US008128957B1

(12) United States Patent
Seth et al.

(10) Patent No.: US 8,128,957 B1
(45) Date of Patent: *Mar. 6, 2012

(54) MODIFIED RELEASE COMPOSITIONS OF AT LEAST ONE FORM OF TRAMADOL

(75) Inventors: Pawan Seth, Irvine, CA (US); Paul J. Maes, Toronto (CA)

(73) Assignee: Valeant International (Barbados) SRL, Welches (BB)

( * ) Notice: Subject to any disclaimer, the term of this patent is extended or adjusted under 35 U.S.C. 154(b) by 6 days.

This patent is subject to a terminal disclaimer.

(21) Appl. No.: 10/933,479

(22) Filed: Sep. 3, 2004

Related U.S. Application Data

(63) Continuation-in-part of application No. 10/434,266, filed on May 9, 2003, now abandoned, which is a continuation-in-part of application No. PCT/US03/04866, filed on Feb. 21, 2003.

(60) Provisional application No. 60/357,851, filed on Feb. 21, 2002.

(51) Int. Cl.
*A61K 9/20* (2006.01)
*A61K 9/58* (2006.01)
*A61K 9/22* (2006.01)
*A61K 9/16* (2006.01)

(52) U.S. Cl. ......... 424/464; 424/462; 424/468; 424/490

(58) Field of Classification Search .................. None
See application file for complete search history.

(56) References Cited

U.S. PATENT DOCUMENTS

| | | | |
|---|---|---|---|
| 4,801,460 A | 1/1989 | Goertz et al. | |
| 5,073,379 A | 12/1991 | Klimesch et al. | |
| 5,478,577 A * | 12/1995 | Sackler et al. | 424/489 |
| 5,601,842 A | 2/1997 | Bartholomaeus | |
| 5,639,476 A | 6/1997 | Oshlack et al. | |
| 5,645,858 A | 7/1997 | Kotwal et al. | |
| 5,648,096 A | 7/1997 | Gander et al. | |
| 5,672,360 A | 9/1997 | Sackler et al. | |
| 5,811,126 A | 9/1998 | Krishnamurthy | |
| 5,891,471 A | 4/1999 | Miller et al. | |
| 5,914,129 A | 6/1999 | Mauskop | |
| 5,919,826 A | 7/1999 | Caruso | |
| 5,929,122 A | 7/1999 | Reimann | |
| 5,955,104 A | 9/1999 | Momberger et al. | |
| 5,958,452 A | 9/1999 | Oshlack et al. | |
| 5,965,161 A | 10/1999 | Oshlack et al. | |
| 5,968,551 A | 10/1999 | Oshlack et al. | |
| 5,980,941 A | 11/1999 | Raiden et al. | |
| 6,001,391 A | 12/1999 | Zeidler et al. | |
| 6,024,980 A | 2/2000 | Hoy | |
| 6,068,855 A | 5/2000 | Leslie et al. | |
| 6,077,532 A | 6/2000 | Malkowska et al. | |
| 6,090,856 A | 7/2000 | Sasaki | |
| 6,103,261 A | 8/2000 | Chasin et al. | |
| 6,117,452 A | 9/2000 | Ahlgren et al. | |
| 6,117,453 A * | 9/2000 | Seth et al. | 424/486 |
| 6,143,322 A | 11/2000 | Sackler et al. | |
| 6,143,327 A * | 11/2000 | Seth | 424/482 |
| 6,156,342 A * | 12/2000 | Sriwongjanya et al. | 424/473 |
| 6,159,501 A | 12/2000 | Skinhog | |
| 6,162,467 A | 12/2000 | Miller et al. | |
| 6,190,591 B1 | 2/2001 | van Lengerich | |
| 6,221,394 B1 | 4/2001 | Gilbert et al. | |
| 6,248,363 B1 | 6/2001 | Patel et al. | |
| 6,254,887 B1 | 7/2001 | Miller et al. | |
| 6,270,805 B1 | 8/2001 | Chen et al. | |
| 6,290,990 B1 | 9/2001 | Grabowski et al. | |
| 6,294,195 B1 | 9/2001 | Oshlack et al. | |
| 6,297,286 B1 | 10/2001 | Huckle | |
| 6,306,438 B1 | 10/2001 | Oshlack et al. | |
| 6,326,027 B1 * | 12/2001 | Miller et al. | 424/468 |
| 6,340,475 B2 | 1/2002 | Shell et al. | |
| 6,342,250 B1 | 1/2002 | Masters | |
| 6,350,471 B1 * | 2/2002 | Seth | 424/480 |
| 6,399,096 B1 | 6/2002 | Miller et al. | |

(Continued)

FOREIGN PATENT DOCUMENTS

CA 2274934 6/1998

(Continued)

OTHER PUBLICATIONS

"Controlled release of tramadol hydrochloride from matrices prepared using glycerol" Obaidot et al., Eur. J. Pharmaceuticals and Biopharmaceutics, 52 (2):231-5 (Sep. 2001) (Biosis Abstract No: 200100535020).

"In vitro/in vivo characterization of a tramadol HCl depot system composed of monoolein and water", Malonne et al., Biol Pharm. Bull. 23(5):627-37 (May 2000) (Biosis Abstract No. 200000356581).

"Microencapsulated and characterization of tramadol-resin completes" Zhang et al, J. Controlled Release 66(2-3):107-113 (May 15, 2000) (Biosis Abstract No. 20000236271).

"Study on controlled-release tablets of tramadol hydrochloride" Cao et al, Zhongguo Yiyao Gungyo Zazhi 30(4):154-6 (1999) (Biosis Abstract No. 199900439938).

(Continued)

*Primary Examiner* — Michael G Hartley
*Assistant Examiner* — Nabila Ebrahim
(74) *Attorney, Agent, or Firm* — Oblon, Spivak, McClelland, Maier & Neustadt, L.L.P.

(57) ABSTRACT

The present invention relates to a modified release composition of at least one form of tramadol which is a delayed and extended release composition for oral administration suitable for once daily dosing. That composition comprises a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient. That composition further comprises a modified release coating which substantially surrounds said core. The compositions of the invention provide delayed and extended release of said at least one form of tramadol such that the mean plasma concentration of the at least one form of tramadol reaches a therapeutically effective level at a time which is after at least about 3 hours after first administration.

35 Claims, 48 Drawing Sheets

U.S. PATENT DOCUMENTS

| | | |
|---|---|---|
| 6,451,350 B1 | 9/2002 | Bartholomaeus et al. |
| 6,488,962 B1 * | 12/2002 | Berner et al. .................. 424/484 |
| 6,558,704 B1 | 5/2003 | Bartholomaeus et al. |
| 6,576,260 B2 | 6/2003 | Bartholomaeus et al. |
| 6,593,373 B2 | 7/2003 | Koegel et al. |
| 6,635,279 B2 | 10/2003 | Kolter et al. |
| 6,673,369 B2 | 1/2004 | Rampal et al. |
| 6,685,964 B1 | 2/2004 | Bartholomaeus et al. |
| 6,723,343 B2 | 4/2004 | Kugelmann et al. |
| 6,780,891 B2 | 8/2004 | Senanayake et al. |
| 6,806,294 B2 | 10/2004 | Wimmer et al. |
| 6,828,345 B2 | 12/2004 | Buschmann et al. |
| 2001/0036477 A1 | 11/2001 | Miller et al. |
| 2002/0015730 A1 | 2/2002 | Hoffmann et al. |
| 2002/0044968 A1 | 4/2002 | van Lengerich |
| 2002/0094992 A1 * | 7/2002 | MacLean ...................... 514/303 |
| 2002/0102300 A1 | 8/2002 | Miller et al. |
| 2002/0150616 A1 | 10/2002 | Vandecruys |
| 2003/0026839 A1 * | 2/2003 | Oshlack et al. ................ 424/469 |
| 2003/0044464 A1 | 3/2003 | Ziegler et al. |
| 2003/0068371 A1 | 4/2003 | Oshlack et al. |
| 2003/0068375 A1 | 4/2003 | Wright et al. |
| 2003/0073714 A1 | 4/2003 | Breder et al. |
| 2003/0091630 A1 | 5/2003 | Louie-Helm et al. |
| 2003/0091635 A1 | 5/2003 | Baichwal et al. |
| 2003/0099711 A1 | 5/2003 | Meadows et al. |
| 2003/0104048 A1 | 6/2003 | Patel et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124184 A1 | 7/2003 | Mezaache et al. |
| 2003/0124185 A1 | 7/2003 | Oshlack et al. |
| 2003/0143270 A1 | 7/2003 | Debroeck et al. |
| 2003/0157168 A1 | 8/2003 | Breder et al. |
| 2003/0175343 A1 | 9/2003 | Razus et al. |
| 2003/0180359 A1 | 9/2003 | Vergnault et al. |
| 2003/0215496 A1 | 11/2003 | Patel et al. |
| 2004/0009219 A1 | 1/2004 | Odidi et al. |
| 2004/0022852 A1 | 2/2004 | Chopra et al. |
| 2004/0076669 A1 | 4/2004 | Bartholomaus et al. |
| 2004/0091528 A1 | 5/2004 | Rogers et al. |

FOREIGN PATENT DOCUMENTS

| | | |
|---|---|---|
| CA | 2295790 | 1/2000 |
| EP | 0864326 | 9/1998 |
| EP | 914823 | 5/1999 |
| EP | 1 020 186 | 7/2000 |
| WO | WO 00/40205 | 7/2000 |
| WO | WO 01/47497 A2 | 7/2001 |
| WO | WO 01/56544 | 8/2001 |
| WO | WO 01/85257 A2 | 11/2001 |
| WO | WO 02/02084 A1 | 1/2002 |

OTHER PUBLICATIONS

"Pharmacokinetic properties of tramodol sustained release capsules: $1^{st}$ communication: investigation of relative bioavailability" Schulz et al, Arzheimittel-Forschung 49(7):582.7 (Jul. 1999) (Biosis Abstract No. 19990383123).

"Pharmacokinetic properties of tramadol sustained release capsules: $3^{rd}$ Communication: Investigation of relative bioavailability under study conditions" Raber et al., Arzeimittel-Forschung 49(7):594-8 (Jul. 1999) (Biosis Abstract No. 199900321598).

"Pharmacokinetic properties of tramadol sustained release capsules" $2^{nd}$ communication: Investigation of relative bioavailability and food Interaction Raber et al., Arzheimittel-Forschung 49(7):588-93 (1999) (Biosis Abstract No. 199900381597).

"Analgesic efficacy and Tolerability of tramadol 100mg sustained-release capsules in patients with moderate to sever chronic low back pain" Drug Invest. 17(6):415-23 (1999) (Biosis Abstract No. 199900319232).

"Comparison of the analgesic efficacy and tolerability of tramadol 100mg sustained release tablets and tramadol 50 mg capsules for the treatment of chronic low back pain." Serge et al., Clin. Drug Invest. 14(3):157-64 (1997) (Biosis Abstract No. 19997997912941).

"Assessment of analgesain in man: Tramadol controlled release formula vs. tramadol stranded formulation." Hummel et al., Eur. J. Colin. Pharmacol. 51(1):3108 (1995) (Biosis Abstract No. 19969205011).

"Dose dependent time course of the analgesic effect of a sustained-release preparation of tramadol an experimental phasic and tonic path." Thuerauf et al., Br. J. Clin. Pharmacol. 41(2):115-23 (1996) (Biosis Abstract No. 199698733219).

* cited by examiner

MODIFIED RELEASE COMPOSITIONS OF AT LEAST ONE FORM OF TRAMADOL

RELATED APPLICATIONS

This application is a continuation-in-part of U.S. patent application Ser. No. 10/434,266 filed May 9, 2003 now abandoned, which is in turn a continuation-in-part of and claims benefit of priority under 35 U.S.C. 120 and 365(c) to PCT/US03/04866 which application designated the United States of American and has an International filing date of Feb. 21, 2003 which itself claims the benefit of U.S. provisional patent application No. 60/357,851 filed Feb. 21, 2002. The contents of all said applications are incorporated herein by reference in their entireties.

FIELD OF THE INVENTION

The present invention relates to modified release compositions for oral administration of at least one form of tramadol, to processes for their preparation and to their medical use. In particular, the present invention relates to a delayed and extended release composition of at least one form of tramadol.

BACKGROUND OF THE INVENTION

An ideal dosage regimen for many medications is that by which an acceptable therapeutic concentration of drug at the site(s) of action is attained immediately and is then maintained constant for the duration of the treatment. Providing dose size and frequency of administration are correct, therapeutic "steady-state" plasma concentrations of a drug can be achieved promptly and maintained by the repetitive administration of conventional peroral dosage forms. However, there are a number of potential limitations associated with conventional peroral dosage forms. These limitations have led pharmaceutical scientists to consider presenting therapeutically active molecules in "extended-release" preparations.

Oral ingestion is the traditionally preferred route of drug administration, providing a convenient method of effectively achieving both local and systemic effects. An ideal oral drug delivery system should steadily deliver a measurable and reproducible amount of drug to the target site over a prolonged period. Extended-release (ER) delivery systems provide a uniform concentration/amount of the drug at the absorption site and thus, after absorption, allow maintenance of plasma concentrations within a therapeutic range over an extended period of time, which can minimize side effects and also reduces the frequency of administration. ER dosage forms release drug slowly, so that plasma concentrations are maintained at a therapeutic level for a prolonged period of time. Typically, these products provide numerous benefits compared with immediate-release compositions, including greater effectiveness in the treatment of chronic conditions, reduced side effects, greater convenience, and higher levels of patient compliance due to a simplified dosing schedule. Because of the above advantages, such systems form a major segment of the drug delivery market.

Over the years many drug delivery systems have been developed with the aim of eliminating the cyclical changes in plasma drug concentration seen after the administration of a conventional delivery system. A variety of terms have been used to describe these systems: delayed release, repeat action, prolonged release, sustained release, extended release, controlled release and modified release. It is interesting to note that the USP considers that the terms controlled release, prolonged release, sustained release and extended-release are interchangeable.

There are at least three types of modified release pharmaceutical compositions in the pharmaceutical art; namely those that are delayed release, those that are extended release, and those that are both delayed and extended release. Delayed release pharmaceutical compositions are often designed to prevent drug release in the upper part of the gastrointestinal tract. Modified release coatings used to prepare this type of pharmaceutical composition are commonly called enteric coatings in the pharmaceutical art. Extended release pharmaceutical compositions are designed to extend drug release over a period of time, a result that is often achieved by the application of a sustained or controlled release coating.

Tramadol, which was first described in U.S. Pat. No. 3,652,589, is in a class of analgesic cycloalkanol-substituted phenol esters having a basic amine group in the cycloalkyl ring and having the chemical name trans-($\pm$)-2-[(dimethylamino)methyl]-1-(3-methoxyphenyl)cyclohexanol. Tramadol is believed to produce an analgesic effect through a mechanism that is neither fully opioid-like nor non-opioid-like because clinical data suggest that tramadol lacks many of the typical side effects of opioid antagonists such as respiratory depression, constipation, tolerance and abuse liability but can produce hot flashes and sweating. Due to the combination of non-opioid and opioid activity, tramadol is a very unique analgesic and many attempts have been made to prepare oral compositions of the drug.

Conventional or immediate release preparations in the form of tablets, capsules, drops and suppositories containing tramadol, or more particularly its hydrochloride salt, have been commercially available for many years for use in the treatment of moderate to severe pain. For example, an immediate release oral composition of tramadol is commercially available in the United States, from Ortho-McNeil Pharmaceutical under the trade name ULTRAM® as tramadol hydrochloride tablets.

The clinical efficacy of immediate release tramadol preparations has been well established in numerous single dose and multiple dose studies, with 70% to 90% of patients obtaining satisfactory pain relief depending on the etiology of the pain. Immediate release tramadol preparations have demonstrated efficacy in obstetrical, gynecologic, orthopedic, abdominal and oral surgery. Immediate-release tramadol preparations have been studied in long-term clinical trials in patients with chronic pain of varying etiology, including low-back pain, osteoarthritis, cancer pain, neuropathic pain and orthopedic pain. The $53^{rd}$ Edition of the Physician's Desk Reference, copyright 1999, p. 2255, states that peak plasma levels of tramadol for the ULTRAM® product occur at about 1.6 hours after a single oral dose (100 mg) and at about 2.3 hours after multiple oral dosing (100 mg q.i.d). Lintz et al. has demonstrated that a plasma concentration of total tramadol (sum of the (+) and (−) enantiomer) of 100 ng/ml is clinically effective in the treatment of mild to moderate pain (Lintz et al. Bioavailability of enteral tramadol formulations. $1^{st}$ communication: capsules. Arzneimittelforschung 1986; 36: 1278-83). The short elimination half-life of tramadol necessitates dosing of patients with immediate-release tramadol preparations every 4-6 hours in order to maintain optimal levels of analgesia in chronic pain. The consequence of this multiple dosing schedule is the inevitable fluctuations of steady state concentrations of the drug in the plasma, and hence at the site(s) of action, leading to a patient being possibly over- or under medicated for periods of time if the values of $C_{max}$ and $C_{min}$, rise or fall, respectively, beyond the therapeutic range.

Another consequence of the multiple dosing schedule for ULTRAM® is that the concentration of tramadol in the plasma and hence at the site(s) of action of the drug fluctuates over successive dosing intervals, even when the so-called "steady-state" condition is achieved. Hence it is not possible to maintain a therapeutic concentration of drug, which remains constant at the site(s) of action for the duration of treatment. At best, the mean value of the maximum and minimum plasma concentrations associated with each successive dose remains constant for the period of drug treatment. Finally, because of the short-elimination half-life of tramadol the multiple dosing schedule for ULTRAM® must be adhered to in order to maintain steady-state plasma concentrations within the therapeutic range. For drugs such as tramadol, the maintenance of therapeutic plasma concentrations is particularly susceptible to the consequence of forgotten doses and the overnight no-dose period. Lack of patient compliance, which is more likely in the case of regimens requiring frequent administration of conventional dosage forms, can be an important reason for therapeutic inefficiency or failure.

Given the clinical efficacy of tramadol and the limitations of a conventional drug delivery system such as ULTRAM®, tramadol is an excellent candidate for an ER drug delivery system wherein the dosing schedule would be reduced to once-daily administration of the ER dosage from. An ER dosage form would be even more advantageous if it could reduce the adverse events or side effects often seen with immediate-release compositions of tramadol. Accordingly, there is a need in the art for an ER dosage form of tramadol exhibiting reduced adverse events or side effects compared to the currently marketed ULTRAM®.

Indeed, various attempts have been made to formulate tramadol into modified-release compositions. For example, such compositions purporting to control the release of tramadol within the gastrointestinal tract, with the purported result that tramadol is delivered at a specific predetermined rate have been described in several patents and patent applications.

U.S. Pat. Nos. 5,958,452, and 6,254,887 to Miller et al. describe a controlled release preparation of tramadol, wherein the tramadol is incorporated into a controlled release matrix. The references also state that the controlled release preparation may comprise a normal release matrix having a controlled release coating, but fail to describe or disclose how such a preparation is to be made. FIGS. 1 and 2 of the '887 reference show that the controlled release tramadol preparation when administered as a single dose releases tramadol without any delay or lag time, and there is no disclosure or teaching relating to making a controlled release tramadol preparation with a delay or lag time. It is known in the art that a relatively quick release of certain irritant drugs may increase the incidence and severity of localized gastrointestinal side effects. While the rate of release of tramadol from the composition described in the '887 reference is admittedly slower than that of the conventional release tramadol drop preparation Tramal®, the reference does not teach if the controlled release composition was able to reduce or at least equal the incidence of any adverse events compared to Tramal®. In fact, neither Miller reference provides any data on the adverse events or side effect profile of the claimed composition.

U.S. Pat. Nos. 5,672,360 and 5,478,577 disclose a method of treating pain in humans comprising orally administering on a once a day basis an oral sustained release dosage form of an opioid analgesic which upon single dose and multiple dose administration provides a time to maximum plasma concentration ($T_{max}$) of said opioid in about 2 to 10 hours and a maximum plasma concentration ($C_{max}$) which is more than twice the plasma level of said opioid at about 24 hours after administration of the dosage form and which dosage form provides effective treatment of pain for about 24 hours or more after administration to the patient.

U.S. Pat. Nos. 5,395,626, 5,474,786, and 5,645,858, all to Kotwal et al., disclose a multilayered controlled release pharmaceutical dosage form comprising a plurality of coated particles comprising a core containing tramadol, hydroxypropyl methylcellulose, polyethylene glycol and propylene glycol overcoated with a controlled release barrier comprising ethylcellulose and which is over coated at least once with a mixture of tramadol, hydroxypropyl methylcellulose, polyethylene glycol and propylene glycol, which is again overcoated with an additional controlled release barrier comprising ethylcellulose. A final outer layer may comprise tramadol intended for substantially immediate release. These references do not provide any comparative data of the performance of the composition taught therein to an immediate-release composition of tramadol, such as ULTRAM®, or to the controlled release compositions of Miller described above. The in vitro dissolution profiles of the Kotwal compositions appear to show a slight delay in the release of tramadol, however pharmacokinetic data have not been presented to determine the efficacy of these compositions nor have any data been presented on the incidence of any adverse events resulting from the administration of the compositions. As a result, it is not known whether the apparent slight delay in in vitro dissolution necessarily results in any delay in in vivo plasma levels. Accordingly, it is not known if the apparent slight in vitro delay in the extended release of the tramadol of the Kotwal compositions has any clinical significance.

U.S. Pat. No. 6,576,260 describes a sustained release formulation of tramadol comprising tramadol saccharinate coated with at least one sustained-release coating. The tramadol saccharinate is itself a poorly soluble salt of tramadol and contributes to the sustained release of the composition. Further retardation is achieved by a sustained release coating. In vivo performance of this formulation is not disclosed.

US Patent Publication No. 2003/0143270A1 discloses a once daily extended release composition containing tramadol. The composition comprises a core containing tramadol or its pharmaceutically acceptable salts, a water soluble insulating membrane separating the tramadol containing core from the controlled release membrane, and a controlled release membrane. The composition in vitro exhibits a biphasic dissolution profile. The composition purports to provide an effective blood concentration of about 24 hours with reduced peak concentrations. The composition provides effective tramadol levels within about 1 to 2 hours after a single administration of the composition where the time to peak tramadol content is at least 10 hours and the peak tramadol concentration is less than three times the concentration obtained after 24 hours of administration. The document does not disclose the side effect or adverse event profile of the composition in comparison to the immediate release formulation.

EP patent Application No. 1190712A1 describes a composition comprising a core containing tramadol or its pharmaceutically acceptable salts, a water soluble insulating membrane separating the tramadol containing core from the controlled release membrane, and a controlled release membrane. The water soluble insulating membrane between the core and the rate controlling releasing membrane reduces the differences of tramadol dissolution rates between batches. The composition provides a time to peak tramadol content of at least about 10 hours versus 2 hours as well as a significantly reduced $C_{max}$ in comparison to the immediate release composition. The document does not disclose the side effect or adverse event profile of the composition in comparison to the immediate release formulation.

U.S. Pat. No. 5,601,842 discloses a tablet containing tramadol and a matrixing agent with a viscosity between 3,000 and 150,000 mPa in a 2% aqueous solution at 20° C.

U.S. Pat. No. 5,811,126 discloses a controlled release pharmaceutical composition containing tramadol and comprising sodium alginate, $C_2$ to $C_{50}$ edible hydrocarbon derivative with melting point range from 25° C. to 90° C. and divalent salt to cross link the alginate. In vivo performance from these formulations is not available.

U.S. Pat. Nos. 5,639,476 and 5,580,578 disclose controlled release dosage forms containing a substrate containing tramadol, said substrate being coated with a plasticized aqueous dispersion of ammonio-methacrylate copolymer having low content of quaternary ammonium groups and a permeability enhancing pore former, said coating being cured for about 24 to about 60 hours to stabilize said formulation.

U.S. Pat. No. 5,955,104 discloses a delayed release tramadol formulation consisting of pellets in a water soluble capsule or in a tablet compressed from said pellets, each pellet having (a) a substantially inert core; (b) an active ingredient layer over the inert core and containing (i) tramadol particles, (ii) with a binder for adhering said tramadol particles over said inert core, and optionally (iii) a pharmaceutically acceptable, inner adjuvant; and (c) a delay coating for retarding the release of tramadol consisting principally of mixtures of ethylcellulose and shellac.

U.S. Pat. No. 5,849,240 describes a process for the manufacture of particles by the "melt-pelletization" process. Tramadol is one of the examples but the in vivo performance of such a formulation is not available.

U.S. Pat. No. 5,965,163 describes a solid dosage form comprising a plurality of particles including tramadol in a matrix, the matrix including a mixture of hydrophobic and hydrophilic fusible carriers having melting point from 35° C. to 150° C., which are produced by the method of "melt-pelletization".

U.S. Pat. No. 5,958,482 describes a sustained release pharmaceutical formulation comprising an extruded blend of tramadol, and one or more hydrophobic fusible carriers having a melting point from about 30 to about 200° C., providing a sustained-release of said therapeutically active agent for a time period of from about 8 to about 24 hours, with a peak plasma level for about 2 to 8 hours.

U.S. Pat. No. 5,891,471 teaches tramadol pharmaceutical particles for once a day administration, which provides a time to peak plasma level of tramadol in about 2 to about 6 hours after administration, produced by a process of "melt-pelletization".

U.S. Pat. No. 5,968,551 describes a sustained release oral analgesic form for once a day administration comprising a unit dose comprising a plurality of pharmaceutically acceptable matrices comprising an analgesically effective amount of tramadol and hydrophobic material, each of said matrices having a diameter of about 0.1 to 3 mm and having a therapeutic effect for about 24 hours or more after oral administration to a human patient. It also discloses a method of treating patients for moderate to severe pain with a once daily oral administration of a unit dose consisting of a plurality of inert pharmaceutically acceptable beads coated with an analgesically effective amount of an opioid and a sustained release coating. The beads have a diameter of 0.1 to 3 mm and provide effective blood levels of the opioid for about 24 hours with peak plasma levels of the opioid in vivo from about 3 to about 10 hours after administration.

U.S. Pat. No. 5,919,826 describes a sustained release tramadol composition providing a time to peak plasma level of about 2 to about 6 hours and produced by a process comprising high speed mixing of tramadol with a hydrophobic or hydrophilic carrier having a melting point from 35° C. to 150° C., and breaking down the agglomerates to give controlled release particles.

U.S. Pat. No. 6,376,550 is directed to a composition and method of treating migraine in which the composition consists essentially of pharmacologically effective amounts of both an antiemetic compound, such as metoclopramide, and tramadol. The reference does not teach, and in fact teaches away from, a composition comprising only tramadol as the pharmaceutically active agent.

U.S. Pat. No. 6,156,342 is directed to a controlled release dosage form for an analgesic that does not contain an expanding polymer and comprising a core containing an analgesic, preferably tramadol or its pharmaceutically acceptable derivatives and a semipermeable membrane coating the core. FIGS. 2 and 3 show a 4-hour delay before plasma tramadol levels are seen to rise. However, the formulation (P97540) cannot be clinically effective as the peak plasma concentration reached in both the fed and fasted state is about 40 ng/ml, which is significantly lower than the expected clinically effective plasma tramadol concentration of 100 ng/ml plasma tramadol reported by Lintz et al. There is no report in the reference to actual clinical or therapeutic effectiveness of the formulation.

International Patent Application No. PCT/CA2003/001638 (published as WO 2004/037222) describes a sustained release tramadol formulation for oral administration, which, upon initial administration of one dose, provides a mean plasma concentration of at least 100 ng/ml within 2 hours of administration and continues to provide a mean plasma concentration of at least 100 ng/ml for at least 22 hours after administration. The composition comprises tramadol and a matrix, wherein the components are associated in such a way that release of tramadol from the matrix is controlled. The matrix is a cross-linked high amylose starch known under the name Contramid®, which is described in U.S. Pat. No. 6,607,748. The matrix core is then coated with a physical mixture of polyvinyl acetate, polyvinylpyrrolidone and tramadol. The coat is formed by dry compression. No data have been provided to show whether the formulation exhibited a reduction in any adverse events compared to an immediate-release or other controlled-release formulation of tramadol.

The in vivo performance of a new oral sustained release dosage form of tramadol is described by Malonne et al. (Malonne et al. 2004. Pharmacokinetic evaluation of a new oral sustained release dosage of tramadol. 57(3): 270-278.). The reference does not teach the composition of the new sustained release dosage form, however, it allegedly provides better in vivo performance than an immediate release composition of tramadol in that it exhibits a significantly lower $C_{max}$ and longer $T_{max}$ compared to an immediate release tramadol composition. Food did not significantly modify any of the pharmacokinetic parameters assessed for the sustained release dosage form. However, the reference reports that the fluctuation and $C_{min}$ were similar for both the sustained release and immediate release compositions. Moreover, the sustained release composition did not appear to reduce the number of adverse events as the number of adverse events is reported to be similar to the immediate release composition.

Despite the many patents and patent applications describing sustained-release/controlled-release once-daily formulations of tramadol, it is noteworthy that as yet none of these compositions or formulations has been commercialized in the US. Given the clinical efficacy of tramadol and the limitations of a conventional drug delivery system such as ULTRAM® together with the fact that a controlled/extended/modified release dosage form of tramadol has yet to be commercially manufactured in the US, there remains a need in the art for a once daily extended release composition of tramadol which would also result in a reduction in the incidence and severity of untoward side-effects.

SUMMARY OF THE INVENTION

The present invention relates to a modified release composition of at least one form of tramadol.

In one embodiment of the invention, the modified release composition of the at least one form of tramadol is a delayed and extended release composition for oral administration suitable for once daily dosing comprising: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a modified release coating which substantially surrounds said core, wherein said composition provides delayed and extended release of said at least one form of tramadol such that the mean plasma concentration of the at least one form of tramadol reaches a therapeutically effective level at a time which is after at least about 3 hours after first administration of said composition in the fasted state.

In another embodiment of the invention the composition provides an in vitro dissolution profile using the USP Basket Method at 75 rpm in 900 ml 0.1 N HCl at 37° C. such that after about 2 hours, from about 0 to about 22% by weight of the at least one form of tramadol is released, after about 4 hours from about 5 to about 30% by weight of said at least one form of tramadol is released, after about 6 hours, from about 15 to about 38% by weight of said at least one form of tramadol is released, and after about 8 hours, more that about 40% by weight of said at least one form of tramadol is released.

In another embodiment of the invention, the composition provides an in vitro dissolution profile using the USP Basket Method at 75 rpm in 900 ml 0.1 N HCl at 37° C. such that after about 2 hours, from about 2 to about 10% by weight of said at least one form of tramadol is released, after about 4 hours from about 12 to about 20% by weight of said at least one form of tramadol is released, after about 6 hours from about 30 to about 38% by weight of said at least one form of tramadol is released, after about 8 hours, from about 48 to about 56% by weight of said at least one form of tramadol is released, after about 10 hours from about 64 to about 72% by weight of said at least one form of tramadol is released, and after about 12 hours, more than about 76% by weight of said at least one form of tramadol is released.

In another embodiment of the invention, the composition when administered to a patient in need thereof provides a mean time to maximum plasma concentration ($T_{max}$) of the at least one form of tramadol ranging from about four to about fourteen hours.

In another embodiment of the invention, the composition when administered once-daily to a patient in need thereof is bioequivalent to an immediate-release composition of tramadol and provides at steady state a fluctuation index equivalent to or lower than an immediate release composition of tramadol when said immediate-release composition is administered three- or four-times daily.

In another embodiment of the invention, the incidence of adverse events resulting from the composition is less than or equal to that of an immediate-release composition of the at least one form of tramadol.

In another embodiment of the invention, the composition exhibits a statistically significant reduction in adverse events when compared to an extended release composition of the at least one form of tramadol.

In another embodiment of the invention, the at least one form of tramadol present in the composition can range from about 70 to about 98% by weight of the core dry weight.

In another embodiment of the invention, the composition comprises from about 100 mg to about 300 mg of the at least one form of tramadol.

In another embodiment of the invention, the at least one form of tramadol is a pharmaceutically acceptable salt thereof. It is preferable that the pharmaceutically acceptable salt is an acid addition salt, most preferably the acid addition salt is the hydrochloride salt.

In another embodiment of the invention, the core of the composition comprises an immediate release core or a controlled release core. Preferably, the core is an immediate release core.

In another embodiment of the invention, the pharmaceutically acceptable excipient is selected from the group consisting of a binder, a lubricant, a filler, a glidant and combinations thereof. The binder is present from about 1 to about 25%, preferably from about 1 to about 10%, and more preferably from about 1 to about 5% by weight of the core dry weight and is selected from the group consisting of starch derivatives, gelatin, polyvinylpyrrolidone, polyvinyl alcohol, hydroxypropylmethylcellulose, hydroxypropylcellulose, xanthan gum, carbomers, caragheen and combinations thereof. The binder is preferably polyvinyl alcohol and is present at about 2% by weight of the core dry weight. The lubricant is present from about 0.5 to about 10%, preferably from about 0.5 to about 5%, and more preferably from about 0.5 to about 2% by weight of the core dry weight and is selected from the group consisting of stearic acid, magnesium stearate, glyceryl behenate, talc, mineral oil (in PEG), sodium stearyl fumarate, hydrogenated vegetable oils, sodium benzoate, calcium stearate and combinations thereof. The lubricant is preferably sodium stearyl fumarate and is present at about 1% by weight of the core dry weight. The glidant, preferably colloidal silicon dioxide, is present at about 1% by weight of the core dry weight. Depending on the size of the tablet, the filler is an optional excipient and can be present from about 1 to about 25% by weight of the core dry weight, preferably from about 1 to about 10%, and more preferably from about 1 to about 5%. A suitable filler is selected from the group consisting of lactose monohydrate, anhydrous lactose, mannitol, sorbitol, microcrystalline cellulose, dibasic calcium, calcium sulfate, pulp cellulose and combinations thereof. The preferred filler, if one is to be used, is microcrystalline cellulose.

In another embodiment, the modified released coating comprises a water-insoluble water-permeable film-forming polymer, a water-soluble polymer and a plasticizer. The water-insoluble water-permeable film-forming polymer is present in an amount from about 20 to about 89% by weight of the coating dry weight and is selected from the group consisting of cellulose ethers, cellulose esters, methacrylic acid derivatives, aqueous ethylcellulose dispersions, aqueous acrylic enteric systems, polyvinyl derivatives, and combinations thereof. The water-insoluble water-permeable film-forming polymer is preferably a cellulose ether such as ethylcellulose and is preferably present from about 53 to about 70% of the coating dry weight and most preferably at about 9% by weight of the composition. The water-soluble polymer is selected from the group consisting of methylcellulose, hydroxypropylmethylcellulose, hydroxypropylcellulose, hydroxyethylcellulose, polyvinyl alcohol, polyvinylpyrrolidone, and combinations thereof, present in an amount from about 10 to about 75%, and preferably from about 20 to about 26% by weight of the coating dry weight. The water-soluble polymer is preferably polyvinylpyrrolidone, present most preferably at about 3.5% by weight of the composition. The plasticizer is present from about 1 to about 30%, and preferably from about 14 to about 18% by weight of the coating dry weight. The plasticizer is preferably an ester such as dibutyl sebacate and is most preferably present at about 2.5% by weight of the composition.

In another embodiment of the invention, the modified release coating is present from about 8% to about 30% and preferably at about 16% by weight of the core dry weight.

In another embodiment of the invention, the pharmaceutical composition for oral administration is in the form of a tablet or capsule. Preferably, the composition is in the form of a tablet.

In another embodiment of the invention, the delayed and extended release pharmaceutical composition for oral administration suitable for once daily dosing comprises: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a coating substantially surrounding said core, said coating comprising a water-insoluble water-permeable film-forming polymer, a water-soluble polymer and a plasticizer, wherein said composition provides delayed and extended release of said at least one form of tramadol such that the mean plasma concentration of the at least one form of tramadol reaches a therapeutically effective level at a time which is after at least about 3 hours after first administration of said composition in the fasted state.

In another embodiment of the invention, the delayed and extended release pharmaceutical composition for oral administration suitable for once daily dosing comprises: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a coating substantially surrounding said core, said coating comprising a water-insoluble water-permeable film-forming polymer, a water-soluble polymer and a plasticizer, wherein said composition provides delayed and extended release of said at least one form of tramadol such that the mean plasma concentration of the at least one form of tramadol reaches a therapeutically effective level at a time which is after at least about 3 hours after the first administration of said composition in the fasted state, is bioequivalent to an immediate-release composition of the at least one form of tramadol and provides at steady state a fluctuation index equivalent to or lower than an immediate-release composition of the at least one form of tramadol administered three or four times daily.

In another embodiment of the invention, the delayed and extended release pharmaceutical composition for oral administration suitable for once daily dosing comprises: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a coating substantially surrounding said core, said coating comprising a water-insoluble water-permeable film-forming polymer, a water-soluble polymer and a plasticizer, wherein said composition provides delayed and extended release of said at least one form of tramadol such that the mean plasma concentration of the at least one form of tramadol reaches a therapeutically effective level at a time which is after at least about 3 hours after first administration of said composition in the fasted state and provides 90% geometric mean confidence intervals for $C_{max}$, $C_{min}$, and $AUC_{0-\tau}$, that fall within the 80-125% limit compared to an immediate release composition of the at least one form of tramadol administered three or four times daily.

In another embodiment of the invention, the delayed and extended release tramadol composition comprises: a) a core comprising at least one form of tramadol selected from the group consisting of from tramadol, racemic mixtures thereof, enantiomers thereof, pharmaceutically acceptable salts thereof, and combinations thereof from about 70 to about 98% by weight of the core dry weight, polyvinyl alcohol from about 1 to about 25% by weight of the core dry weight, and sodium stearyl fumarate from about 0.5 to about 10% by weight of the dry core weight; and b) a coating which substantially surrounds said core, said coating comprising ethylcellulose from about 20 to about 89% by weight of the coating dry weight, polyvinylpyrrolidone from about 10 to about 75% by weight of the coating dry weight, and dibutyl sebacate from about 1 to about 30% by weight of the coating dry weight; wherein said composition provides delayed and extended release of said at least one form of tramadol such that when said composition is administered once-daily to a patient in need thereof it is bioequivalent to an immediate-release composition of the at least one form of tramadol and provides i) a mean plasma concentration of the at least one form of tramadol that reaches a therapeutically effective level at a time which is after at least about 3 hours after first administration of said composition in the fasted state, and ii) provides at steady state a fluctuation index equivalent to or lower than an immediate-release composition of the at least one form of tramadol administered three or four times daily.

In one embodiment of the invention, the delayed and extended release tramadol composition comprises: a) an immediate release core comprising at least one form of tramadol selected from the group consisting of tramadol, racemic mixtures thereof, enantiomers thereof, pharmaceutically acceptable salts thereof, and combinations thereof from about 70 to about 98% by weight of the core dry weight, polyvinyl alcohol at about 2% by weight the core dry weight, sodium stearyl fumarate at about 1% by weight of the core dry weight; and b) a coating substantially surrounding said core present at about 16% by weight of the core dry weight comprising ethylcellulose from about 53 to about 70% by weight of the coating dry weight, polyvinylpyrrolidone from about 20 to about 26% by weight of the coating dry weight, and dibutyl sebacate from about 14 to about 18% by weight of the coating dry weight, said composition when administered once-daily to a patient in need thereof provides i) a steady state 90% geometric mean confidence intervals for $C_{min}$, $C_{max}$, and $AUC_{0-\tau}$, which fall within the 80-125% limit, ii) a steady state fluctuation index equivalent to or lower than an immediate-release composition of the at least one form of tramadol administered three or four times daily, iii) a mean time to maximum plasma concentration ($T_{max}$) of the at least one form of tramadol ranging from about four to about fourteen hours after first administration, iv) an incidence of adverse events which is less than or equal to that of an immediate-release composition of the at least one form of tramadol in the fasted state, vi) a statistically significant reduction in adverse events when compared to an extended but not delayed release composition of the at least one form of tramadol in the fasted state, and vii) a mean plasma concentration of the at least one form of tramadol such that a therapeutically effective level of the at least one form of tramadol is reached after about 3 hours after first administration of said composition in the fasted state.

In one embodiment of the invention, the delayed and extended release pharmaceutical composition for oral administration suitable for once daily dosing comprises: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a modified release coating which substantially surrounds said core, wherein said composition provides delayed and extended release of said at least one form of tramadol in the fed state such that the mean time to maximum plasma concentration of the at least one form of tramadol is delayed by at least about 1 hour after first administration of said composition compared to administration of the composition in the fasted state.

In one embodiment of the invention, the delayed and extended release pharmaceutical composition for oral administration suitable for once daily dosing comprises: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a modified release coating which substantially surrounds said core, wherein said composition provides delayed and extended release of said at least one form of tramadol such that the mean plasma concentration of the at least one form of tramadol reaches a therapeutically effective level at a time which is after at least about 3 hours after first administration of said composition in the fasted state and exhibits reduced side effects compared to an extended but not delayed release composition in the fasted state.

In one embodiment of the invention, the delayed and extended release pharmaceutical composition for oral administration suitable for once daily dosing comprises: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a coating substantially surrounding said core, said coating comprising a water-insoluble water-permeable film-forming polymer, a water-soluble polymer and a plasticizer, wherein said composition provides delayed and extended release of said at least one form of tramadol such that the mean plasma concentration of the at least one form of tramadol reaches a therapeutically effective level at a time which is after at least about 3 hours after first administration of said composition in the fasted state and exhibits reduced side effects compared to an extended but not delayed release composition in the fasted state.

In one embodiment of the invention, the delayed and extended release tramadol tablet comprises:

|  | % w/w | Mg/tablet |
|---|---|---|
| a) a core comprising: | | |
| Tramadol Hydrochloride | 96.3 | 100.00 |
| Colloidal Silicon Dioxide, NF | 0.9 | 1.00 |
| Polyvinyl Alcohol, USP | 1.9 | 2.00 |
| Sodium Stearyl Fumarate, NF and, | 0.9 | 1.00 |
| b) a coating comprising: | | |
| Ethylcellulose 100, NF | 59.9 | 11.39 |
| Polyvinyl Pyrrolidone K-90, USP | 23.2 | 4.4 |
| Dibutyl Sebacate, NF | 16.9 | 3.21 | wherein said composition provides a delayed and extended release of said tramadol hydrochloride.

In another aspect, the invention provides a delayed and extended release pharmaceutical composition for oral administration suitable for once daily dosing comprising at least one form of tramadol selected from the group consisting of tramadol, racemic mixtures thereof, enantiomers thereof, pharmaceutically acceptable salts thereof, and combinations thereof, wherein said composition provides an in vitro dissolution profile using the USP Basket Method at 75 rpm in 900 ml 0.1 N HCl at 37° C. such that after about 2 hours about 0% to about 15% by weight of the at least one form of tramadol is released, preferably about 0% to about 10% after about 2 hours, more preferably about 0% to about 5%; after about 4 hours about 10% to about 40% by weight of the at least one form of tramadol is released, preferably about 10% to about 35%, more preferably about 10% to about 30%; after about 8 hours about 44% to about 85% of the at least one form of tramadol is released, preferably about 45% to about 75%, and most preferably about 50% to about 70%; and after about 16 hours not less than about 80% of the at least one form of tramadol is released, preferably not less than about 85%, and more preferably not less than about 90%.

In a further aspect, the invention provides a delayed and extended release composition for oral administration suitable for once daily dosing comprising: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a modified release coating which substantially surrounds said core, wherein said composition provides an in vitro dissolution profile using the USP Basket Method at 75 rpm in 900 ml 0.1 N HCl at 37° C. such that after about 2 hours, more preferably about 0% to about 5%; after about 4 hours about 10% to about 40% by weight of the at least one form of tramadol is released, preferably about 10% to about 35%, more preferably about 10% to about 30%; after about 8 hours about 44% to about 85% of the at least one form of tramadol is released, preferably about 45% to about 75%, and most preferably about 50% to about 70%; and after about 16 hours not less than about 80% of the at least one form of tramadol is released, preferably not less than about 85%, and more preferably not less than about 90%.

In another aspect, the invention provides a delayed and extended release pharmaceutical composition for oral administration suitable for once daily dosing comprising at least one form of tramadol selected from the group consisting of tramadol, racemic mixtures thereof, enantiomers thereof, pharmaceutically acceptable salts thereof, and combinations thereof, wherein said composition provides an in vitro dissolution profile using the USP Basket Method at 75 rpm in 900 ml 0.1 N HCl, water, pH 6.5 buffer or pH 4.5 buffer, at 37° C. such that after about 2 hours about 0% to about 15% by weight of the at least one form of tramadol is released, preferably about 0% to about 10% after about 2 hours, more preferably about 0% to about 5%; after about 4 hours about 10% to about 40% by weight of the at least one form of tramadol is released, preferably about 10% to about 35%, more preferably about 10% to about 30%; after about 8 hours about 44% to about 85% of the at least one form of tramadol is released, preferably about 45% to about 75%, and most preferably about 50% to about 70%; and after about 16 hours not less than about 80% of the at least one form of tramadol is released, preferably not less than about 85%, and more preferably not less than about 90%.

In a further aspect, the invention provides a delayed and extended release composition for oral administration suitable for once daily dosing comprising: a) a core comprising at least one form of tramadol selected from the group consisting of tramadol, racemic mixtures thereof, enantiomers thereof, pharmaceutically acceptable salts thereof, and combinations thereof in combination with a pharmaceutically acceptable excipient, and b) a modified release coating which substantially surrounds said core, wherein said composition provides an in vitro dissolution profile using the USP Basket Method at 75 rpm in 900 ml 0.1 N HCl, water, pH 6.5 buffer, or pH 4.5 buffer, at 37° C. such that after about 2 hours, more preferably about 0% to about 5%; after about 4 hours about 10% to about 40% by weight of the at least one form of tramadol is released, preferably about 10% to about 35%, more preferably about 10% to about 30%; after about 8 hours about 44% to about 85% of the at least one form of tramadol is released, preferably about 45% to about 75%, and most preferably about 50% to about 70%; and after about 16 hours not less than about 80% of the at least one form of tramadol is released, preferably not less than about 85%, and more preferably not less than about 90%.

BRIEF DESCRIPTION OF THE DRAWINGS

The present invention will be further understood from the following detailed description with reference to the following drawings in which.

DETAILED DESCRIPTION OF THE INVENTION

Figure 1A:
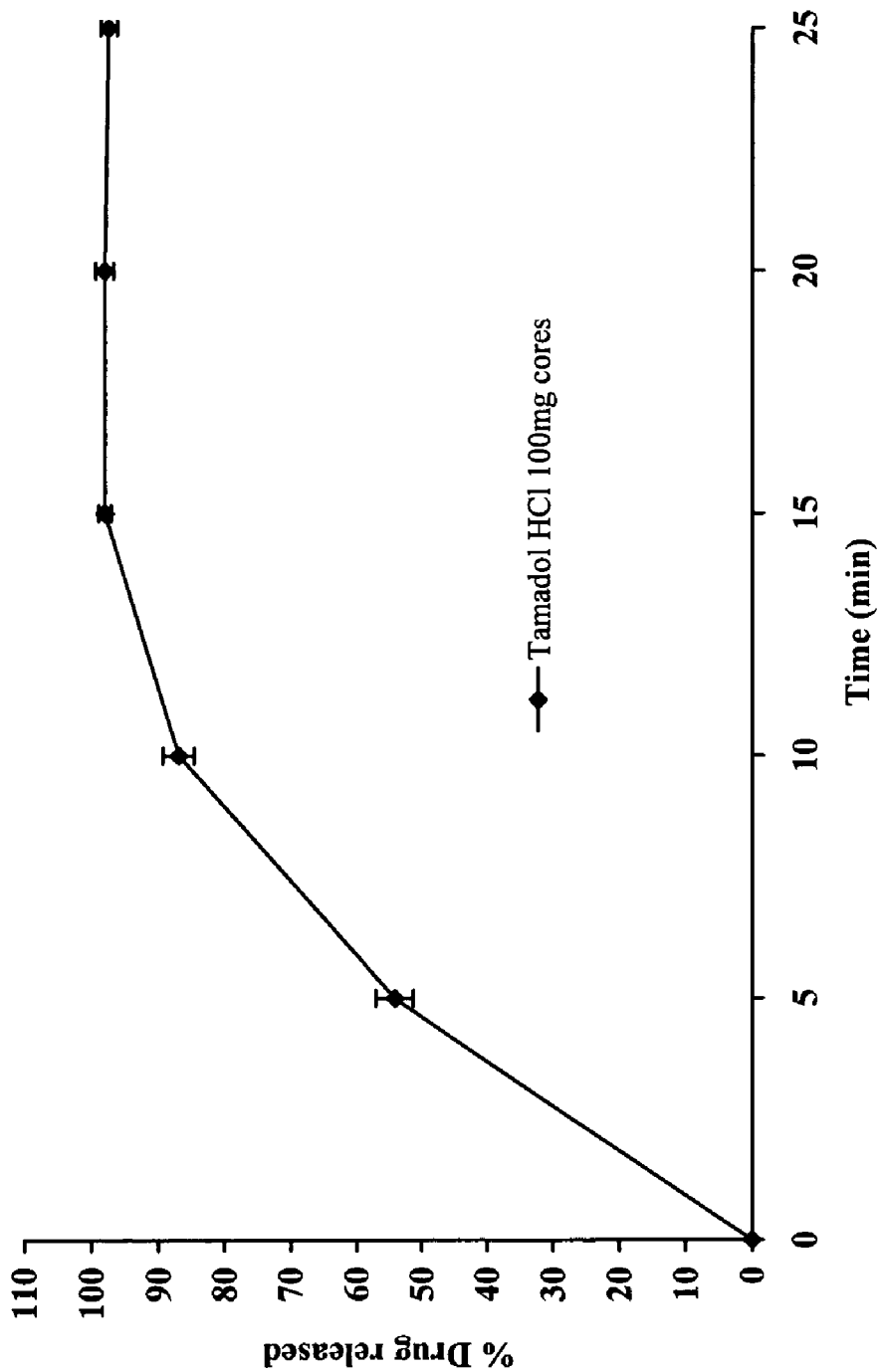
FIG. 1A illustrates the dissolution profile of 100 mg tramadol HCl uncoated cores made according to an embodiment of the invention.

The present invention is directed to a modified release pharmaceutical composition of tramadol. In particular, the composition is a delayed and extended release composition of at least one form of tramadol comprising a core and a modified release coating, which substantially surrounds the core. It will be readily understood by those of ordinary skill in the art that the phrase "delayed and extended release" encompasses compositions with a delayed and extended release as well as delayed extended release compositions. In other words, whether the delayed release alters the extended release properties of the composition, or whether the delayed release has no effect on the extended release properties of the composition is immaterial to the performance of the compositions of the present invention. Either set of release characteristics (delayed and extended or delayed extended) is considered to be within the scope of the present invention.

The Tablet Cores

The core comprises at least one form of tramadol selected from the group consisting of tramadol, racemic mixtures thereof, enantiomers thereof, pharmaceutically acceptable salts thereof, and combinations thereof, and a pharmaceutically acceptable excipient.

The at least one form of tramadol used in the present invention can be any form of tramadol conventional in the pharmaceutical art. The at least one form of tramadol used in the present invention can be tramadol. The at least one form of tramadol used in the present invention can be the individually optically active enantiomers of tramadol, such as for example, (+)-tramadol and (−)-tramadol. The at least one form of tramadol used in the present invention can be pharmaceutically acceptable salts of tramadol. Suitable pharmaceutically acceptable salts of tramadol for use as the at least one form of tramadol according to the present invention are those conventionally known in the art such as, for example, pharmaceutically acceptable acid addition salts. Suitable pharmaceutically acceptable acid addition salts of tramadol for use as the at least one form of tramadol according to the present invention can be the hydrochloride salt, the hydrobromide salt, the hydroiodide salt, the saccharinate salt, etc. The at least one form of tramadol is present in the pharmaceutical composition in an effective amount for the management of moderate to moderately severe pain and can vary from about 25 mg to about 800 mg, preferably from about 50 mg to about 400 mg, and more preferably from about 100 mg to about 400 mg. The term "effective amount" as used herein means that a "pharmaceutically effective amount" is contemplated. A "pharmaceutically effective amount" is the amount or quantity of the at least one form of tramadol in a dosage form of the invention sufficient to elicit an appreciable clinical or therapeutic response when administered, in single or multiple doses, to a patient in need thereof. It will be appreciated that the precise therapeutic dose will depend on the age and condition of the patient and the nature of the condition to be treated and will be at the ultimate discretion of the attendant physician. It is appreciated that the clinically effective level of tramadol in the blood plasma has been reported as being about 100 ng/ml for the treatment of mild to moderate pain (Lintz et al. Bioavailability of enteral tramadol formulations. 1st communication: capsules. Arzneimittelforschung 1986; 36: 1278-83), however, this level can vary from individual to individual and also on the severity and source of the pain. It is well known to the skilled artisan that the therapeutically or clinically effective amount for a certain indication can be determined by conducting clinical studies, such as those some of which have been described herein, using dosage forms that contain a pharmaceutically effective amount of tramadol or its acid addition salts.

With respect to the core, the relative proportion of the at least one form of tramadol can vary from about 70% to about 98% of the core dry weight. Preferably, the at least one form of tramadol is a salt of tramadol having a solubility of greater than 100 mg/ml in water and/or aqueous fluids at 25° C. (see U.S. Pat. No. 5,723,343 to Kugelmann). The preferred tramadol salt is the hydrochloride salt (tramadol hydrochloride (HCl)) and is present at about 82% of the composition or about 96% of the core dry weight.

In addition to the at least one form of tramadol, the core also comprises at least one pharmaceutical excipient. Excipients ensure that the operation of the composition can run satisfactorily and to ensure that compositions of specified quality are prepared. Depending on the intended main function, excipients to be used in formulating compositions are subcategorized into different groups. However, one excipient can affect the properties of a composition in a series of ways, and many excipients used in compositions can thus be described as being multifunctional.

In addition to the at least one form of tramadol, the core ideally comprises at least one lubricant and at least one binder.

A binder (also sometimes called adhesive) is added to a drug composition to ensure that granules and tablets can be formed with the required mechanical strength. Non-limiting examples of binders useful for use in the present invention include starch derivatives and water-soluble polymers such as gelatin, polyvinylpyrrolidone, polyvinyl alcohol, hydroxypropylmethylcellulose, hydroxypropylcellulose, xanthan gum, carbomers, and caragheen. Mixtures of the binders can also be used. The amount of binder can be present from about 1% to about 25% by weight of the core dry weight. The preferred binder is polyvinyl alcohol and is present preferably at about 2% of the core dry weight.

Lubricants are added to pharmaceutical formulations to ensure that tablet formation and ejection can occur with low friction between the solid and the die wall. High friction during tabletting can cause a series of problems, including inadequate tablet quality (capping or even fragmentation of tablets during ejection, and vertical scratches on tablet edges) and can even stop production. Non-limiting examples of lubricants for use in the present invention include stearic acid, magnesium stearate, glyceryl behenate, talc, mineral oil (in PEG), sodium stearyl fumarate, hydrogenated vegetable oils, sodium benzoate, and calcium stearate. Mixtures of the lubricants can also be used. The amount of lubricant can be present from about 0.5% to about 10% of the core dry weight. The preferred lubricant is sodium stearyl fumarate and is present preferably at about 1% by weight of the core dry weight.

At this stage, the core formulation is an immediate release formulation. For example, a core composition comprising 100 mg of the at least one form of tramadol, preferably tramadol HCl, will release about 100% of the active by about 15-20 minutes, a core composition comprising 200 mg of the at least one form of tramadol, preferably tramadol HCl, will release about 100% of the active by about 15-20 minutes, and a core composition comprising about 300 mg of the at least one form of tramadol, preferably tramadol HCl, will release about 100% of the active by about 15-20 minutes. Preferably the core comprises only an effective pharmaceutical amount of the at least one form of tramadol, a binder, preferably polyvinyl alcohol, and a lubricant, preferably sodium stearyl fumarate. However, if necessary, additional inert excipients consistent with the objects of the invention can be added to the core formulation. The additional inert excipients can be added to facilitate the preparation and/or improve patient acceptability of the final modified-release tramadol dosage form as described herein. The additional inert excipients are well known to the skilled artisan and can be found in the relevant literature, for example in the Handbook of Pharmaceutical Excipients (Rowe et al., eds. 4th Ed., Pharmaceutical Press (2003)).

For example, some oral dosage forms require the incorporation of an excipient into the dosage form to increase the bulk volume of the powder and hence the size of the dosage forms. Accordingly, the core can further comprise at least one filler (or diluent). Non-limiting examples of the at least one filler useful for the oral dosage form described herein include lactose monohydrate, anhydrous lactose, mannitol, sorbitol, microcrystalline cellulose, dibasic calcium, calcium sulfate, and pulp cellulose. Mixtures of fillers can also be used. The at least one filler is preferably present up to about 25% by weight of the core dry weight. The preferred filler, if one is to be used, is microcrystalline cellulose.

Another excipient which can be added is a glidant. Glidants improve the flowability of the powder. This is especially important during tablet production at high production speeds and during direct compaction. The glidant, if present, is preferably present at about 1% by weight of the dry core weight. The at least one glidant which can be used is preferably colloidal silicon dioxide. The colloidal silicon dioxide can suitably be, for example, AEROSIL® as supplied by Degussa. Similar colloidal silicon dioxides are also available from other suppliers. Preferably, the colloidal silicon dioxide used is AEROSIL® 200.

An exemplary method of manufacturing the core is as follows. The at least one form of tramadol is first granulated with the at least one binder, in one embodiment in a granulator, but not necessarily a fluidized bed granulator. The at least one binder is first dissolved or dispersed in a suitable solvent, in one embodiment water. The solution or suspension of the at least one binder is then sprayed onto the at least one form of tramadol in a granulator, in one embodiment a fluidized bed granulator. For example, fluidized bed granulators manufactured by Glatt (Germany) or Aeromatic (Switzerland) can be used for this operation. An alternative process can be to use a conventional or high shear mixer. If necessary, the at least one form of tramadol can be mixed with a filler, prior to the granulation step. Granules once dried can be mixed with the other pharmaceutically acceptable excipients, especially with the at least one lubricant, but also with at least one glidant and any other pharmaceutically acceptable excipient suitable to improve processing. The mixture of granules (in one embodiment with the at least one lubricant), and optionally at least one glidant, is pressed into tablets. Alternatively, the at least one form of tramadol and the at least one lubricant can be mixed in a granulator, in one embodiment a fluidized bed granulator, and heated to the melting point of the at least one lubricant to form granules. This mixture can then be mixed with at least one suitable filler and compressed into tablets. Also, it is possible to mix the at least one form of tramadol and the at least one lubricant (in one embodiment sodium stearyl fumarate) in a granulator, in one embodiment a fluidized bed granulator, and then to press the resulting granules into tablets. Tablets can be obtained by standard techniques, in one embodiment on a (rotary) press (for example Manesty Betapress®) fitted with suitable punches. The resulting tablets are hereinafter referred to as tablet cores.

The preferred tablet core comprises 96% tramadol, 2% binder, 1% lubricant and 1% glidant.

The Modified Release Coating

The modified release coating is a coating designed to achieve a delayed and extended release of the at least one form of tramadol over about a 24 hour period. The preferred modified release coating comprises at least one water-insoluble water-permeable film forming polymer, at least one water-soluble polymer and at least one plasticizer.

The at least one insoluble water-permeable film-forming polymer used in the coating can include for example a cellulose ether, such as ethylcellulose, a cellulose ester, such as cellulose acetate, methacrylic acid derivatives, aqueous ethylcellulose dispersions such as Surelease®, aqueous acrylic enteric systems such as Acryl-EZE®, and polyvinyl derivatives such as Kollidon® SR. Combinations of these polymers are permissible. The at least one water-permeable film-forming polymer is present in an amount from about 20% to about 89% and preferably from about 53% to about 70% of the coating dry weight. The preferred at least one water-insoluble, water-permeable film-forming polymer is ethylcellulose. The ethylcellulose can suitably be, for example, ETHOCEL® as supplied by Dow Chemical Company. Similar ethylcelluloses are also available from other suppliers. Preferably, the ethylcellulose used is ETHOCEL® PR, more preferably ETHOCEL® PR100.

The at least one water-soluble polymer or substance can be a partially or totally water-soluble hydrophilic substance intended to modulate the film permeability to the outside aqueous medium. Non-limiting examples of the at least one water-soluble polymer or substances can be water-soluble cellulose ethers, vinylic polymers and combinations thereof. The water-soluble cellulose ethers include but are not limited to, methylcellulose, hydroxypropylmethylcellulose, non-ionic water-soluble cellulose ethers, and combinations thereof. The non-ionic water-soluble cellulose ethers include, but are not limited to, hydroxypropylcellulose, hydroxyethylcellulose, and combinations thereof. The vinylic polymers include, but are not limited to, polyvinyl alcohol, polyvinylpyrrolidone, and combinations thereof. The amount of the at least one water-soluble polymer is present from about 10% to about 75% and preferably from about 20% to about 26% of the coating dry weight. The preferred at least one water-soluble polymer is polyvinylpyrrolidone and can suitably be, for example, KOLLIDON® as supplied by BASF AG. Similar polyvinylpyrrolidones are also available from other suppliers. Preferably, the polyvinylpyrrolidone used is KOLLIDON® 90F.

Plasticizers are generally added to film coating formulations to modify the physical properties of the polymer to make it more usable. The amount and choice of the plasticizer contributes to the hardness of a tablet and can even affect its dissolution or disintegration characteristics, as well as its physical and chemical stability. One important property of plasticizers is their ability to make a coat elastic and pliable, thereby decreasing the coat's brittleness. Non-limiting examples of the at least one plasticizer useful for the preferred polymer coat include polyols, such as polyethylene glycol of various molecular weights, organic esters, such as diethyl phthalate or triethyl citrate, dibutyl sebacate, dibutyl pthalate, and oils/glycerides such as fractionated coconut oil or castor oil. Combinations are permitted. The at least one plasticizer is present in an amount from about 5% to about 30% and preferably from about 14% to about 18% of the coating dry weight. The preferred at least one plasticizer is an ester; most preferably the ester is dibutyl sebacate.

The relative amounts of ingredients in the coating are preferably as follows. The proportion of the at least one water-insoluble, water-permeable polymer (in one embodiment ethylcellulose) in the coating may vary between about 20% and about 90% of the coating dry weight. The proportion of the at least one water-soluble polymer (in one embodiment polyvinylpyrollidone) in the coating may vary between about 10% and about 75% of the coating dry weigh. The proportion of the at least one plasticizer (in one embodiment dibutyl sebacate) in the coating may vary between about 5% and about 30% of the coating dry weight. The relative proportions of ingredients, notably the ratio of the at least one water-insoluble, water-permeable film-forming polymer to the at least one water-soluble polymer, can be varied depending on the desired release profile (where a more delayed release is desired, it is generally obtained with a higher amount of the at least one water-insoluble, water-permeable film-forming polymer).

In another aspect, the relative proportions of the preferred polymer coat ingredients, notably the ratio of the at least one water-insoluble, water-permeable film-forming polymer:the at least one water-soluble polymer or substance:the at least one plasticizer, can be varied depending on the desired rate of release. The skilled artisan will appreciate that controlling the permeability and/or the amount of coating applied to the tablet cores can control the release of the active. For example, the permeability of the preferred polymer coat, can be altered by varying the ratio of the at least one water-insoluble, water-permeable film-forming polymer:the at least one water-soluble polymer:the at least one plasticizer and/or the quantity of coating applied to the tablet cores. A more delayed and extended-release is generally obtained with a higher amount of water-insoluble, water-permeable film forming polymer and/or by increasing the amount of the coating solution applied to the tablet cores. Alternatively, a faster rate of release, if so desired, can be obtained by increasing the amount of the water-soluble polymer and/or by decreasing the amount of coating solution applied. The addition of other excipients to the tablet core can also alter the permeability of the modified release coating. For example, if it is desired that the tablet core further comprise an expanding agent, the amount of plasticizer in the control-releasing coat should be increased to make the coat more pliable as the pressure exerted on a less pliable coat by the expanding agent would rupture the coat. Other excipients such as pigments and taste-masking agents can also be added to the coating formulation.

The amount of coating applied can also be a factor in regulating the rate of release of the at least one form of tramadol. The amount of coat applied can vary from about 8 to about 30%, preferably about 16% of the core dry weight. An exemplary process of preparing the coating can be as follows, using methods and equipment that are well known to those of ordinary skill in the art. The at least one water-insoluble, water-permeable film-forming polymer, the at least one water-soluble polymer and the at least one plasticizer are dissolved in a solvent such as denatured alcohol using a stirrer until complete dissolution is achieved. The resulting solution can optionally be passed through a high pressure homogenizer. The resulting solution is coated onto tablet cores, as described elsewhere herein, to substantially surround those cores using for example a perforated coating pan.

The delayed and extended release composition comprising at least one form of tramadol of the invention provides an in-vitro dissolution profile using the USP Basket Method at 75 rpm in 900 ml 0.1 N HCl at 37° C. such that after about 2 hours, from about 0 to about 22% by weight of the at least one form of tramadol is released, after about 4 hours from about 5 to about 30% by weight of said at least one form of tramadol is released, after about 6 hours, from about 15 to about 38% by weight of said at least one form of tramadol is released, and after about 8 hours, more that about 40% by weight of said at least one form of tramadol is released. Preferably, the dissolution profile is such that after about 2 hours, from about 2 to about 10% by weight of said at least one form of tramadol is released, after about 4 hours from about 12 to about 20% by weight of said at least one form of tramadol is released, after about 6 hours from about 30 to about 38% by weight of said at least one form of tramadol is released, after about 8 hours, from about 48 to about 56% by weight of said at least one form of tramadol is released, after about 10 hours from about 64 to about 72% by weight of said at least one form of tramadol is released, and after about 12 hours, more than about 76% by weight of said at least one form of tramadol is released.

The delayed and extended release composition of the at least one form of tramadol is bioequivalent to the reference product ULTRAM®. In-vivo, the delayed and extended release of the at least one form of tramadol, preferably tramadol HCl, should be such that a therapeutically effective level of the at least one form of tramadol, preferably tramadol hydrochloride, is reached after about 3 hours following first administration of the composition in the fasted state. "First administration" as used herein means the first single dose of the composition administered to a patient or the first dose administered to a patient after a suitable washout period. In certain individuals it can be preferable that the mean time to maximum plasma concentration ($C_{max}$), in other words the $T_{max}$, of the at least one form of tramadol, preferably tramadol hydrochloride, be further delayed. In such cases, the composition can be administered in the fed state, in which case the $T_{max}$ of the at least one form of tramadol, preferably tramadol hydrochloride, is delayed by about 1 or more hours following first administration of the composition when compared to first administration of the composition in the fed state. Preferably, the $T_{max}$ in the fed state is delayed by about 4 hours relative to the fasted state, and more preferably, by about 2 hours. The delayed and extended release composition of the at least one form of tramadol of the invention, preferably tramadol hydrochloride, provides a mean plasma concentration of preferably about 44 ng/ml, more preferably about 50 ng/ml, and even more preferably about 70 ng/ml before about 3 hours after the first administration of the composition.

It is preferable that the core of the composition be an immediate-release core. However, a core with a controlled-release matrix can also be used in conjunction with the coating formulation described above to obtain a delayed and extended release of the at least one form of tramadol. Such controlled release matrix cores have been described, for example, in U.S. Pat. Nos. 5,958,452, 6,254,887, 5,395,626, 5,474,786, and 5,645,858, the entire contents of which are incorporated herein by reference. Depending on the extent of release provided by the controlled-release matrix itself, the ratio of the water-insoluble water-permeable film-forming polymer:water-soluble polymer:plastisizer can be altered to provide the desired in-vitro dissolution profile as well as the in-vivo delay of the release of the at least one form of tramadol. For example, at one extreme, if the controlled-release matrix significantly controls the release of the at least one form of tramadol, the composition of the coating can be altered such that a higher proportion of the water-soluble polymer and/or a lower proportion of the water-insoluble water-permeable film forming polymer is used to obtain the desired in-vivo delay. At the other extreme, if the controlled release matrix hardly controls the release of the at least one form of tramadol, the coating composition can be altered such that a higher proportion of the water-insoluble water-permeable film forming polymer and/or a lower proportion of the water-soluble polymer is used to obtain the desired in-vivo delay. At the same time, the proportion of the plasticizer may also have to be altered to make the coating more or less elastic and pliable.

The forms of administration according to the invention are preferably suitable for oral administration. The preferred form of administration according to the invention is a tablet. However, the composition of the invention can also take the form of pellets, beads or microtablets, which can then be packaged into capsules or compressed into a unitary solid dosage form. Other solid oral dosage forms, as disclosed herein, can be prepared by workers of ordinary skill in the art, despite the fact that such other solid oral dosage forms can be more difficult to commercially manufacture.

Further details of the preferred embodiments of the present invention are illustrated in the following examples, which are understood to be non-limiting.

EXAMPLE 1

100 mg Delayed and Extended Release Tramadol HCl Tablets

I. Formulation

The following tablet core formulations were prepared:

TABLE 1A (Core Formulation)

| Ingredients | Quantity (mg) | % |
|---|---|---|
| Tramadol HCl | 100.00 | 96.15 |
| Polyvinyl Alcohol | 2.00 | 1.92 |
| Colloidal Silicon Dioxide (AEROSIL ® 200) | 1.00 | 0.96 |
| Sodium Stearyl Fumarate | 1.00 | 0.96 |
| Purified Water | 41.60 * | |
| Core Total Weight | 104.00 | 99.99 |

* evaporated during process

The cores were prepared as follows. Tramadol HCl and colloidal silicon dioxide were mixed and passed through a 1.0 mm screen. Polyvinyl alcohol was dissolved in purified water. The mixed tramadol HCl and colloidal silicon dioxide powder was granulated with the aqueous solution of polyvinyl alcohol in a fluidized bed granulator, Glatt GPCG1 and then dried. After granulation, the granules were blended with sodium stearyl fumarate and then passed through a 1.0 mm screen. The blend was then compressed into tablet cores using a Manesty Betapress.

The dissolution profile of the uncoated 100 mg tablet cores was determined under the same conditions shown in Table 1F below. The results are presented in Table 1B as % release of the total tramadol in the core:

TABLE 1B (Dissolution Profile of 100 mg Uncoated Tramadol Tablet Cores)

| Time (min) | Tramadol HCl 100 mg cores | SD | Max | Min |
|---|---|---|---|---|
| 0 | 0 | 0 | 0 | 0 |
| 5 | 54.15 | 2.86 | 59.42 | 50.75 |
| 10 | 87 | 2.37 | 90.67 | 84.6 |
| 15 | 98.14 | 0.91 | 99.53 | 97.12 |
| 20 | 98.15 | 1.3 | 100.4 | 97.06 |
| 25 | 97.53 | 1.26 | 99.67 | 96.16 |
| 30 | 96.3 | 1.3 | 98.55 | 94.96 |

The data in Table 1B is graphically presented in FIG. 1A

The following coating formulation was prepared as shown in Table 1C:

TABLE 1C (Coating Formulation)

| | Mg/tablet | | |
|---|---|---|---|
| Ingredients | Composition A Quantity (mg) | Composition B Quantity (mg) | Composition C Quantity (mg) |
| Ethylcellulose (ETHOCEL ® PR 100) | 9.20 | 9.81 | 9.54 |
| Polyvinylpyrrolidone (KOLLIDON ® 90F) | 4.14 | 3.53 | 3.80 |
| Dibutyl Sebacate | 2.66 | 2.66 | 2.66 |
| Denatured Alcohol | 170.00 * | 170.00 * | 170.00 * |

* evaporated during process

The coating formulation was prepared as follows. The ethyl alcohol and isopropanol were weighed and mixed. Dibutyl sebacate and ethylcellulose were added to and dissolved in the ethyl alcohol and isopropyl alcohol while stirring using a propeller stirrer, Coframo RZR1. The ethylcellulose and dibutyl sebacate were allowed to dissolve completely. The polyvinylpyrrolidone was added. The solution was stirred until all components were dissolved. The solution was passed through a high-pressure homogenizer, Mini DeBee 2000 with #7 nozzle, Bee International. The tablet cores were coated using the coating solution in a perforated coating pan, O'Hara Labcoat III 36" Pan, Vector LCDS.

The coating parameters are as shown in Tables 1D and 1E:

TABLE 1D (Coating Parameters)

| Inlet Temperature | 48.5-49.5° C. |
|---|---|
| Outlet Temperature | 38.5-39.5° C. |
| Bed Temperature | 37.5-38.5° C. |
| Spray Rate | 300 g/min |
| Atomizing Air/Pattern | 25/25 psi |
| Distance gun/Bed | 6" |
| Distance between guns | 6" |
| Pan speed | 12.0 rpm |

TABLE 1E (Coating Amount)

| Diameter | 6 mm |
|---|---|
| Thickness | 4.65 mm |
| Cup Height | 1.02 mm |
| Surface | 112 mm$^2$ |
| Percentage | 100% |
| Amount | 16 mg |

In vitro dissolution studies were conducted on 100 mg tramadol HCl delayed and extended release tablets formulated according to Composition A, Composition B and Composition C. Table 1F shows the dissolution conditions used for all of the in vitro dissolution studies conducted herein for determining the in vitro dissolution profiles of delayed and extended release tablets:

TABLE 1F (Dissolution Conditions)

| Apparatus | USP Basket (10 mesh) |
|---|---|
| Dissolution medium | 0.1 N HCl |
| Volume (vessels) | 900 ml |
| Bath temperature | 37° C. (±0.5° C.) |

TABLE 1F-continued (Dissolution Conditions)

| | | |
|---|---|---|
| Wavelength | 271 | nm |
| Flow cell thickness | 1 | cm |
| Rotation speed | 75 | rpm |
| Total run time | 900 | min |
| Sampling interval | 30 | min |

The dissolution profile is presented in Table 1G below:

TABLE 1G (Dissolution Profile)

| Time | % Dissolved | | |
|---|---|---|---|
| (min.) | Composition A | Composition B | Composition C |
| 0 | 0 | 0 | 0 |
| 30 | 1.1 | 0.1 | 0.3 |
| 60 | 5.7 | 0.3 | 2.0 |
| 90 | 12.8 | 1.4 | 5.1 |
| 120 | 21.3 | 2.9 | 9.1 |
| 180 | 41.6 | 7.0 | 19.8 |
| 240 | 62.4 | 12.8 | 33.4 |
| 300 | 77.8 | 20.2 | 48.7 |
| 360 | 87.3 | 29.4 | 62.7 |
| 420 | 92.6 | 40.3 | 73.5 |
| 480 | 95.9 | 50.8 | 81.7 |
| 540 | 97.5 | 59.9 | 87.2 |
| 600 | 98.7 | 67.6 | 91.1 |
| 660 | 99.2 | 73.7 | 94.1 |
| 720 | 99.6 | 78.2 | 96.0 |
| 780 | 99.9 | 81.9 | 97.2 |
| 840 | | 84.9 | 97.8 |
| 900 | | 86.9 | 98.5 |
| 960 | | 88.5 | 99.0 |

Figure 2:
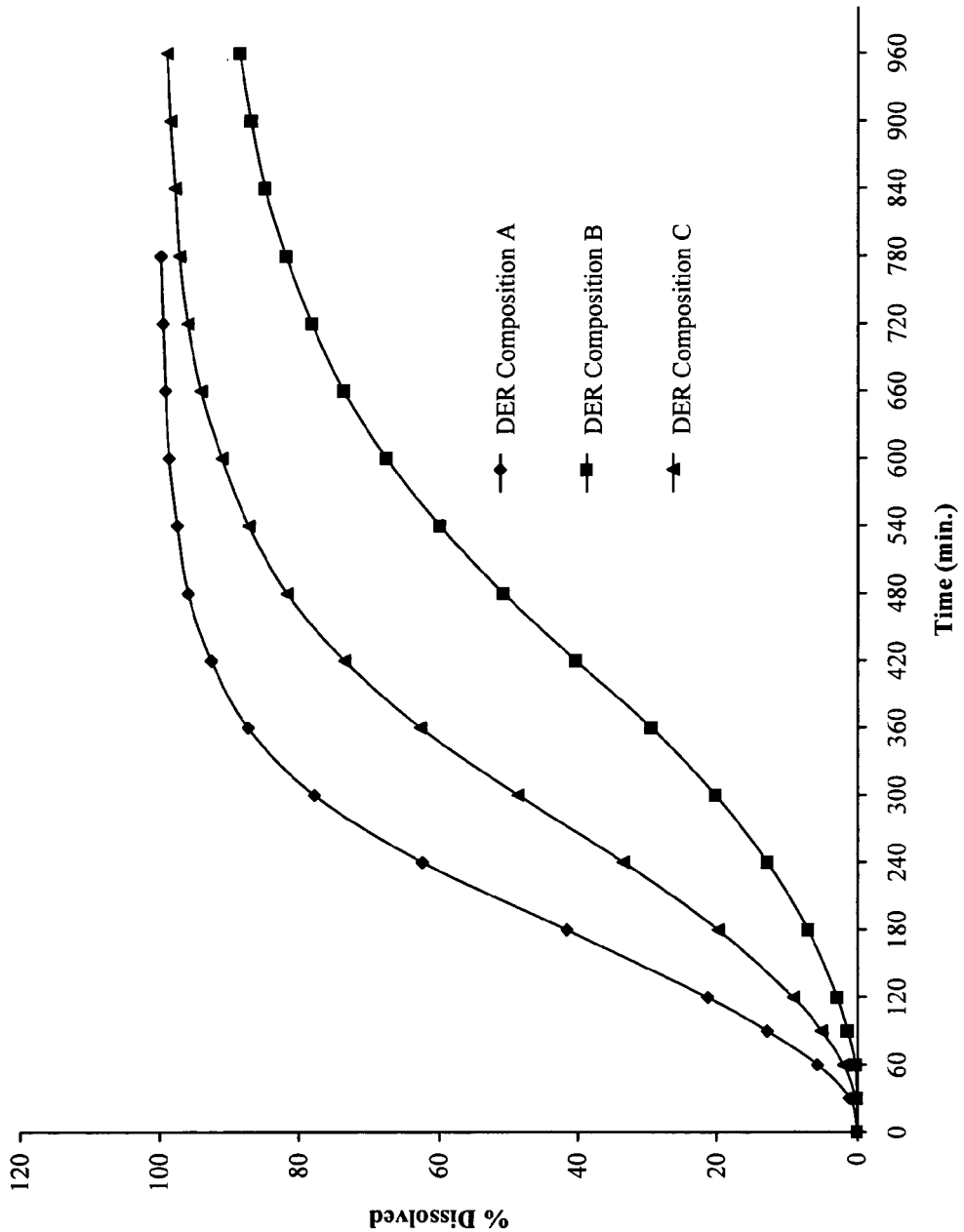
FIG. 2 is a graph comparing the in vitro dissolution profiles of 100 mg delayed and extended release (DER) tramadol HCl tablets with three different release rates made according to an aspect of the invention.

FIG. 2 compares the in vitro dissolution profiles of 100 mg tramadol HCl delayed and extended release tablets formulated according to Compositions A, B, and C.

II. Pharmacokinetic Studies

A. Pilot Four-Way, Single-Dose, Open-Label, Fasting, Comparative Bioavailability Study of Three Formulations (A, B, and C) of Tramadol Hydrochloride Delayed and Extended Release Tablets (2×100 mg) Versus ULTRAM® Tablets (50 mg q.i.d) in Normal, Healthy, Non-Smoking Male Volunteers.

This study evaluated the bioavailability of compositions A, B, and C (2×100 mg) against ULTRAM® (Ortho-McNeil Pharmaceuticals) Tablets (50 mg q.i.d.) under fasting conditions.

This study was a randomized, balanced, four-period, four-treatment, four-sequence crossover study design in sixteen (16) normal, healthy, non-smoking male volunteers and two (2) alternates.

Eighteen (18) subjects were entered into the study. Fourteen (14) subjects completed the study; there were fourteen (14) evaluable subjects. All subjects were non-smoking, between 18 and 45 years of age (inclusive), and with body weights no more than ±15% of the ideal weight for the subject's height and frame as determined by the Table of Desirable Weights for Men and Women.

The study periods were separated by a one-week washout period. Blood sampling for drug content analysis was carried out at 0.0 (pre-drug), 1.0, 2.0, 3.0, 4.0, 6.0, 8.0, 10.0, 12.0, 16.0, 20.0, 24.0, 30.0, 36.0, and 48.0 hours post-drug when each test drug was administered. Blood sampling for drug content analysis was carried out at 0.0 (pre-drug), 1.0, 2.0, 3.0, 4.0, 5.0 (pre-drug), 6.0, 7.0, 8.0, 9.0, 10.0, 11.0 (pre-drug), 12.0, 13.0, 14.0, 15.0 (pre-drug), 16.0, 17.0, 18.0, 20.0, 24.0, 30.0, 36.0, and 48.0 hours post-drug when the reference drug was administered.

| Treatments: | A: | DER tramadol HC1 2 × 100 mg tablets q.d. Composition A |
|---|---|---|
| | B: | DER tramadol HC1 2 × 100 mg tablets q.d. Composition B |
| | C: | DER tramadol HC1 2 × 100 mg tablets q.d. Composition C |
| | D: | ULTRAM ® 50 mg Tablets Control Number: CDA 2225 (Ortho-McNeil Pharmaceuticals, U.S.A.) |

Figure 3:
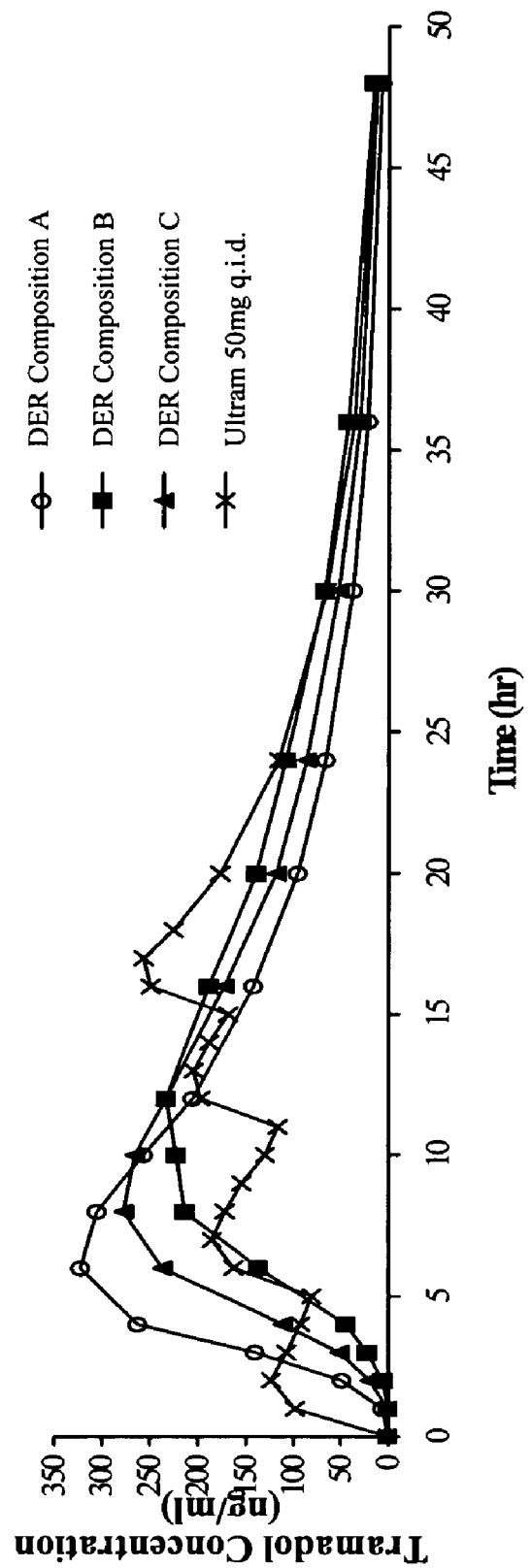
FIG. 3 is a graph comparing the mean plasma tramadol concentrations over time following once-a-day administration of the DER tablets of FIG. 2 (100 mg×2) compared to the immediate-release reference product ULTRAM® (50 mg q.i.d.).
Figure 4:
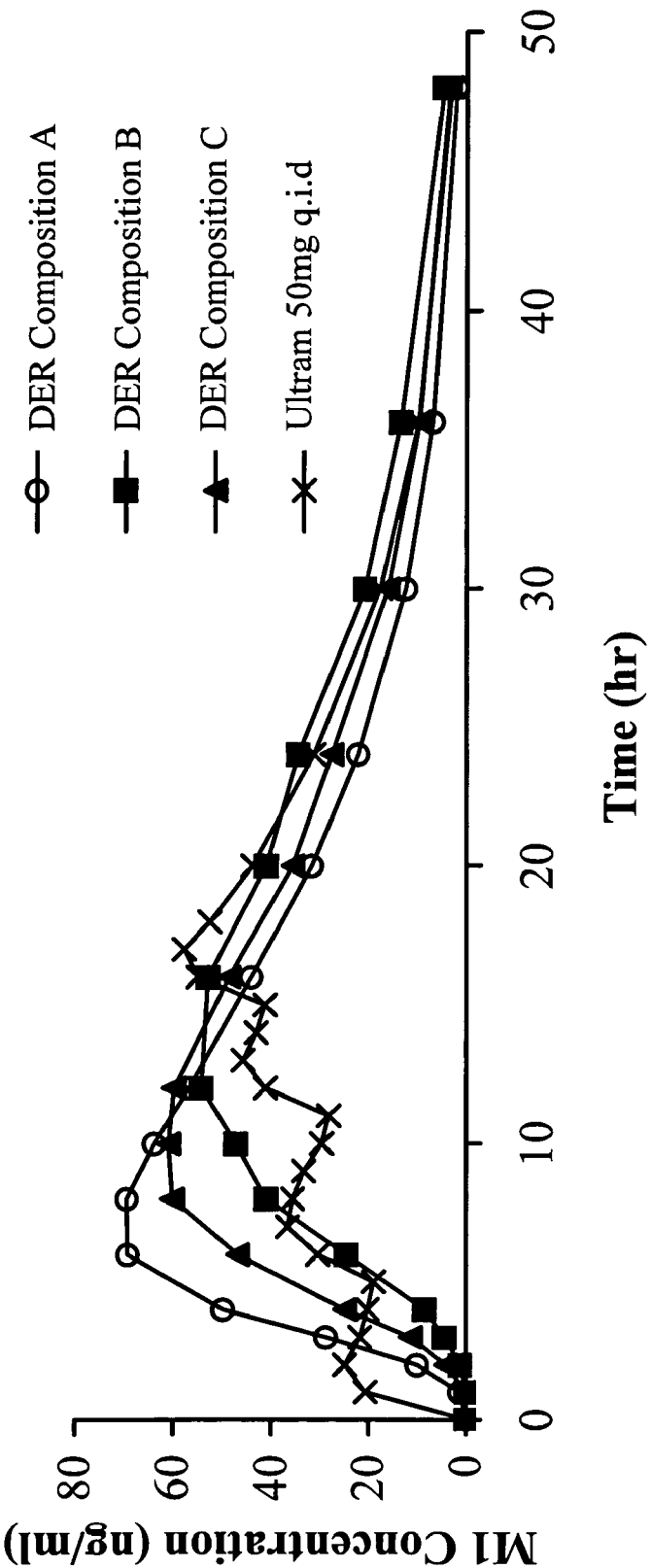
FIG. 4 is a graph illustrating the mean plasma desmethyltramadol (M1) concentrations following once-a-day administration of the DER tablets of FIG. 2 (100 mg×2) compared to the immediate-release reference product ULTRAM® (50 mg q.i.d.).

The three 100 mg delayed and extended release tramadol formulations tested (2×100 mg once a day) demonstrated prolonged tramadol and mono-O-desmethyltramadol (also referred to herein as M1, desmethyltramadol, and/or O-desmethyltramadol) plasma concentration-time profiles relative to the ULTRAM® tablet (1×50 mg) when administered 4 times a day ($2^{nd}$, $3^{rd}$ and $4^{th}$ doses at 5, 11 and 15 hours post-$1^{st}$ dose, respectively) (See FIGS. 3 and 4). In addition, the DER formulations yielded equivalent AUCs relative to an equivalent dose of the ULTRAM® immediate release tablet. The 90% geometric mean confidence intervals for $AUC_t$ and $AUC_\infty$ were within the 80%-125% range for all three novel formulations. Compositions B and C also yielded equivalent $C_{max}$ values versus ULTRAM® as evidenced by 90% geometric confidence intervals within the 80-125% range. The mean plasma concentrations for tramadol and desmethyltramadol for each of compositions A, B, and C are provided in Table 1AA-AB for composition A, Table 1BA-BB for composition B and Table 1CA-CB for composition C. The mean pharmacokinetic parameters and 90% confidence interval for ratio of the geometric mean AUC and $C_{max}$ are presented in Tables 1H and 1I for tramadol and in Tables 1J and 1K for O-desmethyltramadol. Table 1H also shows that overall there was no apparent difference in the ratio of metabolite ($AUC_\infty$ of M1/tramadol) among the DER tramadol formulations and the immediate release tablet. The half-life following ULTRAM® treatment was slightly shorter compared to the delayed and extended release formulations.

TABLE 1AA (Mean ± SD Plasma Tramadol Concentrations for Composition A)

| | Hours | | | | |
|---|---|---|---|---|---|
| | 0.0 | 1.0 | 2.0 | 3.0 | 4.0 |
| Average | 0.00 | 6.35 | 50.70 | 145.06 | 267.81 |
| SD | 0.00 | 3.62 | 14.01 | 49.59 | 77.19 |

| | Hours | | | | |
|---|---|---|---|---|---|
| | 6.0 | 8.0 | 10.0 | 12.0 | 16.0 |
| Average | 332.81 | 306.33 | 257.59 | 206.64 | 142.92 |
| SD | 90.38 | 109.94 | 94.79 | 82.61 | 75.64 |

| | Hours | | | | |
|---|---|---|---|---|---|
| | 20.0 | 24.0 | 30.0 | 36.0 | 48.0 |
| Average | 97.20 | 67.70 | 39.03 | 22.81 | 8.51 |
| SD | 59.42 | 46.52 | 33.90 | 26.15 | 13.95 |

TABLE 1AB (Mean ± SD Plasma Desmethyltramadol Concentrations for Composition A)

| | Hours | | | | |
|---|---|---|---|---|---|
| | 0.0 | 1.0 | 2.0 | 3.0 | 4.0 |
| Average | 0.00 | 1.31 | 10.15 | 28.68 | 48.11 |
| SD | 0.00 | 1.62 | 5.23 | 14.34 | 21.10 |

| | Hours | | | | |
|---|---|---|---|---|---|
| | 6.0 | 8.0 | 10.0 | 12.0 | 16.0 |
| Average | 66.71 | 65.13 | 60.01 | 53.37 | 41.73 |
| SD | 27.06 | 26.89 | 26.33 | 23.08 | 20.92 |

| | Hours | | | | |
|---|---|---|---|---|---|
| | 20.0 | 24.0 | 30.0 | 36.0 | 48.0 |
| Average | 30.37 | 21.56 | 12.33 | 6.71 | 2.03 |
| SD | 16.57 | 11.65 | 7.43 | 4.14 | 1.95 |

TABLE 1BA (Mean ± SD Plasma Tramadol Concentrations for Composition B)

| | Hours | | | | |
|---|---|---|---|---|---|
| | 0.0 | 1.0 | 2.0 | 3.0 | 4.0 |
| Average | 0.00 | 0.00 | 6.07 | 21.96 | 44.57 |
| SD | 0.00 | 0.00 | 2.46 | 5.98 | 25.91 |

| | Hours | | | | |
|---|---|---|---|---|---|
| | 6.0 | 8.0 | 10.0 | 12.0 | 16.0 |
| Average | 137.20 | 213.88 | 222.36 | 233.04 | 188.81 |
| SD | 67.93 | 83.71 | 78.50 | 77.62 | 64.70 |

| | Hours | | | | |
|---|---|---|---|---|---|
| | 20.0 | 24.0 | 30.0 | 36.0 | 48.0 |
| Average | 139.33 | 108.40 | 66.83 | 41.64 | 15.44 |
| SD | 55.51 | 46.02 | 32.06 | 27.31 | 16.84 |

TABLE 1BB (Mean ± SD Plasma Desmethyltramadol Concentrations for Composition B)

| | Hours | | | | |
|---|---|---|---|---|---|
| | 0.0 | 1.0 | 2.0 | 3.0 | 4.0 |
| Average | 0.00 | 0.00 | 1.19 | 4.34 | 8.28 |
| SD | 0.00 | 0.00 | 1.01 | 2.45 | 4.65 |

| | Hours | | | | |
|---|---|---|---|---|---|
| | 6.0 | 8.0 | 10.0 | 12.0 | 16.0 |
| Average | 24.81 | 39.92 | 47.12 | 53.63 | 52.08 |
| SD | 14.46 | 18.84 | 19.21 | 20.70 | 21.13 |

TABLE 1BB-continued (Mean ± SD Plasma Desmethyltramadol Concentrations for Composition B)

| | Hours | | | | |
|---|---|---|---|---|---|
| | 20.0 | 24.0 | 30.0 | 36.0 | 48.0 |
| Average | 40.19 | 34.35 | 20.99 | 13.62 | 4.75 |
| SD | 17.94 | 17.70 | 11.16 | 8.23 | 3.98 |

TABLE 1CA (Mean ± SD Plasma Tramadol Concentrations for Composition C)

| | Hours | | | | |
|---|---|---|---|---|---|
| | 0.0 | 1.0 | 2.0 | 3.0 | 4.0 |
| Average | 0.00 | 1.09 | 19.74 | 52.51 | 115.01 |
| SD | 0.00 | 1.55 | 4.96 | 14.10 | 46.95 |

| | Hours | | | | |
|---|---|---|---|---|---|
| | 6.0 | 8.0 | 10.0 | 12.0 | 16.0 |
| Average | 243.15 | 281.96 | 269.25 | 236.06 | 176.39 |
| SD | 107.87 | 121.65 | 106.69 | 89.21 | 84.10 |

| | Hours | | | | |
|---|---|---|---|---|---|
| | 20.0 | 24.0 | 30.0 | 36.0 | 48.0 |
| Average | 120.20 | 88.14 | 53.51 | 31.17 | 12.62 |
| SD | 66.83 | 48.38 | 36.10 | 26.68 | 15.26 |

TABLE 1CB (Mean ± SD Plasma Desmethyltramadol Concentrations for Composition C)

| | Hours | | | | |
|---|---|---|---|---|---|
| | 0.0 | 1.0 | 2.0 | 3.0 | 4.0 |
| Average | 0.00 | 0.17 | 3.96 | 11.04 | 24.39 |
| SD | 0.00 | 0.45 | 2.53 | 5.39 | 12.73 |

| | Hours | | | | |
|---|---|---|---|---|---|
| | 6.0 | 8.0 | 10.0 | 12.0 | 16.0 |
| Average | 44.92 | 56.96 | 56.73 | 55.29 | 46.24 |
| SD | 19.97 | 23.98 | 23.07 | 21.98 | 19.66 |

| | Hours | | | | |
|---|---|---|---|---|---|
| | 20.0 | 24.0 | 30.0 | 36.0 | 48.0 |
| Average | 33.21 | 26.18 | 15.26 | 9.09 | 3.22 |
| SD | 15.57 | 11.62 | 8.26 | 5.77 | 2.89 |

TABLE 1H (Mean Pharmacokinetic Parameters for Plasma Tramadol (n = 14))

| Parameter | Composition A 2 × 100 mg Mean (CV %) | Composition B 2 × 100 mgmg Mean (CV %) | Composition C 2 × 100 mg Mean (CV %) | ULTRAM® 50 × 2 mg q.i.d Mean (CV %) |
|---|---|---|---|---|
| $AUC_t$ (hr * ng/mL) | 4796.83 (42.92) | 4663.89 (34.42) | 4827.94 (44.08) | 4915.71 (43.81) |
| $AUC_\infty$ (hr * ng/mL) | 4936.23 (45.71) | 4897.97 (38.96) | 5028.36 (46.36) | 5118.72 (47.88) |
| $C_{max}$ (ng/mL) | 351.60 (28.89) | 246.46 (32.13) | 298.30 (38.34) | 284.70 (36.17) |
| $T_{max}$ (hr) | 5.86 (21.02) | 9.86 (21.74) | 8.43 (19.03) | 14.07 (37.03) |
| Half-life (hr) | 6.90 (32.10) | 7.94 (32.96) | 7.49 (37.02) | 6.73 (37.46) |
| M1/Tramadol | 0.29 (50.96) | 0.30 (45.62) | 0.29 (49.35) | 0.29 (52.92) |
| MRT (hr) | 13.70 (24.08) | 19.48 (18.19) | 16.57 (22.61) | 17.79 (19.03) |
| Lag Time (hr) | 0.00 (0.00) | 1.00 (0.00) | 0.64 (77.35) | 0.00 (0.00) |

FIG. 3 illustrates the mean plasma tramadol concentrations (ng/ml) over time following once a day delayed and extended release tramadol HCl tablet (100 mg×2) formulated according to Compositions A, B, and C vs ULTRAM® (50 mg×2) q.i.d.

B. Pilot Two-Way, Multiple-Dose, Open-Label, Fasting, Comparative Bioavailability Study of Tramadol Hydrochloride Delayed and Extended-Release Tablets (2×100 mg) Versus ULTRAM® in Normal, Healthy, Non-Smoking Male and Female Volunteers.

TABLE 1I (Ratio of Means & 90% C.I. for Plasma Tramadol)

| | AUC (0-t) | | | AUC (0-∞) | | | Cmax | | |
|---|---|---|---|---|---|---|---|---|---|
| | 90% CI | Ratio of Means | CV (%) | 90% CI | Ratio of Means | CV (%) | 90% CI | Ratio of Means | CV (%) |
| Composition A | 90.1-105.1 | 97.3 | 11.5 | 89.2-104.4 | 96.5 | 11.7 | 114.2-140.0 | 126.5 | 15.2 |
| Composition B | 93.1-109.6 | 101 | 11.5 | 93.7-110.7 | 101.9 | 11.7 | 80.5-101.1 | 90.7 | 15.2 |
| Composition C | 94.0-109.6 | 101.5 | 11.5 | 94.0-110.1 | 101.7 | 11.7 | 99.0-121.4 | 109.6 | 15.2 |

TABLE 1J (Mean Pharmacokinetic Parameters for Plasma O-desmethyltramadol (n = 12))

| Parameter | Composition A 2 × 100 mg Mean (CV %) | Composition B 2 × 100 mg Mean (CV %) | Composition C 2 × 100 mg Mean (CV %) | ULTRAM® 2 × 50 mg q.i.d Mean (CV %) |
|---|---|---|---|---|
| $AUC_t$ (hr * ng/mL) | 1193.78 (44.84) | 1230.54 (40.02) | 1169.03 (39.15) | 1166.74 (33.21) |
| $AUC_\infty$ (hr * ng/mL) | 1226.20 (44.26) | 1295.76 (41.06) | 1218.22 (39.68) | 1201.62 (32.42) |
| $C_{max}$ (ng/mL) | 68.91 (39.65) | 56.49 (36.64) | 61.75 (39.92) | 60.72 (35.05) |
| $T_{max}$ (hr) | 7.29 (23.11) | 13.29 (21.78) | 10.14 (29.41) | 16.71 (4.35) |
| Half-life (hr) | 7.56 (30.98) | 8.80 (36.96) | 8.16 (28.65) | 7.50 (32.79) |

FIG. 4 illustrates the mean plasma desmethyltramadol concentrations (ng/ml) following once a day delayed and extended release tramadol HCl tablet (100 mg×2) formulated according to compositions A, B, and C vs ULTRAM® (50 mg×2) q.i.d.

TABLE 1K (Ratio of Means & 90% C.I. for Plasma O-desmethyltramadol)

| | AUC (0-t) | | AUC (0-∞) | | Cmax | |
|---|---|---|---|---|---|---|
| | 90% CI | Ratio of Means | 90% CI | Ratio of Means | 90% CI | Ratio of Means |
| Composition A | 87.8-109.7 | 98.1 | 87.6-108.9 | 97.7 | 98.3-124.6 | 110.7 |
| Composition B | 91.0-115.2 | 102.4 | 93.0-117.1 | 104.3 | 80.7-103.7 | 91.4 |
| Composition C | 89.0-111.2 | 99.5 | 89.7-111.6 | 100.1 | 89.4-113.3 | 100.7 |

The objective of this study was to compare the rate and extent of absorption of a delayed and extended-release formulation of tramadol hydrochloride (2×100 mg) of the invention against ULTRAM® (50 mg q.i.d.) under steady-state conditions in normal healthy male and female volunteers. This comparison reflects the administration of ULTRAM® under clinical conditions.

This steady-state study was a randomized, two-way crossover study design in sixteen (16) normal, healthy, non-smoking male and female volunteers and four (4) alternates (total 11 males and 9 females).

Twenty (20) subjects were entered into the study. Fifteen (15) subjects completed the study; there were fifteen (15) evaluable subjects. All subjects were non-smoking, between 18 and 45 years of age (inclusive), and with body weights no more than ±15% of the weight for the subject's height and frame as determined by the Table of Desirable Weights for Men and Women. All female subjects were non-lactating, had negative pregnancy tests, and were taking an acceptable method of contraception.

The study periods were separated by a one-week washout period. Blood sampling for drug content analysis was carried out as follows for the test product (DER Composition B tablets (2×100 mg), treatment A): Day 1—0.0 (pre-dose), 1.0, 2.0, 3.0, 4.0, 6.0, 8.0, 10.0, 12.0, 16.0, 20.0, 24.0; Day 2, 3, and 4—0.0 (pre-dose); Day 5—0.0 (pre-dose), 1.0, 2.0, 3.0, 4.0, 6.0, 8.0, 10.0, 12.0, 16.0, 20.0, 24.0, 30.0, 36.0, and 48.0 hours post-drug administration.

Blood sampling for drug content analysis was carried out as follows for the reference product (ULTRAM® 50 mg tablets q.i.d., treatment B): Day 1—0.0 (pre-dose), 1.0, 2.0, 3.0, 4.0, 5.0 (pre-dose), 6.0, 7.0, 8.0, 9.0, 10.0, 11.0 (pre-dose), 12.0, 13.0, 14.0, 15.0 (pre-dose), 16.0, 17.0, 18.0, 20.0 and 24.0; Days 2, 3, and 4—0.0 (pre-dose); Day 5—0.0 (pre-dose), 1.0, 2.0, 3.0, 4.0, 5.0 (pre-dose), 6.0, 7.0, 8.0, 9.0, 10.0, 11.0 (pre-dose), 12.0, 13.0, 14.0, 15.0 (pre-dose), 16.0, 17.0, 18.0, 20.0, 24.0, 30.0, 36.0, and 48.0 hours post-drug administration.

Treatments:  A:  2 Tablets of Tramadol HCl DER 100 mg tablets (Composition B) once a day (approximately 7 AM) for 5 consecutive days.

-continued

B:  ULTRAM ® (Tramadol HCl 50 mg tablet, Ortho-McNeil Pharmaceutical, USA) (Lot# CDA2225) q.i.d. (approximately 7 AM, 12 PM, 6 PM and 10 PM) for 5 consecutive days.

In the instant study, DER Composition B tablet was compared to immediate release ULTRAM® under multiple-dose conditions. The delayed and extended release formulation performed consistently under both single and multiple doses. The overall half-life after multiple-dose for tramadol was 7.3 hours and 6.7 hours, respectively, following DER Composition B tablet and ULTRAM®. Steady state levels of tramadol were achieved by the third dose (day 3 of the study) for DER Composition B tablets, and by the fifth dose (Day 2 of the study) for ULTRAM®. The mean pharmacokinetic data for single dose and multiple dose of tramadol and the M1 are presented in tables 1L-1M and 1N-1O, respectively. Steady-state bioequivalence between the DER tramadol HCl-Composition B tablets and immediate-release ULTRAM® was established. The 90% confidence intervals for AUC and $C_{max}$ were within the 80-125% limits for both unchanged drug and O-desmethyltramadol. DER tramadol HCl-Composition B tablets given once daily exhibited lower percent fluctuation at steady state (70%) than ULTRAM® given four times a day.

TABLE 1L (Mean Pharmacokinetic Parameters for Plasma Tramadol (N = 15))

| Parameter | DER Composition B (2 × 100 mg) q.d. | | ULTRAM ® 50 mg q.i.d. | |
| --- | --- | --- | --- | --- |
| | Day 1 | Day 5 | Day 1 | Day 5 |
| $AUC_{0-}$ (ng · hr/mL) | 5089.010 (37.55) | 7715.89 (35.69) | 5000.73 (37.94) | 7004.37 (27.81) |
| $C_{max}$ (ng/mL) | 365.62 (40.34) | 431.58 (34.06) | 348.23 (36.73) | 406.95 (26.88) |
| $T_{max}$ (hr) | 13.47 (19.82) | 12.80 (21.13) | 16.00 (10.02) | 15.80 (26.23) |
| $t1/2_{el}$ (hr) | | 7.32 (16.41) | | 6.67 (20.24) |
| % Fluctuation | | 70.19 (24.19) | | 81.82 (20.28) |

| $C_{min}$ (ng/mL) | Composition B (2 × 100 mg) q.d. | ULTRAM ® 50 mg q.i.d. |
| --- | --- | --- |
| Day 1 | 161.37 (70.23) | 147.52 (49.96) |
| Day 2 | 213.43 (52.38) | 178.52 (47.03) |
| Day 3 | 235.13 (56.41) | 183.89 (36.33) |
| Day 4 | 231.44 (44.66) | 176.41 (44.24) |
| Day 5 | 253.55 (46.44) | 201.20 (26.12) |

Figure 5:
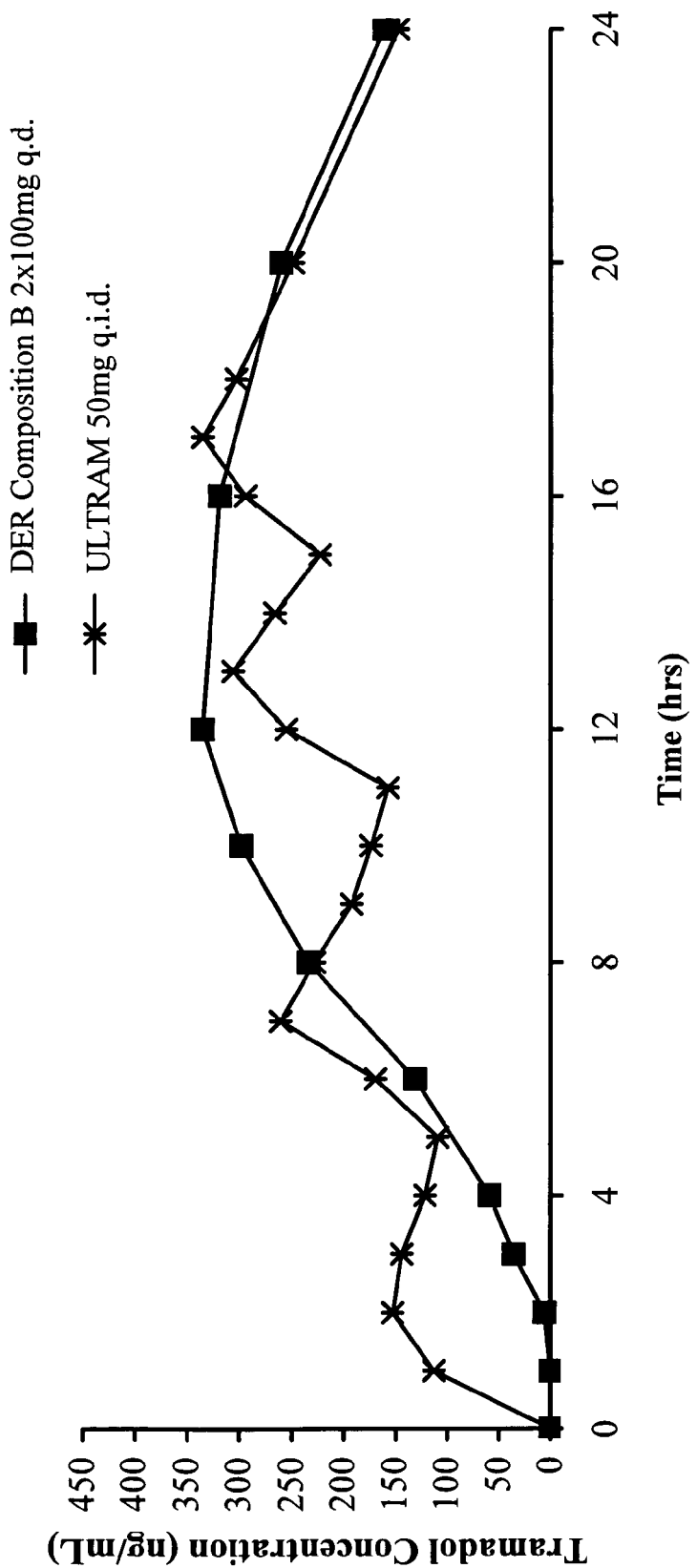
FIG. 5 is a graph illustrating the mean plasma tramadol concentrations over time of a multiple dose study on Day 1 of a five day dosing regimen following once-a-day administration of one DER tramadol HCl tablet made according to an aspect of the invention (100 mg×2) compared to the immediate-release reference product ULTRAM® (50 mg q.i.d.).

FIG. 5 illustrates the mean plasma tramadol concentrations over time on Day 1 of the five day dosing regimen following once a day tramadol HCl tablets (100 mg×2) formulated according to Composition B vs. ULTRAM® (50 mg×2) q.i.d.

Figure 6:
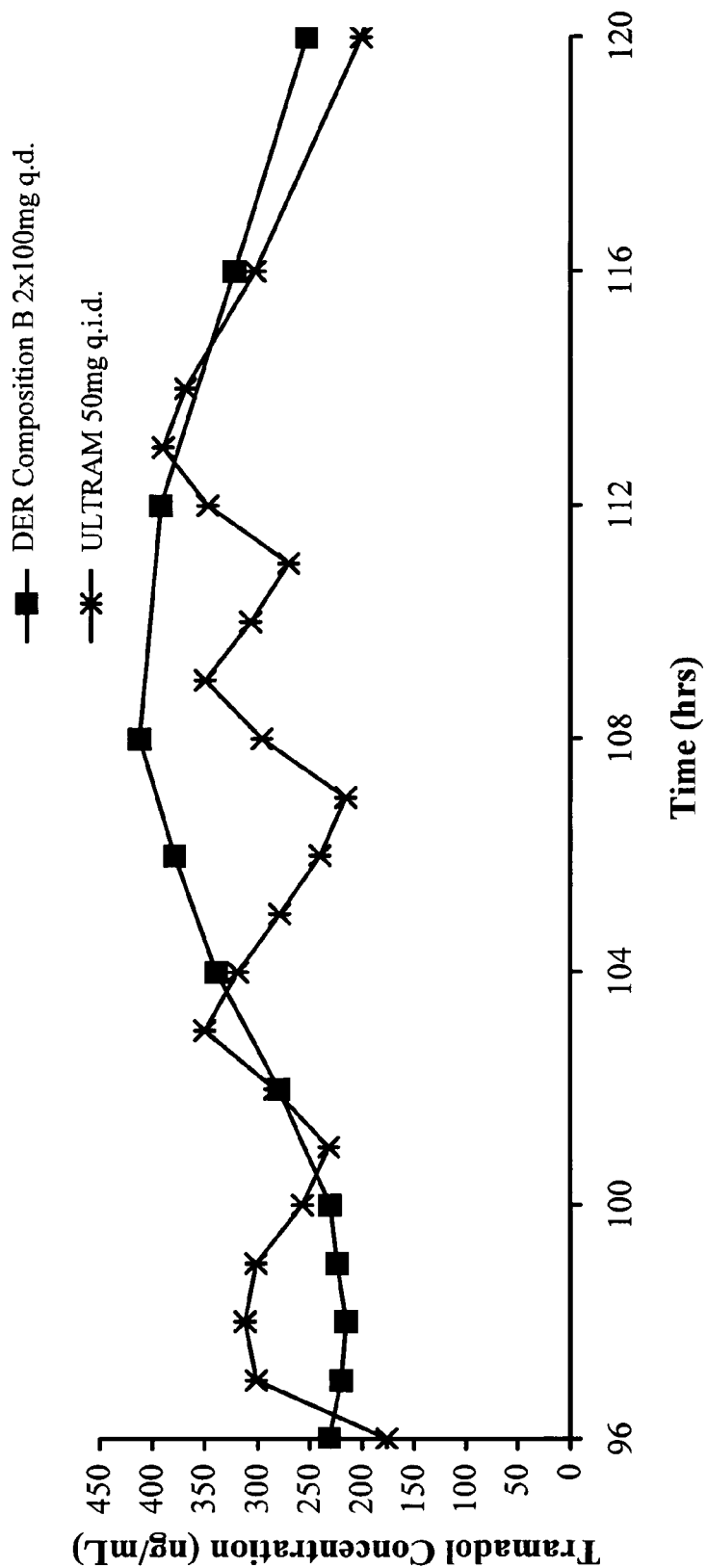
FIG. 6 is a graph illustrating the mean plasma tramadol concentrations over time of a multiple dose study on Day 5 of a five day dosing regimen following once-a-day administration of the DER tablet of FIG. 5 (100 mg×2) compared to the immediate-release reference product ULTRAM® (50 mg q.i.d.).

FIG. 6 illustrates the mean plasma tramadol concentrations over time on Day 5 of a five day dosing regimen following once a day tramadol HCl tablets (100 mg×2) formulated according to Composition B vs. ULTRAM® (50 mg×2) q.i.d.

TABLE 1M (Ratio of Means & 90% C. I. for Plasma Tramadol)

| Statistical Analysis (ANOVA) | Treatment Comparisons | Ratio[1] | 90 % Geometric C.I.[2] | |
|---|---|---|---|---|
| | | | Lower | Upper |
| $AUC_{0-t}$ | Composition B vs ULTRAM ® | 108.6% | 104.2% | 113.2% |
| $C_{max}$ | Composition B vs ULTRAM ® | 104.9% | 98.6% | 111.6% |

[1]Ratio of least squares means
[2]Calculated from log-transformed data

TABLE 1N (Mean Pharmacokinetic Parameters for Plasma O-desmethyltramadol (n = 15))

| Parameter | Composition B (2 × 100 mg) q.d. | | ULTRAM ® 50 mg q.i.d. | |
|---|---|---|---|---|
| | Day 1 | Day 5 | Day 1 | Day 5 |
| $AUC_{0-\square}$ (ng · hr/mL) | 1037.71 (40.22) | 1550.55 (37.21) | 1105.30 (37.74) | 1540.17 (39.07) |
| $C_{max}$ (ng/mL) | 70.85 (39.87) | 79.75 (36.94) | 72.82 (37.02) | 80.97 (41.13) |
| $T_{max}$ (hr) | 14.27 (21.76) | 13.73 (16.39) | 16.87 (8.34) | 13.47 (41.43) |
| $t1/2_{el}$ (hr) | | 8.49 (14.28) | | 7.15 (12.75) |
| % Fluctuation | | 49.46 (22.71) | | 55.08 (33.22) |

| $C_{min}$ (ng/mL) | Composition B (2 × 100 mg) q.d. | ULTRAM ® 50 mg q.i.d. |
|---|---|---|
| Day 1 | 40.05 (45.16) | 41.34 (38.83) |
| Day 2 | 54.73 (39.72) | 49.41 (37.52) |
| Day 3 | 56.67 (36.46) | 50.03 (37.94) |
| Day 4 | 56.55 (37.43) | 47.35 (40.18) |
| Day 5 | 55.19 (38.43) | 50.86 (39.67) |

Figure 7:
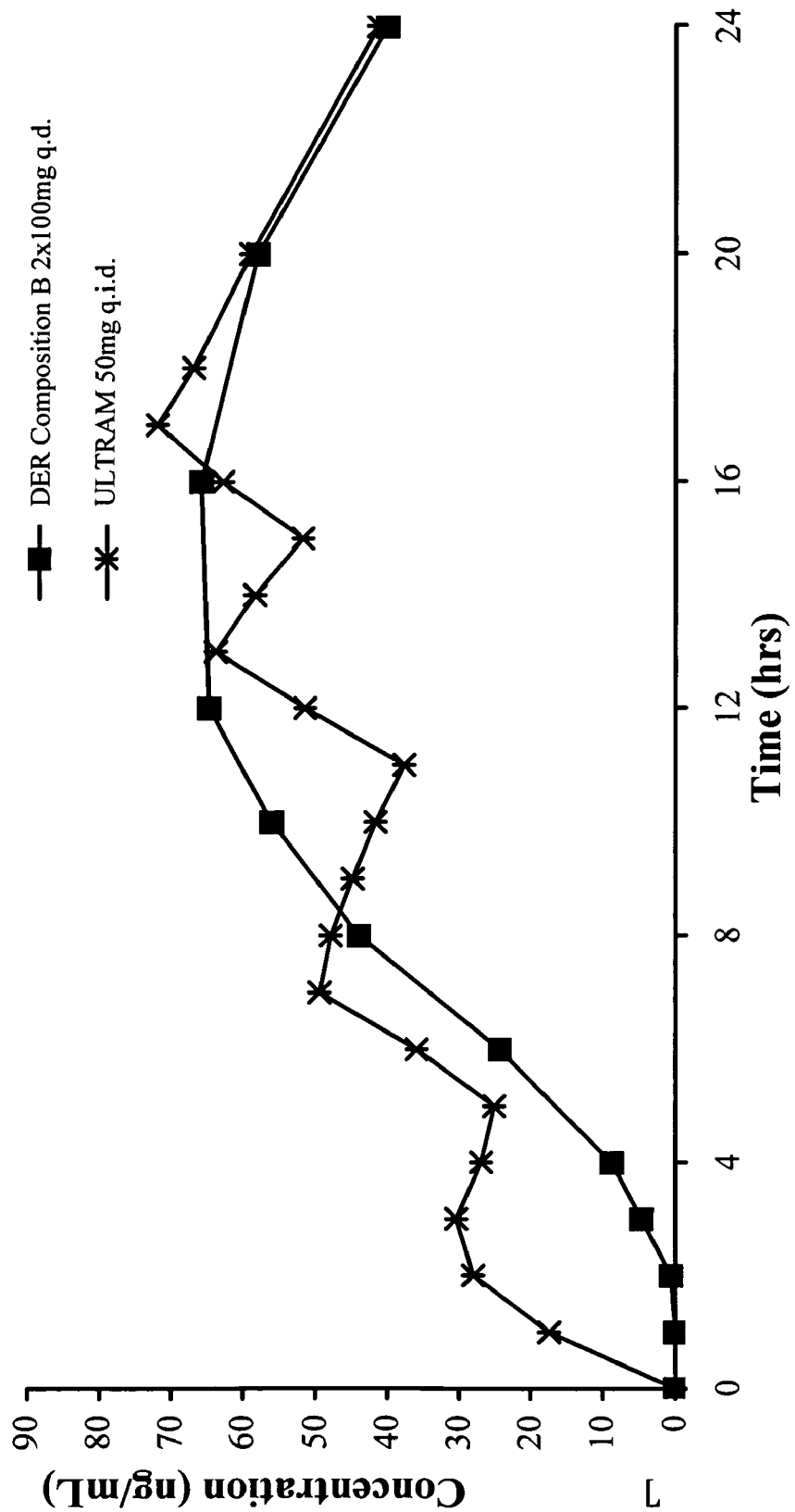
FIG. 7 is a graph illustrating the mean plasma desmethyltramadol (M1) concentrations over time of a multiple dose study on Day 1 of a five day dosing regimen following once-a-day administration of the DER tablet of FIG. 5 (100 mg×2) compared to the immediate-release reference product ULTRAM® (50 mg q.i.d.).

FIG. 7 illustrates the mean plasma desmethyltramadol concentrations on Day 1 of a five day dosing regimen following once a day DER tramadol HCl tablets (100 mg×2) formulated according to Composition B vs. ULTRAM® (50 mg×2) q.i.d.

Figure 8:
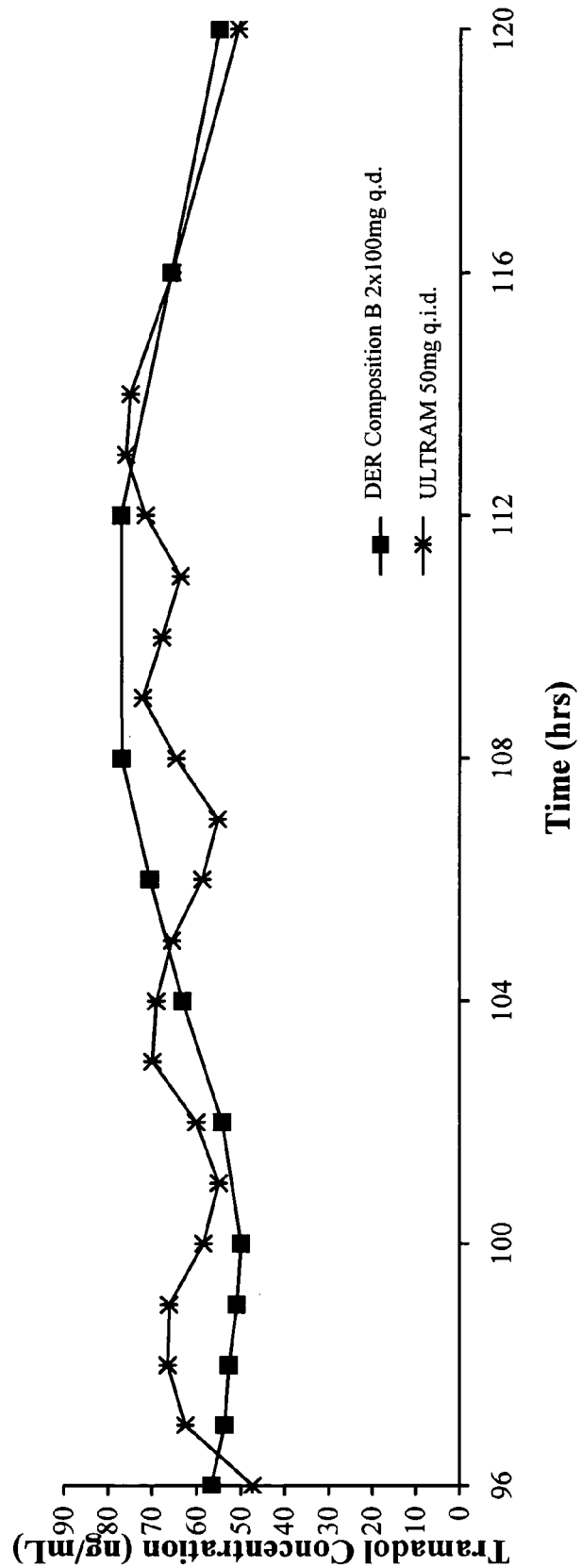
FIG. 8 is a graph illustrating the mean plasma desmethyltramadol (M1) concentrations over time of a multiple dose study on Day 5 of a five day dosing regimen following once-a-day administration of the DER tablet of FIG. 5 (100 mg×2) compared to the immediate-release reference product ULTRAM® (50 mg q.i.d.).

FIG. 8 illustrates the mean plasma desmethyltramadol concentrations on Day 5 of a five day dosing regimen following once a day DER tramadol HCl tablets (100 mg×2) formulated according to Composition B vs. ULTRAM® (50 mg×2) q.i.d.

TABLE 1O (Ratio of Means & 90% C. I. for Plasma O-desmethyltramadol)

| Statistical Analysis (ANOVA) | Treatment Comparisons | Ratio[1] | 90 % Geometric C.I.[2] | |
|---|---|---|---|---|
| | | | Lower | Upper |
| $AUC_{0-t}$ | Tramadol HCl DER vs ULTRAM ® | 101.5% | 97.2% | 106.0% |
| $C_{max}$ | Tramadol HCl DER vs ULTRAM ® | 100.0% | 94.2% | 106.2% |

[1]Ratio of least squares means
[2]Calculated from log-transformed data

C. Pilot Three-Way, Multiple-Dose, Open-Label, Fasting, Comparative Bioavailability Study of Two Formulations of DER Tramadol Hydrochloride Tablets (3×100 mg) Administered Once a Day Versus ULTRAM® Tablets (2×50 mg) Administered Three Times a Day in Normal, Healthy, Non-Smoking Male and Female Volunteers.

The objective of this study was to compare the rate and extent of absorption of two delayed and extended-release formulations of tramadol hydrochloride (3×100 mg) administered once daily against ULTRAM® (2×50 mg) administered three times a day under steady-state conditions in normal healthy male and female volunteers. This comparison reflects the administration of ULTRAM® under clinical conditions.

This steady-state study was a randomized, three-way crossover study design in fifteen (15) normal, healthy, non-smoking male and female volunteers and three (3) alternates (total 11 males and 9 females). Eighteen (18) subjects were entered into the study. Fourteen (14) subjects completed the study; there were fourteen (14) evaluable subjects. All subjects were non-smoking, between 18 and 45 years of age (inclusive), and with body weights no more than ±15% of the ideal weight for the subject's height and frame as determined by the Table of Desirable Weights for Men and Women. All female subjects were non-lactating, had negative pregnancy tests, and were taking an acceptable method of contraception.

The study periods were separated by a one-week washout period. Blood sampling for drug content analysis was carried out as follows for the two test products (DER tramadol HCl tablets (3×100 mg), treatment A (Composition B) and treatment B (Composition C)): Day 1—0.0 (pre-dose), 1.0, 2.0, 3.0, 4.0, 6.0, 8.0, 10.0, 12.0, 16.0, 20.0, Day 2, 3, and 4—0.0 (pre-dose); Day 5—0.0 (pre-dose), 1.0, 2.0, 3.0, 4.0, 6.0, 8.0, 10.0, 12.0, 16.0, 20.0, 24.0, 30.0, 36.0 and 48.0 hours post-drug administration.

Blood sampling for drug content analysis was carried out as follows for the reference product (ULTRAM® 50 mg tablets q.i.d., treatment C): Day 1—0.0 (pre-dose), 1.0, 2.0, 3.0, 4.0, 5.0 (pre-dose), 6.0, 7.0, 8.0, 9.0, 10.0, 11.0 (pre-dose), 12.0, 13.0, 14.0, 16.0, and 20.0 hours; Days 2, 3, and 4—0.0 (pre-dose); Day 5—0.0 (pre-dose), 1.0, 2.0, 3.0, 4.0, 5.0 (pre-dose), 6.0, 7.0, 8.0, 9.0, 10.0, 11.0 (pre-dose), 12.0, 13.0, 14.0, 16.0, 20.0, 24.0, 30.0, 36.0, and 48.0 hours post-drug administration.

| Treatments: | A: | 3 Tablets of DER tramadol HCl 100 mg Tablets (Composition B) once a day (approximately 7 AM) for 5 consecutive days. |
|---|---|---|
| | B: | 3 Tablets of DER tramadol HCl 100 mg Tablets (Composition C) once a day (approximately 7 AM) for 5 consecutive days. |
| | C: | 2 Tablets of ULTRAM ® (Tramadol HCl 50 mg tablet, Ortho-McNeil Pharmaceutical, USA) (Lot# CDA2225) t.i.d. (approximately 7 AM, 12 PM and 6 PM) for 5 consecutive days. |

The instant study was undertaken to compare two DER tramadol HCl tablet formulations according to an embodiment of the invention (Compositions B and C) (3×100 mg) administered once daily against ULTRAM® (2×50 mg) administered three times a day under steady-state conditions in normal healthy male and female volunteers. This comparison reflects the administration of ULTRAM® under clinical conditions.

The delayed and extended release formulations performed consistently both under single and multiple dose conditions. The overall half-life after multiple-dose for tramadol was 7.3 hours following the DER tramadol HCl tablets (Composition B), 6.9 hours following DER tramadol HCl tablets (Composition C), and 6.4 hours immediate release ULTRAM®. Steady state levels of tramadol were achieved by the third dose (day 3 of the study) for the DER tramadol HCl tablets, (Compositions B and C) and by the seventh dose (day 3 of the study) for ULTRAM®. The mean pharmacokinetic data for single dose and multiple doses of tramadol and M1 are presented in tables 1P-1Q and 1R-1S respectively. Steady-state bioequivalence between the DER tramadol HCl tablets (Compositions B and C) and immediate-release ULTRAM® was established. The 90% confidence intervals for unchanged drug and O-desmethyltramadol AUC and $C_{max}$ for the DER tramadol HCl Tablets (Composition B), and the 90% confidence intervals for unchanged drug and O-desmethyltramadol AUC for the DER tramadol HCl tablets (Composition C) were within the 80-125% limits. O-desmethyltramadol $C_{max}$ for Composition C was within the limits.

Composition B demonstrates steady-state bioequivalence versus both t.i.d. and q.i.d. administration of ULTRAM® as evidenced by 90% C.I. values for AUC and $C_{max}$ within 80-125% limits for both tramadol and O-desmethyltramadol. Composition B also exhibited lower percent fluctuation versus ULTRAM® when given t.i.d. and q.i.d.

TABLE 1P (Mean Pharmacokinetic Parameters for Plasma Tramadol (n = 15))

| Parameter | DER Tramadol HCl tablet (3 × 100 mg) q.d. Composition B | | DER tramadol HCl tablet (3 × 100 mg) q.d. Composition C | | ULTRAM ® 2 × 50 mg q.i.d. | |
|---|---|---|---|---|---|---|
| | Day 1 | Day 5 | Day 1 | Day 5 | Day 1 | Day 5 |
| $AUC_{0-\square}$ (ng · hr/mL) | 6407.95 (27.03) | 9849.28 (23.65) | 6977.91 (27.97) | 10116.75 (23.97) | 6854.57 (25.77) | 9611.88 (19.12) |
| $C_{max}$ (ng/mL) | 457.65 (28.37) | 585.17 (21.58) | 540.76 (24.05) | 699.76 (22.32) | 464.67 (23.46) | 621.66 (20.06) |
| $T_{max}$ (hr) | 10.40 (20.80) | 10.90 (27.70) | 7.90 (18.6) | 8.40 (21.20) | 12.20 (34.20) | 9.60 (36.10) |
| t½ $_{el}$ (hr) | | 7.32 (23.58) | | 6.91 (17.33) | | 6.40 (14.20) |
| % Fluctuation | | 84.73 (36.04) | | 125.39 (24.96) | | 114.47 (15.79) |

| $C_{min}$ (ng/mL) | DER tramadol HCl tablet (3 × 100 mg) q.d. Composition B | DER tramadol HCL tablet (3 × 100 mg) q.d. Composition C | ULTRAM ® 2 × 50 mg q.i.d. |
|---|---|---|---|
| Day 2 | 174.56 (40.90) | 134.96 (51.01) | 142.63 (36.88) |
| Day 3 | 213.73 (41.07) | 156.63 (37.89) | 154.99 (39.36) |
| Day 4 | 218.78 (44.50) | 175.36 (46.91) | 150.46 (32.52) |
| Day 5 | 250.77 (43.26) | 186.04 (47.41) | 166.85 (31.67) |

TABLE 1Q (Ratio of Means & 90% C. I. for Plasma Tramadol)

| Statistical Analysis | Treatment | | 90 % Geometric C.I.[2] | |
|---|---|---|---|---|
| (ANOVA) | Comparisons | Ratio[1] | Lower | Upper |
| $AUC_{0-t}$ | Tramadol DER vs ULTRAM ® | 101.9% | 95.4% | 108.8% |
| | Tramadol DER vs ULTRAM ® | 104.9% | 98.2% | 112.0% |
| $C_{max}$ | Tramadol DER vs ULTRAM ® | 93.1% | 83.9% | 103.4% |
| | (Lot# CDA2225) Tramadol DER vs ULTRAM ® | 114.1% | 102.8% | 126.7% |

[1]Ratio of least squares means
[2]Calculated from log-transformed data

TABLE 1R (Mean Pharmacokinetic Parameters for Plasma O-desmethyltramadol (n = 15))

| Parameter | DER tramadol HCl tablet (3 × 100 mg) q.d. Composition B | | DER tramadol HCl tablet (3 × 100 mg) q.d. Composition C | | ULTRAM ® 2 × 50 mg q.i.d. | |
|---|---|---|---|---|---|---|
| | Day 1 | Day 5 | Day 1 | Day 5 | Day 1 | Day 5 |
| $AUC_{0-\square}$ (ng · hr/mL) | 1896.02 (26.07) | 2554.04 (26.68) | 2133.71 (32.64) | 2478.46 (32.46) | 2096.32 (24.41) | 2475.64 (25.10) |
| $C_{max}$ (ng/mL) | 130.64 (30.58) | 138.37 (24.02) | 150.67 (33.05) | 145.57 (29.10) | 127.43 (24.32) | 138.26 (26.73) |
| $T_{max}$ (hr) | 11.60 (19.80) | 12.60 (22.00) | 9.60 (14.60) | 9.20 (18.80) | 13.20 (29.90) | 13.20 (14.30) |

| $C_{min}$ (ng/mL) | DER tramadol HCl tablet (3 × 100 mg) q.d. | DER tramadol HCl tablet (3 × 100 mg) q.d. | ULTRAM ® 2 × 50 mg q.i.d. |
|---|---|---|---|
| Day 2 | 64.24 (34.32) | 52.92 (46.34) | 57.74 (25.59) |
| Day 3 | 70.48 (33.65) | 55.29 (41.81) | 56.61 (28.78) |
| Day 4 | 76.09 (41.83) | 60.05 (44.08) | 57.67 (28.81) |
| Day 5 | 76.87 (38.41) | 59.65 (45.35) | 58.82 (30.95) |

TABLE 1S (Ratio of Means & 90% C.I. for Plasma O-desmethyltramadol)

| Statistical Analysis (ANOVA) | Treatment Comparisons | Ratio[1] | 90 % Geometric C.I.[2] | |
|---|---|---|---|---|
| | | | Lower | Upper |
| $AUC_{0-t}$ | DER Composition B vs ULTRAM ® | 102.4% | 96.9% | 108.1% |
| | DER Composition C vs ULTRAM ® | 98.6% | 93.4% | 104.2% |
| $C_{max}$ | DER Composition B) vs ULTRAM ® | 100.4% | 95.0% | 106.0% |
| | DER Composition C vs ULTRAM ® | 105.3% | 99.7% | 111.3% |

[1]Ratio of least squares means
[2]Calculated from log-transformed data

Figure 9:
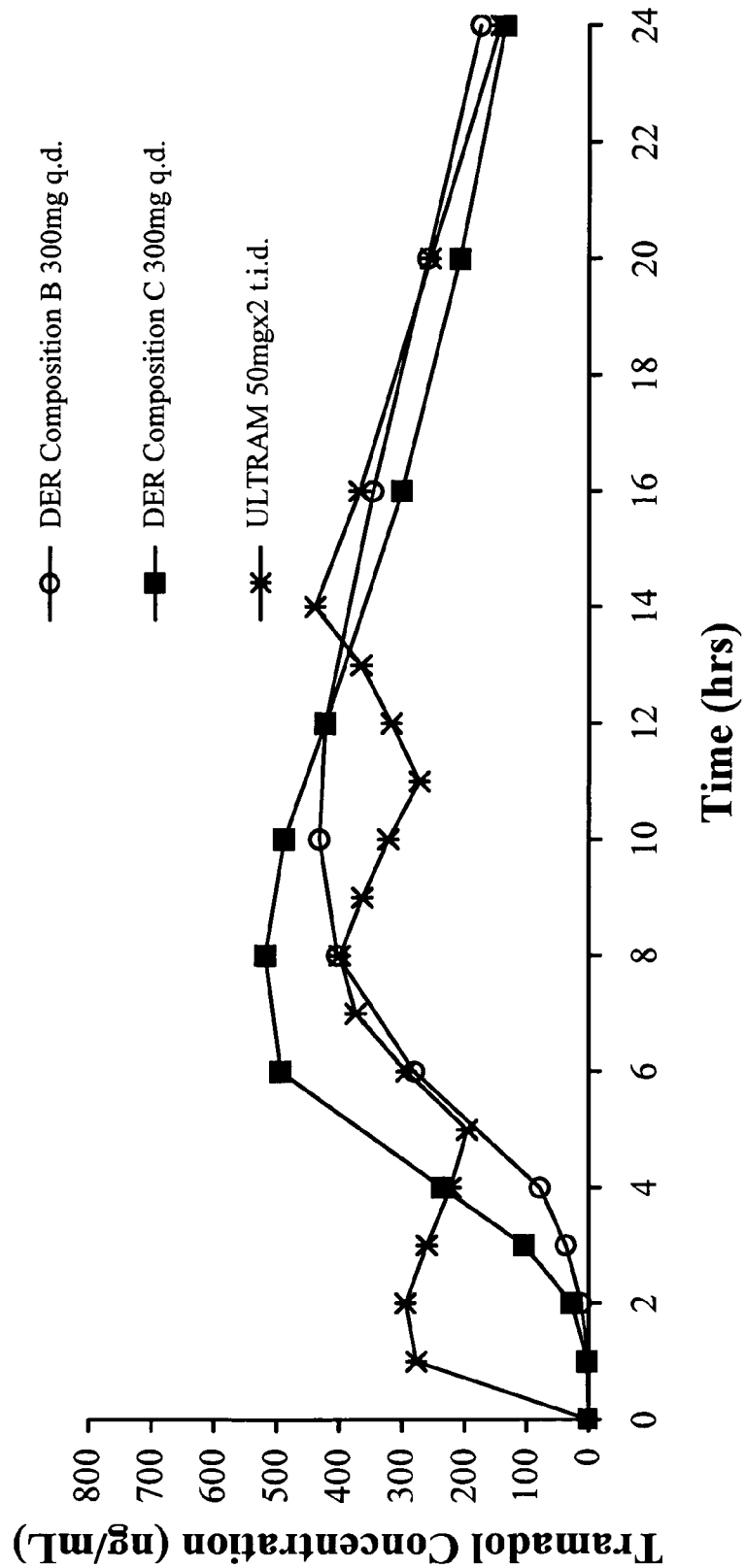
FIG. 9 is a graph illustrating the mean plasma tramadol concentrations over time of a single dose study on Day 1 of a five day dosing regimen following a once-a-day administration of the DER tramadol HCl tablet of FIG. 5 (100 mg×3) and another DER tramadol HCl tablet of FIG. 2 (100 mg×3) with a faster release rate compared to the immediate-release reference product ULTRAM® (50 mg×2 t.i.d).

FIG. 9 illustrates the mean plasma tramadol concentrations on Day 1 of a five day dosing regimen following once a day DER tramadol HCl tablets (100 mg×3) formulated according to Compositions B and C vs. ULTRAM® (50 mg×2) t.i.d.

Figure 10:
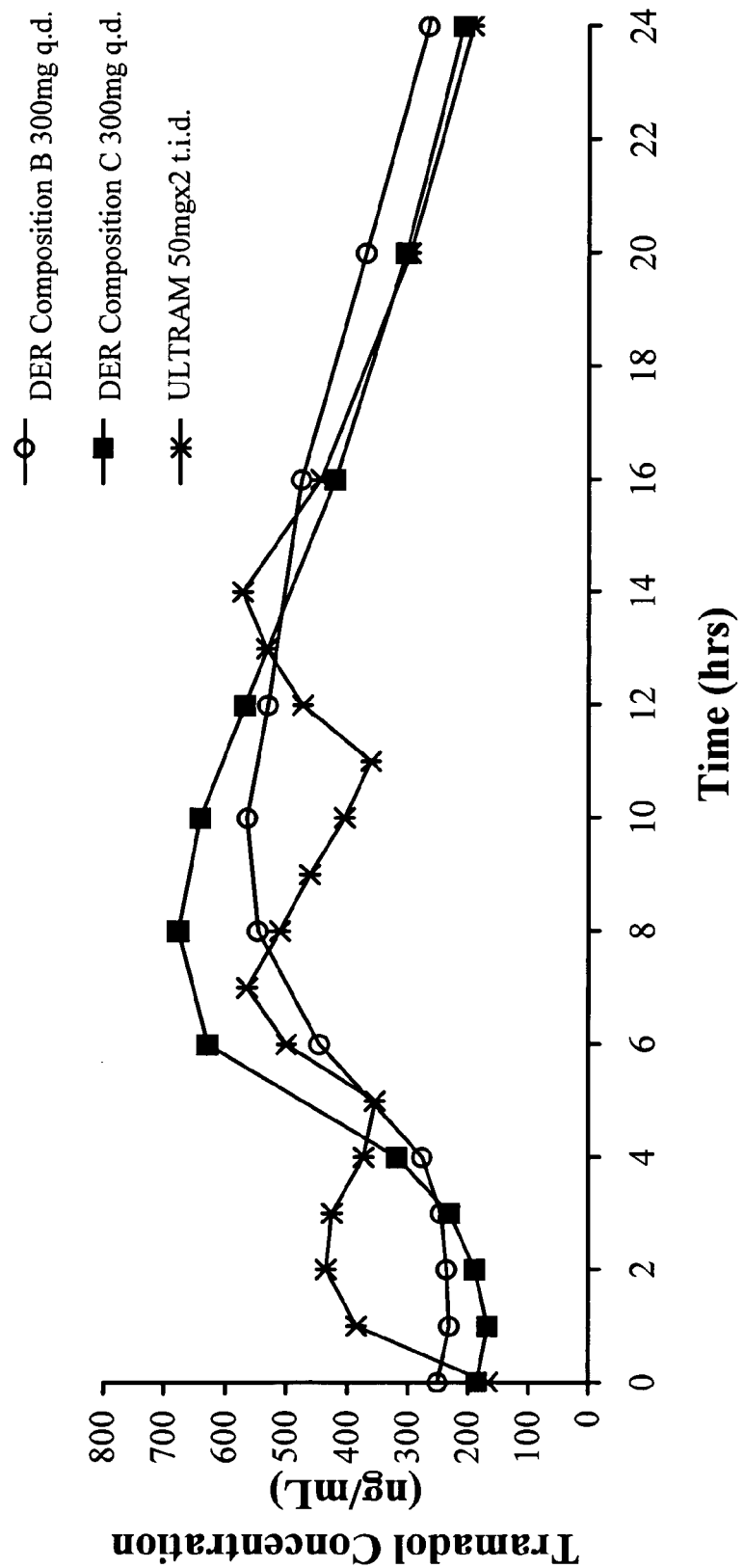
FIG. 10 is a graph illustrating the mean plasma tramadol concentrations over time of a single dose study on Day 5 of a five day dosing regimen following administration of the tablets of FIG. 9.

FIG. 10 illustrates the mean plasma tramadol concentrations on Day 5 of a five day dosing regimen following once a day DER tramadol HCl tablets (100 mg×3) formulated according to Compositions B and C vs. ULTRAM® (50 mg×2) t.i.d.

Figure 11:
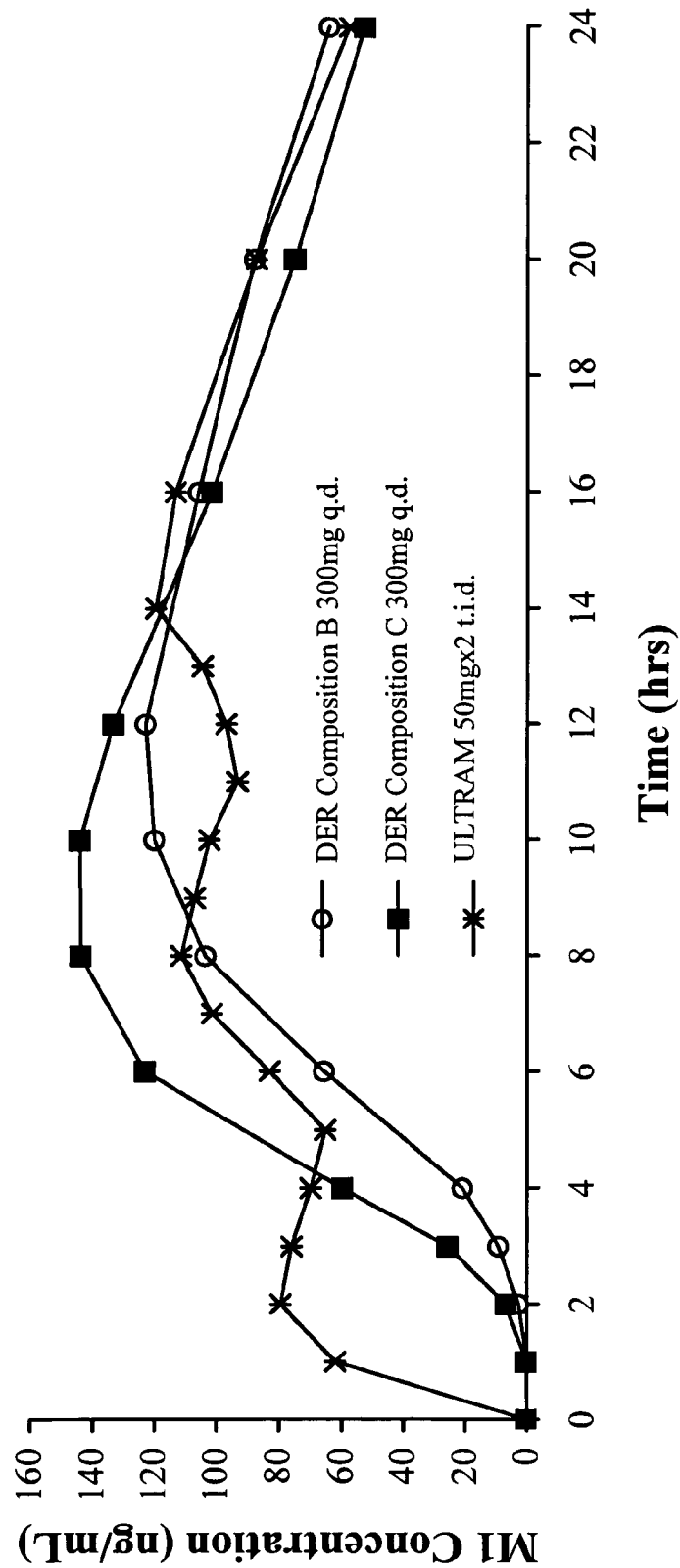
FIG. 11 is a graph illustrating the mean plasma desmethyltramadol (M1) concentrations over time of a single dose study on Day 1 of a five day dosing regimen following administration of the tablets of FIG. 9.

FIG. 11 illustrates the mean plasma desmethyltramadol concentrations on Day 1 of a five day dosing regimen following once a day DER tramadol HCl tablets (100 mg×3) formulated according to Compositions B and C vs. ULTRAM® (50 mg×2) t.i.d.

Figure 12:
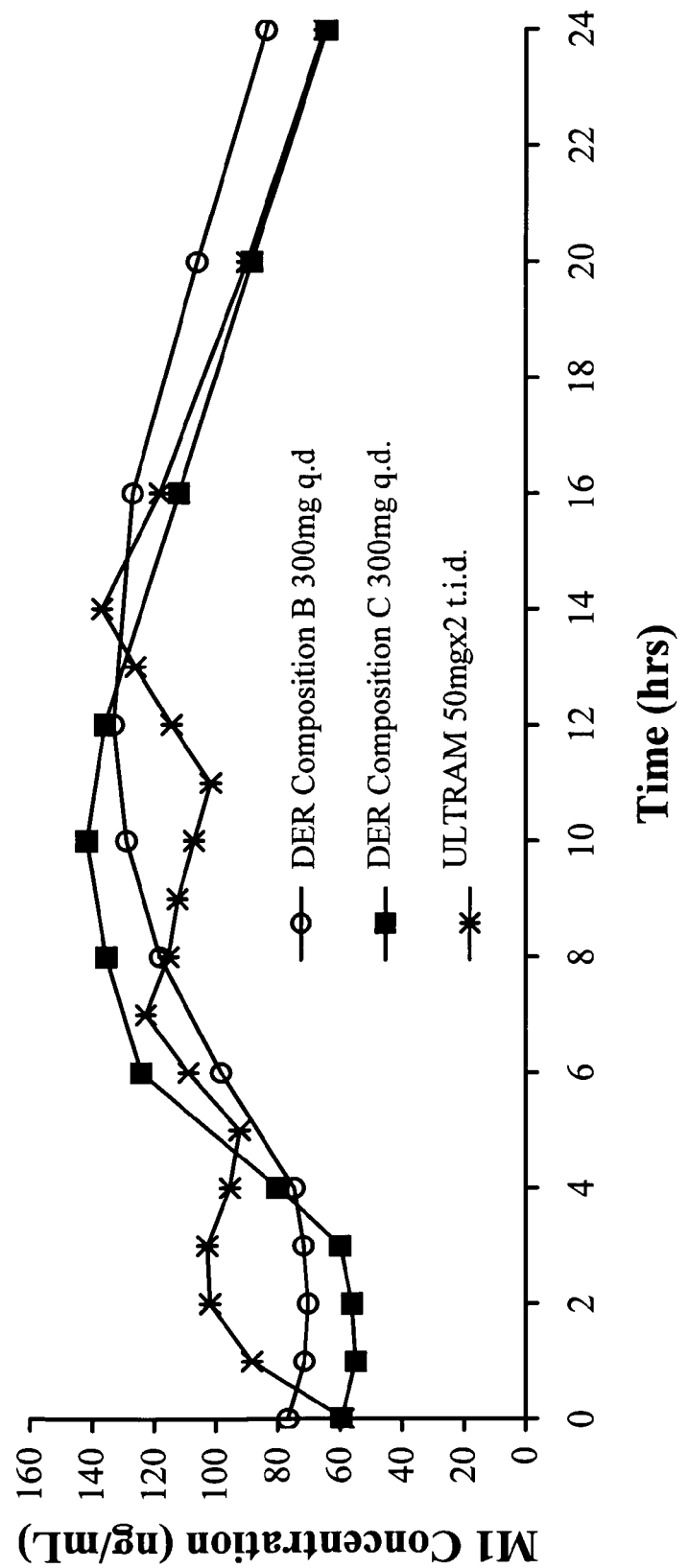
FIG. 12 is a graph illustrating the mean plasma desmethyltramadol (M1) concentrations over time of a single dose study on Day 5 of a five day dosing regimen following administration of the tablets of FIG. 9.

FIG. 12 illustrates the mean plasma desmethyltramadol concentrations on Day of a five day dosing regimen following once a day DER tramadol HCl tablets (100 mg×3) formulated according to Compositions B and C vs. ULTRAM® (50 mg×2) t.i.d.

EXAMPLE 2

100 mg Delayed and Extended Release Tramadol HCl Tablets

I. Formulation

The tablet core formulation was that of Example 1. The tablet core was prepared according to the process described in Example 1.

The coating formulation was as shown in Table 2A:

TABLE 2A (Coating Formulation)

| Ingredients | Quantity (mg) | % |
|---|---|---|
| Ethylcellulose (ETHOCEL ® PR 100) | 9.73 | 73.00 (of coating polymer) |
| Polyvinylpyrrolidone (KOLLIDON ® 90F) | 3.60 | 27.00 (of coating polymer) |
| Dibutyl Sebacate | 2.67 | 20.00 (of total polymer) |
| Total dry material: 8.5% of the solution | | |
| Ethyl Alcohol 200 Proof | 163.62 * | 95% (of total solvent) |
| Isopropyl Alcohol 99% | 8.61 * | 5% (of total solvent) |
| Coated Tablet | 120.00 | |

* evaporated during process

The coating parameters used were as shown in Table 2B:

TABLE 2B (Coating Parameters)

| Spray Pressure | 30 psi |
|---|---|
| Product Temperature | 40° C. |
| Spray Rate | 5 g/min/kg |

EXAMPLE 3

100 mg Delayed and Extended Release Tramadol HCl Tablets

I. Formulation

The tablet core formulation was that of Example 1. The tablet core was prepared according to the process described in Example 1.

The coating composition was as shown in Table 3A:

TABLE 3A (Coating Formulation)

| | Mg/tablet | | | |
|---|---|---|---|---|
| Ingredients | Coating Formulation A Quantity (mg) | Coating Formulation B Quantity (mg) | Coating Formulation C Quantity (mg) | Coating Formulation D Quantity (mg) |
| Ethylcellulose (ETHOCEL ® PR 100) | 9.87 | 9.87 | 9.60 | 9.60 |
| Polyvinylpyrrolidone (KOLLIDON ® 90F) | 3.47 | 3.47 | 3.73 | 3.73 |
| Dibutyl Sebacate | 2.67 | 2.67 | 2.67 | 2.67 |
| Ethyl Alcohol 200 Proof | 153.94 * | 153.94 * | 153.94 * | 153.94 * |
| Isopropyl Alcohol 99% USP | 8.09 * | 8.09 * | 8.09 * | 8.09 * |

* evaporated during process

The tablet core coating solution was prepared according to the process described in Example 1. The coating parameters were as shown in Table 3B:

TABLE 3B (Coating Parameters)

| Parameter | Coating Parameter A | Coating Parameter B | Coating Parameter C | Coating Parameter D |
|---|---|---|---|---|
| Inlet Temperature C. ° | 41-42 | 56-57 | 56-57 | 48.5-49.5 |
| Outlet Temperature C. ° | 32-33 | 44-45 | 44-45 | 38.5-39.5 |
| Bed Temperature C. ° | ND | 45-46 | 45-46 | 37.5-38.5 |
| Spray Rate g/min | 300 | 300-310 | 300-310 | 300 |
| Atomizing Air/Pattern Psi | 25/20 | 25/25 | 25/25 | 25/25 |
| Distance gun/Bed | 6" | 6" | 6" | 6" |
| Distance between guns | 6" | 6" | 6" | 6" |
| Pan speed rpm | 12.0 | 12.0 | 12.0 | 12.0 |

In vitro dissolution studies were carried out as described in Example 1. The dissolution profile is presented in Table 3C:

TABLE 3C (Dissolution Profile)

| | % Dissolved | | | |
|---|---|---|---|---|
| Time (min.) | Coating Formulation A/Coating Parameter A | Coating Formulation B/Coating Parameter B | Coating Formulation C/Coating Parameter C | Coating Formulation D/Coating Parameter D |
| 0 | 0 | 0 | 0 | 0 |
| 120 | 0.5 | 3.34 | 7.81 | 5.13 |
| 240 | 0.85 | 7.94 | 26.68 | 15.23 |
| 360 | 1.39 | 13.06 | 50.97 | 34.94 |
| 480 | 2.43 | 20.72 | 70.16 | 54.58 |
| 600 | 4.04 | 30.15 | 83.27 | 70.10 |
| 720 | 6.89 | 41.77 | 91.40 | 81.89 |

Figure 13:
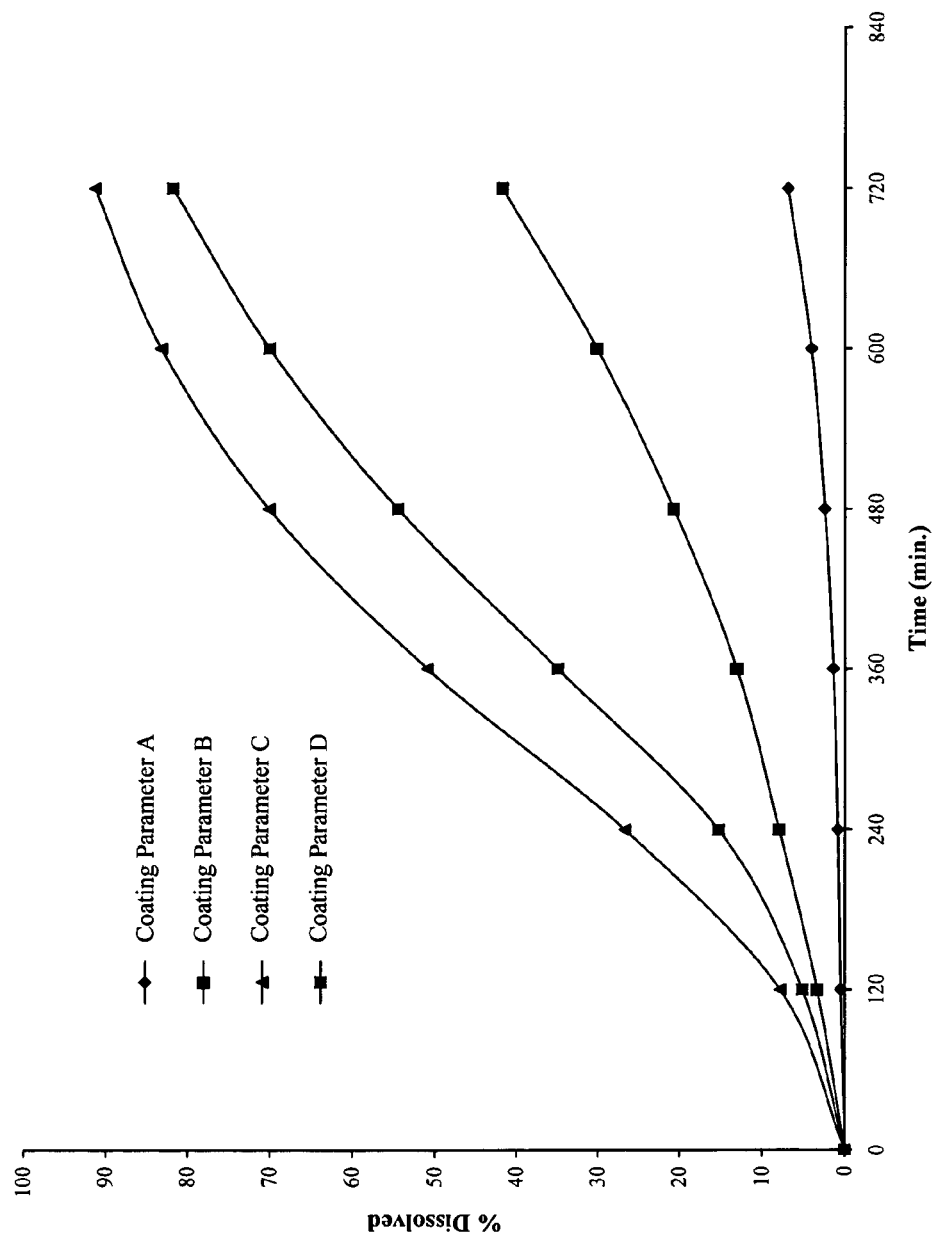
FIG. 13 is a graph illustrating the in-vitro dissolution profile over the first six hours of four 100 mg DER tramadol HCl tablets made according to an embodiment of the invention coated using four coating parameters.

A graphical representation of the data in Table 3C is presented in FIG. 13.

EXAMPLE 3A

In Vitro In Vivo Correlation (IVIVC) Studies

I. Formulation

The core composition of a Fast, Target (Medium) and Slow Release formulation is as shown in Table 3A':

TABLE 3A'

(Core Formulations for Fast, Medium and Slow Release Composition)

| Ingredients | Fast 100 Quantity (mg) | Medium 100 Quantity (mg) | Slow 100 Quantity (mg) |
|---|---|---|---|
| Tramadol HCl | 100.00 | 100.00 | 100.00 |
| Polyvinyl Alcohol | 2.00 | 2.00 | 2.00 |
| Colloidal Silicon Dioxide (AEROSIL ® 200) | 1.00 | 1.00 | 1.00 |
| Sodium Stearyl Fumarate | 1.00 | 1.00 | 1.00 |
| Purified Water | * | * | * |
| Core Total Weight | 104.00 | 104.00 | 104.00 |

* evaporated during process

The cores were prepared as described in Example 1.

The coating formulation for each Fast, Medium, and Slow release formulations is as shown in Table 3B':

TABLE 3B'

(Coating Formulations For Fast, Medium, and Slow Release Compositions)

| Ingredients | Fast Quantity (mg) | Medium (Target) Quantity (mg) | Slow Quantity (mg) |
|---|---|---|---|
| Ethylcellulose (ETHOCEL ® PR100) | 8.39 | 11.39 | 15.58 |
| Polyvinylpyrrolidone (KOLLIDON ® K90) | 3.25 | 4.4 | 6.03 |
| Dibutyl Sebacate NF | 2.36 | 3.21 | 4.39 |
| Ethyl Alcohol 200 Proof | * | * | * |
| Isopropyl Alcohol USP | * | * | * |

* evaporated during process

The cores were coated as described in Example 1, with the following coating parameters:

TABLE 3C'

(Coating Parameters)

| | Fast release Composition | Medium (Target) Release Composition | Slow Release Composition |
|---|---|---|---|
| Exhaust Temperature | 40.4° C. | 42.3° C. | 40.4° C. |
| Product Temperature | 38.1° C. | 40.0° C. | 38.1° C. |

TABLE 3C'-continued (Coating Parameters)

| | Fast release Composition | Medium (Target) Release Composition | Slow Release Composition |
|---|---|---|---|
| Dew Point Temperature | 4.2-10° C. | 6.4-8.6° C. | 4.2-10° C. |
| Air Flow | 910 CFM | 910 CFM | 910 CFM |
| Liquid Atomization/ Pattern | 25/28 psi | 25/28 psi | 25/28 psi |
| Spray Rate | 221 g/min | 223 g/min | 221 g/min |
| Pan speed | 13.0 rpm | 13.0 rpm | 13.0 rpm |

In vitro dissolution studies were carried out as described in Example 1. The dissolution profile is presented below in Table 3D':

TABLE 3D'

(Coating Formulations For Fast, Medium, and Slow Release Compositions)

| | Fast Release Composition | | Medium (Target) Release composition | | Slow Release Composition | |
|---|---|---|---|---|---|---|
| Time (hr) | Mean | Std. Dev | Mean | Std. Dev | Mean | Std. Dev |
| 0 | 0.05 | 0.07 | 0.01 | 0.07 | 0.16 | 0.05 |
| 1 | 3.08 | 0.37 | 1.33 | 1.43 | 0.32 | 0.10 |
| 2 | 11.78 | 1.15 | 4.33 | 0.86 | 2.06 | 0.31 |
| 3 | 24.92 | 2.12 | 10.42 | 1.50 | 5.39 | 0.69 |
| 4 | 40.13 | 2.69 | 18.76 | 2.44 | 10.15 | 1.19 |
| 5 | 54.59 | 2.92 | 29.38 | 3.26 | 16.44 | 1.81 |
| 6 | 67.08 | 2.84 | 40.90 | 3.74 | 24.48 | 2.62 |
| 7 | 77.05 | 2.54 | 51.83 | 3.84 | 33.88 | 3.25 |
| 8 | 84.50 | 2.23 | 61.58 | 3.75 | 43.58 | 3.47 |
| 9 | 89.93 | 1.91 | 70.01 | 3.53 | 52.63 | 3.48 |
| 10 | 93.73 | 1.63 | 77.02 | 3.23 | 60.77 | 3.39 |
| 11 | 97.15 | 1.47 | 82.44 | 2.79 | 67.88 | 3.20 |
| 12 | 98.13 | 1.37 | 86.83 | 2.42 | 73.95 | 3.00 |
| 13 | 99.40 | 1.29 | 90.37 | 2.17 | 79.06 | 2.75 |
| 14 | 100.29 | 1.24 | 93.08 | 1.97 | 83.31 | 2.55 |
| 15 | 100.96 | 1.21 | 94.96 | 1.82 | 86.77 | 2.32 |
| 16 | 101.41 | 1.22 | 96.46 | 1.72 | 89.61 | 2.16 |
| 17 | 101.73 | 1.20 | 97.78 | 1.68 | 91.87 | 2.00 |
| 18 | 102.00 | 1.22 | 98.70 | 1.65 | 93.69 | 1.89 |
| 19 | 102.20 | 1.21 | 99.38 | 1.62 | 95.02 | 1.89 |
| 20 | 102.36 | 1.21 | 99.88 | 1.60 | 96.13 | 1.85 |
| 21 | 102.46 | 1.21 | 100.33 | 1.58 | 97.13 | 1.76 |
| 22 | 102.51 | 1.21 | 100.62 | 1.56 | 97.90 | 1.78 |
| 23 | 102.62 | 1.20 | 100.89 | 1.57 | 98.55 | 1.76 |
| 24 | 102.65 | 1.22 | 101.08 | 1.60 | 99.05 | 1.77 |

Figure 13A:
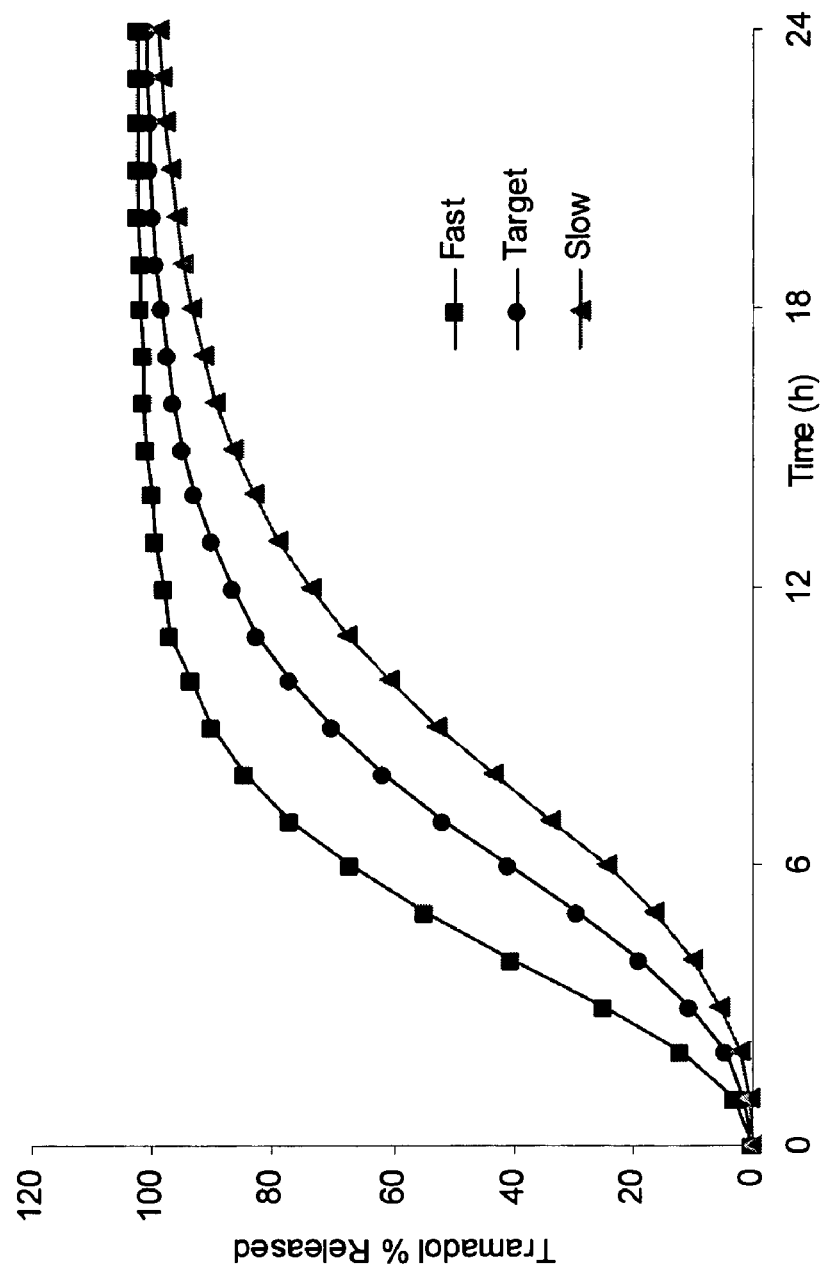
FIG. 13A is a graph illustrating the in vitro dissolution profiles of the 100 mg DER tramadol HCl tablets formulated according to the Fast, Medium and Slow release formulations of one aspect of the invention.

FIG. 13A compares the in vitro dissolution profiles of the 100 mg DER tramadol HCl tablets formulated according to the Fast, Medium and Slow release formulations.

Figure 13B:
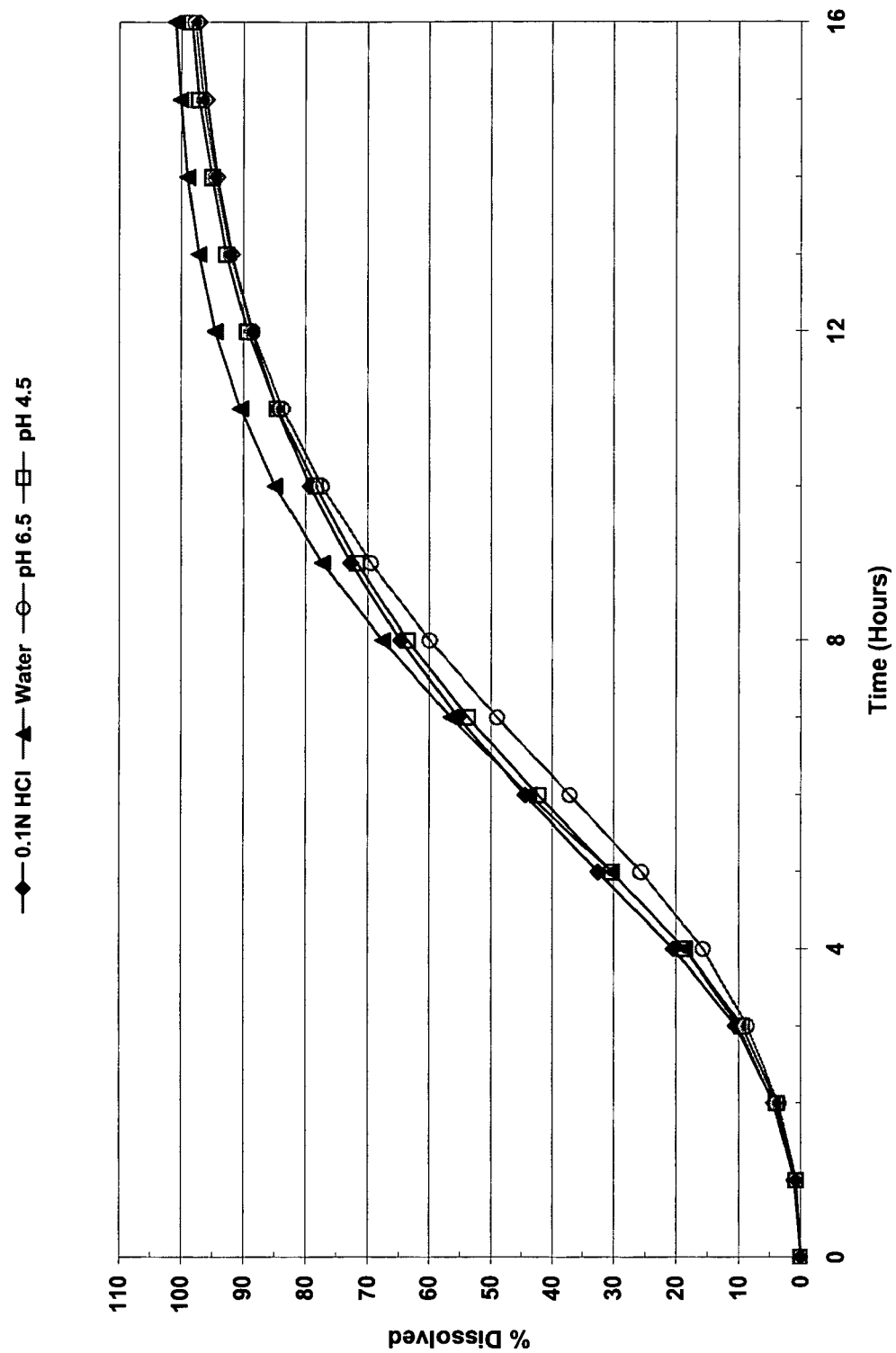
FIG. 13B is a graph illustrating the in-vitro dissolution profile of a 100 mg DER tramadol HCl tablet in different dissolution media.

FIG. 13B compares the in vitro dissolution profiles of the 100 mg DER tramadol HCL tablets in 0.1 N HCl, water, pH 6.5 media, and pH 4.5 media. The dissolution studies were carried out using the same apparatus and conditions as described in Example 1.

II. Pharmacokinetic Studies

Figure 13C:
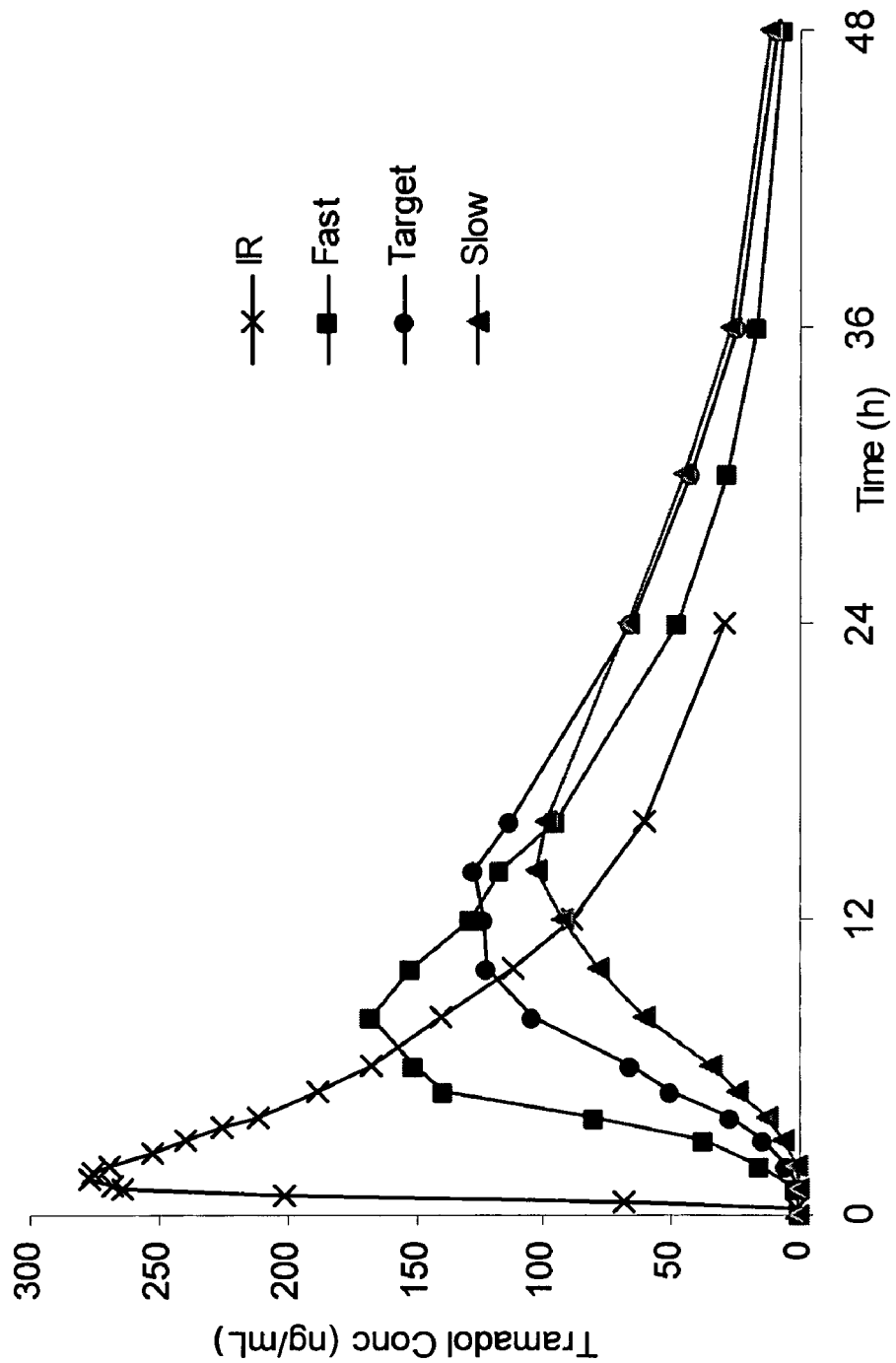
FIG. 13C is a graph illustrating the mean plasma tramadol profiles of the tablets of FIG. 13A compared to the immediate-release product, ULTRAM®.
Figure 13D:
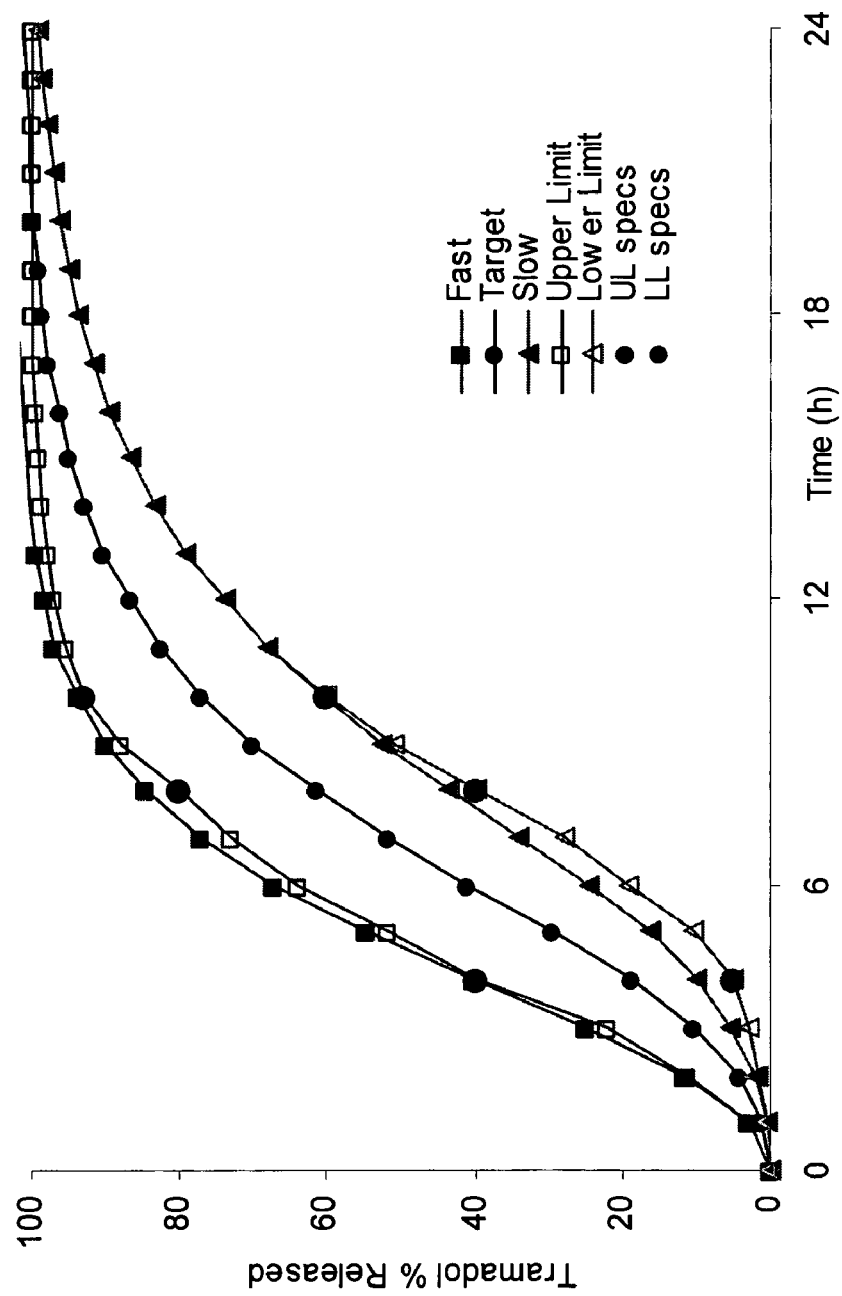
FIG. 13D is a graph illustrating the correlation between the predicted and observed in vitro dissolution profiles of the tablets of FIG. 13A.
Figure 13E:
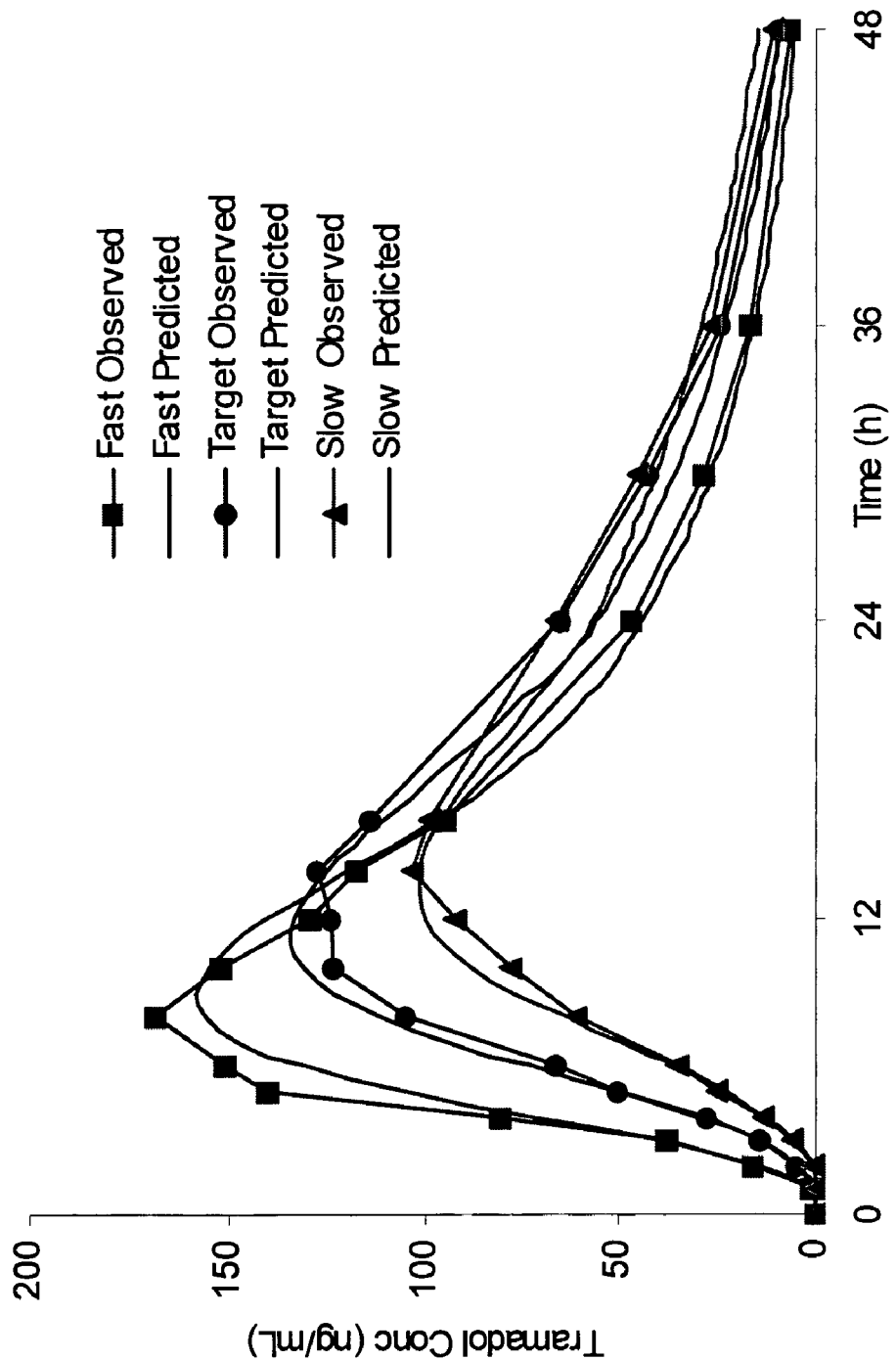
FIG. 13E is a graph illustrating the correlation between the predicted and observed mean plasma tramadol profiles of the tablets of FIG. 13A.

A Four-Way, Four-Treatment, Crossover, Open-Label, Single-Dose, Fasting, in-Vitro/In-Vivo Correlation Pharmacokinetic Study Of Three Formulations Of Tramadol HCl Extended Release 1×100 mg Tablets (Fast Fraction, Medium Fraction And Slow Fraction Formulations) Versus ULTRAM® 2×50 mg Tablets in Normal Healthy Non-Smoking Male Subjects This four-way single dose fasting study was carried out in 16 subjects to determine the pharmacokinetic profile of three formulations (Fast, Target, Slow Release) of the DER formulations of the present invention and ULTRAM® Tablets. The dataset was generated for the development of an in-vivo/in-vitro correlation for the DER formulation. Subjects were given either a single dose of the 100 mg strength DER formulation (Fast, Medium (Target) or Slow Release Formulation) or a single dose of 2×50 mg of ULTRAM® Tablets after a 10 hour overnight fast in four study periods separated by a one week washout. Blood samples for pharmacokinetic analysis were collected from 0 to 48 hours for the three DER formulations and 0 to 24 hours for ULTRAM®. The mean plasma concentration versus time profiles, in-vitro dissolution profiles of the DER formulations, IVIVC correlations and resulting fits are shown in FIGS. 13C-13E. The mean pharmacokinetic parameters for tramadol are presented in Table 3E'. The IVIVC model parameters, and prediction errors are presented in Table 3F'. The in vitro release data of tramadol HCl DER 100 mg tablets determined with an official USP dissolution method could be linked mathematically with their in vivo release kinetics by a Level A in vitro-in vivo correlation. The correlation between the in vitro and in vivo data sets indicates that the selected in vitro test is biorelevant.

TABLE 3E'

(Pharmacokinetic Parameters for Tramadol for Fast, medium and Slow Release DER Compositions)

| Pharmacokinetic Parameters | Tramadol HCl DER 100 mg Tablets (Fast) (N = 16) (Mean ± SD) | Tramadol HCl DER 100 mg Tablets (Target) (N = 16) (Mean ± SD) | Tramadol HCl DER 100 mg Tablets (Slow) (N = 16) (Mean ± SD) | ULTRAM® 2 × 50 mg Tablets (N = 16) (Mean ± SD) |
|---|---|---|---|---|
| $AUC_{0-t}$ (ng · hr/mL) | 2779.34 ± 1021.77 | 2706.20 ± 1030.08 | 2300.30 ± 1104.01 | 2649.53 ± 816.53 |
| $AUC_{0-\infty}$ (ng · hr/mL) | 2876.72 ± 1095.03 | 2841.74 ± 1112.57 | 2458.92 ± 1222.91 | 2985.06 ± 1071.17 |
| $C_{max}$ (ng/mL) | 179.33 ± 48.78 | 139.27 ± 45.16 | 109.87 ± 45.04 | 325.28 ± 64.08 |
| $T_{max}$ (hr) | 7.69 ± 1.81 | 12.00 ± 2.19 | 13.50 ± 2.68 | 1.41 ± 0.45 |
| $t_{1/2}$ (hr) | 7.47 ± 1.92 | 8.13 ± 2.06 | 8.72 ± 1.72 | 6.84 ± 1.69 |
| M1/Tramadol Ratio | 0.399 ± 0.183 | 0.410 ± 0.178 | 0.400 ± 0.184 | 0.388 ± 0.175 |

TABLE 3E'-continued (Pharmacokinetic Parameters for Tramadol for Fast, medium and Slow Release DER Compositions)

| Pharmacokinetic Parameters | Tramadol HCl DER 100 mg Tablets (Fast) (N = 16) (Mean ± SD) | Tramadol HCl DER 100 mg Tablets (Target) (N = 16) (Mean ± SD) | Tramadol HCl DER 100 mg Tablets (Slow) (N = 16) (Mean ± SD) | ULTRAM ® 2 × 50 mg Tablets (N = 16) (Mean ± SD) |
|---|---|---|---|---|
| M5/Tramadol Ratio | 0.126 ± 0.041 | 0.123 ± 0.035 | 0.122 ± 0.040 | 0.128 ± 0.038 |

TABLE 3F'

(IVIVC Model Parameters and Prediction Errors)

| PK Parameters | Internal Validation | | | | | | | | | MAPPE (%) |
|---|---|---|---|---|---|---|---|---|---|---|
| | Fast | | | Target | | | Slow | | | |
| | Predicted | Observed | % PE | Predicted | Observed | % PE | Predicted | Observed | % PE | |
| $C_{max}$ (ng/mL) | 157.77 | 168.00 | −6.09 | 133.64 | 127.52 | 4.80 | 101.50 | 103.05 | −1.50 | 4.13 |
| $AUC_{0-48h}$ (ng · hr/mL) | 2656.96 | 2745.40 | −3.22 | 2611.01 | 2674.40 | −2.37 | 2264.17 | 2270.20 | −0.27 | 1.95 |

The validated Level-A IVIVC was then applied to find the bioequivalent side batches of the "Target" tramadol HCl formulation. Based on the properties of the drug substance and its extended release formulation, as well as the robust Level-A IVIVC, in vitro release specifications wider than the traditional 10% range around the target formulation are justified. In this particular case asymmetric release specifications resulted from the calculations.

EXAMPLE 4

200 mg Delayed and Extended Release Tramadol HCl Tablets

I. Formulation

The core composition is as shown in Table 4A:

TABLE 4A (Core Formulation for 200 mg DER tramadol HCl Tablets)

| Ingredients | Quantity (mg) |
|---|---|
| Tramadol HCl | 200.00 |
| Polyvinyl Alcohol | 4.00 |
| Colloidal Silicon Dioxide (AEROSIL ® 200) | 2.00 |
| Sodium Stearyl Fumarate | 2.00 |
| Purified Water | 83.20 * |
| Core Total Weight | 208.00 |

* evaporated during process

The tablet core was prepared according to the process described in Example 1.

The dissolution profile of the uncoated 200 mg tablet cores was determined under the same conditions shown in Example 1. The results are presented in Table 4B as release of the total tramadol in the core:

TABLE 4B (Dissolution Profile of 200 mg Uncoated Tramadol Tablet Cores)

| Time (min) | Tramadol HCl 200 mg cores | SD | Max | Min |
|---|---|---|---|---|
| 0 | 0 | 0 | 0 | 0 |
| 5 | 43.71 | 2.18 | 47.84 | 42.38 |
| 10 | 77.91 | 1.6 | 80.9 | 76.53 |
| 15 | 95.79 | 1.34 | 97.48 | 93.53 |
| 20 | 99.54 | 2.15 | 102.4 | 96.49 |
| 25 | 99.48 | 2.13 | 102.26 | 96.48 |

Figure 1B:
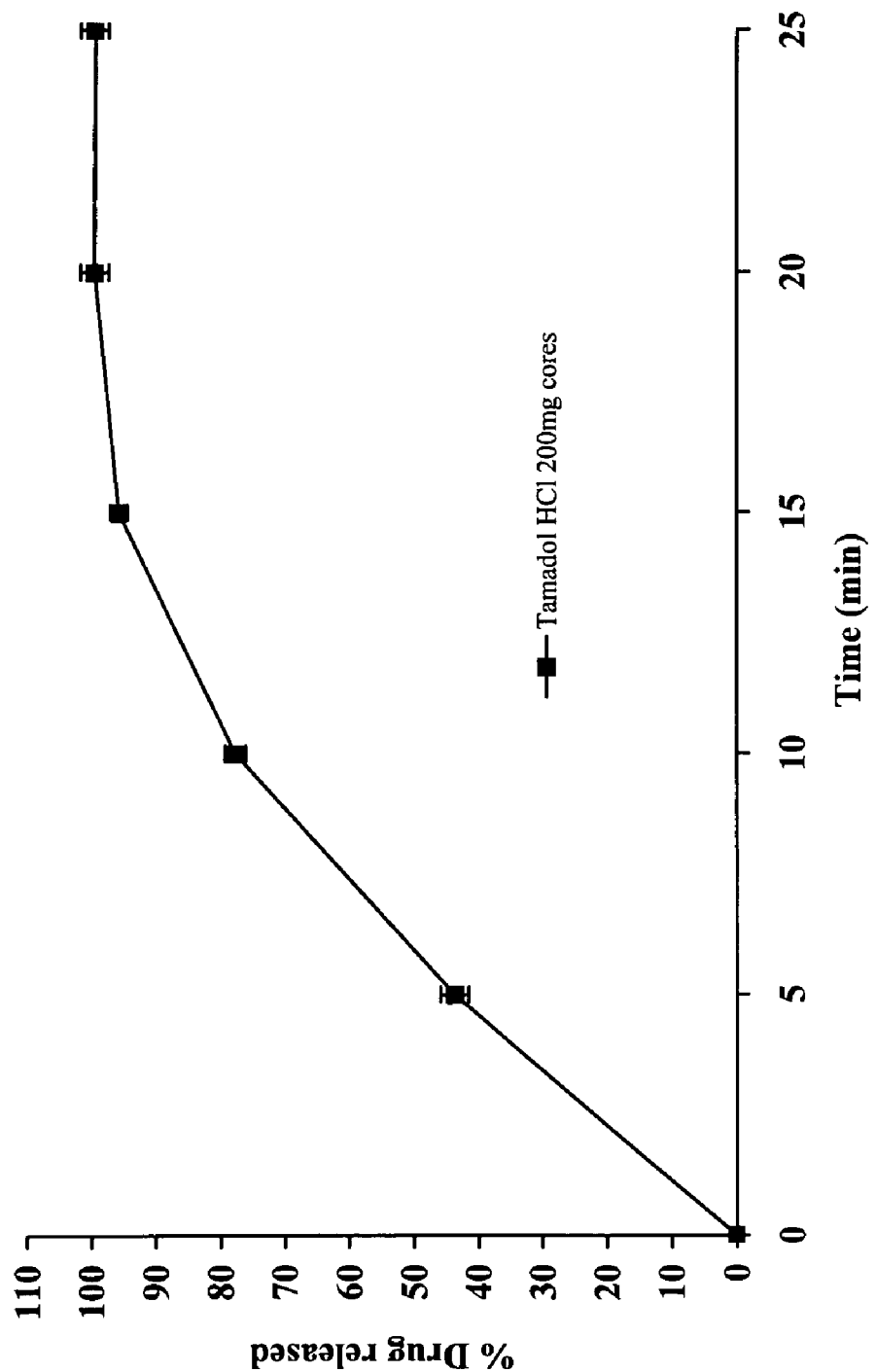
FIG. 1B illustrates the dissolution profile of 200 mg tramadol HCl uncoated cores made according to an embodiment of the invention.

The data in Table 4B is graphically presented in FIG. 1B

The coating formulation is as shown in Table 4B:

TABLE 4B (Coating Formulation for 200 mg DER tramadol HCl Tablets)

| Ingredients | Quantity (mg) |
|---|---|
| Ethylcellulose (ETHOCEL ® PR 100) | 12.28 |
| Polyvinylpyrrolidone (KOLLIDON ® K90) | 6.05 |
| Dibutyl Sebacate NF | 3.67 |
| Ethyl Alcohol 200 Proof | 154.24 * |
| Isopropyl Alcohol USP | 8.12 * |

* evaporated during process

The tablet core coating solution was prepared and applied to the tablet cores essentially according to the process described in Example 1.

In vitro dissolution studies were carried out as described in Example 1. The dissolution profile is presented below in Table 4C:

TABLE 4C (Dissolution Profile)

| Time (min.) | % Dissolved |
|---|---|
| 0 | 0 |
| 60 | 1.13 |
| 120 | 6.05 |
| 180 | 13.80 |
| 240 | 22.87 |
| 300 | 32.18 |
| 360 | 41.17 |
| 420 | 49.43 |
| 480 | 56.85 |
| 540 | 63.33 |
| 600 | 68.87 |
| 660 | 73.55 |
| 720 | 77.55 |
| 780 | 80.72 |
| 840 | 83.43 |
| 900 | 85.77 |
| 960 | 87.75 |
| 1020 | 89.20 |
| 1080 | 90.70 |
| 1140 | 91.62 |

Figure 14:
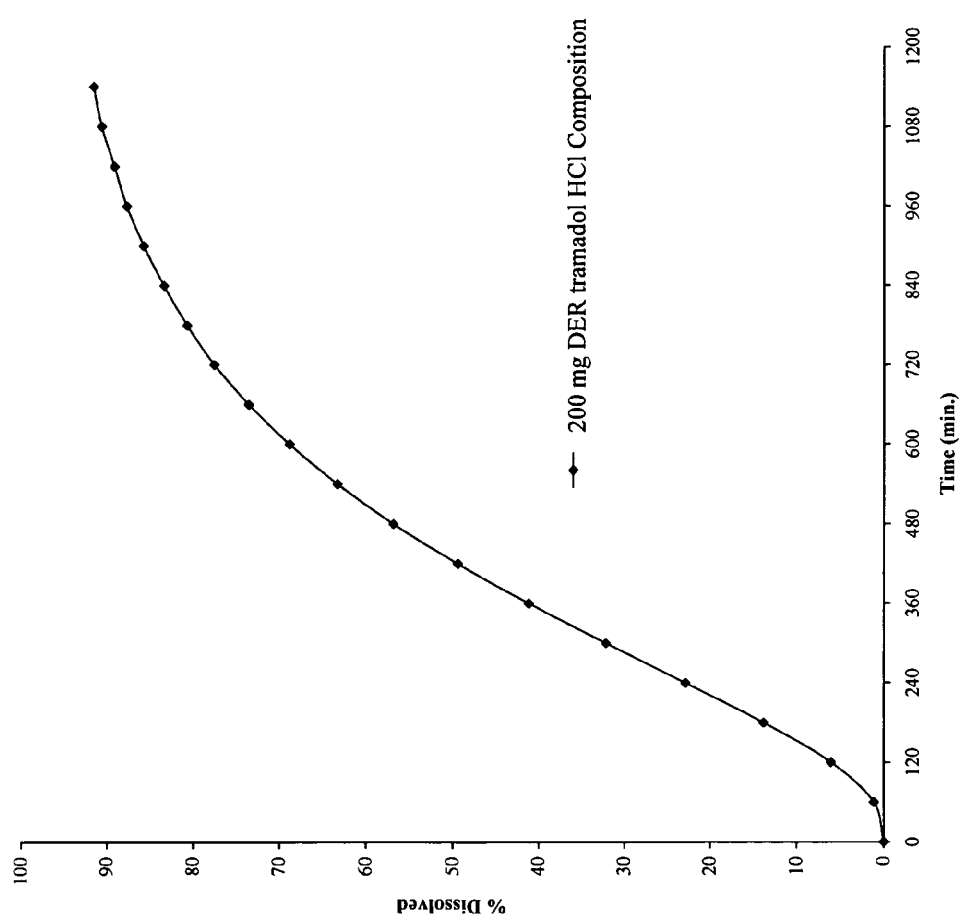
FIG. 14 is a graph illustrating the in vitro dissolution profile of a 200 mg DER tramadol HCl composition made according to an embodiment of the invention.

FIG. 14 illustrates the in vitro dissolution profile of a 200 mg DER tramadol HCl tablet of the invention.

EXAMPLE 5

200 mg DER Tramadol HCl Tablets

I. Formulation

The tablet core formulation was that of Example 4 and was prepared according to the process described in Example 1.

The coating formulation is as shown in Table 5A:

TABLE 5A (Coating Formulation)

| Ingredients | Quantity (mg) | % |
|---|---|---|
| Ethylcellulose (ETHOCEL ® PR 100) | 13.38 | 73.00 (of coating polymer) |
| Polyvinylpyrrolidone (KOLLIDON ® 90F) | 4.95 | 27.00 (of coating polymer) |
| Dibutyl Sebacate | 3.67 | 20.00 (of above polymer) |
| Total dry material: 9% of the solution | | |
| Ethyl Alcohol 200 Proof | 211.32 * | 95% (of total solvent) |
| Isopropyl Alcohol 99% | 11.12 * | 5% (of total solvent) |
| Coated Tablet | 230.00 | |

* evaporated during process

The coating process was carried out with the parameters shown in Table 2E.

EXAMPLE 6

200 mg DER Tramadol HCl Tablets

I. Formulation

The following tablet core formulation was that of Example 4 and was prepared according to the process described in Example 1.

The coating formulation is as shown in Table 6A:

TABLE 6A (Coating Formulation)

| Ingredient | Quantity (mg) |
|---|---|
| Ethylcellulose (ETHOCEL ® PR 100) | 15.60 |
| Polyvinylpyrrolidone (KOLLIDON ® 90F) | 6.07 |
| Dibutyl Sebacate | 4.33 |
| Ethyl Alcohol 200 Proof | 249.75 * |
| Isopropyl Alcohol 99% | 13.15 * |

* evaporated during process

The tablet core coating solution was prepared according to the process described in Example 1. The coating parameters tested are shown in Table 6B:

TABLE 6B (Coating Parameters)

| Parameter | Coating Parameter E | Coating Parameter F | Coating Parameter G |
|---|---|---|---|
| Inlet Temperature C. ° | 49-50 | 50-51.5 | 50-51.5 |
| Outlet Temperature C. ° | 38.5-39.5 | 39.5-40.5 | 39.5-40.5 |
| Bed Temperature C. ° | 37.5-38.5 | 37.5-39 | 37.5-39 |
| Spray Rate g/min | 300 | 300 | 300 |
| Atomizing Air/Pattern Psi | 25/25 | 25/25 | 25/25 |
| Distance gun/Bed | 6" | 6" | 6" |
| Distance between guns | 6" | 6" | 6" |
| Pan speed rpm | 12.0 | 12.0 | 12.0 |

The dissolution method was performed according to the method described in Example 1. The dissolution data is presented in Table 6C.

TABLE 6C (Dissolution Profile)

| | % Dissolved Tablet Core coated with: | | |
|---|---|---|---|
| Time (min.) | Coating Parameter E | Coating Parameter F | Coating Parameter G |
| 0 | 0 | 0 | 0 |
| 120 | 5.54 | 4.13 | 5.37 |
| 240 | 14.71 | 14.29 | 15.76 |
| 360 | 29.25 | 31.83 | 33.48 |
| 480 | 46.40 | 50.16 | 51.62 |
| 600 | N/A | 65.64 | 66.42 |
| 720 | N/A | 76.8 | 77.49 |

Figure 15:
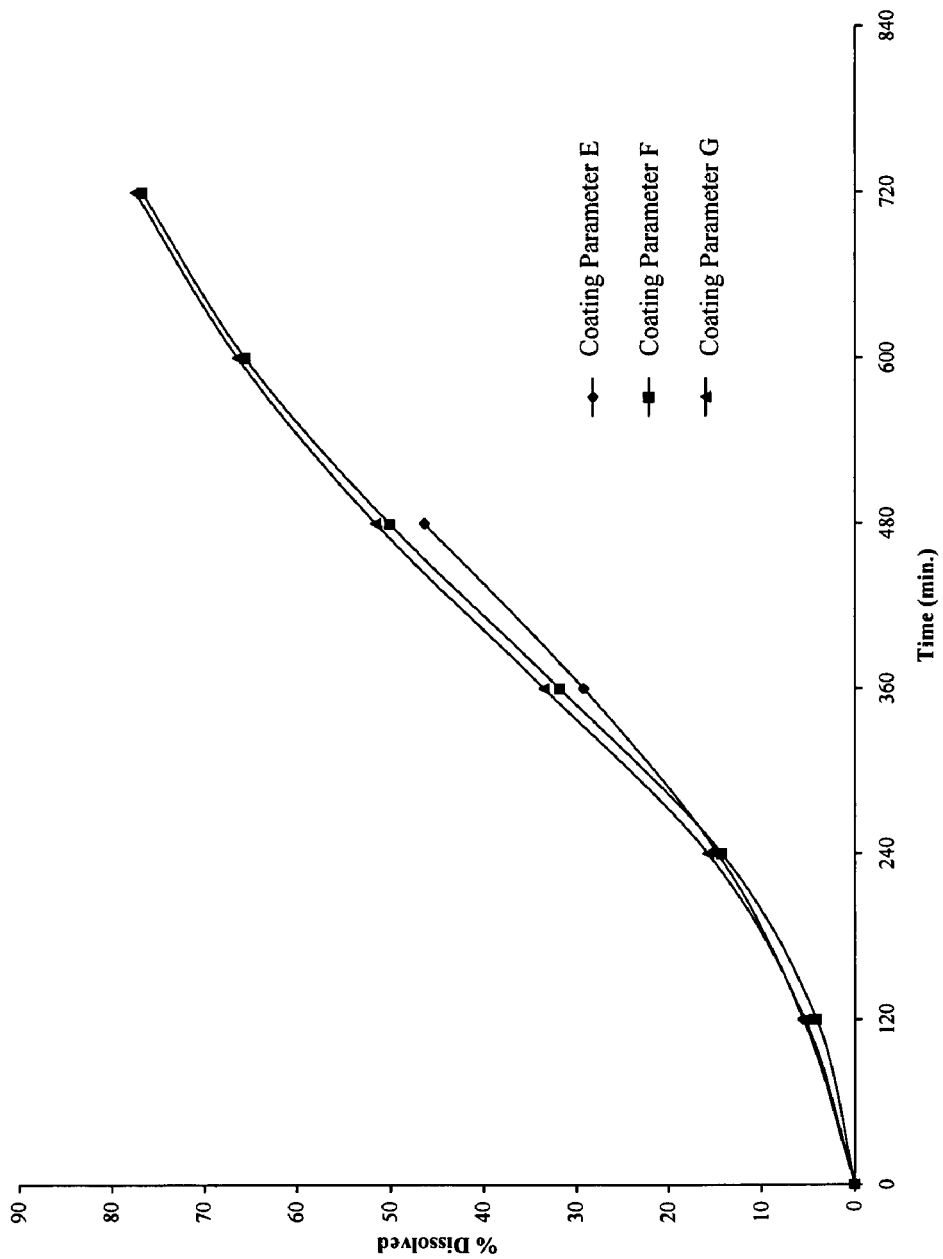
FIG. 15 is a graph illustrating the in-vitro dissolution profile over the first six hours of three 200 mg DER tramadol HCl tablets made according to an embodiment of the invention coated under different coating parameters.

FIG. 15 illustrates the in vitro dissolution profiles of 200 mg DER tramadol HCl tablets coated according to coating parameters E, F, and G.

EXAMPLE 7

300 mg Delayed and Extended Release Tramadol HCl Tablets

I. Formulation

The tablet core formulation is as shown in Table 7A:

TABLE 7A (Core Formulation)

| Ingredients | Quantity (mg) | % |
|---|---|---|
| Tramadol HCl | 300.00 | 96.15 |
| Polyvinyl Alcohol | 6.00 | 1.92 |
| Colloidal Silicon Dioxide (AEROSIL ® 200) | 3.00 | 0.96 |
| Sodium Stearyl Fumarate | 3.00 | 0.96 |
| Purified Water | 124.8* | |
| Core Total Weight | 312.0 | 99.99 |

*evaporated during process

The cores were prepared as described in Example 1.

The dissolution profile of the uncoated 100 mg tablet cores was determined under the same conditions shown in Table 1F. The results are presented in Table 7B as % release of the total tramadol in the core:

TABLE 7B (Dissolution Profile of 300 mg Uncoated Tramadol Tablet Cores)

| Time (min) | Tramadol HCl 300 mg cores (Average) | SD | Max | Min |
|---|---|---|---|---|
| 0 | 0 | 0 | 0 | 0 |
| 5 | 40.66 | 6.898628 | 47.59 | 31.25 |
| 10 | 76.085 | 8.166768 | 85.08 | 65.58 |
| 15 | 94.235 | 4.263938 | 99.05 | 88.97 |
| 20 | 99.185 | 0.658761 | 100.09 | 98.51 |
| 25 | 99.4075 | 0.582602 | 100.1 | 98.75 |
| 30 | 99.39 | 0.640781 | 100.12 | 98.65 |

Figure 1C:
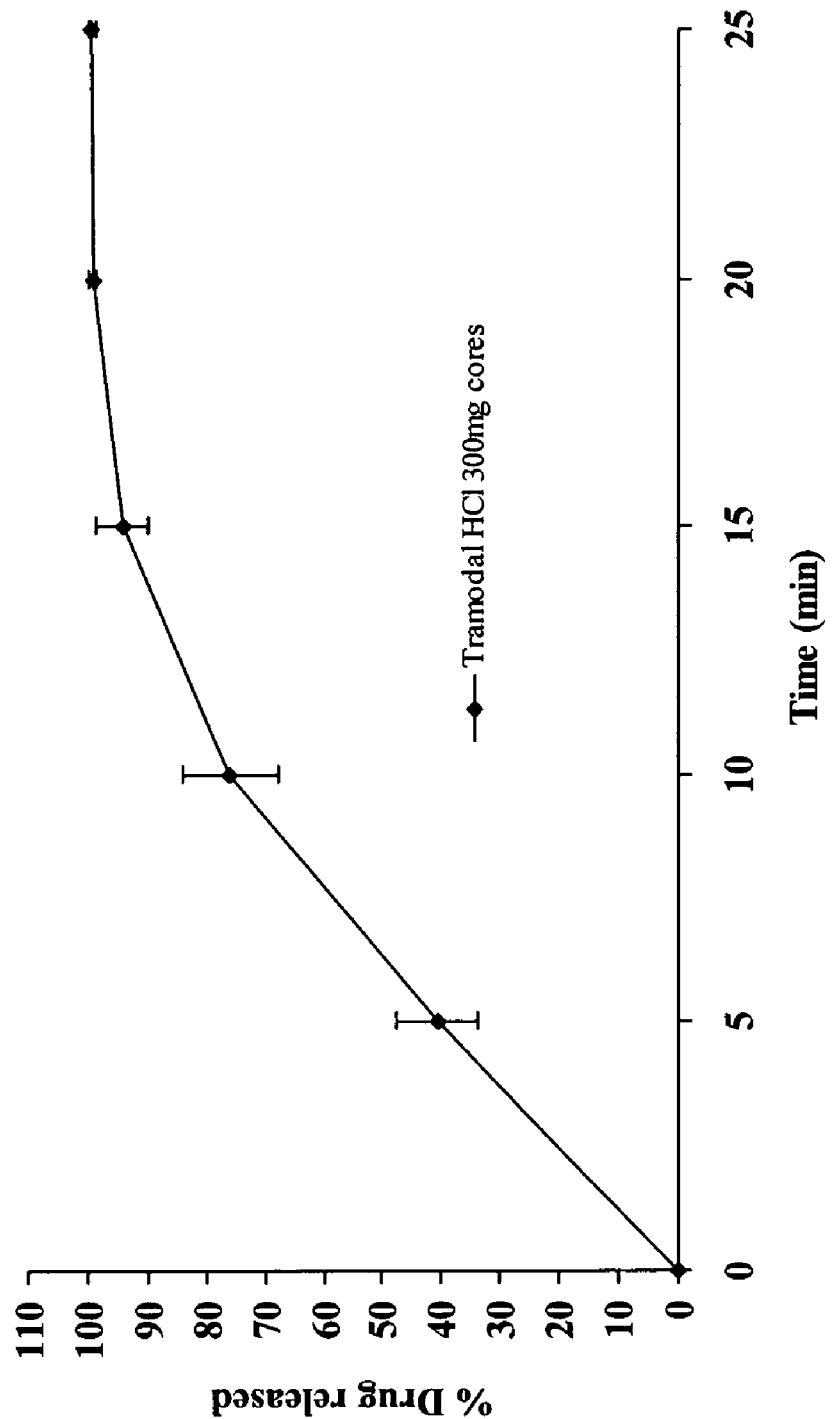
FIG. 1C illustrates the dissolution profile of 300 mg tramadol HCl uncoated cores made according to an embodiment of the invention.

The data in Table 7B is graphically presented in FIG. 1C. The coating formulation is as shown in Table 7C:

TABLE 7C (Coating Formulation)

| Ingredients | Quantity (mg) | % w/w |
|---|---|---|
| Ethylcellulose (ETHOCEL ® PR 100) | 19.23 | 5.4 |
| Polyvinylpyrrolidone (KOLLIDON ® 90F) | 7.47 | 2.1 |
| Dibutyl Sebacate | 5.33 | 1.5 |
| Total dry material: 9.0% of the solution | | |
| Ethyl Alcohol 200 Proof | 307.37* | 86.45 |
| Isopropyl Alcohol 99% | 16.18* | 4.55 |

*evaporated during process

The coating parameters used are as shown in Table 7D:

TABLE 7D (Coating Parameters)

| Parameters | |
|---|---|
| Pan speed (rpm) | 13 |
| Exhaust air temperature (° C.) | 44 ± 2 |
| Inlet air temperature (° C.) | 54 ± 2 |
| Nozzle diameter (mm) | 1 |
| Spray rate (g/min) | 250 ± 50 |
| Atomizing air pressure (psi) | 30 ± 2 |
| Pattern air pressure (psi) | 25 ± 2 |
| Air flow (CFM) | 910 ± 10 |
| Product temperature (° C.) | 40 ± 2 |

EXAMPLE 8

I. Pharmacokinetic Studies

The following two pharmacokinetic studies were conducted comparing the dosage strength proportionality of 2×100 mg vs 1×200 mg DER tramadol HCl tablets.

A. A Two-Way, Crossover, Open-Label, Single-Dose, Fasting, Comparative Bioavailability Study of DER Tramadol HCl Tablets (2×100 mg vs 1×200 mg) in Normal Healthy Non-Smoking Male Subjects was Conducted.

Based on data from 12 completing subjects, the 200 mg strength DER tramadol HCl tablets are proportional to the 100 mg strength given as 2×100 mg.

This study was designed to determine the dosage strength proportionality of two strengths of DER tramadol HCl tablets (2×100 mg vs 1×200 mg) under single dose fasting conditions.

A single-dose, open-label, two-way, two-sequence, crossover design study was conducted. The treatments were separated by a one (1) week washout period. On day 1 of each period, subjects received one of the following treatments on two (2) separate occasions according to the randomization scheme.

| | |
|---|---|
| Treatment A: | Two DER tramadol HCl 100 mg tablets of Example 3 (Coating Formulation B/Coating Parameter B) with 240 mL of water at 0.0 hour following a 10-hour overnight fast (Total Daily Dose = 200 mg) |
| Treatment B: | One DER tramadol HCl 200 mg tablet of Example 4 with 240 mL of water at 0.0 hour following a 10 hour overnight fast (Total Daily Dose = 200 mg) |

This study was intended to determine the dosage strength proportionality of two strengths of DER tramadol HCl tablets (2×100 mg vs 1×200 mg) under single dose fasting conditions. A total of 12 male subjects were dosed. Pharmacokinetic and statistical analyses were conducted with plasma data from 12 completing subjects for tramadol, and M1 metabolite. The mean plasma concentrations for tramadol and desmethyltramadol for treatments A and B are provided in Table 8AA-AB for treatment A and Table 8BA-BB for treatment B. The mean plasma concentrations vs time plots based on 12 completing subjects for tramadol, and M1 metabolite are presented in FIGS. 16 and 17, respectively. Individual pharmacokinetic parameters are shown in Tables 8A-D.

With all subjects, the ratio of geometric means (1×200 mg/2×100 mg) for tramadol $AUC_{0-t}$ and $C_{max}$ were 1.11 and 1.17, respectively. The corresponding 90% confidence intervals were 97%-125% and 103%-133%, respectively. For the M1 metabolite, the ratio of geometric means (1×200 mg/2×100 mg) for $AUC_{0-t}$ and $C_{max}$ were 1.05 and 1.11, respectively. The corresponding 90% confidence intervals were 96%-116% and 102%-121%, respectively.

In conclusion, the 200 mg strength DER tramadol HCl tablets were proportional to the 100 mg strength given as 2×100 mg since the 90% confidence intervals for $AUC_{0-t}$ and $C_{max}$ for all analytes were found to be within the 80%-125% limits.

TABLE 8AA (Mean ± SD Plasma Tramadol Concentrations for Treatment A)

|  | Hours | | | | | | | |
| --- | --- | --- | --- | --- | --- | --- | --- | --- |
|  | 0.0 | 1.0 | 2.0 | 3.0 | 4.0 | 5.0 | 6.0 | 8.0 |
| Average | 0.00 | 0.89 | 22.86 | 83.82 | 144.62 | 202.36 | 229.42 | 254.46 |
| SD | 0.00 | 1.34 | 10.19 | 28.67 | 46.77 | 39.73 | 34.59 | 50.74 |

|  | Hours | | | | | | | |
| --- | --- | --- | --- | --- | --- | --- | --- | --- |
|  | 10.0 | 12.0 | 16.0 | 20.0 | 24.0 | 30.0 | 36.0 | 48.0 |
| Average | 259.93 | 225.06 | 185.67 | 141.97 | 97.56 | 55.15 | 31.93 | 11.91 |
| SD | 65.43 | 64.91 | 71.53 | 67.89 | 47.54 | 41.26 | 29.63 | 15.43 |

TABLE 8AB (Mean ± SD Plasma Desmethyltramadol Concentrations for Treatment A)

|  | Hours | | | | | | | |
| --- | --- | --- | --- | --- | --- | --- | --- | --- |
|  | 0.0 | 1.0 | 2.0 | 3.0 | 4.0 | 5.0 | 6.0 | 8.0 |
| Average | 0.00 | 0.00 | 6.31 | 23.33 | 43.42 | 62.30 | 69.79 | 85.51 |
| SD | 0.00 | 0.00 | 3.27 | 11.64 | 21.46 | 28.49 | 30.10 | 36.45 |

|  | Hours | | | | | | | |
| --- | --- | --- | --- | --- | --- | --- | --- | --- |
|  | 10.0 | 12.0 | 16.0 | 20.0 | 24.0 | 30.0 | 36.0 | 48.0 |
| Average | 94.55 | 85.01 | 73.15 | 60.18 | 44.15 | 24.54 | 12.91 | 4.15 |
| SD | 38.25 | 32.09 | 24.98 | 20.77 | 14.25 | 8.07 | 4.33 | 1.80 |

TABLE 8BA (Mean ± SD Plasma Tramadol Concentrations for Treatment B)

|  | Hours | | | | | | | |
| --- | --- | --- | --- | --- | --- | --- | --- | --- |
|  | 0.0 | 1.0 | 2.0 | 3.0 | 4.0 | 5.0 | 6.0 | 8.0 |
| Average | 0.00 | 0.68 | 14.12 | 34.84 | 89.41 | 165.29 | 198.21 | 230.88 |
| SD | 0.00 | 1.25 | 3.16 | 8.79 | 48.73 | 79.82 | 73.38 | 79.81 |

|  | Hours | | | | | | | |
| --- | --- | --- | --- | --- | --- | --- | --- | --- |
|  | 10.0 | 12.0 | 16.0 | 20.0 | 24.0 | 30.0 | 36.0 | 48.0 |
| Average | 231.48 | 217.23 | 185.57 | 139.00 | 102.86 | 57.88 | 32.15 | 11.92 |
| SD | 93.03 | 84.60 | 77.04 | 60.32 | 47.15 | 35.76 | 25.83 | 14.93 |

TABLE 8BB (Mean ± SD Plasma Desmethyltramadol Concentrations for Treatment B)

|  | Hours | | | | | | | |
| --- | --- | --- | --- | --- | --- | --- | --- | --- |
|  | 0.0 | 1.0 | 2.0 | 3.0 | 4.0 | 5.0 | 6.0 | 8.0 |
| Average | 0.00 | 0.00 | 6.31 | 23.33 | 43.42 | 62.30 | 69.79 | 85.51 |
| SD | 0.00 | 0.00 | 3.27 | 11.64 | 21.46 | 28.49 | 30.10 | 36.45 |

|  | Hours | | | | | | | |
| --- | --- | --- | --- | --- | --- | --- | --- | --- |
|  | 10.0 | 12.0 | 16.0 | 20.0 | 24.0 | 30.0 | 36.0 | 48.0 |
| Average | 94.55 | 85.01 | 73.15 | 60.18 | 44.15 | 24.54 | 12.91 | 4.15 |
| SD | 38.25 | 32.09 | 24.98 | 20.77 | 14.25 | 8.07 | 4.33 | 1.80 |

TABLE 8A ($C_{max}$ for Plasma Tramadol)

| | 1 × 200 mg | | | 2 × 100 mg | | | 1 × 200 mg/2 × 100 mg |
|---|---|---|---|---|---|---|---|
| Subject | $T_{max}$ | $C_{max}$ | ln $C_{max}$ | $T_{max}$ | $C_{max}$ | ln $C_{max}$ | $C_{max}$ Ratio |
| 1 | 8 | 244.69 | 5.50 | 8 | 258.32 | 5.55 | 0.95 |
| 2 | 10 | 277.87 | 5.63 | 12 | 339.09 | 5.83 | 0.82 |
| 3 | 8 | 243.47 | 5.50 | 10 | 330.78 | 5.80 | 0.74 |
| 4 | 10 | 268.04 | 5.59 | 10 | 226.90 | 5.42 | 1.18 |
| 5 | 6 | 227.80 | 5.43 | 8 | 200.75 | 5.30 | 1.13 |
| 6 | 8 | 259.13 | 5.56 | 10 | 216.91 | 5.38 | 1.19 |
| 7 | 5 | 261.09 | 5.56 | 10 | 155.44 | 5.05 | 1.68 |
| 8 | 8 | 226.11 | 5.42 | 8 | 98.86 | 4.59 | 2.29 |
| 9 | 8 | 278.90 | 5.63 | 10 | 232.96 | 5.45 | 1.20 |
| 10 | 10 | 195.36 | 5.27 | 8 | 148.30 | 5.00 | 1.32 |
| 11 | 8 | 353.25 | 5.87 | 8 | 330.44 | 5.80 | 1.07 |
| 12 | 10 | 435.46 | 6.08 | 10 | 404.39 | 6.00 | 1.08 |
| Mean | 8.25 | 272.60 | 5.59 | 9.33 | 245.26 | 5.43 | 1.22 |
| SD | 1.60 | 64.10 | 0.21 | 1.30 | 90.97 | 0.41 | 0.41 |
| CV | 19.42 | 23.51 | 3.77 | 13.96 | 37.09 | 7.50 | 33.90 |
| Min | 5.00 | 195.36 | 5.27 | 8.00 | 98.86 | 4.59 | 0.74 |
| Max | 10.00 | 435.46 | 6.08 | 12.00 | 404.39 | 6.00 | 2.29 |
| Geo Mean | 8.09 | 266.71 | 5.58 | 9.25 | 228.55 | 5.42 | 1.17 |

$C_{max}$ Ratio

| | Mean | Geo Mean | 90% C.I. | 90% C.I. (Excluding Subject 8) |
|---|---|---|---|---|
| 200 mg/2 × 100 mg | 1.11 | 1.17 (SAS) | 103-133 | 100-123 |

TABLE 8B ($AUC_T$ FOR PLASMA TRAMADOL)

| | 200 mg | | 2 × 100 mg | | 200 mg/2 × 100 mg |
|---|---|---|---|---|---|
| Subject | $AUC_t$ | ln $AUC_t$ | $AUC_t$ | ln $AUC_t$ | $AUC_t$ Ratio |
| 1 | 4604.23 | 8.43 | 4446.02 | 8.40 | 1.04 |
| 2 | 6485.28 | 8.78 | 6343.27 | 8.76 | 1.02 |
| 3 | 5324.71 | 8.58 | 6067.74 | 8.71 | 0.88 |
| 4 | 6975.11 | 8.85 | 6292.41 | 8.75 | 1.11 |
| 5 | 4284.83 | 8.36 | 4045.08 | 8.31 | 1.06 |
| 6 | 3919.08 | 8.27 | 3944.65 | 8.28 | 0.99 |
| 7 | 4096.54 | 8.32 | 3521.10 | 8.17 | 1.16 |
| 8 | 3279.62 | 8.10 | 1382.53 | 7.23 | 2.37 |
| 9 | 4260.44 | 8.36 | 4423.57 | 8.39 | 0.96 |
| 10 | 2923.70 | 7.98 | 2714.23 | 7.91 | 1.08 |
| 11 | 4911.47 | 8.50 | 4882.50 | 8.49 | 1.01 |
| 12 | 8824.82 | 9.09 | 8323.14 | 9.03 | 1.06 |
| Mean | 4990.82 | 8.47 | 4698.85 | 8.37 | 1.14 |
| SD | 1687.36 | 0.32 | 1852.43 | 0.47 | 0.39 |
| CV | 33.81 | 3.73 | 39.42 | 5.60 | 34.34 |
| Min | 2923.70 | 7.98 | 1382.53 | 7.23 | 0.88 |
| Max | 8824.82 | 9.09 | 8323.14 | 9.03 | 2.37 |
| Geo Mean | 4759.37 | 8.46 | 4307.55 | 8.36 | 1.10 |

AUCt Ratio

| | Mean | Geo Mean | 90% C.I. | 90% C.I. (Excluding Subject 8) |
|---|---|---|---|---|
| 200 mg/2 × 100 mg | 1.06 | 1.11 (SAS) | 97-125 | 99-107 |

Figure 16:
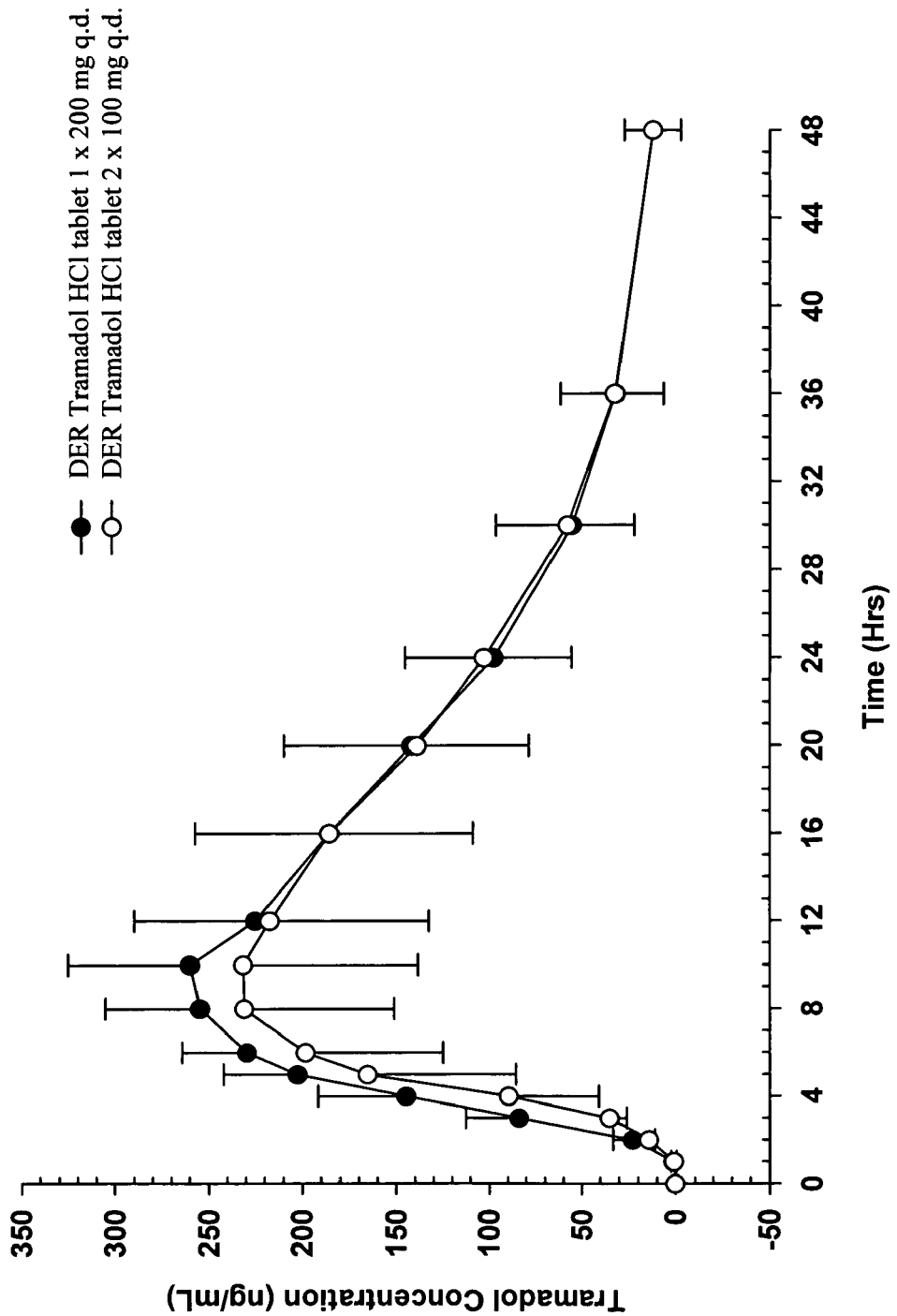
FIG. 16 is a graph illustrating the comparison of the mean tramadol plasma concentration-time profiles resulting from the single dose administration of the 100 mg tramadol HCl DER tablets (2×100 mg once a day) and 200 mg tramadol HCl DER tablets (1×200 mg once a day) formulated according to an embodiment of the present invention.

FIG. 16 illustrates the comparison of the mean tramadol plasma concentration-time profiles resulting from the oral administration of the DER tramadol HCl 100 mg tablets (2×100 mg once a day) and the DER tramadol HCl 200 mg tablets (1×200 mg once a day) formulated according to an embodiment of the present invention.

TABLE 8C ($C_{MAX}$ FOR DESMETHYLTRAMADOL)

| | 200 mg | | | 2 × 100 mg | | | 200 mg/2 × 100 mg |
|---|---|---|---|---|---|---|---|
| Subject | $T_{max}$ | $C_{max}$ | ln $C_{max}$ | $T_{max}$ | $C_{max}$ | ln $C_{max}$ | $C_{max}$ Ratio |
| 1 | 10 | 104.54 | 4.65 | 12 | 110.02 | 4.70 | 0.95 |
| 2 | 10 | 98.85 | 4.59 | 12 | 105.22 | 4.66 | 0.94 |
| 3 | 10 | 96.35 | 4.57 | 10 | 97.49 | 4.58 | 0.99 |
| 4 | 20 | 23.51 | 3.16 | 16 | 25.50 | 3.24 | 0.92 |
| 5 | 12 | 75.83 | 4.33 | 20 | 66.86 | 4.20 | 1.13 |
| 6 | 10 | 142.03 | 4.96 | 10 | 118.45 | 4.77 | 1.20 |
| 7 | 10 | 110.74 | 4.71 | 10 | 84.57 | 4.44 | 1.31 |
| 8 | 10 | 102.54 | 4.63 | 8 | 58.72 | 4.07 | 1.75 |
| 9 | 8 | 127.10 | 4.84 | 10 | 135.05 | 4.91 | 0.94 |
| 10 | 10 | 93.51 | 4.54 | 10 | 90.31 | 4.50 | 1.04 |
| 11 | 10 | 139.85 | 4.94 | 10 | 107.20 | 4.67 | 1.30 |
| 12 | 16 | 30.01 | 3.40 | 16 | 27.27 | 3.31 | 1.10 |
| Mean | 11.33 | 95.40 | 4.44 | 12.00 | 85.56 | 4.34 | 1.13 |
| SD | 3.34 | 37.38 | 0.57 | 3.52 | 34.68 | 0.55 | 0.24 |

TABLE 8C-continued ($C_{MAX}$ FOR DESMETHYLTRAMADOL)

| CV | 29.47 | 39.18 | 12.91 | 29.30 | 40.53 | 12.66 | 21.07 |
|---|---|---|---|---|---|---|---|
| Min | 8.00 | 23.51 | 3.16 | 8.00 | 25.50 | 3.24 | 0.92 |
| Max | 20.00 | 142.03 | 4.96 | 20.00 | 135.05 | 4.91 | 1.75 |
| Geo Mean | 10.98 | 85.03 | 4.40 | 11.59 | 76.53 | 4.30 | 1.11 |

$C_{max}$ Ratio

| | Mean | Geo Mean | 90% C.I. | 90% C.I. (Excluding Subject 8) |
|---|---|---|---|---|
| 200 mg/2 × 100 mg | 1.12 | 1.11 | 102-121 | 100-115 |

TABLE 8D ($AUC_T$ FOR PLASMA DESMETHYLTRAMADOL)

| | 200 mg | | 2 × 100 mg | | 200 mg/2 × 100 mg |
|---|---|---|---|---|---|
| Subject | AUCt | ln AUCt | AUCt | ln AUCt | AUCt Ratio |
| 1 | 2386.29 | 7.78 | 2404.81 | 7.79 | 0.99 |
| 2 | 2367.19 | 7.77 | 2244.63 | 7.72 | 1.05 |
| 3 | 2150.65 | 7.67 | 2139.59 | 7.67 | 1.01 |
| 4 | 718.62 | 6.58 | 750.69 | 6.62 | 0.96 |
| 5 | 1862.16 | 7.53 | 1773.47 | 7.48 | 1.05 |
| 6 | 2474.58 | 7.81 | 2359.88 | 7.77 | 1.0 |
| 7 | 2079.14 | 7.64 | 2137.31 | 7.67 | 0.97 |
| 8 | 1717.15 | 7.45 | 958.31 | 6.87 | 1.79 |
| 9 | 2262.49 | 7.72 | 2661.79 | 7.89 | 0.85 |
| 10 | 1657.30 | 7.41 | 1800.10 | 7.50 | 0.92 |
| 11 | 2373.89 | 7.77 | 2072.75 | 7.64 | 1.15 |
| 12 | 722.24 | 6.58 | 666.77 | 6.50 | 1.08 |
| Mean | 1897.64 | 7.48 | 1830.84 | 7.42 | 1.07 |
| SD | 611.42 | 0.44 | 674.61 | 0.48 | 0.24 |
| CV | 32.22 | 5.87 | 36.85 | 6.45 | 22.33 |
| Min | 718.62 | 6.58 | 666.77 | 6.50 | 0.85 |
| Max | 2474.58 | 7.81 | 2661.79 | 7.89 | 1.79 |
| Geo Mean | 1766.50 | 7.46 | 1676.26 | 7.41 | 1.05 |

AUCt Ratio

| | Mean | Geo Mean | 90% C.I. | 90% C.I. (Excluding Subject 8) |
|---|---|---|---|---|
| 200 mg/2 × 100 mg | 1.04 | 1.05 | 96-116 | 96-105 |

Figure 17:
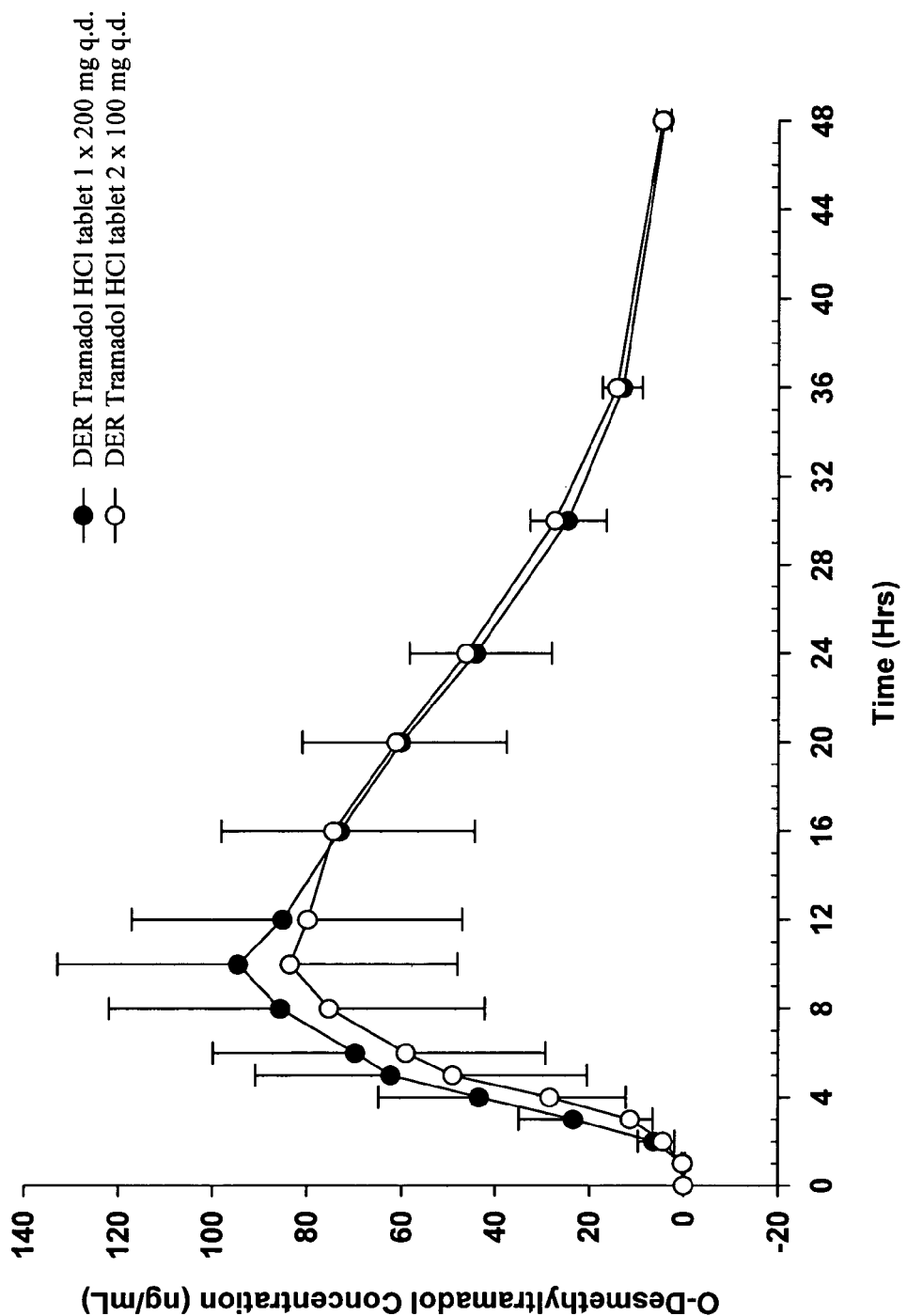
FIG. 17 is a graph illustrating the comparison of the mean desmethyltramadol (M1) plasma concentration-time profiles resulting from the single dose administration of the tablets of FIG. 16.

FIG. 17 illustrates the comparison of the mean M1 plasma concentration-time profiles resulting from the oral administration of the DER tramadol HCl 100 mg tablets (2×100 mg once a day) and the DER tramadol HCl 200 mg tablets (1×200 mg once a day) formulated according to an embodiment of the present invention.

B. A Two-Way, Crossover, Open-Label, Single-Dose, Fasting, Comparative Bioavailability Study of DER Tramadol HCl Tablets (2×100 mg vs 1×200 mg) in Normal Healthy Non-Smoking Male Subjects.

Based on data from 23 completing subjects, the 200 mg strength tramadol HCl ER Tablets are proportional to the 100 mg strength given as 2×100 mg.

This study was designed to determine the dosage strength proportionality of two strengths of DER tramadol HCl tablets (2×100 mg (Tablets of Example 3 (Coating Formulation C/Coating Parameter C)) vs 1×200 mg (Tablet of Example 6 (Coating Parameter F)) under single dose fasting conditions.

A single-dose, open-label, two-way, two-sequence, crossover design study was conducted. The treatments were separated by a one (1) week washout period. On day 1 of each period, subjects received one of the following treatments on two (2) separate occasions according to the randomization scheme.

Treatment A: Two DER tramadol HCl 100 mg tablets of Example 3 (Coating Formulation C/Coating Parameter C) with 240 mL of water at 0.0 hour following a 10-hour overnight fast (Total Daily Dose = 200 mg)

Treatment B: One DER tramadol HCl 200 mg tablet of Example 6 (Coating Parameter F) with 240 mL of water at 0.0 hour following a 10 hour overnight fast (Total Daily Dose = 200 mg)

This study was intended to determine the dosage strength proportionality of two strengths of DER tramadol HCl tablets (2×100 mg vs 1×200 mg) under single dose fasting conditions. A total of 24 male subjects were dosed. Pharmacokinetic and statistical analyses were conducted with plasma data from 23 completing subjects for tramadol, M1 and M5 metabolites. The mean plasma concentrations for tramadol, desmethyltramadol, and didesmethyltramadol for treatments A and B are provided in Table 8EA-EC for treatment A and Table 8FA-FC for treatment B. The mean plasma concentrations vs time plots based on 23 completing subjects for tramadol, M1 and M5 metabolites are presented in FIGS. 18, 19 and 20, respectively. Individual pharmacokinetic parameters are shown in Tables 8E, 8F and 8G.

With all subjects, the ratio of geometric means (1×200 mg/2×100 mg) for tramadol $AUC_{0-t}$ and $C_{max}$ were 1.00 and 1.00, respectively. The corresponding 90% confidence intervals were 96.3%-104.17% and 92.2%-109.12%, respectively. For the M1 metabolite, the ratio of geometric means (1×200 mg/2×100 mg) for $AUC_{0-t}$ and $C_{max}$ were 1.00 and 0.97, respectively. The corresponding 90% confidence intervals were 95.6%-104.61% and 90.3%-104.39%, respectively. For the M5 metabolite, the ratio of geometric means (1×200 mg/2×100 mg) for $AUC_{0-t}$ and $C_{max}$ were 0.98 and 0.99, respectively. The corresponding 90% confidence intervals were 92.6%-104.72% and 90.9%-107.25%, respectively.

In conclusion, the 200 mg strength DER tramadol HCl tablets were proportional to the 100 mg strength DER tramadol HCl tablets given as 2×100 mg since the 90% confidence intervals for $AUC_{0-t}$ and $C_{max}$ for all analytes were found to be within 80%-125%.

TABLE 8EA (Mean ± SD Plasma Tramadol Concentrations for Treatment A)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.00 | 6.60 | 20.70 | 40.39 | 88.42 | 122.59 | 175.88 |
| SD | 0.00 | 0.00 | 3.38 | 8.44 | 18.19 | 55.38 | 61.83 | 83.32 |

| | Hours | | | | | | | |
|---|---|---|---|---|---|---|---|---|
| | 10.0 | 12.0 | 14.0 | 16.0 | 20.0 | 24.0 | 30.0 | 36.0 | 48.0 |
| Average | 211.01 | 230.72 | 242.46 | 228.62 | 193.44 | 150.49 | 93.07 | 55.00 | 19.27 |
| SD | 89.60 | 102.26 | 105.74 | 97.24 | 85.39 | 77.48 | 55.77 | 36.33 | 16.10 |

TABLE 8EB (Mean ± SD Plasma Desmethyltramadol Concentrations for Treatment A)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.00 | 1.52 | 5.36 | 10.91 | 21.04 | 29.91 | 48.48 |
| SD | 0.00 | 0.00 | 0.95 | 2.85 | 5.08 | 13.61 | 19.10 | 27.81 |

| | Hours | | | | | | | |
|---|---|---|---|---|---|---|---|---|
| | 10.0 | 12.0 | 14.0 | 16.0 | 20.0 | 24.0 | 30.0 | 36.0 | 48.0 |
| Average | 62.85 | 70.66 | 78.43 | 79.72 | 75.33 | 61.07 | 39.42 | 23.75 | 8.80 |
| SD | 26.61 | 25.92 | 25.26 | 25.52 | 26.01 | 22.24 | 16.83 | 13.22 | 6.86 |

TABLE 8EC (Mean ± SD Plasma Didestmethyltramadol Concentrations for Treatment A)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.00 | 0.00 | 1.59 | 3.51 | 6.53 | 10.08 | 17.21 |
| SD | 0.00 | 0.00 | 0.00 | 1.19 | 1.56 | 3.65 | 6.33 | 9.64 |

| | Hours | | | | | | | |
|---|---|---|---|---|---|---|---|---|
| | 10.0 | 12.0 | 14.0 | 16.0 | 20.0 | 24.0 | 30.0 | 36.0 | 48.0 |
| Average | 24.57 | 28.16 | 31.12 | 33.55 | 31.87 | 27.40 | 19.89 | 13.24 | 5.60 |
| SD | 12.01 | 12.03 | 12.83 | 12.75 | 11.56 | 10.30 | 7.68 | 6.42 | 3.57 |

TABLE 8FA (Mean ± SD Plasma Tramadol Concentrations for Treatment B)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.00 | 7.64 | 22.36 | 45.61 | 104.38 | 133.59 | 183.29 |
| SD | 0.00 | 0.00 | 5.19 | 10.45 | 26.84 | 63.54 | 82.61 | 109.48 |

| | Hours | | | | | | | |
|---|---|---|---|---|---|---|---|---|
| | 10.0 | 12.0 | 14.0 | 16.0 | 20.0 | 24.0 | 30.0 | 36.0 | 48.0 |
| Average | 211.85 | 231.00 | 247.59 | 239.83 | 199.78 | 156.93 | 93.18 | 52.85 | 18.06 |
| SD | 115.62 | 112.36 | 119.50 | 119.72 | 105.16 | 86.47 | 55.86 | 35.92 | 14.31 |

TABLE 8FB (Mean ± SD Plasma Desmethyltramadol Concentrations for Treatment B)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.00 | 1.52 | 5.73 | 12.25 | 24.22 | 33.83 | 49.90 |
| SD | 0.00 | 0.00 | 1.36 | 2.92 | 7.14 | 14.86 | 21.54 | 29.71 |

| | Hours | | | | | | | |
|---|---|---|---|---|---|---|---|---|
| | 10.0 | 12.0 | 14.0 | 16.0 | 20.0 | 24.0 | 30.0 | 36.0 | 48.0 |
| Average | 63.21 | 72.33 | 79.44 | 80.68 | 73.50 | 62.24 | 39.72 | 21.95 | 8.14 |
| SD | 33.26 | 33.35 | 30.29 | 30.12 | 21.73 | 18.38 | 13.58 | 9.25 | 4.26 |

TABLE 8FC (Mean ± SD Plasma Didesmethyltramadol Concentrations for Treatment B)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.06 | 0.26 | 1.64 | 3.93 | 7.54 | 11.33 | 17.97 |
| SD | 0.00 | 0.26 | 0.52 | 1.26 | 2.27 | 4.58 | 7.53 | 12.33 |

| | Hours | | | | | | | |
|---|---|---|---|---|---|---|---|---|
| | 10.0 | 12.0 | 14.0 | 16.0 | 20.0 | 24.0 | 30.0 | 36.0 | 48.0 |
| Average | 24.98 | 28.33 | 31.10 | 32.10 | 31.38 | 28.04 | 20.34 | 12.41 | 5.41 |
| SD | 16.90 | 16.69 | 14.75 | 14.44 | 12.03 | 10.16 | 7.74 | 5.51 | 3.03 |

TABLE 8E (Summary of Plasma Pharmacokinetic Parameters for Tramadol)

| | B DER Tramadol HCl 1 × 200 mg | | | A DER tramadol HCl 2 × 100 mg | | | B/A Ratio | |
|---|---|---|---|---|---|---|---|---|
| Subject | AUC | $C_{max}$ | $T_{max}$ | AUC | $C_{max}$ | $T_{max}$ | AUC | $C_{max}$ |
| 1 | 3772.72 | 125.97 | 24.00 | 4465.15 | 207.76 | 8.00 | 0.84 | 0.61 |
| 2 | 6989.42 | 361.35 | 14.00 | 7563.59 | 416.83 | 12.00 | 0.92 | 0.87 |
| 3 | 9967.41 | 440.03 | 14.00 | 8773.22 | 374.54 | 16.00 | 1.14 | 1.17 |
| 4 | 10503.26 | 528.11 | 16.00 | 10727.13 | 517.12 | 14.00 | 0.98 | 1.02 |
| 5 | 4315.08 | 244.26 | 12.00 | 4439.38 | 209.95 | 16.00 | 0.97 | 1.16 |
| 7 | 3539.99 | 151.93 | 16.00 | 4128.98 | 234.12 | 8.00 | 0.86 | 0.65 |
| 8 | 7752.67 | 368.21 | 14.00 | 6369.64 | 369.49 | 8.00 | 1.22 | 1.00 |
| 9 | 5413.87 | 281.50 | 14.00 | 5561.14 | 244.18 | 16.00 | 0.97 | 1.15 |
| 10 | 3640.04 | 162.12 | 12.00 | 4354.42 | 179.31 | 14.00 | 0.84 | 0.90 |
| 11 | 3442.46 | 147.72 | 20.00 | 3394.52 | 162.28 | 16.00 | 1.01 | 0.91 |
| 12 | 2763.51 | 190.15 | 10.00 | 2722.78 | 150.02 | 10.00 | 1.01 | 1.27 |
| 13 | 3746.10 | 203.07 | 8.00 | 4084.60 | 183.27 | 16.00 | 0.92 | 1.11 |
| 14 | 6394.67 | 311.42 | 16.00 | 5107.43 | 239.83 | 8.00 | 1.25 | 1.30 |
| 15 | 3093.78 | 178.86 | 12.00 | 2806.92 | 128.49 | 16.00 | 1.10 | 1.39 |
| 16 | 8363.96 | 465.15 | 10.00 | 7811.02 | 369.66 | 14.00 | 1.07 | 1.26 |
| 17 | 2410.07 | 130.62 | 14.00 | 2647.52 | 135.74 | 14.00 | 0.91 | 0.96 |
| 18 | 9336.37 | 469.34 | 8.00 | 9475.49 | 409.69 | 16.00 | 0.99 | 1.15 |
| 19 | 9125.11 | 437.92 | 14.00 | 8440.88 | 322.16 | 14.00 | 1.08 | 1.36 |
| 20 | 4983.63 | 209.73 | 10.00 | 4444.82 | 226.82 | 12.00 | 1.12 | 0.92 |
| 21 | 3337.64 | 151.75 | 12.00 | 3818.74 | 220.36 | 12.00 | 0.87 | 0.69 |
| 22 | 2868.24 | 164.88 | 16.00 | 2595.66 | 163.49 | 8.00 | 1.11 | 1.01 |
| 23 | 4233.82 | 179.29 | 16.00 | 4310.37 | 238.80 | 16.00 | 0.98 | 0.75 |
| 24 | 7311.78 | 329.98 | 20.00 | 7105.46 | 307.21 | 20.00 | 1.03 | 1.07 |
| Mean | 5535.03 | 271.02 | 14.00 | 5441.25 | 261.35 | 13.22 | 1.01 | 1.03 |
| SD | 2591.09 | 128.34 | 3.86 | 2376.20 | 104.90 | 3.45 | 0.11 | 0.22 |
| CV | 46.81 | 47.36 | 27.58 | 43.67 | 40.14 | 26.10 | 11.32 | 21.60 |
| Geo Mean | 4992.59 | 244.00 | 13.51 | 4979.67 | 242.83 | 12.74 | 1.00 | 1.00 |

TABLE 8E-continued (Summary of Plasma Pharmacokinetic Parameters for Tramadol)

| Min | 2410.07 | 125.97 | 8.00 | 2595.66 | 128.49 | 8.00 | 0.84 | 0.61 |
|---|---|---|---|---|---|---|---|---|
| Max | 10503.26 | 528.11 | 24.00 | 10727.13 | 517.12 | 20.00 | 1.25 | 1.39 |

1 × 200 mg/2 × 100 mg Ratio

|  | Means | Geo Means | LS Means % | 90% CI |
|---|---|---|---|---|
| AUC | 1.02 | 1.00 | 100.11 | 96.3-104.17 |
| $C_{max}$ | 1.04 | 1.00 | 100.29 | 92.2-109.12 |

Figure 18:
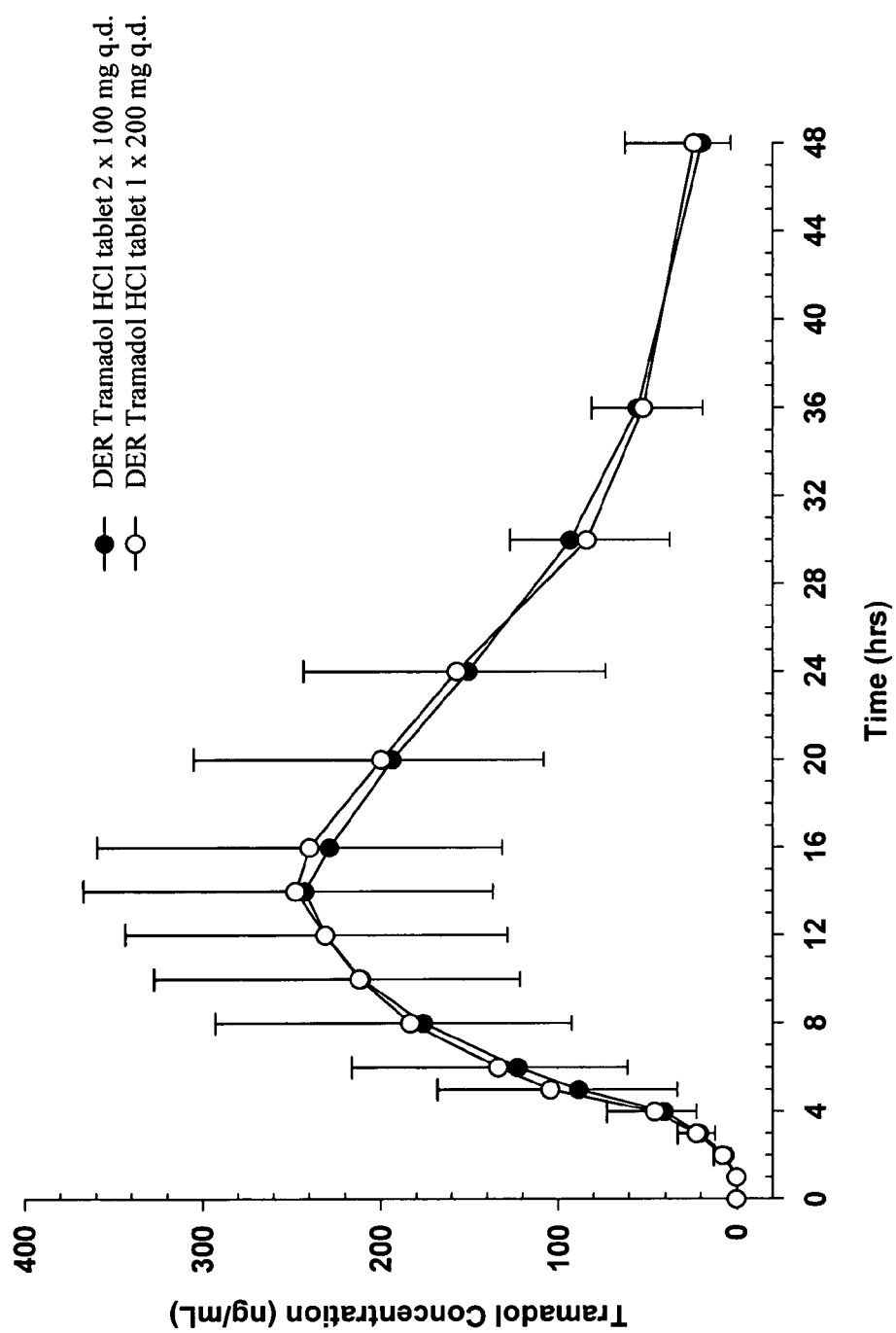
FIG. 18 is a graph illustrating the mean plasma tramadol concentrations over time after two single dose 100 mg tramadol HCl DER tablets formulated according to an embodiment of the present invention or after one single dose 200 mg tramadol HCl DER tablet formulated according to an embodiment of the present invention following a 10 hour overnight fast.

FIG. 18 illustrates the mean plasma tramadol concentrations (ng/ml) over time after two 100 mg DER tramadol HCl tablets formulated according to an embodiment of the present invention or after one 200 mg DER tramadol HCl tablet formulated according to an embodiment of the present invention following a 10 hour overnight fast.

Figure 19:
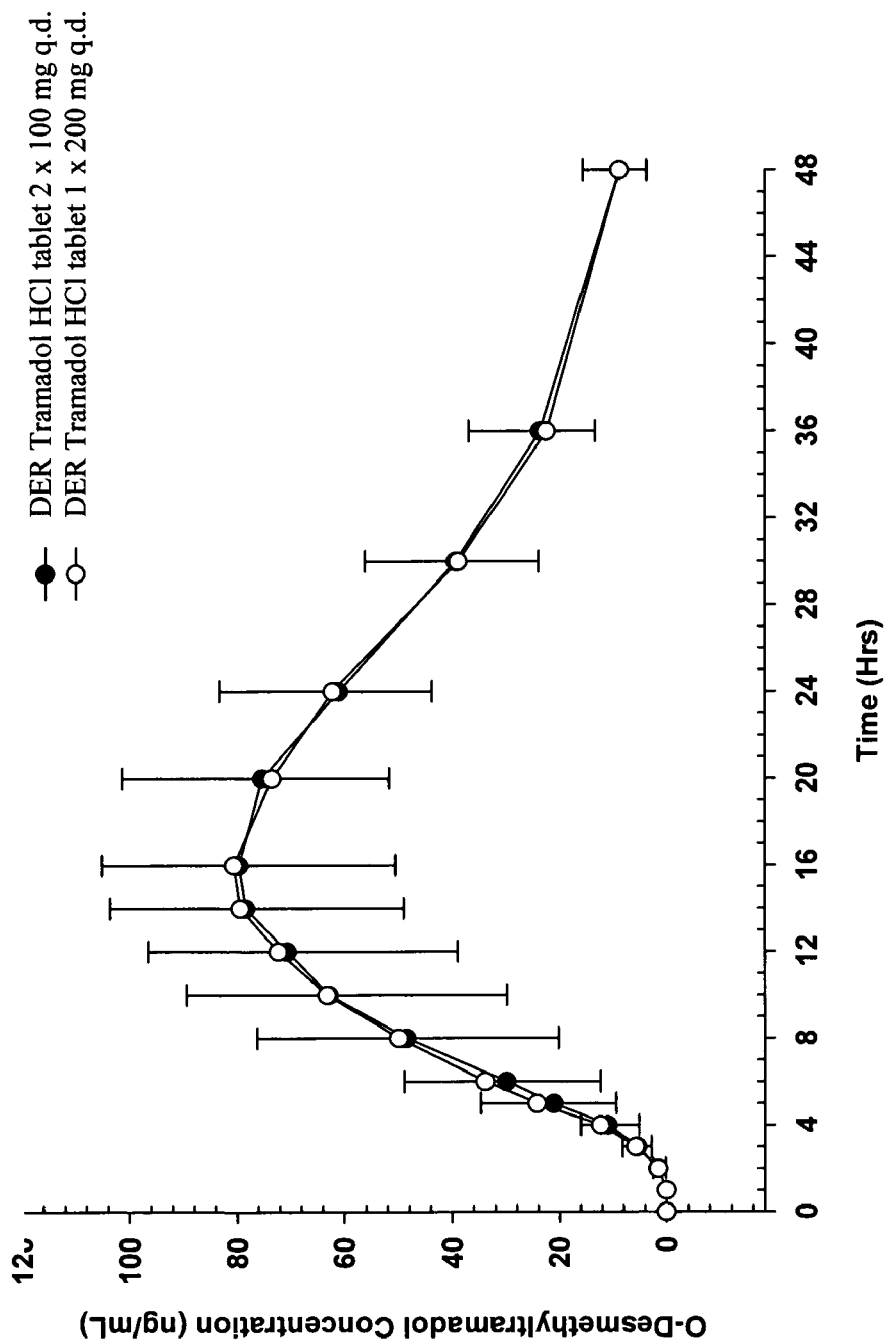
FIG. 19 is a graph illustrating the mean plasma desmethyltramadol (M1) concentrations over time following administration of the tablets of FIG. 18 following a 10-hour overnight fast.

FIG. 19 illustrates the mean plasma M1 concentrations (ng/ml) over time after two 100 mg DER tramadol HCl tablets formulated according to an embodiment of the present invention or after one 200 mg DER tramadol HCl tablet formulated according to an embodiment of the present invention following a 10 hour overnight fast.

TABLE 8F (Summary of Plasma Pharmacokinetic Parameters for Desmethyltramadol (M1))

| | B DER tramadol HCl 1 × 200 mg | | | A DER tramadol HCl 2 × 100 mg | | | B/A Ratio | |
|---|---|---|---|---|---|---|---|---|
| Subject | AUC | $C_{max}$ | $T_{max}$ | AUC | $C_{max}$ | $T_{max}$ | AUC | $C_{max}$ |
| 1 | 1672.89 | 57.88 | 24.00 | 2022.04 | 80.50 | 16.00 | 0.83 | 0.72 |
| 2 | 970.95 | 43.44 | 14.00 | 1156.80 | 54.21 | 12.00 | 0.84 | 0.80 |
| 3 | 1774.74 | 69.27 | 20.00 | 1789.62 | 70.05 | 20.00 | 0.99 | 0.99 |
| 4 | 1076.19 | 48.16 | 16.00 | 1050.38 | 44.32 | 16.00 | 1.02 | 1.09 |
| 5 | 1979.48 | 96.47 | 14.00 | 1657.77 | 72.52 | 14.00 | 1.19 | 1.33 |
| 7 | 953.92 | 36.57 | 24.00 | 1330.47 | 68.82 | 8.00 | 0.72 | 0.53 |
| 8 | 1414.94 | 61.68 | 24.00 | 1116.16 | 53.67 | 12.00 | 1.27 | 1.15 |
| 9 | 2484.11 | 113.99 | 14.00 | 2406.74 | 108.07 | 20.00 | 1.03 | 1.05 |
| 10 | 1721.50 | 73.76 | 14.00 | 1906.22 | 74.23 | 16.00 | 0.90 | 0.99 |
| 11 | 1829.82 | 80.76 | 24.00 | 1850.88 | 88.60 | 16.00 | 0.99 | 0.91 |
| 12 | 2144.82 | 109.30 | 10.00 | 2095.44 | 101.89 | 14.00 | 1.02 | 1.07 |
| 13 | 2111.31 | 90.98 | 10.00 | 2036.17 | 89.08 | 20.00 | 1.04 | 1.02 |
| 14 | 2130.45 | 93.13 | 16.00 | 2122.92 | 91.06 | 16.00 | 1.00 | 1.02 |
| 15 | 2360.46 | 115.08 | 12.00 | 2128.12 | 97.80 | 16.00 | 1.11 | 1.18 |
| 16 | 3234.30 | 130.32 | 12.00 | 3507.19 | 134.18 | 20.00 | 0.92 | 0.97 |
| 17 | 1922.21 | 90.47 | 16.00 | 1977.41 | 91.02 | 14.00 | 0.97 | 0.99 |
| 18 | 3490.68 | 135.80 | 12.00 | 3521.34 | 138.38 | 16.00 | 0.99 | 0.98 |
| 19 | 1154.33 | 49.30 | 16.00 | 991.16 | 38.21 | 20.00 | 1.16 | 1.29 |
| 20 | 2303.91 | 96.21 | 14.00 | 2269.27 | 110.63 | 14.00 | 1.02 | 0.87 |
| 21 | 1853.29 | 72.48 | 16.00 | 1983.58 | 95.39 | 12.00 | 0.93 | 0.76 |
| 22 | 2637.81 | 153.39 | 16.00 | 2464.84 | 144.41 | 8.00 | 1.07 | 1.06 |
| 23 | 1970.96 | 81.98 | 24.00 | 1870.67 | 96.76 | 16.00 | 1.05 | 0.85 |
| 24 | 1867.23 | 89.74 | 20.00 | 1673.09 | 78.73 | 20.00 | 1.12 | 1.14 |
| Mean | 1959.14 | 86.53 | 16.61 | 1953.40 | 87.94 | 15.48 | 1.01 | 0.99 |
| SD | 639.46 | 30.56 | 4.69 | 647.00 | 27.94 | 3.58 | 0.12 | 0.18 |
| CV | 32.64 | 35.32 | 28.23 | 33.12 | 31.77 | 23.12 | 12.11 | 18.40 |
| Geo Mean | 1857.57 | 81.15 | 16.00 | 1855.19 | 83.46 | 15.03 | 1.00 | 0.97 |
| Min | 953.92 | 36.57 | 10.00 | 991.16 | 38.21 | 8.00 | 0.72 | 0.53 |
| Max | 3490.68 | 153.39 | 24.00 | 3521.34 | 144.41 | 20.00 | 1.27 | 1.33 |

1 × 200 mg/2 × 100 mg Ratio

|  | Means | Geo Means | LS Means % | 90% CI |
|---|---|---|---|---|
| AUC | 1.00 | 1.00 | 100.01 | 95.6-104.61 |
| $C_{max}$ | 0.98 | 0.97 | 97.06 | 90.3-104.39 |

TABLE 8G (Summary of Pharmacokinetic Parameters for Didesmethyltramadol (M5))

| | B DER tramadol HCl 1 × 200 mg | | | A DER tramadol HCl 2 × 100 mg | | | B/A Ratio | |
|---|---|---|---|---|---|---|---|---|
| Subject | AUC | $C_{max}$ | $T_{max}$ | AUC | $C_{max}$ | $T_{max}$ | AUC | $C_{max}$ |
| 1 | 586.48 | 19.01 | 30.00 | 669.49 | 26.43 | 16.00 | 0.88 | 0.72 |
| 2 | 1011.03 | 39.82 | 20.00 | 1156.49 | 43.27 | 16.00 | 0.87 | 0.92 |
| 3 | 479.82 | 18.04 | 20.00 | 606.97 | 21.98 | 24.00 | 0.79 | 0.82 |
| 4 | 597.78 | 23.35 | 24.00 | 709.78 | 25.47 | 24.00 | 0.84 | 0.92 |
| 5 | 638.62 | 28.06 | 12.00 | 652.44 | 28.32 | 16.00 | 0.98 | 0.99 |
| 7 | 505.59 | 18.07 | 20.00 | 794.87 | 34.53 | 14.00 | 0.64 | 0.52 |
| 8 | 1105.91 | 49.06 | 24.00 | 1022.61 | 39.84 | 14.00 | 1.08 | 1.23 |
| 9 | 765.91 | 32.10 | 14.00 | 860.60 | 35.68 | 20.00 | 0.89 | 0.90 |
| 10 | 986.85 | 41.59 | 14.00 | 973.22 | 38.01 | 16.00 | 1.01 | 1.09 |
| 11 | 492.42 | 20.37 | 24.00 | 565.44 | 24.25 | 16.00 | 0.87 | 0.84 |
| 12 | 1566.17 | 75.38 | 16.00 | 1481.53 | 71.45 | 14.00 | 1.06 | 1.06 |
| 13 | 1044.20 | 43.60 | 16.00 | 974.90 | 39.62 | 20.00 | 1.07 | 1.10 |
| 14 | 843.42 | 35.36 | 16.00 | 809.01 | 33.16 | 16.00 | 1.04 | 1.07 |
| 15 | 967.94 | 46.14 | 14.00 | 867.23 | 36.72 | 16.00 | 1.12 | 1.26 |
| 16 | 987.92 | 44.60 | 20.00 | 1019.98 | 38.32 | 20.00 | 0.97 | 1.16 |
| 17 | 630.21 | 29.71 | 16.00 | 607.88 | 25.47 | 20.00 | 1.04 | 1.17 |
| 18 | 1889.26 | 66.43 | 14.00 | 1865.13 | 67.08 | 20.00 | 1.01 | 0.99 |
| 19 | 813.41 | 31.21 | 20.00 | 584.26 | 19.99 | 20.00 | 1.39 | 1.56 |
| 20 | 841.90 | 34.50 | 14.00 | 640.29 | 27.74 | 14.00 | 1.31 | 1.24 |
| 21 | 829.00 | 33.19 | 16.00 | 940.72 | 42.90 | 14.00 | 0.88 | 0.77 |
| 22 | 617.32 | 33.20 | 16.00 | 639.87 | 37.09 | 10.00 | 0.96 | 0.90 |
| 23 | 908.93 | 38.57 | 24.00 | 759.38 | 40.38 | 16.00 | 1.20 | 0.96 |
| 24 | 743.29 | 33.02 | 20.00 | 717.33 | 30.83 | 20.00 | 1.04 | 1.07 |
| Mean | 863.19 | 36.28 | 18.43 | 866.06 | 36.02 | 17.22 | 1.00 | 1.01 |
| SD | 334.21 | 14.20 | 4.51 | 308.56 | 12.52 | 3.45 | 0.17 | 0.22 |
| CV | 38.72 | 39.15 | 24.47 | 35.63 | 34.76 | 20.04 | 16.59 | 21.38 |
| Geo Mean | 812.38 | 33.87 | 17.94 | 825.19 | 34.29 | 16.88 | 0.98 | 0.99 |
| Min | 479.82 | 18.04 | 12.00 | 565.44 | 19.99 | 10.00 | 0.64 | 0.52 |
| Max | 1889.26 | 75.38 | 30.00 | 1865.13 | 71.45 | 24.00 | 1.39 | 1.56 |

| 1 × 200 mg/2 × 100 mg Ratio | | | | |
|---|---|---|---|---|
| | Means | Geo Means | LS Means % | 90% CI |
| AUC | 1.00 | 0.98 | 98.45 | 92.6-104.72 |
| $C_{max}$ | 1.01 | 0.99 | 98.77 | 90.9-107.25 |

Figure 20:
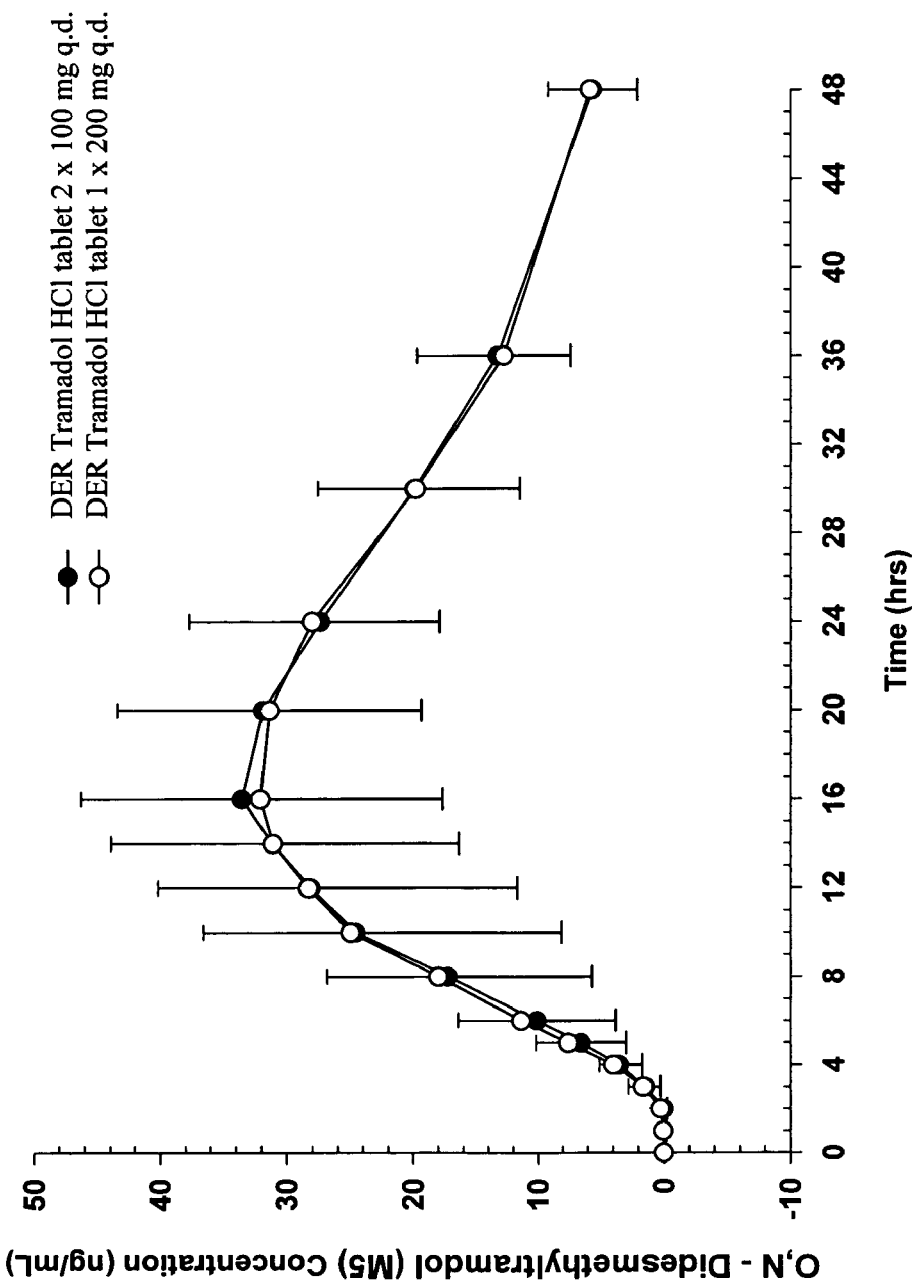
FIG. 20 is a graph illustrating the mean plasma didesmethyltramadol (also sometimes referred to herein as M5 or O,N-di-desmethyltramadol) concentrations over time following administration of the tablets of FIG. 18 following a 10-hour overnight fast.

FIG. 20 illustrates the mean plasma M5 concentrations (ng/ml) over time after two 100 mg DER tramadol HCl tablets formulated according to an embodiment of the present invention or after one 200 mg DER tramadol HCl tablet formulated according to an embodiment of the present invention following a 10 hour overnight fast.

EXAMPLE 9

I. Pharmacokinetic Study

A Two-Way, Crossover, Open-Label, Single-Dose, Food Effect, Comparative Bioavailability Study of DER Tramadol HCl 200 mg Tablets in Normal Healthy Non-Smoking Male Subjects.

Based on data from 20 completing subjects, the presence of food significantly decreased the rate and extent of absorption of tramadol, M1 and M5 metabolites of 200 mg DER tramadol HCl tablets of Example 6 (Coating Parameter F) following single dose administration.

This study was designed to evaluate the effect of food on the DER tramadol HCl 200 mg tablets following single dose administration.

A single-dose, open-label, two-way, two-sequence, crossover design study was conducted. The treatments were separated by a one (1) week washout period. On day 1 of each period, subjects received one of the following treatments following a 10-hour overnight fast on two (2) separate occasions according to the randomization scheme Treatment A: One DER tramadol HCl 200 mg tablet of Example 6 (Coating Parameter F) with 240 mL of water at 0.0 hour within 5 minutes of complete ingestion of a high fat content breakfast.

Treatment B: One DER tramadol HCl 200 mg tablet of Example 6 (Coating Parameter F) with 240 mL of water at 0.0 hour following a 10 hour overnight fast This study was intended to evaluate the effect of food on the DER tramadol HCl 200 mg tablets following single dose administration. A total of 24 male subjects were dosed. Pharmacokinetic and statistical analyses were conducted with plasma data from 22 completing subjects. The mean plasma concentrations for tramadol, desmethyltramadol, and didesmethyltramadol for treatments A and B are provided in Table 9AA-AC for treatment A and Table 9BA-BC for treatment B. The mean plasma concentrations vs time plots based on 20 completing subjects for tramadol, M1 and M5 metabolites are presented in FIGS. 21, 22 and 23, respectively. Individual pharmacokinetic parameters are shown in Tables 9A, 9B and 9C.

With all subjects, the ratio of geometric means (Fed/Fasting) for tramadol $AUC_{0-t}$ and $C_{max}$ were 0.76 and 0.73, respectively. For the M1 metabolite, the ratio of geometric means (Fed/Fasting) for $AUC_{0-t}$ and $C_{max}$ were 0.75 and 0.76, respectively. For the M5 metabolite, the ratio of geometric means (Fed/Fasting) for $AUC_{0-t}$ and $C_{max}$ were 0.73 and 0.73, respectively.

When data analysis was carried out in the absence of subject #12 and #18, the ratio of geometric means for tramadol $AUC_{0-t}$ and $C_{max}$ were 0.79 and 0.73, respectively. For the M1 metabolite, the ratio of geometric means (Fed/Fasting) for $AUC_{0-t}$ and $C_{max}$ were 0.78 and 0.76, respectively. For the M5 metabolite, the ratio of geometric means (Fed/Fasting) for $AUC_{0-t}$ and $C_{max}$ were 0.75 and 0.72, respectively.

Based on the results, it was concluded that a significant food effect was observed for the DER tramadol HCl 200 mg tablets. In the presence of food, the rate and extent of absorption of tramadol and its metabolites resulting from a single dose of the DER tramadol HCl 200 mg tablet were significantly lower when compared to administration without food.

TABLE 9AA (Mean ± SD Plasma Tramadol Concentrations for Treatment A)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.44 | 6.28 | 16.69 | 28.33 | 40.26 | 46.79 | 64.08 |
| SD | 0.00 | 2.05 | 4.82 | 7.08 | 12.49 | 22.67 | 30.78 | 41.27 |
| | Hours | | | | | | | |
| | 10.0 | 12.0 | 14.0 | 16.0 | 20.0 | 24.0 | 36.0 | 48.0 |
| Average | 91.97 | 122.20 | 148.84 | 154.77 | 155.96 | 157.74 | 66.70 | 29.47 |
| SD | 57.28 | 84.95 | 92.02 | 85.71 | 85.51 | 132.86 | 42.74 | 26.20 |

TABLE 9AB (Mean ± SD Plasma Desmethyltramadol Concentrations for Treatment A)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.09 | 0.90 | 3.35 | 6.03 | 8.98 | 11.05 | 17.11 |
| SD | 0.00 | 0.41 | 1.28 | 2.01 | 2.92 | 4.41 | 5.93 | 11.54 |
| | Hours | | | | | | | |
| | 10.0 | 12.0 | 14.0 | 16.0 | 20.0 | 24.0 | 36.0 | 48.0 |
| Average | 26.87 | 34.72 | 43.98 | 50.80 | 57.43 | 51.44 | 26.27 | 12.52 |
| SD | 18.46 | 24.31 | 29.57 | 30.78 | 34.27 | 23.69 | 14.09 | 11.30 |

TABLE 9AC (Mean ± SD Plasma Didesmethyltramadol Concentrations for Treatment A)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.00 | 0.05 | 0.57 | 1.67 | 2.67 | 3.52 | 5.90 |
| SD | 0.00 | 0.00 | 0.21 | 0.73 | 0.75 | 1.08 | 1.64 | 3.35 |
| | Hours | | | | | | | |
| | 10.0 | 12.0 | 14.0 | 16.0 | 20.0 | 24.0 | 36.0 | 48.0 |
| Average | 9.11 | 11.51 | 14.95 | 18.32 | 21.48 | 20.67 | 13.45 | 7.12 |
| SD | 5.37 | 7.55 | 9.16 | 9.83 | 11.39 | 9.30 | 7.32 | 5.99 |

TABLE 9BA (Mean ± SD Plasma Tramadol Concentrations for Treatment B)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.81 | 9.89 | 25.36 | 43.89 | 79.52 | 107.46 | 163.45 |
| SD | 0.00 | 2.31 | 7.37 | 12.24 | 21.67 | 43.83 | 73.24 | 98.59 |

TABLE 9BA-continued (Mean ± SD Plasma Tramadol Concentrations for Treatment B)

| | Hours | | | | | | | |
|---|---|---|---|---|---|---|---|---|
| | 10.0 | 12.0 | 14.0 | 16.0 | 20.0 | 24.0 | 36.0 | 48.0 |
| Average | 200.96 | 225.08 | 246.32 | 227.57 | 189.68 | 144.29 | 56.37 | 23.11 |
| SD | 102.49 | 92.16 | 86.81 | 74.75 | 60.80 | 54.54 | 29.23 | 15.90 |

TABLE 9BB (Mean ± SD Plasma Desmethyltramadol Concentrations for Treatment B)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.23 | 2.05 | 6.15 | 10.83 | 17.31 | 23.26 | 37.95 |
| SD | 0.00 | 0.76 | 2.59 | 4.23 | 5.87 | 9.03 | 14.01 | 21.25 |

| | Hours | | | | | | | |
|---|---|---|---|---|---|---|---|---|
| | 10.0 | 12.0 | 14.0 | 16.0 | 20.0 | 24.0 | 36.0 | 48.0 |
| Average | 53.11 | 62.25 | 71.10 | 73.93 | 70.09 | 57.07 | 23.72 | 10.52 |
| SD | 25.12 | 24.60 | 24.65 | 22.89 | 21.20 | 15.79 | 8.11 | 5.37 |

TABLE 9BC (Mean ± SD Plasma Didesmethyltramadol Concentrations for Treatment B)

| | Hours | | | | | | | |
|---|---|---|---|---|---|---|---|---|
| | 0.0 | 1.0 | 2.0 | 3.0 | 4.0 | 5.0 | 6.0 | 8.0 |
| Average | 0.00 | 0.00 | 0.18 | 1.56 | 3.07 | 5.03 | 7.21 | 12.29 |
| SD | 0.00 | 0.00 | 0.58 | 1.04 | 1.33 | 2.49 | 4.31 | 6.09 |

| | Hours | | | | | | | |
|---|---|---|---|---|---|---|---|---|
| | 10.0 | 12.0 | 14.0 | 16.0 | 20.0 | 24.0 | 36.0 | 48.0 |
| Average | 18.13 | 21.77 | 26.07 | 28.61 | 28.53 | 24.37 | 12.48 | 6.22 |
| SD | 7.63 | 9.24 | 10.73 | 10.87 | 11.03 | 9.52 | 6.01 | 4.38 |

TABLE 9A (Summary of Pharmacokinetic Parameters for Tramadol)

| | DER tramadol 200 mg, Fed | | | DER tramadol 200 mg, Fasting | | | Fed/Fasting | |
|---|---|---|---|---|---|---|---|---|
| Subject | AUC | $C_{max}$ | $T_{max}$ | AUC | $C_{max}$ | $T_{max}$ | AUC | $C_{max}$ |
| 1 | 3944.30 | 149.33 | 24.00 | 4013.96 | 205.64 | 14.00 | 0.98 | 0.73 |
| 2 | 4078.64 | 139.34 | 24.00 | 6969.14 | 355.35 | 14.00 | 0.59 | 0.39 |
| 3 | 6818.20 | 251.76 | 20.00 | 6939.38 | 342.62 | 10.00 | 0.98 | 0.73 |
| 4 | 2021.34 | 72.15 | 24.00 | 4218.92 | 234.01 | 14.00 | 0.48 | 0.31 |
| 5 | 2330.34 | 142.73 | 20.00 | 2848.84 | 140.20 | 16.00 | 0.82 | 1.02 |
| 6 | 4636.19 | 225.35 | 20.00 | 5154.28 | 340.84 | 12.00 | 0.90 | 0.66 |
| 7 | 1901.40 | 128.41 | 14.00 | 3554.14 | 173.63 | 16.00 | 0.53 | 0.74 |
| 8 | 4585.55 | 137.09 | 14.00 | 5674.75 | 263.32 | 14.00 | 0.81 | 0.52 |
| 9 | 7727.96 | 320.14 | 14.00 | 7827.31 | 290.33 | 20.00 | 0.99 | 1.10 |
| 10 | 3783.07 | 170.80 | 14.00 | 4258.28 | 203.68 | 16.00 | 0.89 | 0.84 |
| 11 | 7079.58 | 263.39 | 14.00 | 7252.23 | 285.04 | 14.00 | 0.98 | 0.92 |
| 13 | 3342.06 | 171.38 | 16.00 | 3019.69 | 138.26 | 12.00 | 1.11 | 1.24 |
| 15 | 4424.02 | 190.87 | 16.00 | 4935.58 | 255.62 | 14.00 | 0.90 | 0.75 |

TABLE 9A-continued (Summary of Pharmacokinetic Parameters for Tramadol)

| 16 | 7296.94 | 328.00 | 16.00 | 6632.83 | 342.80 | 12.00 | 1.10 | 0.96 |
|---|---|---|---|---|---|---|---|---|
| 17 | 1070.08 | 43.56 | 4.00 | 8377.65 | 384.17 | 10.00 | 0.13 | 0.11 |
| 20 | 4209.33 | 215.06 | 14.00 | 5340.01 | 288.25 | 12.00 | 0.79 | 0.75 |
| 21 | 3451.99 | 173.23 | 14.00 | 3886.46 | 205.50 | 10.00 | 0.89 | 0.84 |
| 22 | 3937.39 | 155.94 | 16.00 | 3596.43 | 152.88 | 14.00 | 1.09 | 1.02 |
| 23 | 4539.31 | 200.08 | 20.00 | 5569.65 | 244.83 | 16.00 | 0.82 | 0.82 |
| 24 | 8472.81 | 669.76 | 24.00 | 6400.85 | 312.84 | 16.00 | 1.32 | 2.14 |
| Mean | 4482.52 | 207.42 | 17.10 | 5323.52 | 257.99 | 13.80 | 0.85 | 0.83 |
| SD | 2042.83 | 130.14 | 4.96 | 1647.23 | 75.37 | 2.50 | 0.26 | 0.41 |
| CV | 45.57 | 62.74 | 29.02 | 30.94 | 29.21 | 18.15 | 30.93 | 49.48 |
| Geo Mean | 3999.75 | 178.85 | 16.16 | 5076.49 | 246.69 | 13.59 | 0.79 | 0.73 |
| Min | 1070.08 | 43.56 | 4.00 | 2848.84 | 138.26 | 10.00 | 0.13 | 0.11 |
| Max | 8472.81 | 669.76 | 24.00 | 8377.65 | 384.17 | 20.00 | 1.32 | 2.14 |

| | Fed/Fasting Ratio | | | Fed/Fasting Ratio (Including Subject #12 and #18 who vomited during post-dose) | |
|---|---|---|---|---|---|
| | Geo Means | LS Means % | | Geo Means | LS Means % |
| AUC | 0.79 | 78.93 | AUC | 0.76 | 75.62 |
| $C_{max}$ | 0.73 | 72.27 | $C_{max}$ | 0.73 | 72.38 |

Figure 21:
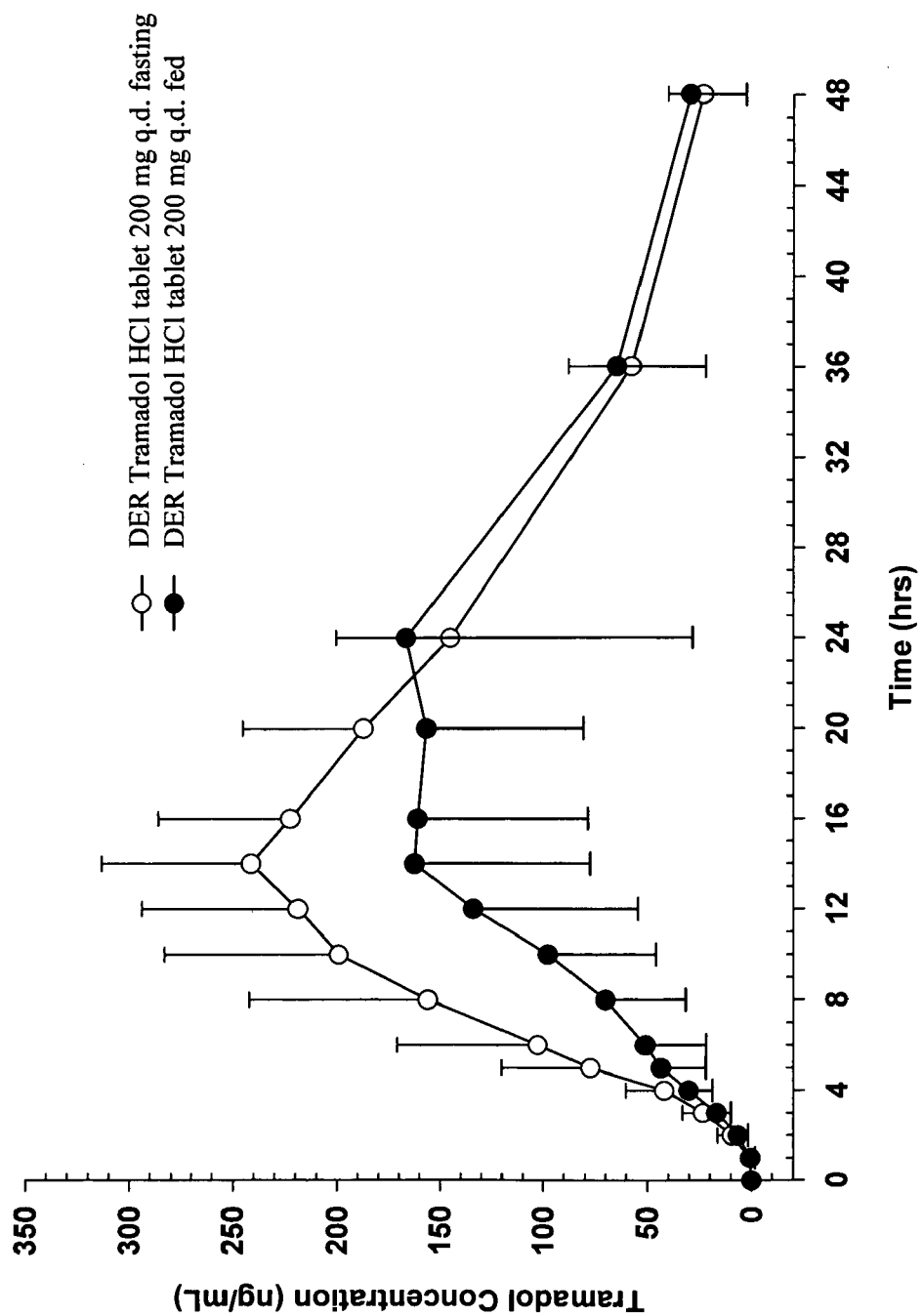
FIG. 21 is a graph illustrating the mean plasma tramadol concentrations over time after a single dose of one 200 mg tramadol HCl DER tablet formulated according to an embodiment of the present invention under fasting or fed conditions.

FIG. 21 illustrates the mean plasma tramadol concentrations (ng/ml) over time after a single dose of one 200 mg DER tramadol HCl tablet formulated according to an embodiment of the present invention under fasting or fed conditions.

Figure 22:
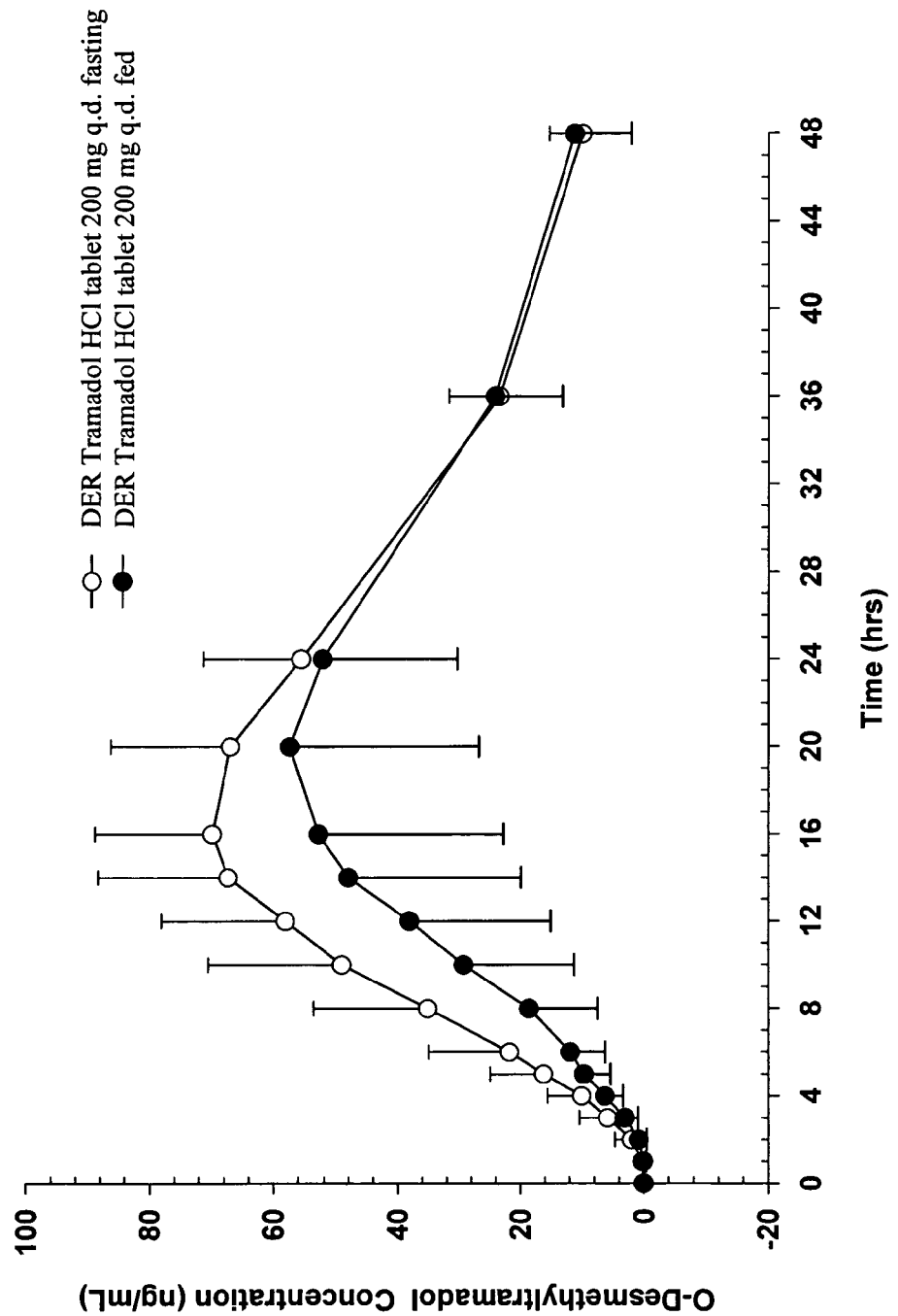
FIG. 22 is a graph illustrating the mean plasma desmethyltramadol (M1) concentrations over time following administration of the tablets of FIG. 21 under fasting or fed conditions.

FIG. 22 illustrates the mean plasma M1 concentrations (ng/ml) over time after a single dose of one DER 200 mg tramadol HCl tablet formulated according to an embodiment of the present invention under fasting or fed conditions.

TABLE 9B (Summary of Pharmacokinetic Parameters for Desmethyltramadol (M1))

| | DER tramadol 200 mg, Fed | | | DER tramadol 200 mg, Fasting | | | Fed/Fasting | |
|---|---|---|---|---|---|---|---|---|
| Subject | AUC | $C_{max}$ | $T_{max}$ | AUC | $C_{max}$ | $T_{max}$ | AUC | $C_{max}$ |
| 1 | 1921.05 | 75.67 | 24.00 | 2116.84 | 90.06 | 20.00 | 0.91 | 0.84 |
| 2 | 1278.59 | 45.95 | 24.00 | 2158.62 | 86.81 | 20.00 | 0.59 | 0.53 |
| 3 | 1159.73 | 42.64 | 20.00 | 1183.17 | 46.50 | 10.00 | 0.98 | 0.92 |
| 4 | 542.48 | 19.92 | 24.00 | 1223.87 | 58.17 | 14.00 | 0.44 | 0.34 |
| 5 | 1894.84 | 117.77 | 20.00 | 1982.93 | 96.08 | 20.00 | 0.96 | 1.23 |
| 6 | 1887.04 | 91.91 | 20.00 | 1761.13 | 105.91 | 12.00 | 1.07 | 0.87 |
| 7 | 1130.02 | 60.88 | 16.00 | 1901.17 | 77.45 | 16.00 | 0.59 | 0.79 |
| 8 | 1674.77 | 51.91 | 24.00 | 2013.76 | 75.57 | 16.00 | 0.83 | 0.69 |
| 9 | 1511.07 | 52.51 | 24.00 | 1487.99 | 53.84 | 24.00 | 1.02 | 0.98 |
| 10 | 1322.65 | 54.89 | 16.00 | 1702.91 | 70.92 | 16.00 | 0.78 | 0.77 |
| 11 | 1335.58 | 51.01 | 20.00 | 1286.31 | 46.10 | 24.00 | 1.04 | 1.11 |
| 13 | 2269.80 | 100.16 | 16.00 | 1796.92 | 70.38 | 14.00 | 1.26 | 1.42 |
| 15 | 1018.82 | 46.97 | 20.00 | 1168.38 | 52.96 | 16.00 | 0.87 | 0.89 |
| 16 | 1270.79 | 56.22 | 16.00 | 1382.61 | 71.49 | 16.00 | 0.92 | 0.79 |
| 17 | 183.63 | 5.70 | 24.00 | 1555.20 | 63.67 | 14.00 | 0.12 | 0.09 |
| 20 | 2275.30 | 101.30 | 20.00 | 2439.33 | 116.53 | 14.00 | 0.93 | 0.87 |
| 21 | 1257.39 | 60.38 | 20.00 | 1339.50 | 64.90 | 12.00 | 0.94 | 0.93 |
| 22 | 1749.84 | 66.63 | 20.00 | 2118.35 | 79.93 | 24.00 | 0.83 | 0.83 |
| 23 | 2201.99 | 91.33 | 24.00 | 2577.88 | 107.78 | 20.00 | 0.85 | 0.85 |
| 24 | 1373.21 | 77.04 | 24.00 | 1575.86 | 65.39 | 20.00 | 0.87 | 1.18 |
| Mean | 1462.93 | 63.54 | 20.80 | 1738.64 | 75.02 | 76.25 | | 0.84 |
| SD | 543.09 | 27.58 | 3.07 | 419.16 | 20.30 | 4.18 | 0.25 | 0.29 |
| CV | 37.12 | 43.40 | 14.76 | 24.11 | 27.07 | 24.44 | 29.56 | 34.89 |
| Geo Mean | 1311.89 | 55.00 | 20.57 | 1691.12 | 72.48 | 16.61 | 0.78 | 0.76 |
| Min | 183.63 | 5.70 | 16.00 | 1168.38 | 46.10 | 10.00 | 0.12 | 0.09 |
| Max | 2275.30 | 117.77 | 24.00 | 2577.88 | 116.53 | 24.00 | 1.26 | 1.42 |

| | Fed/Fasting Ratio | | | Fed/Fasting Ratio (Including Subject #12 and #18 who vomited during post-dose | |
|---|---|---|---|---|---|
| | Geo Means | LS Means % | | Geo Means | LS Means % |
| AUC | 0.78 | 77.89 | AUC | 0.75 | 75.27 |
| $C_{max}$ | 0.76 | 176.07 | $C_{max}$ | 0.76 | |

TABLE 9C (Summary of Pharmacokinetic Parameters for Didesmethyltramadol (M5))

| | DER tramadol 200 mg, Fed | | | DER tramadol 200 mg, Fasting | | | Fed/Fasting | |
|---|---|---|---|---|---|---|---|---|
| Subject | AUC | $C_{max}$ | $T_{max}$ | AUC | $C_{max}$ | $T_{max}$ | AUC | $C_{max}$ |
| 1 | 748.53 | 27.50 | 20.00 | 897.15 | 39.14 | 20.00 | 0.83 | 0.70 |
| 2 | 511.56 | 16.27 | 24.00 | 915.79 | 36.24 | 20.00 | 0.56 | 0.45 |
| 3 | 658.62 | 21.94 | 24.00 | 678.13 | 22.05 | 24.00 | 0.97 | 1.00 |
| 4 | 536.16 | 20.64 | 36.00 | 1281.12 | 58.25 | 20.00 | 0.42 | 0.35 |
| 5 | 371.79 | 21.38 | 20.00 | 406.02 | 17.27 | 20.00 | 0.92 | 1.24 |
| 6 | 851.56 | 38.97 | 20.00 | 732.06 | 40.97 | 12.00 | 1.16 | 0.95 |
| 7 | 298.02 | 16.33 | 16.00 | 535.16 | 21.77 | 16.00 | 0.56 | 0.75 |
| 8 | 764.80 | 21.96 | 24.00 | 1100.54 | 38.46 | 24.00 | 0.69 | 0.57 |
| 9 | 1066.70 | 31.87 | 24.00 | 1054.70 | 33.20 | 24.00 | 1.01 | 0.96 |
| 10 | 547.25 | 21.77 | 20.00 | 674.38 | 26.28 | 16.00 | 0.81 | 0.83 |
| 11 | 582.46 | 22.11 | 24.00 | 565.57 | 19.86 | 24.00 | 1.03 | 1.11 |
| 13 | 446.45 | 19.72 | 16.00 | 399.37 | 16.12 | 14.00 | 1.12 | 1.22 |
| 15 | 629.68 | 26.27 | 20.00 | 746.10 | 30.50 | 16.00 | 0.84 | 0.86 |
| 16 | 943.41 | 33.73 | 20.00 | 1024.16 | 44.47 | 16.00 | 0.92 | 0.76 |
| 17 | 41.47 | 1.49 | 24.00 | 341.34 | 12.37 | 14.00 | 0.12 | 0.12 |
| 20 | 939.16 | 36.75 | 20.00 | 1125.74 | 52.09 | 14.00 | 0.83 | 0.71 |
| 21 | 599.05 | 26.91 | 20.00 | 617.38 | 26.32 | 14.00 | 0.97 | 1.02 |
| 22 | 674.58 | 23.94 | 20.00 | 782.20 | 28.83 | 16.00 | 0.86 | 0.83 |
| 23 | 555.68 | 21.00 | 24.00 | 755.53 | 30.14 | 20.00 | 0.74 | 0.70 |
| 24 | 644.69 | 24.87 | 24.00 | 826.43 | 31.25 | 20.00 | 0.78 | 0.80 |
| Mean | 620.58 | 23.77 | 22.00 | 772.94 | 31.28 | 18.20 | 0.81 | 0.80 |
| SD | 236.47 | 8.13 | 4.21 | 259.24 | 11.96 | 3.89 | 0.25 | 0.28 |
| CV | 38.10 | 34.21 | 19.11 | 33.54 | 38.23 | 21.36 | 30.63 | 35.05 |
| Geo Mean | 542.98 | 21.07 | 21.67 | 728.60 | 29.09 | 17.81 | 0.75 | 0.72 |
| Min | 41.47 | 1.49 | 16.00 | 341.34 | 12.37 | 12.00 | 0.12 | 0.12 |
| Max | 1066.70 | 38.97 | 36.00 | 1281.12 | 58.25 | 24.00 | 1.16 | 1.24 |

| | Fed/Fasting Ratio | | | Fed/Fasting Ratio (Including Subject #12 and #18 who vomited during post-dose | |
|---|---|---|---|---|---|
| | Geo Means | LS Means % | | Geo Means | LS Means % |
| AUC | 0.75 | 74.62 | AUC | 0.73 | 73.24 |
| $C_{max}$ | 0.72 | 72.23 | $C_{max}$ | 0.73 | 73.45 |

Figure 23:
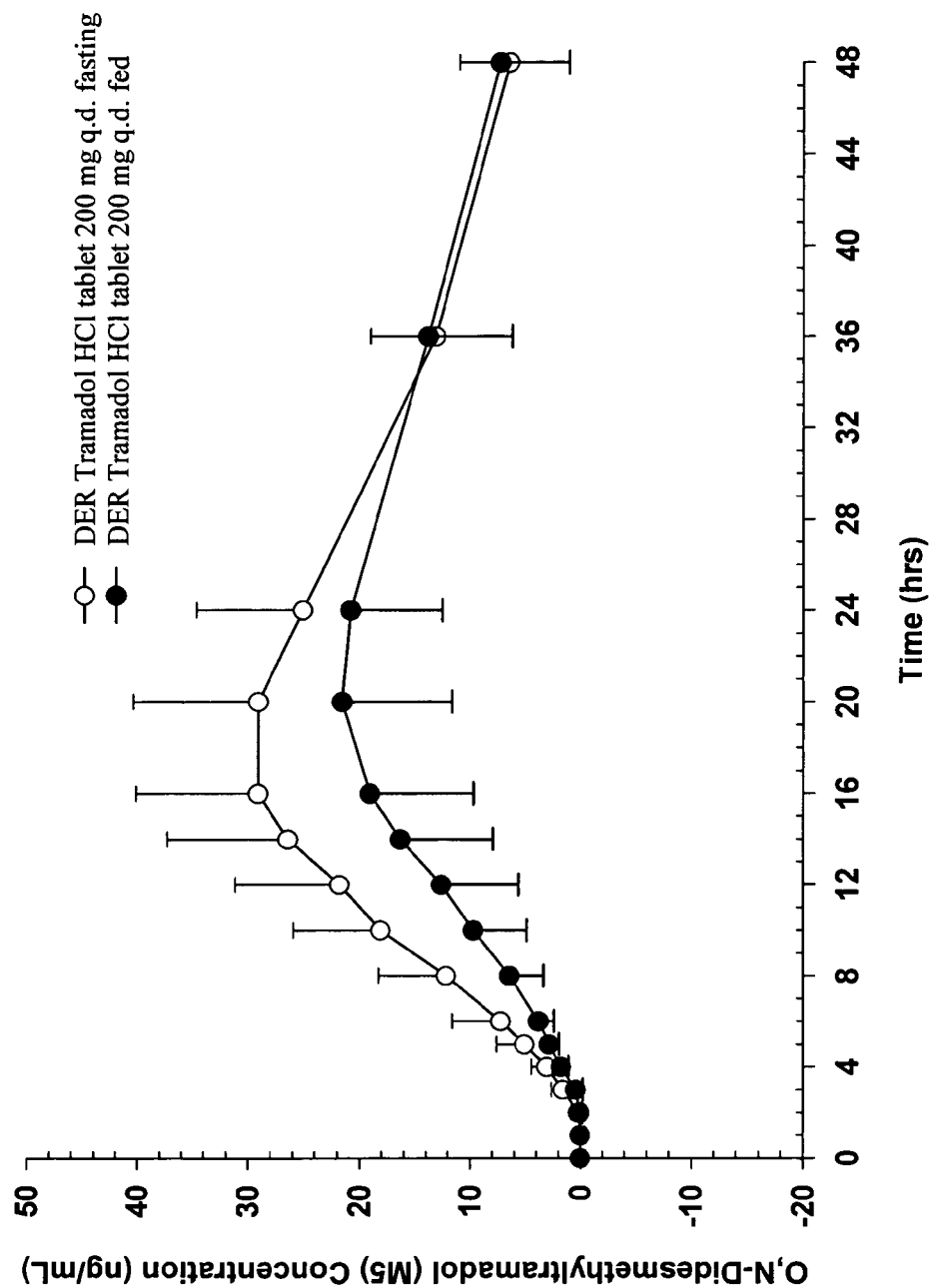
FIG. 23 is a graph illustrating the mean plasma didesmethyltramadol (M5) concentrations over time after administration of the tablets of FIG. 21 under fasting or fed conditions.

FIG. 23 illustrates the mean plasma M5 concentrations (ng/ml) over time after a single dose of one DER 200 mg tramadol HCl tablet formulated according to an embodiment of the present invention under fasting or fed conditions.

EXAMPLE 10

DER Tramadol Osteoarthritis Study

I. Overall Study Design and Plan

A 12-week, multi-center double blind, randomized, dose-titration, parallel-group comparison of the efficacy and safety of the DER tramadol tablets of Example 3 (Coating Formulation B/Coating Parameter B) and placebo in the treatment of osteoarthritis of the knee was conducted. Approximately 245 patients from 18 to 75 years of age with moderate to severe pain associated with Functional Class I-III osteoarthritis of the knee were planned for study enrollment to ensure that a minimum of 140 patients completed the study. After signing the informed consent, patients who met the inclusion and exclusion criteria at screening entered a 2 to 7 day washout period during which all analgesic use was discontinued. At the start of the first week of the study (Baseline, Visit 2), eligible patients who reported pain intensity≧40 mm on a visual analog scale (VAS) in the index knee joint were randomly assigned to either the DER tramadol tablets or placebo.

Patients assigned to DER tramadol tablets were initiated on 100 mg q.d. and maintained on their dose for at least 3 days. On Day 4, and for the remainder of the week (until their return to the clinic for Visit 3), patients were permitted to have their dose increased to 200 mg q.d., based upon the tolerability of side effects. Beginning at Visit 3, patients must have been maintained on a minimum DER tramadol tablet dose of 200 mg q.d., and the dose titrated upwards if required based upon the adequacy of pain relief and tolerability of side effects. Patients randomized to the placebo group underwent sham dose increases. Further dose escalation and de-escalation was permitted provided that a minimum dose of 200 mg q.d. was maintained from Week 1 (Visit 3) to Week 12 (Visit 7). In patients with pain unresponsive to appropriate dosage adjustments, or with unacceptable side effects, treatment was discontinued and alternate analgesia therapy initiated, as appropriate. Patients returned for efficacy and safety evaluations at Week 1 (Visit 3), Week 2 (Visit 4), Week 4 (Visit 5), Week 8 (Visit 6) and Week 12 (Visit 7) or at Early Termination.

II. Efficacy Variables

The primary measure of efficacy was the Arthritis Pain Intensity VAS (visual analog scale) Score from patient visits. The arthritis VAS is the most commonly used, validated tool to assess pain intensity and one recommended by FDA to evaluate the analgesic potential of a drug product.

Pain was also assessed as a secondary measure of efficacy using the WOMAC Osteoarthritis Index. The WOMAC is a validated, internationally recognized and widely used multi-dimensional instrument for assessing response to therapy in osteoarthritis. It assesses pain, joint stiffness and physical function, the three major bothersome symptoms in osteoarthritis. In addition, patients and physicians provided a global assessment of disease and patients recorded their response on a sleep questionnaire as other secondary measures of efficacy.

III. Results

A total of 246 patients were randomized and evaluable for safety. Of these, 219 were evaluable for the intent-to-treat (ITT) population. The ITT population included all safety evaluable patients who had primary efficacy information recorded at the baseline visit (Visit 2) and at the Week 1 visit (Visit 3), the first primary efficacy variable collection point on treatment. The ITT population also included all patients who dropped out before the Week 1 visit due to lack of treatment efficacy. The mean daily dose of DER tramadol following the flexible dosing regimen was approximately 300 mg. The median age of patients who enrolled was 61 years and the median duration of osteoarthritis was 10 years.

DER tramadol produced statistically significant and clinically meaningful reductions in pain intensity associated with osteoarthritis of the knee compared to placebo for the primary efficacy variable and all secondary variables evaluated.

IV. Response to Primary Variable

Figure 24:
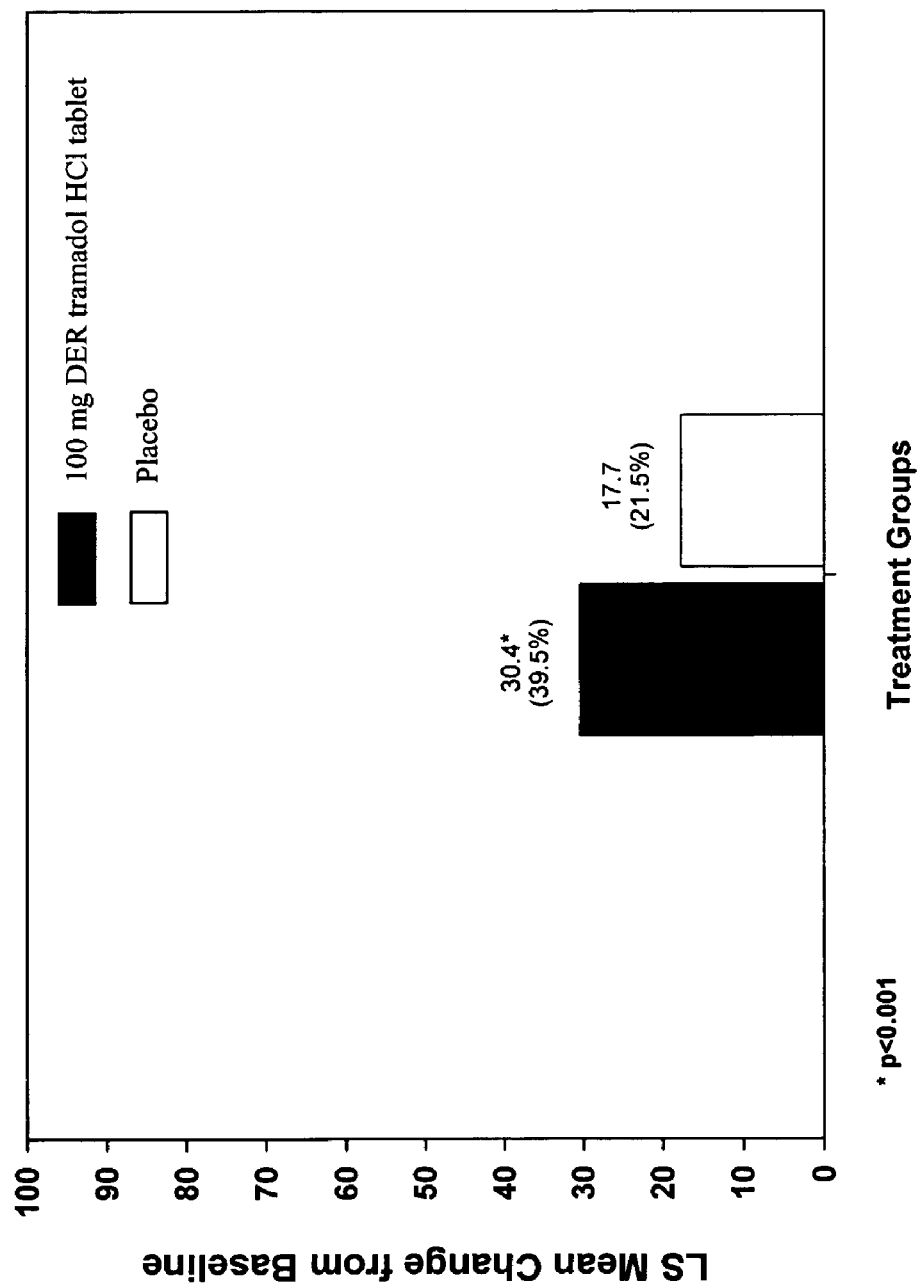
FIG. 24 is a comparison of the LS mean change from baseline to average of weeks 1-12 in arthritis pain intensity VAS scores (primary variables) for the tramadol HCl DER tablets according to an embodiment of the invention and placebo.
Figure 25:
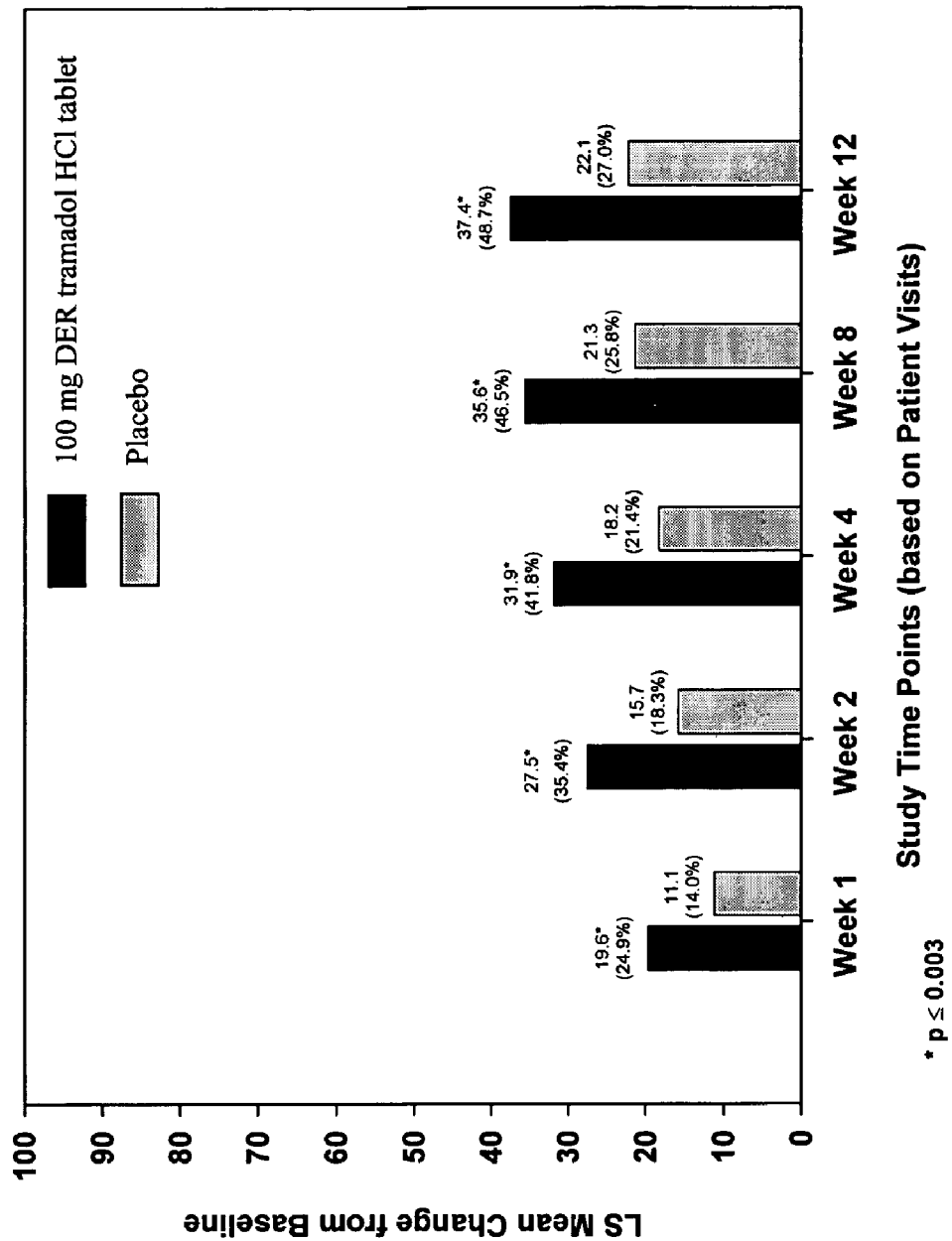
FIG. 25 is a comparison of the LS mean change from baseline to different study time points in arthritis pain intensity VAS scores (primary variables) for the tramadol HCl DER tablets according to an embodiment of the invention and placebo.

FIG. 24 compares the LS (least square) mean change from baseline in VAS score for DER tramadol and placebo based upon the average of Weeks 1-12. On the primary endpoint (LS mean change from baseline over 12 weeks), there was a 39.5% (30.4 mm) and 21.5% (17.7 mm) change from baseline in the arthritis pain intensity VAS in the DER tramadol tablets and placebo groups, respectively (LS mean difference 12.7 mm, p<0.001). FIG. 25 shows the weekly LS mean changes from baseline for the two treatment groups. Treatment differences emerged at the first return visit (Week 1) when patients were receiving either a 100 mg or 200 mg dose of DER tramadol (change from baseline 24.8% [19.6 mm] vs. 14.0% [11.1 mm], LS mean difference 8.5 mm, p=0.003). At the end of the second week of treatment, the response to the DER tramadol increased relative to placebo (change from baseline 35.7% [27.4 mm] vs. 19.3% [15.7 mm], LS mean difference 11.7 mm, p<0.001). By Week 12, the response to the DER tramadol tablet (LS mean change from baseline) was 48.6% [37.4 mm] while that for placebo was 27.0% [22.1 mm]. The LS mean difference was 15.3 mm (p<0.001).

V. Response on the Secondary Variables

Figure 26:
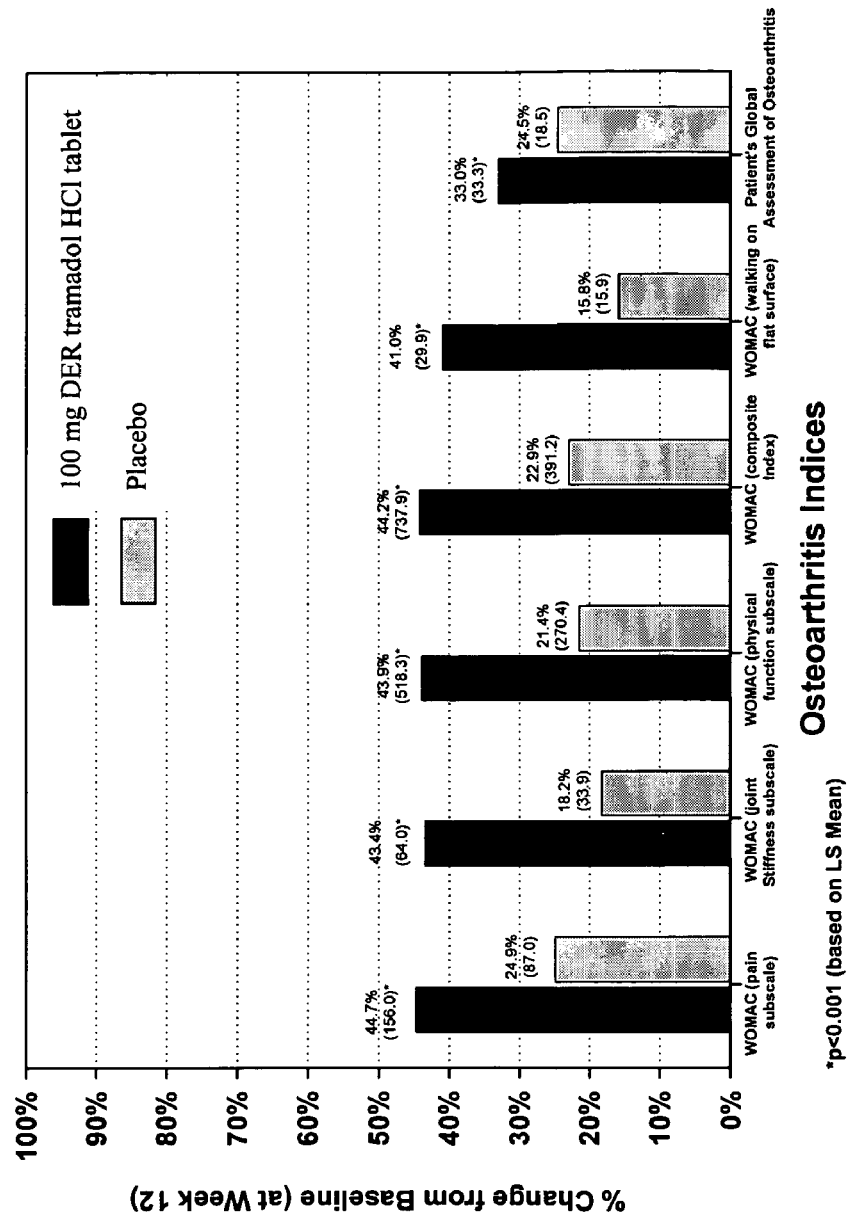
FIG. 26 is a comparison of the LS mean changes from baseline to Week 12 for the tramadol HCl DER tablets according to an embodiment of the invention and placebo for each of the secondary variables.

FIG. 26 compares the LS mean changes from baseline to Week 12 for the DER tramadol tablets and placebo for each of the secondary variables.

WOMAC Subscales

Results on the three dimensions of the WOMAC, namely pain, stiffness and physical function were similar to the main findings. The DER tramadol tablets were significantly better than placebo in improving pain, stiffness and physical function on the WOMAC.

At Week 12, on the WOMAC Pain Subscale, the DER tramadol was significantly different from placebo (change from baseline 44.6% [155.9 mm] vs. 24.8% [86.9 mm], LS mean difference on 0-100 mm Scale 13.8 mm, p<0.001).

At Week 12, on the WOMAC Stiffness Subscale, DER tramadol was significantly different from placebo (change from baseline 43.4% [63.9 mm] vs. 18.1% [33.8 mm], LS mean difference on 0-100 mm Scale 15.0 mm, p<0.001).

At Week 12, on the WOMAC Physical Function Subscale, DER tramadol was significantly different from placebo (change from baseline 43.8% [518.3 mm] vs. 21.3% [270.4 mm], LS mean difference on 0-100 mm Scale 14.6 mm, p<0.001).

At Week 12, on the WOMAC Composite Score, DER tramadol was significantly different from placebo (change from baseline 42.2% [737.9 mm] vs. 22.8% [391.2 mm], LS mean difference on 0-100 mm Scale 14.4 mm, p<0.001).

WOMAC Pain Walking on a Flat Surface

In the past, some studies have utilized one item from the WOMAC pain subscale as the primary endpoint. Since some of the questions on the WOMAC subscale relate to walking "up" or "down stairs" (and some areas of the country preferred by the elderly have few stairs, e.g., Arizona, New Mexico, Florida, etc), the WOMAC pain subscale question, "Pain Walking on a Flat Surface" is preferred by some biometricians.

At Week 12, on the WOMAC Pain Walking on Flat Surface, DER tramadol was significantly different from placebo (change from baseline 40.9% [29.9 mm] vs. 15.7% [15.9 mm], LS mean difference 14 mm, p<0.001). This is also shown in FIG. 26.

VI. Patient Global Assessment of Osteoarthritis

At Week 12, on the Patient Global Assessment of Arthritis, DER tramadol was significantly different from placebo (change from baseline 33.0% [33.2 mm] vs. 24.4% [18.5 mm], LS mean difference 14.7 mm, p<0.001).

VII. Safety Results

This was a placebo-controlled study without a positive control. Consequently, direct comparison with data on ULTRAM® product are not possible. However, indirect comparisons with the ULTRAM® product package insert are possible. Table 10 provides data on the cumulative incidence of adverse events on ULTRAM® in chronic non-malignant pain. The 90-day comparison is the most appropriate, given the 12 weeks duration of the present study. Adverse events were qualitatively similar. However, the incidence of the most commonly observed adverse events were generally lower for DER tramadol after up to 90 days compared to only 7 days of treatment with ULTRAM®.

TABLE 10

Cumulative Incidence of Adverse Reactions for ULTRAM ® in Chronic Trials of Nonmalignant Pain (N = 427). Data on a DER tramadol HCl tablet of Example 3 (Coating Formulation B/Coating Parameter B) from the 12-Week OA Study (N = 124) are Provided in Parenthesis for Comparison

|  | Up to 7 Days | Up to 30 Days | Up to 90 Days |
| --- | --- | --- | --- |
| Dizziness/Vertigo | 26% | 31% | 33% (33%) |
| Nausea | 24% | 34% | 40% (24.2%) |
| Constipation | 24% | 38% | 46% (25.8%) |
| Headache | 18% | 26% | 32% (14.5%) |
| Somnolence | 16% | 23% | 25% (8.1%) |
| Vomiting | 9% | 13% | 17% (6.5%) |
| Pruritus | 8% | 10% | 11% (6.5%) |
| "CNS Stimulation"[1] | 7% | 11% | 14% (ND) |
| Asthenia | 6% | 11% | 12% (ND) |
| Sweating | 6% | 7% | 9% (4%) |
| Dyspepsia | 5% | 9% | 13% (1.6%) |
| Dry Mouth | 5% | 9% | 10% (1.6%) |
| Diarrhea | 5% | 6% | 10% (9.7%) |

[1]"CNS Stimulation" is a composite of nervousness, anxiety, agitation, tremor, spasticity, euphoria, emotional lability and hallucinations.

VIII. Conclusion

DER tramadol produced statistically significant and clinically meaningful reductions in pain associated with osteoarthritis compared to placebo following a flexible dosing regimen in which the once-daily tablet formulation was titrated upward or downward over 12 weeks in doses of 200 mg, 300 mg or 400 mg based upon adequacy of pain relief and tolerability of side effects. The mean daily dose of DER tramadol was estimated to be about 300 mg. The primary efficacy variable was pain relief as measured on a visual analog scale (VAS). Secondary measures of efficacy were the pain intensity, stiffness and physical function subscales of WOMAC Osteoarthritis Index, the Patient's and Physician's Global Assessment of Arthritis, patient withdrawal due to inadequate pain relief, and patient assessment of sleep.

At the end of the first week of treatment and at all subsequent weeks, DER tramadol was statistically superior to placebo in reducing pain. The magnitude pain improvement (change from baseline) for the DER tramadol cohort increased weekly throughout the 12 weeks of therapy (25% at Week 1 and 47% at Week 12). By Week 12, patients treated with tramadol reported a clinically important 15 mm difference in mean pain relief score compared to placebo. This difference was highly statistically significant ($p<0.001$). Based upon the average of Weeks 1 through 12, the DER tramadol treated patients achieved a highly statistically significant and clinically meaningful 14 mm difference in mean pain relief score compared to placebo ($p<0.001$). The results for the secondary variables paralleled those of the primary with all results statistically significant in favor of DER tramadol.

The adverse events reported were qualitatively similar to that for ULTRAM®. However, the incidence was generally lower for DER tramadol than for that previously reported for ULTRAM®.

The results of this 12 week placebo controlled study demonstrate that DER tramadol, when given at a dose of 200 to 400 mg q.d., results in significant improvements in the cardinal symptoms of osteoarthritis, namely pain, stiffness and physical function. The safety profile of DER tramadol is consistent with that for ULTRAM®, although the frequency of some adverse events appears to be lower than historical controls.

IX. Clinical Implications

In the present study, using conventional endpoints for evaluating efficacy, DER tramadol demonstrated a 30.4 mm and 37.4 mm change from baseline in Arthritis Pain Intensity VAS, when expressed as a mean over 12 weeks (primary endpoint) and at the 12-Week time point, respectively. However, consistent with most such studies, the placebo treatment demonstrates a 17.7 mm and 22.1 mm change from baseline in Arthritis Pain Intensity VAS, when expressed as a mean over 12 weeks (primary endpoint) and at the 12-Week time point, respectively. Consequently, the actual treatment difference (response on DER tramadol less response on placebo) is a 12.7 mm and 15.3 mm change from baseline in Arthritis Pain Intensity VAS, when expressed as a mean over 12 weeks (primary endpoint) and at the 12-Week time point, respectively.

A close examination of the time course and magnitude of the pharmacological response (on the primary and secondary variables) following treatment with DER tramadol indicates that this is a clear drug effect: the magnitude of the response increases over time and all of the effects (pain, stiffness, physical function, patient global) are directionally consistent and generally of comparable size.

There are two available benchmarks for determining the robustness of the analgesic response to DER tramadol in osteoarthritis. One approach involves using the perspectives from the academic rheumatology community. The other involves using the results of pivotal studies in osteoarthritis from recently approved and commercially successful drugs.

In a consensus development (3-round Delphi exercise) involving academic rheumatologists, a 15 mm treatment difference in patients overall assessment of pain was considered to be the minimum clinically important difference (MCID) for clinical trial purposes (Bellamy N, Carette S, Ford P M et al. Osteoarthritis Antirheumatic Drug Trials. II. Tables for calculating sample size for clinical trials. J Rheumatol 1992; 19:444-50; Bellamy N, Carette S, Ford P M et al. Osteoarthritis Antirheumatic Drug Trials. III. Delta for Clinical Trials—Results of a Consensus Development (Delphi) Exercise. J Rheumatology 1992; 19:3, 451-457). However, in a recently published study, the minimum clinically perceptible improvement (MCPI) on the three dimensions of WOMAC pain, stiffness and physical function subscale scores (expressed using a 0-100 mm scale) were 9.7, 9.3 and 10 mm, respectively (Beaton D E, Bombardier C, Katz J et al. Looking for important change/difference in studies of responsiveness. J Rheumatol 2001; 28; 400-405.).

Data from other approved analgesics for which the NDA contained pivotal clinical trials in osteoarthritis were obtained from the FDA under a Freedom of Information (FOI) request. Although a direct comparison with other drugs is not possible and no drugs exist in the tramadol class (combined serotonergic, noradrenergic and opioidergic effects), data on other analgesics provide a context for the results of the DER tramadol study.

Rofecoxib (VIOXX®) is approved for the treatment of osteoarthritis at a daily dose of 12.5 mg; with the comment that some patients may derive a benefit from an increase in does to 25 mg per day (maximum dose). The efficacy studies with rofecoxib in osteoarthritis were 6 weeks in duration. The WOMAC variable "pain walking on a flat surface" was used as the primary endpoint. In most cases, the LS mean change from baseline over 6-weeks formed the basis of comparison. The mean difference between rofecoxib 12.5 mg and placebo was 14.3 mm (Study No. 029), 12.4 mm (Study No. 033), 15.4 mm (Study No. 040) and 9.0 (Study No. 058). Similarly, the mean difference between the positive control and placebo was 13.5 mm (Ibuprofen, 2400 mg, Study No. 033), 14.6 mm (Ibuprofen, 2400 mg, Study No. 040) and 10 mm (Nabumetone [Relafen], 1500 mg, Study No. 058).

Celecoxib (CELEBREX®) is approved for the treatment of osteoarthritis at a daily dose of 200 mg. Pivotal clinical trials were placebo controlled studies of either 6 or 12 weeks duration and used naproxen as the positive control. Study No. 020 and 054 served as pivotal clinical trials and Studies 040 and 087 were placebo controlled evaluations of celecoxib 100 mg BID vs. 200 mg QD. There were multiple primary endpoints in each of the studies, including Patients Assessment of Arthritis Pain VAS. The LS mean difference in pain VAS change from baseline between celecoxib 100 mg BID and placebo was 8.0 mm (12 weeks; Study No. 020), 12.2 mm (12 weeks; Study No. 054), 13.9 mm (6 weeks; Celecoxib 100 mg BID; Study No. 040) and 13.1 mm (6 weeks; Celecoxib 200 mg QD; Study No. 040), 6.2 mm (6 weeks; Celecoxib 100 mg BID; Study No. 087) and 8.5 mm (6 weeks; Celecoxib 100 mg BID; Study No. 087). Similarly, the mean difference between the positive control and placebo was 7.6 mm (Naproxen 500 mg BID, Study No. 020) and 11.2 mm (Naproxen 500 mg BID, Study No. 054).

The results of the present study demonstrate that DER tramadol at an approximate dose of 300 mg q.d. (range of about 200 to about 400 mg) provides a robust analgesic response in OA. The magnitude of the response is at least equal, if not superior to that of NSAIDs and COX-2 inhibitors. With its advantage of once daily dosing, DER tramadol will be an important addition to the therapeutic armamentarium of clinicians treating chronic pain.

EXAMPLE 11

DER Tramadol Chronic Low Back Pain Study

A double-blind, placebo-controlled, parallel-group comparison of the efficacy and safety of a 2×100 mg q.d. and a 3×100 mg DER tramadol HCl tablet of Example 3 (Coat Composition B/Coating Parameter B) to placebo in the treatment of chronic low back pain was conducted.

A multicenter, multiple-dose, randomized, placebo-controlled, parallel-group study involving a minimum of 360 patients designed to compare the analgesic efficacy and safety of the delayed and extended release tramadol (DER tramadol) 300 mg and 200 mg orally (PO) once-daily (q.d.) to placebo in patients with chronic low back pain.

I. Subjects

Patients with chronic 6 months) low back pain requiring daily treatment with an analgesic.

II. Design

An open-label run-in period followed by a double blind, randomized, multiple-dose, placebo-controlled study. Patients could rollover into an ongoing 1-year open-label extension study.

III. Treatment Regimen

A 3-week, open-label run-in period, including 2 weeks of dose titration on DER tramadol, beginning with 100 mg, to attain a tolerable dose of 300 mg q.d., followed by 1 week on a stable maintenance dose of DER tramadol 300 mg q.d. Following the run-in period, patients were randomized to one of the following double-blind treatments:

Treatment A: DER tramadol 3×100 mg q.d. (tablet of Example 3, Coating Composition B/Coating Parameter B) at 8:00 A.M.;

Treatment B: DER tramadol 2×100 mg q.d. (tablet of Example 3, Coating Composition B/Coating Parameter B) at 8:00 A.M.;

Treatment C: Placebo q.d. at 8:00 A.M.

IV. Enrollment Period 5 months

V. Treatment Period

At Screening (Visit 1), eligible patients underwent laboratory testing, and then entered a 2 to 7 day washout period during which all analgesic use was discontinued. At Visit 2 (Week −3), eligible patients who reported a pain intensity of ≧40 mm on a visual analog scale entered a 3-week, open-label run-in period. Patients were initiated on DER tramadol 100 mg q.d. and maintained at their dose for at least 3 days. On Day 4, and for the remainder of the week (until their return to the clinic for Visit 3, Week −2), patients had their dose increased to 200 mg q.d., based on the tolerability of side effects. Beginning at Visit 3 (Week −2), patients were maintained on a minimum DER tramadol dose of 200 mg q.d., and the dose titrated upwards (i.e. to 300 mg q.d.) based on the tolerability of side effects. Beginning at Visit 4 (Week −1), patients escalated their DER tramadol dose to 300 mg q.d. and maintained that dose for 1 week. No further dose adjustments were permitted during the remainder of the run-in period. In patients with pain unresponsive to appropriate dosage adjustments, or with unacceptable side effects, treatment was discontinued and alternate analgesic therapy initiated, as appropriate. Eligible patients receiving DER tramadol 300 mg q.d. at the end of the 3-week run-in period were entered into a 12-week, double-blind, randomized study. At Visit 5 (Week 0), patients were randomly assigned to receive tramadol 300 mg q.d., DER tramadol 200 mg q.d., or placebo q.d. Study medication dosing occurred daily at 8:00 A.M. No dose adjustments were permitted in the double-blind period. Patients unable to tolerate the double-blind study medication and those with unacceptable pain control were dropped from the study. Patients returned for efficacy and safety evaluations at Week 1 (Visit 6), Week 2 (Visit 7), Week 4 (Visit 8), Week 8 (Visit 9), and Week 12 (Visit 10), or Early Termination. Study medication was discontinued at Visit 10 and patients were treated with non-opioid analgesics until they returned to the clinic after 1 week for a post-study medication visit (Visit 11, Week 13). Patients were contacted by telephone between Visit 10 and Visit 11 to ensure that they were not taking opioid analgesics, including tramadol. Visit 11 was scheduled earlier than 1 week after Visit 10, in the event that patient pain could not be managed with nonopioid analgesics, and intervention with opioid analgesics or tramadol was necessary. At Visit 11, patients completed assessments for physical dependence and adverse events.

VI. No. of Centers

30 Centers

VII. No. of Subjects

Approximately 600 patients were enrolled to provide a minimum of 360 patients (120 patients per treatment).

IX. Efficacy

At each visit, patients were asked to rate their current pain intensity and their pain intensity since their previous visit, using a visual analog scale (VAS), and they provided an overall global assessment of study medication. The primary efficacy measure was the patient's pain intensity VAS score since the previous visit. Secondary measures included the patient's current pain intensity, the patient's global assessment, the Roland Disability Index, the patient's assessment of sleep and premature study termination due to inefficacy.

X. Safety

Safety was assessed at each visit by vital signs (heart rate, respiratory rate, supine or sitting and standing blood pressure) and a non-directed adverse events questionnaire. At Screening and at each visit, including Early Termination, patients were evaluated for the occurrence of syncope, orthostasis, dizziness, drop attacks and flushing (vasodilation). Adverse events were monitored throughout the study. Physical examination was performed at Screening (Visit 1) and at the Final Visit (Visit 11), or at Early Termination. Clinical laboratory testing was performed at Screening (Visit 1), at Week −3 (Visit 2), at Baseline (Week 0, Visit 5), at Week 1 (Visit 6), and at Week 12 (Visit 10) or Early Termination. In females of childbearing potential, serum pregnancy tests were performed at Screening (Visit 1), at Week −3 (Visit 2), at Baseline (Week 0, Visit 5), at Week 1 (Visit 6), at Week 4 (Visit 8), at Week 8 (Visit 9), and at Week 12 (Visit 10) or Early Termination. If the Screening (Visit 1) serum pregnancy results were not available from the central laboratory at the start of the run-in period (Visit 2), then the site obtained a urine pregnancy test locally. EKGs were performed at Screening (Visit 1), at Baseline (Week 0, Visit 5) and at Week 12 (Visit 10) or at Early Termination. The Addiction Research Center Inventory (ARCI) Short-form was completed by patients at each visit following the Screening Visit. The Physical Dependence Questionnaire was completed by patients at the start of the run-in period (Visit 2), at Week 12 (Visit 10), and at Week 13 (Visit 11) or at Early Termination.

Adverse events of all causalities that occurred during the double-blind period for at least 5% of all patients in the safety population are summarized by duration of exposure in Table 11A, and adverse events of all causalities that occurred during the run-in period for at least 5% of all patients in the population of all entered patients are summarized in Table 11B.

TABLE 11A

Adverse Events of All Causalities With Onset During the Double-Blind Period (≧5% of All Patients). Safety Population

| Duration of Treatment Exposure<br>Body System<br>Adverse event | Number (%) of Patients | | | |
|---|---|---|---|---|
| | Tramadol HCl ER 300 mg (N = 128) | Tramadol HCl ER 200 mg (N = 129) | Placebo (N = 127) | p-value[a] |
| Any event | 97 (75.8%) | 79 (61.2%) | 72 (56.7%) | 0.003 |
| 1 Week (1-7 days) | | | | |
| Gastrointestinal disorders | | | | |
| Nausea | 11 (8.6%) | 2 (1.6%) | 8 (6.3%) | 0.029 |
| Nervous system disorders | | | | |
| Headache | 11 (8.6%) | 6 (4.7%) | 6 (4.7%) | 0.346 |
| 4 Weeks (1-28 days) | | | | |
| Gastrointestinal disorders | | | | |
| Constipation | 16 (12.5%) | 5 (3.9%) | 1 (0.8%) | <0.001 |
| Nausea | 21 (16.4%) | 5 (3.9%) | 9 (7.1%) | 0.002 |
| Nervous system disorders | | | | |
| Dizziness | 12 (9.4%) | 8 (6.2%) | 9 (7.1%) | 0.635 |
| Headache | 17 (13.3%) | 13 (10.1%) | 12 (9.4%) | 0.619 |
| 12 Weeks (1-84 days) | | | | |
| Gastrointestinal disorders | | | | |
| Constipation | 19 (14.8%) | 7 (5.4%) | 1 (0.8%) | <0.001 |
| Diarrhea | 5 (3.9%) | 9 (7.0%) | 7 (5.5%) | 0.568 |
| Nausea | 25 (19.5%) | 10 (7.8%) | 9 (7.1%) | 0.003 |
| Nervous system disorders | | | | |
| Dizziness | 18 (14.1%) | 13 (10.1%) | 12 (9.4%) | 0.464 |
| Headache | 19 (14.8%) | 15 (11.6%) | 14 (11.0%) | 0.640 |
| Insomnia | 13 (10.2%) | 5 (3.9%) | 6 (4.7%) | 0.093 |

[a]Significant p-values are in bold.

TABLE 11B

Adverse Events of All Causalities With Onset During the Run-In Period (≧5% of All Patients). All Entered Patients

| Duration of Treatment Exposure<br>Body System<br>Adverse event | Number (%) or Patients | | | | |
|---|---|---|---|---|---|
| | Tramadol HCl ER 300 mg (N = 128) | Tramadol HCl ER 200 mg (N = 129) | Placebo (N = 129) | Not Randomized (N = 233) | p-value[a] |
| 1 Week (1-7 days) | | | | | |
| Gastrointestinal disorders | | | | | |
| Constipation | 18 (14.1%) | 12 (9.3%) | 12 (9.3%) | 21 (9.0%) | 0.425 |
| Nausea | 23 (18.0%) | 29 (22.5%) | 28 (21.7%) | 57 (24.5%) | 0.644 |
| Vomiting | 4 (3.1%) | 5 (3.9%) | 6 (4.7%) | 24 (10.3%) | 0.945 |
| Nervous system disorders | | | | | |
| Dininess | 12 (9.4%) | 12 (9.3%) | 16 (12.4%) | 66 (28.3%) | 0.665 |
| Headache | 7 (5.5%) | 15 (11.6%) | 14 (10.9%) | 25 (10.7%) | 0.184 |
| Somnolence | 7 (5.5%) | 12 (9.3%) | 16 (12.4%) | 30 (12.9%) | 0.159 |
| Skin & subcutaneous disorders | | | | | |
| Pruritus | 12 (9.4%) | 8 (6.2%) | 7 (5.4%) | 16 (6.9%) | 0.477 |
| Vascular disorders | | | | | |
| Flushing | 8 (6.3%) | 6 (4.7%) | 2 (1.6%) | 17 (7.3%) | 0.116 |

TABLE 11B-continued

Adverse Events of All Causalities With Onset During the Run-In Period (≧5% of All Patients). All Entered Patients

| | Number (%) or Patients | | | | |
|---|---|---|---|---|---|
| Duration of Treatment Exposure Body System Adverse event | Tramadol HCl ER 300 mg (N = 128) | Tramadol HCl ER 200 mg (N = 129) | Placebo (N = 129) | Not Randomized (N = 233) | p-value[a] |
| 2 Weeks (1 - 14 days) Gastrointestinal disorders | | | | | |
| Constipation | 28 (21.9%) | 23 (17.8%) | 21 (16.3%) | 31 (13.3%) | 0.490 |
| Nausea | 32 (25.0%) | 34 (26.4%) | 35 (27.1%) | 66 (28.3%) | 0.936 |
| Vomiting | 6 (4.7%) | 8 (6.2%) | 7 (5.4%) | 30 (12.9%) | 0.960 |
| General disorders and adminisiration site conditions | | | | | |
| Fatigue | 9 (7.0%) | 7 (5.4%) | 6 (4.7%) | 12 (5.2%) | 0.679 |
| Nervous system disorders | | | | | |
| Dizziness | 16 (12.5%) | 17 (13.2%) | 19 (14.7%) | 73 (31.3%) | 0.897 |
| Headache | 9 (7.0%) | 20 (15.5%) | 16 (12.4%) | 29 (12.4%) | 0.091 |
| Somnolence | 12 (9.4%) | 17 (13.2%) | 16 (12.4%) | 36 (15.5%) | 0.625 |
| Vascular disorders | | | | | |
| Flushing | 10 (7.8%) | 9 (7.0%) | 5 (3.9%) | 23 (9.9%) | 0.352 |

[a]Significant p-values are in bold.

EXAMPLE 12

A Two-Way, Crossover, Open-Label, Fasting, Single-Dose And Multiple-Dose Bioavailability Study Of Delayed and Extended Release Tramadol Hydrochloride 200 mg Tablets (Once Daily) Versus ULTRAM® 50 mg Tablets (Four Times Daily) In Normal Healthy Non-Smoking Male And Female Subjects was conducted.

I. Objectives

The objectives of this study were to determine the relative bioavailability of delayed and extended Release Tramadol HCl 200 mg tablets of Example 6 (Coating Parameter F) administered as a 200 mg dose (once daily) compared to ULTRAM® 50 mg Tablets administered as 50 mg (four times daily) under single-dose and steady-state conditions, and to investigate the extended release characteristics of the novel formulation.

II. Experimental Design

A two-way, crossover, open-label, single-dose and multiple-dose, fasting design.

III. Subjects

Thirty-six (36) normal, healthy, non-smoking male and female subjects.

IV. Drug Administration

Subjects received one of the following treatments, specific to the study-dosing day, during each of the two (2) 12-day study periods, according to the following dosage regimen in:
Treatment A: One (1) DER tramadol HCl 200 mg tablet (q.d.)
Treatment B: One (1) ULTRAM® 50 mg Tablet (q.i.d.)

Day 1:
Treatment A (q.d.):
One (1) DER tramadol HCl 200 mg tablet at 0.0 hour with 240 mL of ambient temperature water following an overnight fast of at least ten (10) hours.
(Total dose=200 mg).
Treatment B (Four Times Daily):
One (1) ULTRAM® 50 mg tablet was administered at 0.0 hour with 240 mL of ambient temperature water following an overnight fast of at least ten (10) hours.
A second dose of one (1) ULTRAM® 50 mg tablet was administered at 6.0 hours with 240 mL of ambient temperature water after a fast of at least one (1) hour.
A third dose of one (1) ULTRAM® 50 mg tablet was administered at 12.0 hours with 240 mL of ambient temperature water after a fast of at least one (1) hour.
A fourth dose of one (1) ULTRAM® 50 mg tablet was administered at 18.0 hours with 240 mL of ambient temperature water after a fast of at least one (1) hour.
(Total daily dose=200 mg).

Day 2:
No drug administration.

Days 3-10:
Treatment A (Once Daily):
One (1) DER tramadol HCl 200 mg tablet was administered at 0.0 hour with 240 mL of ambient temperature water following an overnight fast of at least ten (10) hours.
(Total dose=200 mg).
Treatment B (Four Times Daily):
One (1) ULTRAM® 50 mg tablet was administered at 0.0 hour with 240 mL of ambient temperature water following an overnight fast of at least ten (10) hours.
A second dose of one (1) ULTRAM® 50 mg tablet was administered at 6.0 hours with 240 mL of ambient temperature water after a fast of at least one (1) hour.
A third dose of one (1) ULTRAM® 50 mg tablet was administered at 12.0 hours with 240 mL of ambient temperature water after a fast of at least one (1) hour.
A fourth dose of one (1) ULTRAM® 50 mg tablet was administered at 18.0 hours with 240 mL of ambient temperature water after a fast of at least one (1) hour.
(Total daily dose=200 mg).

Washout Period:
At least a two (2) week washout period between the last dose of Period I to the first dose of Period II.

Sample Collection:
Treatment A had a total of twenty-nine (29) blood samples (7 mL each) drawn in each period. Treatment B had a total of fifty-five (55) blood samples (7 mL each) drawn in each period for drug content analysis at the following times and relative to the 0.0 hour drug administration of each study-dosing day, as follows:

Treatment A:
Days 1-3:
0.0 (pre-dose), 1.0, 2.0, 3.0, 4.0, 6.0, 8.0, 10.0, 12.0, 16.0, 20.0, 24.0 (Day 2), 36.0 and 48.0 (Day 3) hours post-drug administration.
Days 7, 8, 9:
0.0 (pre-dose)
Day 10:
0.0 (pre-dose), 1.0, 2.0, 3.0, 4.0, 6.0, 8.0, 10.0, 12.0, 16.0, 20.0 and 24.0 (Day 11) hours post-drug administration.

Treatment B:
Days 1-3:
0.0 (pre-dose), 0.5, 1.0, 1.5, 2.0, 4.0, 6.0, 6.5, 7.0, 7.5, 8.0, 10.0, 12.0, 12.5, 13.0, 13.5, 14.0, 16.0, 18.0, 18.5, 19.0, 19.5, 20.0, 22.0, 24.0 (Day 2), 36.0 and 48.0 (Day 3) hours post-drug administration.
Days 7, 8, 9:
0.0 (pre-dose). Pre-Dose samples not required for 6.0, 12.0 and 18.0 drug administration.
Day 10:
0.0 (pre-dose), 0.5, 1.0, 1.5, 2.0, 4.0, 6.0, 6.5, 7.0, 7.5, 8.0, 10.0, 12.0, 12.5, 13.0, 13.5, 14.0, 16.0, 18.0, 18.5, 19.0, 19.5, 20.0, 22.0 and 24.0 (Day 11) hours post-drug administration.

All blood samples, which coincided with drug administration, were drawn within 10 minutes prior to dosing.

There were no blood draws for drug content analysis on Days 4, 5, and 6.

Thirty-six subjects completed the study. Day 7 of dosing for each treatment attained steady state plasma levels of all analytes. Both products demonstrated similar AUC for tramadol under single dose (Ratio=90%; 90% C.I.=83-99%) and at steady state (Ratio=89%; 90% C.I.=84-94%). $T_{max}$ from DER tramadol was significantly longer (p<0.05). In conclusion, a once daily product, DER tramadol made according to one aspect of the invention, was found to demonstrate similar AUC relative to ULTRAM® given four times daily. The plasma concentration vs time profile demonstrated prolonged systemic delivery of tramadol. This product is suitable for once daily administration.

Tables 12A-F provide the mean plasma concentration time profiles for tramadol, desmethyltramadol, and didesmethyltramadol when the DER tramadol HCl tablets are administered under a single- or multiple-dosing regimen compared to ULTRAM®, Tables 12G-L summarizes the pharmacokinetic parameters for tramadol, desmethyltramadol, and didesmethyltramadol when the DER tramadol HCL tablets are administered compared to ULTRAM® under a single- or multiple-dosing regimen, and Tables 12M-R provide the relative bioavailability analysis for tramadol, desmethyltramadol, and didesmethyltramadol, of the DER tramadol tablets versus ULTRAM° under a single- or multiple dosing regimen.

TABLE 12A (Mean (±SD) Plasma Concentration-Time Profiles for Tramadol (ng/mL) Single-Dose))

| Hours | Treatment A (1 × 200 mg) Mean ± SD | Treatment B (4 × 50 mg) Mean ± SD |
|---|---|---|
| 0.0 | 0.000 ± 0.000 | 0.000 ± 0.000 |
| 0.5 | — | 39.661 ± 40.840 |
| 1.0 | 0.167 ± 0.659 | 114.496 ± 47.058 |

TABLE 12A-continued (Mean (±SD) Plasma Concentration-Time Profiles for Tramadol (ng/mL) Single-Dose))

| Hours | Treatment A (1 × 200 mg) Mean ± SD | Treatment B (4 × 50 mg) Mean ± SD |
|---|---|---|
| 1.5 | — | 132.150 ± 34.078 |
| 2.0 | 6.711 ± 4.128 | 132.958 ± 31.526 |
| 3.0 | 17.604 ± 8.289 | — |
| 4.0 | 32.372 ± 15.414 | 102.362 ± 24.944 |
| 6.0 | 95.112 ± 73.170 | 81.425 ± 23.267 |
| 6.5 | — | 85.634 ± 36.967 |
| 7.0 | — | 113.144 ± 70.267 |
| 7.5 | — | 140.204 ± 74.667 |
| 8.0 | 144.273 ± 85.625 | 158.469 ± 70.587 |
| 10.0 | 176.680 ± 78.128 | 172.499 ± 46.685 |
| 12.0 | 210.190 ± 75.483 | 131.122 ± 38.911 |
| 12.5 | — | 137.865 ± 53.363 |
| 13.0 | — | 166.699 ± 70.529 |
| 13.5 | — | 181.891 ± 68.216 |
| 14.0 | — | 203.898 ± 77.579 |
| 16.0 | 214.278 ± 92.105 | 184.824 ± 58.359 |
| 18.0 | — | 154.686 ± 57.060 |
| 18.5 | — | 150.269 ± 52.568 |
| 19.0 | — | 182.943 ± 68.067 |
| 19.5 | — | 205.774 ± 86.967 |
| 20.0 | 173.782 ± 82.192 | 205.561 ± 81.945 |
| 22.0 | — | 198.821 ± 66.916 |
| 24.0 | 132.108 ± 64.445 | 156.779 ± 55.024 |
| 36.0 | 46.269 ± 28.195 | 35.899 ± 21.273 |
| 48.0 | 16.538 ± 11.611 | 10.854 ± 8.540 |

Figure 27:
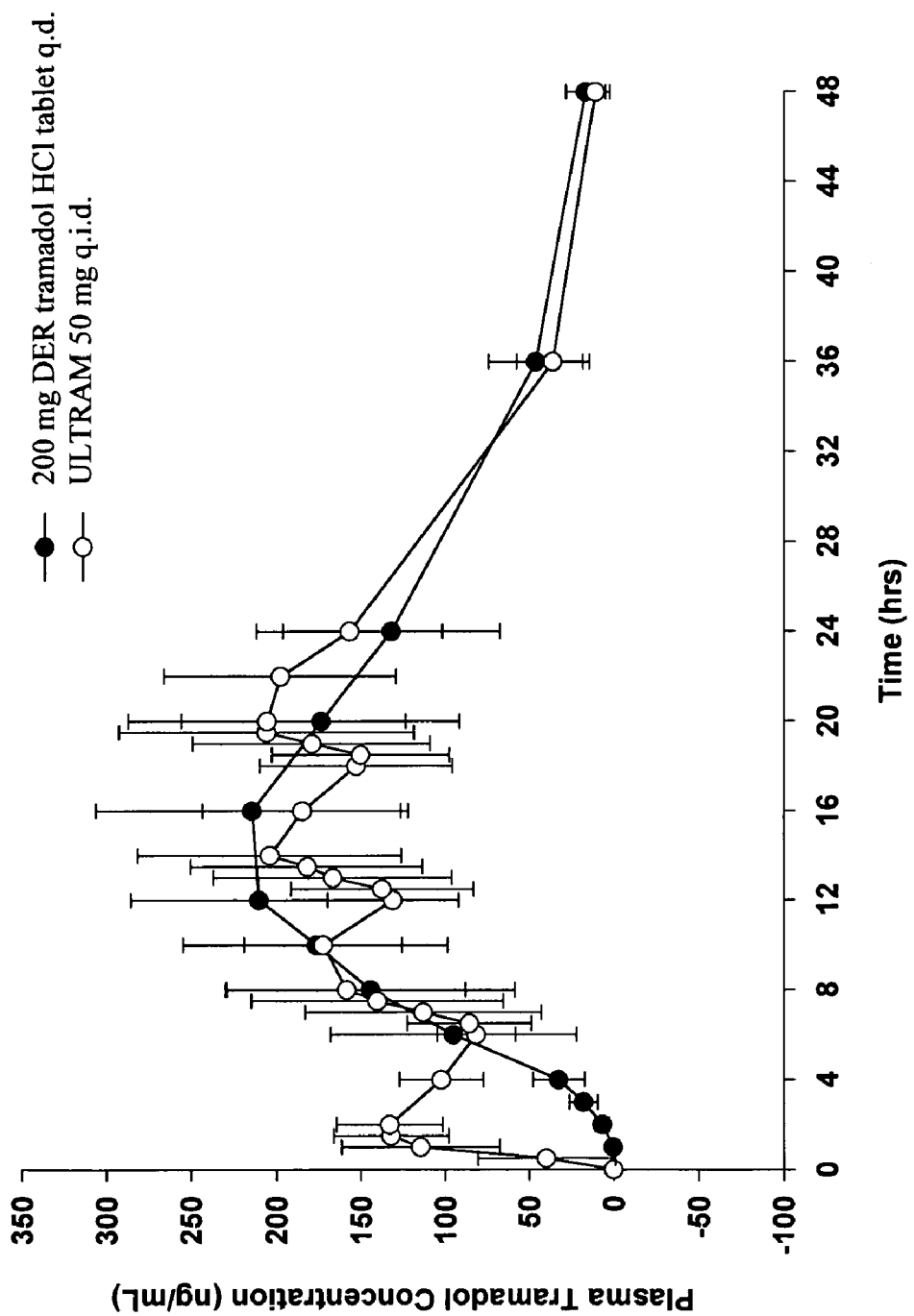
FIG. 27 is a graph illustrating the mean plasma tramadol concentrations over time on Day 1 of a 12 day study period following administration of a single dose and multiple dose of a 200 mg DER tramadol HCl tablet q.d. according to an embodiment of the invention compared to ULTRAM® 50 mg q.i.d. under fasting conditions.

Table 12A is graphically presented in FIG. 27.

TABLE 12B (Mean (±SD) Plasma Concentration-Time Profiles for Desmethyltramadol (M1) (ng/mL) (Single-Dose))

| Hours | Treatment A (1 × 200 mg) Mean ± SD | Treatment B (4 × 50 mg) Mean ± SD |
|---|---|---|
| 0.0 | 0.037 ± 0.206 | 0.112 ± 0.357 |
| 0.5 | — | 11.053 ± 9.212 |
| 1.0 | 0.142 ± 0.639 | 27.751 ± 13.640 |
| 1.5 | — | 35.973 ± 14.295 |
| 2.0 | 1.731 ± 1.809 | 40.539 ± 15.659 |
| 3.0 | 5.041 ± 2.820 | — |
| 4.0 | 10.055 ± 5.107 | 40.038 ± 12.828 |
| 6.0 | 25.784 ± 19.323 | 35.316 ± 9.899 |
| 6.5 | — | 34.500 ± 10.271 |
| 7.0 | — | 38.802 ± 14.763 |
| 7.5 | — | 46.329 ± 18.867 |
| 8.0 | 42.046 ± 26.865 | 50.819 ± 18.902 |
| 10.0 | 56.091 ± 29.637 | 60.828 ± 17.240 |
| 12.0 | 69.206 ± 28.447 | 53.430 ± 13.917 |
| 12.5 | — | 53.748 ± 14.135 |
| 13.0 | — | 58.758 ± 16.934 |
| 13.5 | — | 62.088 ± 18.937 |
| 14.0 | — | 67.873 ± 19.433 |
| 16.0 | 78.978 ± 27.318 | 68.941 ± 18.913 |
| 18.0 | — | 63.529 ± 16.684 |
| 18.5 | — | 62.565 ± 16.374 |
| 19.0 | — | 69.658 ± 22.827 |
| 19.5 | — | 74.614 ± 23.383 |
| 20.0 | 71.897 ± 23.204 | 77.648 ± 22.610 |
| 22.0 | — | 80.164 ± 22.591 |
| 24.0 | 57.593 ± 18.702 | 72.071 ± 21.221 |
| 36.0 | 21.983 ± 9.678 | 20.144 ± 7.539 |
| 48.0 | 8.883 ± 4.982 | 6.728 ± 3.447 |

Figure 29:
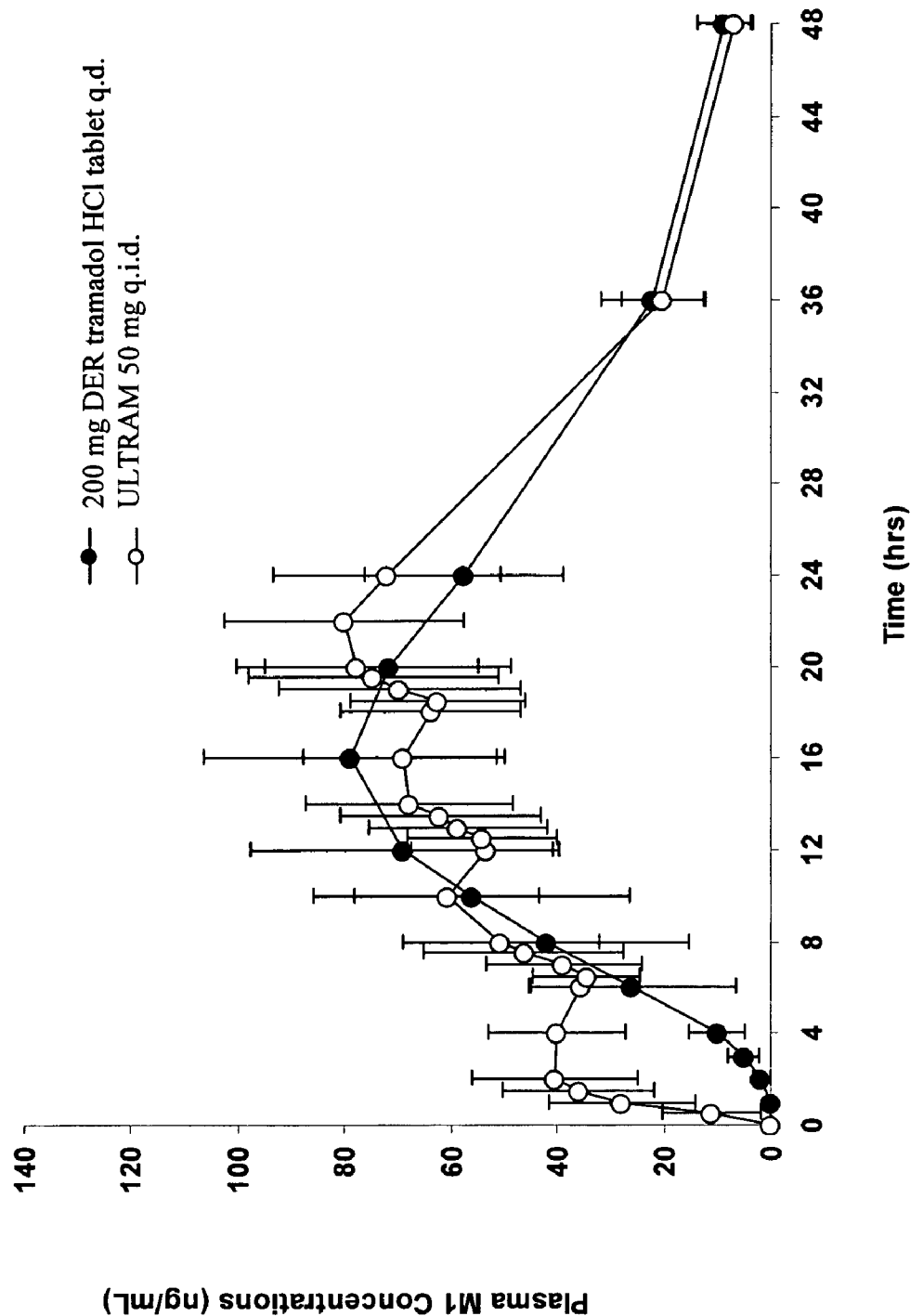
FIG. 29 is a graph illustrating the mean plasma desmethyltramadol (M1) concentrations over time on Day 1 of a 12-day study period following administration of a single dose and multiple dose of the tablets of FIG. 27 under fasting conditions.

Table 12B is graphically presented in FIG. 29

TABLE 12C (Mean (±SD) Plasma Concentration-Time Profiles for Didesmethyltramadol (M5) (ng/mL) (Single-Dose))

| Hours | Treatment A (1 × 200 mg) Mean ± SD | Treatment B (4 × 50 mg) Mean ± SD |
|---|---|---|
| 0.0 | 0.035 ± 0.198 | 0.000 ± 0.000 |
| 0.5 | — | 3.098 ± 2.980 |
| 1.0 | 0.000 ± 0.000 | 7.527 ± 3.531 |
| 1.5 | — | 9.681 ± 3.242 |
| 2.0 | 0.037 ± 0.209 | 11.296 ± 4.092 |
| 3.0 | 1.113 ± 0.926 | — |
| 4.0 | 2.601 ± 1.299 | 12.490 ± 3.697 |
| 6.0 | 7.334 ± 4.693 | 12.705 ± 4.030 |
| 6.5 | — | 12.164 ± 4.144 |
| 7.0 | — | 13.729 ± 5.616 |
| 7.5 | — | 15.904 ± 6.562 |
| 8.0 | 12.755 ± 7.109 | 17.113 ± 6.973 |
| 10.0 | 18.183 ± 8.743 | 20.775 ± 6.235 |
| 12.0 | 22.901 ± 9.137 | 20.422 ± 6.731 |
| 12.5 | — | 20.205 ± 7.432 |
| 13.0 | — | 21.781 ± 8.533 |
| 13.5 | — | 22.008 ± 9.527 |
| 14.0 | — | 24.100 ± 9.418 |
| 16.0 | 27.475 ± 9.428 | 25.002 ± 8.947 |
| 18.0 | — | 24.097 ± 8.027 |
| 18.5 | — | 23.184 ± 7.930 |
| 19.0 | — | 25.554 ± 8.895 |
| 19.5 | — | 26.620 ± 9.318 |
| 20.0 | 25.968 ± 9.122 | 28.049 ± 9.668 |
| 22.0 | — | 29.282 ± 9.248 |
| 24.0 | 22.063 ± 8.843 | 26.052 ± 9.107 |
| 36.0 | 9.968 ± 5.073 | 9.631 ± 4.623 |
| 48.0 | 4.225 ± 2.774 | 3.387 ± 2.289 |

Figure 31:
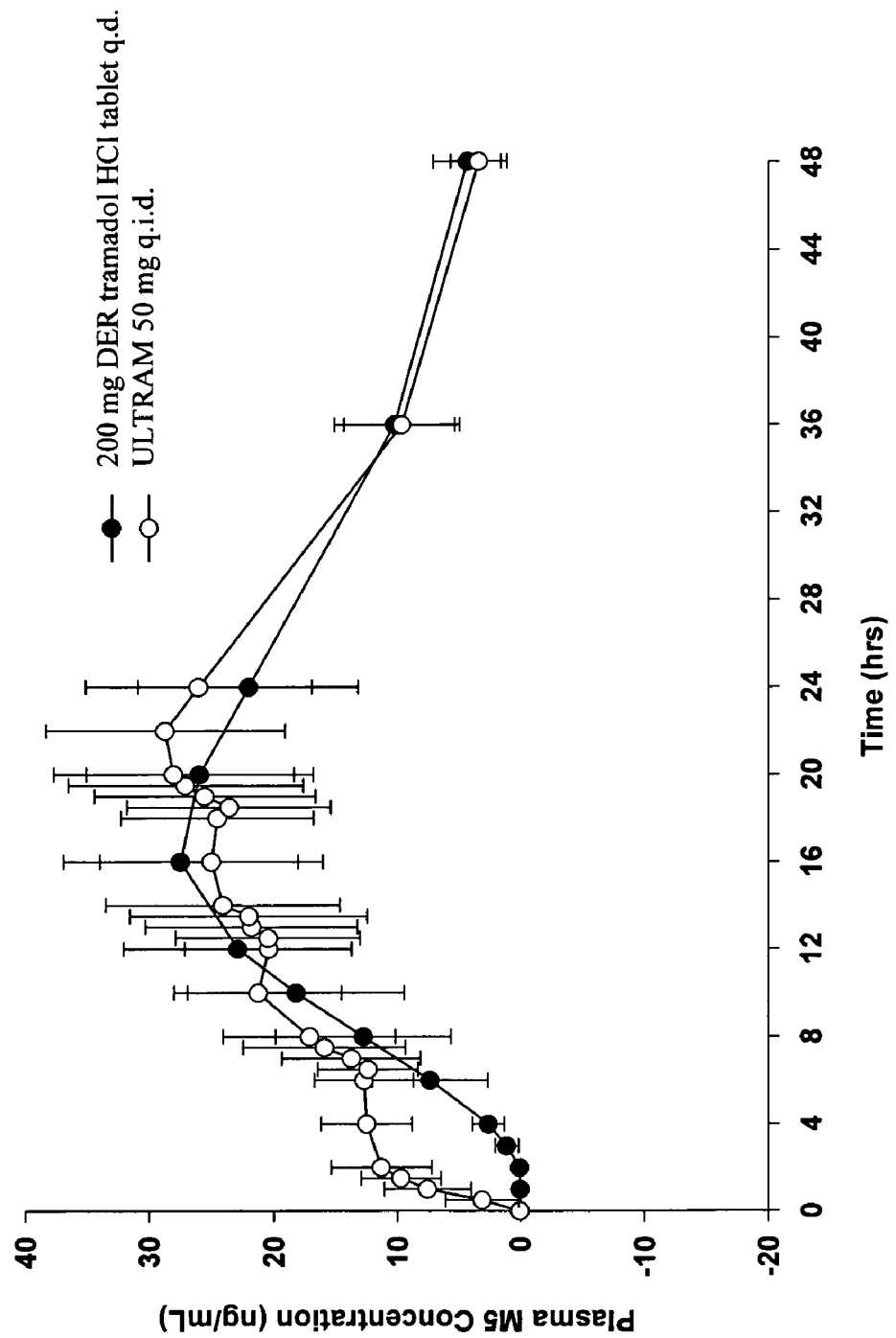
FIG. 31 is a graph illustrating the mean plasma didesmethyltramadol (M5) concentrations over time on Day 1 of a 12-day study period following administration of a single dose and multiple dose of the tablets of FIG. 27 under fasting conditions.

Table 12C is presented graphically in FIG. 31

TABLE 12D (Mean (±SD) Plasma Concentration-Time Profiles for Tramadol (ng/mL) (Multiple-Dose))

| Hours | Treatment A (1 × 200 mg) Mean ± SD | Treatment B (4 × 50 mg) Mean ± SD |
|---|---|---|
| Day 7 | 172.260 ± 86.654 | 222.253 ± 74.822 |
| Day 8 | 165.631 ± 89.639 | 208.205 ± 69.644 |
| Day 9 | 178.611 ± 70.424 | 208.345 ± 67.377 |
| Day 10 0.0 | 181.080 ± 75.681 | 217.318 ± 73.031 |
| 0.5 | — | 239.237 ± 81.718 |
| 1.0 | 169.850 ± 76.343 | 305.008 ± 82.624 |
| 1.5 | — | 324.188 ± 79.985 |
| 2.0 | 168.811 ± 73.497 | 322.966 ± 79.327 |
| 3.0 | 176.662 ± 77.092 | — |
| 4.0 | 185.678 ± 76.516 | 278.551 ± 83.145 |
| 6.0 | 244.557 ± 100.530 | 227.146 ± 74.007 |
| 6.5 | — | 250.215 ± 69.072 |
| 7.0 | — | 295.069 ± 72.288 |
| 7.5 | — | 309.479 ± 81.004 |
| 8.0 | 291.578 ± 117.818 | 317.119 ± 87.116 |
| 10.0 | 311.004 ± 107.742 | 294.493 ± 94.117 |
| 12.0 | 311.222 ± 103.406 | 228.819 ± 75.602 |
| 12.5 | — | 240.710 ± 88.065 |
| 13.0 | — | 272.966 ± 109.605 |
| 13.5 | — | 286.259 ± 113.756 |
| 14.0 | — | 303.417 ± 107.971 |
| 16.0 | 290.068 ± 98.332 | 269.550 ± 90.764 |
| 18.0 | — | 220.034 ± 77.524 |
| 18.5 | — | 230.974 ± 78.174 |
| 19.0 | — | 298.965 ± 97.855 |
| 19.5 | — | 317.634 ± 86.238 |
| 20.0 | 232.071 ± 83.494 | 314.616 ± 86.295 |
| 22.0 | — | 270.906 ± 82.463 |
| 24.0 | 186.538 ± 69.511 | 227.680 ± 72.362 |

Figure 28:
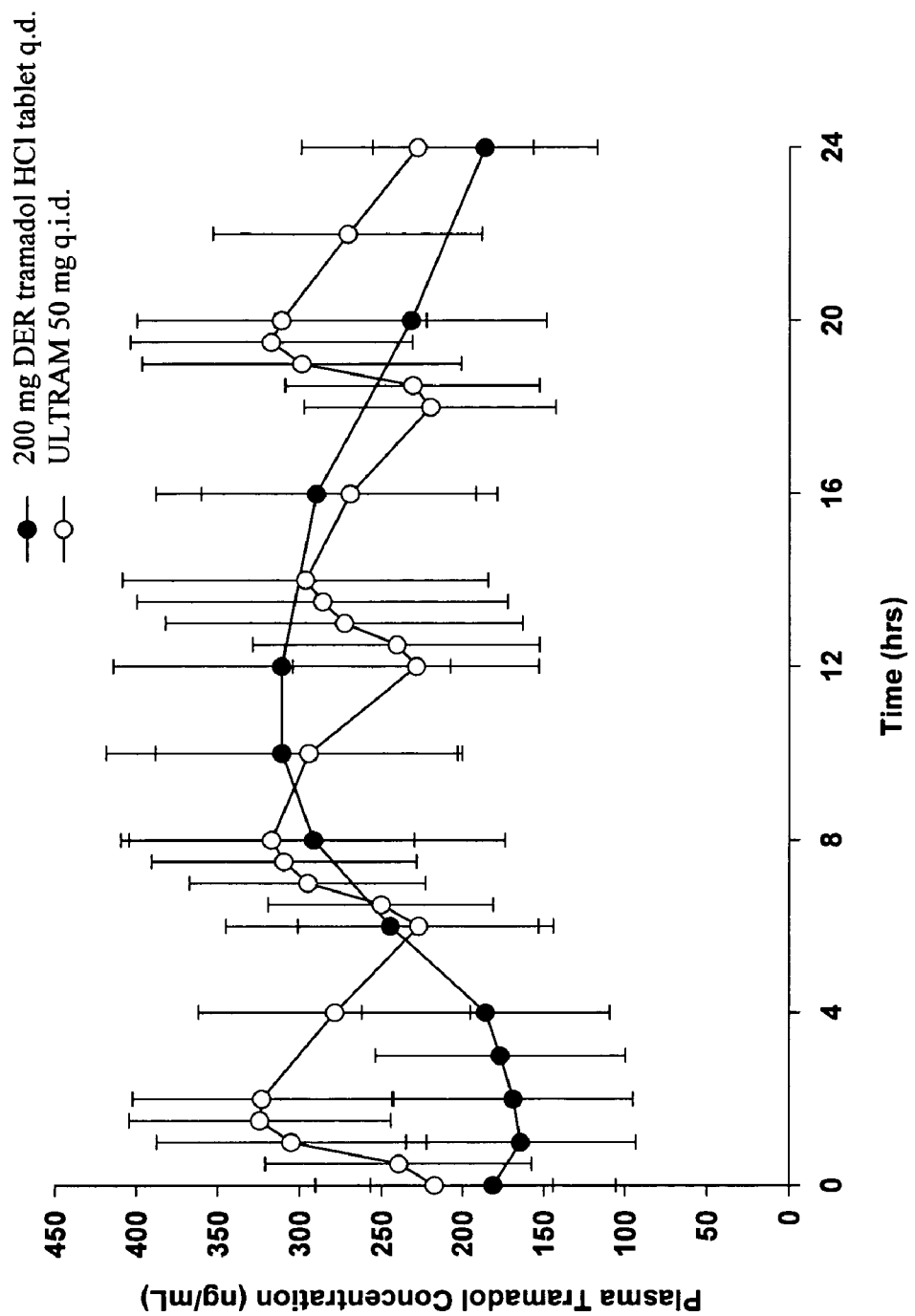
FIG. 28 is a graph illustrating the mean plasma tramadol concentrations over time on Day 10 of a 12-day study period following administration of a single dose and multiple dose of the tablets of FIG. 27 under fasting conditions.

Table 12D is presented graphically in FIG. 28

TABLE 12E (Mean (±SD) Plasma Concentration-Time Profiles for Desmethyltramadol (M1) (ng/mL) (Multiple-Dose))

| Hours | Treatment A (1 × 200 mg) Mean ± SD | Treatment B (4 × 50 mg) Mean ± SD |
|---|---|---|
| Day 7 | 64.165 ± 23.744 | 81.109 ± 22.933 |
| Day 8 | 64.118 ± 27.384 | 80.275 ± 22.049 |
| Day 9 | 70.204 ± 20.574 | 80.300 ± 21.690 |
| Day 10 0.0 | 66.667 ± 20.879 | 77.732 ± 21.598 |
| 0.5 | — | 81.556 ± 19.798 |
| 1.0 | 62.713 ± 19.753 | 90.092 ± 19.924 |
| 1.5 | — | 93.349 ± 19.781 |
| 2.0 | 61.044 ± 19.222 | 94.693 ± 20.198 |
| 3.0 | 61.783 ± 19.580 | — |
| 4.0 | 62.575 ± 19.225 | 90.586 ± 22.032 |
| 6.0 | 70.432 ± 19.820 | 80.339 ± 20.357 |
| 6.5 | — | 83.446 ± 22.673 |
| 7.0 | — | 89.370 ± 25.446 |
| 7.5 | — | 88.847 ± 25.183 |
| 8.0 | 80.975 ± 23.261 | 91.298 ± 25.550 |
| 10.0 | 87.936 ± 24.747 | 92.109 ± 24.126 |
| 12.0 | 89.795 ± 23.229 | 79.121 ± 24.414 |
| 12.5 | — | 79.632 ± 25.149 |
| 13.0 | — | 82.772 ± 28.524 |
| 13.5 | — | 85.220 ± 29.459 |
| 14.0 | — | 86.631 ± 28.178 |
| 16.0 | 90.703 ± 23.351 | 84.720 ± 25.744 |
| 18.0 | — | 77.673 ± 23.522 |
| 18.5 | — | 79.629 ± 24.830 |
| 19.0 | — | 90.084 ± 26.437 |
| 19.5 | — | 94.817 ± 24.915 |
| 20.0 | 81.932 ± 21.785 | 96.805 ± 25.489 |
| 22.0 | — | 90.633 ± 23.673 |
| 24.0 | 69.142 ± 20.703 | 81.981 ± 22.364 |

Figure 30:
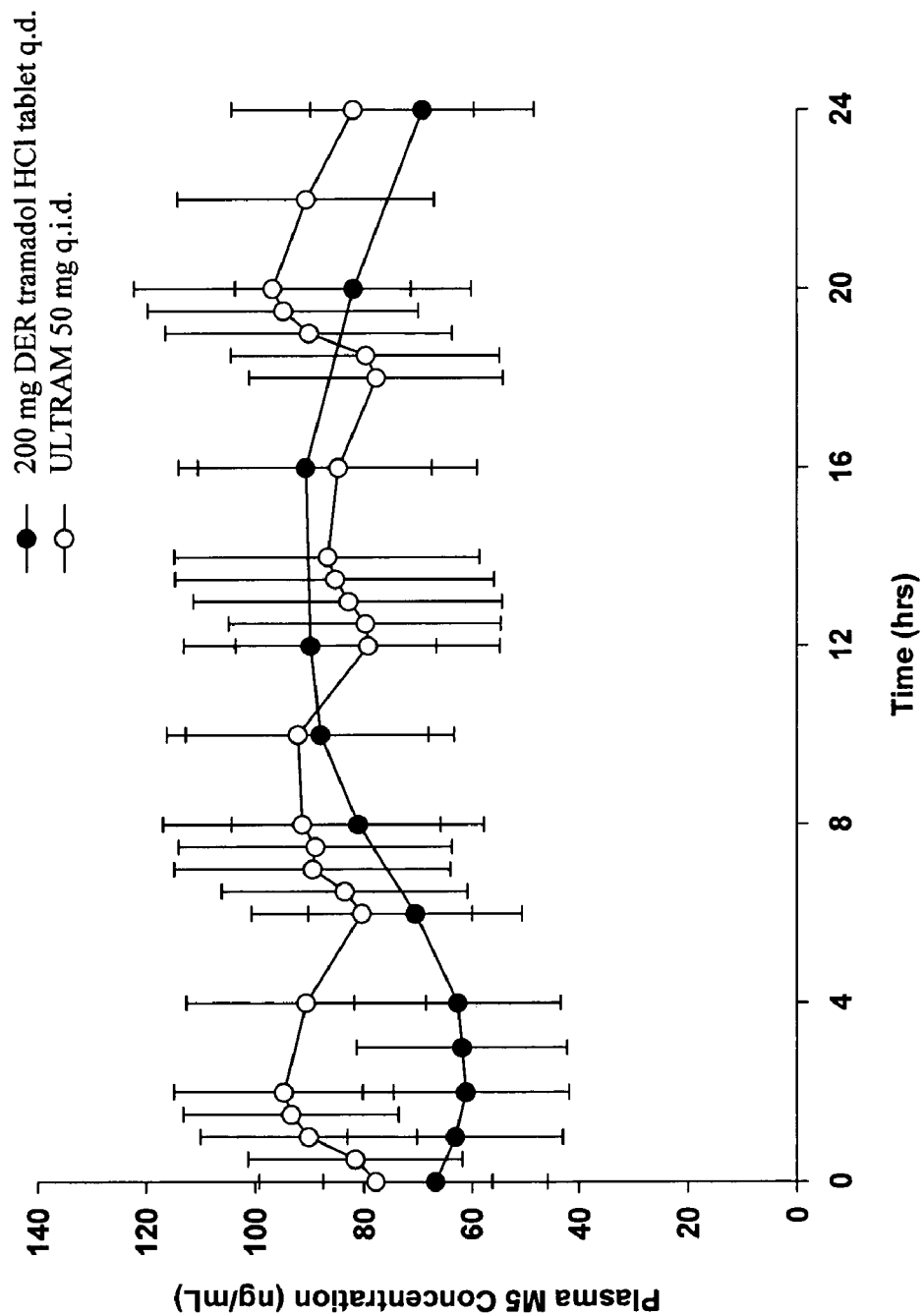
FIG. 30 is a graph illustrating the mean plasma desmethyltramadol (M1) concentrations over time on Day 10 of a 12-day study period following administration of a single dose and multiple dose of the tablets of FIG. 27 under fasting conditions.

The data in Table 12E is presented graphically in FIG. 30

TABLE 12F (Mean (±SD) Plasma Concentration-Time Profiles for Didesmethyltramadol (M5) (ng/mL) (Multiple-Dose))

| Hours | Treatment A (1 × 200 mg) Mean ± SD | Treatment B (4 × 50 mg) Mean ± SD |
|---|---|---|
| Day 7 | 35.089 ± 14.474 | 42.440 ± 12.849 |
| Day 8 | 31.976 ± 13.547 | 38.980 ± 12.616 |
| Day 9 | 34.426 ± 14.884 | 39.204 ± 12.311 |
| Day 10 0.0 | 36.667 ± 15.036 | 41.238 ± 14.662 |
| 0.5 | — | 42.378 ± 13.491 |
| 1.0 | 33.625 ± 13.860 | 44.544 ± 13.517 |
| 1.5 | — | 45.317 ± 14.018 |
| 2.0 | 32.958 ± 13.611 | 45.891 ± 13.966 |
| 3.0 | 32.519 ± 12.585 | — |
| 4.0 | 32.455 ± 12.388 | 45.654 ± 14.599 |
| 6.0 | 35.541 ± 13.014 | 42.998 ± 13.319 |
| 6.5 | — | 44.058 ± 14.122 |
| 7.0 | — | 45.558 ± 14.828 |
| 7.5 | — | 44.926 ± 15.465 |
| 8.0 | 39.531 ± 13.868 | 45.444 ± 14.043 |
| 10.0 | 44.265 ± 15.256 | 47.752 ± 13.720 |
| 12.0 | 44.814 ± 15.160 | 42.781 ± 14.071 |
| 12.5 | — | 43.175 ±_ 14.871 |
| 13.0 | — | 43.881 ± 15.852 |
| 13.5 | — | 44.448 ± 15.400 |
| 14.0 | — | 45.590 ± 15.522 |
| 16.0 | 46.887 ± 15.866 | 44.679 ± 15.591 |
| 18.0 | — | 42.633 ± 14.258 |
| 18.5 | — | 42.781 ± 14.482 |
| 19.0 | — | 45.742 ± 14.501 |
| 19.5 | — | 47.028 ± 14.852 |
| 20.0 | 45.335 ± 17.055 | 47.271 ± 14.722 |
| 22.0 | — | 45.744 ± 15.384 |
| 24.0 | 38.305 ± 17.317 | 43.580 ± 15.859 |

Figure 32:
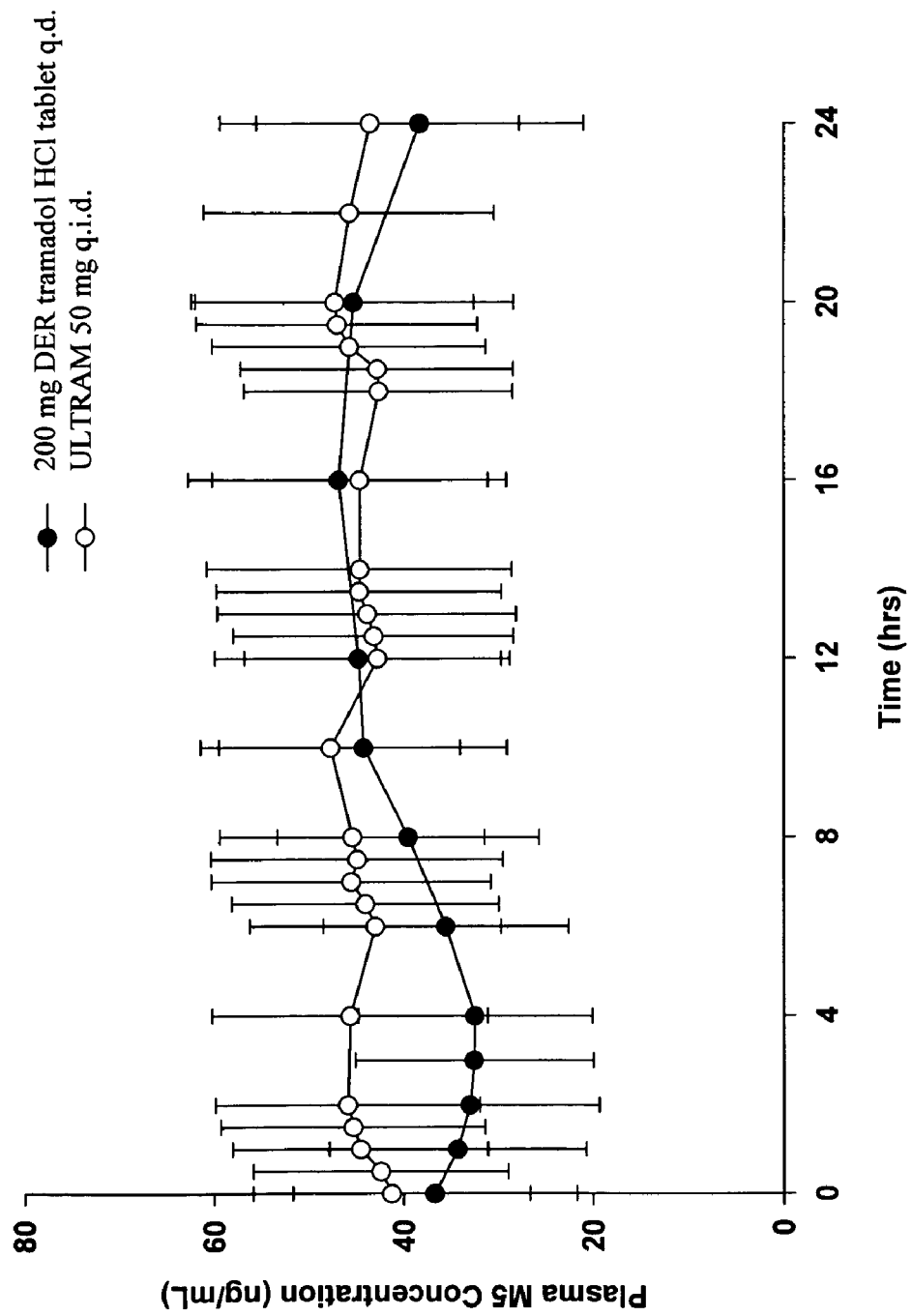
FIG. 32 is a graph illustrating the mean plasma didesmethyltramadol (M5) concentrations over time on Day 10 of a 12-day study period following administration of a single dose and multiple dose of the tablets of FIG. 27 under fasting conditions.

Table 12F is presented graphically in FIG. 32.

TABLE 12G (Pharmacokinetic Parameters for Tramadol Single-Dose)

| Pharmacokinetic Parameter | Tramadol HCl 200 mg Extended Release Tablets (A) N = 32 Mean ± SD | ULTRAM ® 4 × 50 mg Tablets (B) N = 32 Mean ± SD |
|---|---|---|
| $AUC_{0-t}$ (ng.hr/mL) | 4792.17 ± 2017.83 | 5095.20 ± 1595.42 |
| $AUC_{0-inf}$ (ng.hr/mL) | 4999.94 ± 2139.00 | 5174.38 ± 1687.68 |
| $C_{max}$ (ng/mL) | 234.23 ± 90.43 | 257.98 ± 69.04 |
| $T_{max}$ (hour) | 13.57 ± 3.76 | 2.22 ± 1.36 |
| $t_{1/2}$ (hour) | 7.66 ± 1.76 | 5.76 ± 1.15 |
| $K_{el}$ (hour$^{-1}$) | 0.096 ± 0.024 | 0.125 ± 0.025 |
| MRT (hours) | 2.22 ± 1.47 | 1.03 ± 0.69 |

TABLE 12H (Pharmacokinetic Parameters for Tramadol Multiple-Dose)

| Pharmacokinetic Parameter | Tramadol HCl 200 mg Extended Release Tablets (A) N = 32 Mean ± SD | ULTRAM ® 4 × 50 mg Tablets (B) N = 32 Mean ± SD |
|---|---|---|
| $AUC_\tau$ (ng.hr/mL) | 5975.03 ± 2027.42 | 6612.66 ± 1790.04 |
| $C_{max}$ (ng/mL) | 335.44 ± 116.11 | 382.49 ± 79.86 |
| $C_{min}$ (ng/mL) | 186.54 ± 69.51 | 227.68 ± 72.36 |
| $T_{max}$ (hour) | 11.88 ± 3.17 | 1.49 ± 0.63 |
| Degree of Fluctuation (%) | 61.03 ± 34.51 | 59.36 ± 20.77 |
| Degree of Swing (%) | 103.76 ± 103.14 | 76.30 ± 34.17 |
| $C_{avg}$ (ng/mL) | 248.96 ± 84.48 | 275.53 ± 74.59 |

TABLE 12I (Pharmacokinetic Parameters for O-desmethyltramadol (M1) Single-Dose)

| Pharmacokinetic Parameter | Tramadol HCl 200 mg Extended Release Tablet (A) N = 32 Mean ± SD | ULTRAM ® 4 × 50 mg Tablets (B) N = 32 Mean ± SD |
|---|---|---|
| $AUC_{0-t}$ (ng.hr/mL) | 1856.01 ± 596.66 | 2063.81 ± 501.78 |
| $AUC_{0-inf}$ (ng.hr/mL) | 1984.59 ± 636.68 | 2168.12 ± 527.97 |
| $C_{max}$ (ng/mL) | 83.42 ± 27.52 | 88.79 ± 21.21 |
| $T_{max}$ (hour) | 15.57 ± 3.16 | 2.97 ± 1.57 |
| $t_{1/2}$ (hour) | 8.95 ± 2.20 | 6.90 ± 1.22 |
| $K_{el}$ (hour$^{-1}$) | 0.082 ± 0.022 | 0.104 ± 0.020 |
| MRT (hours) | 3.91 ± 2.70 | 1.85 ± 1.10 |
| M/P ratio | 0.4747 ± 0.2121 | 0.4901 ± 0.2056 |

TABLE 12J (Pharmacokinetic Parameters for O-desmethyltramadol (M1) Multiple-Dose)

| Pharmacokinetic Parameter | Tramadol HCl 200 mg Extended Release Tablets (A) N = 32 Mean ± SD | ULTRAM ® 4 × 50 mg Tablets (B) N = 32 Mean ± SD |
|---|---|---|
| $AUC_\tau$ (ng.hr/mL) | 1889.96 ± 481.47 | 2095.37 ± 539.58 |
| $C_{max}$ (ng/mL) | 95.44 ± 23.09 | 104.35 ± 24.57 |
| $C_{min}$ (ng/mL) | 69.14 ± 20.70 | 81.98 ± 22.36 |
| $T_{max}$ (hour) | 14.63 ± 3.92 | 1.94 ± 1.10 |
| Degree of Fluctuation (%) | 33.50 ± 24.21 | 26.10 ± 12.23 |
| Degree of Swing (%) | 45.56 ± 46.27 | 30.03 ± 20.41 |
| $C_{avg}$ (ng/mL) | 78.75 ± 20.06 | 87.31 ± 22.48 |
| M/P ratio | 0.3610 ± 0.1192 | 0.3510 ± 0.1041 |

TABLE 12K

Pharmacokinetic Parameters for O,N-di-desmethyltramadol (M5) Single-Dose

| Pharmacokinetic Parameter | Tramadol HCl 200 mg Extended Release Tablets (A) N = 32 Mean ± SD | ULTRAM ® 4 × 50 mg Tablets (B) N = 32 Mean ± SD |
|---|---|---|
| $AUC_{0-t}$ (ng.hr/mL) | 684.84 ± 244.04 | 765.01 ± 239.00 |
| $AUC_{0-inf}$ (ng.hr/mL) | 757.34 ± 282.87 | 804.97 ± 264.89 |
| $C_{max}$ (ng/mL) | 29.00 ± 9.09 | 31.03 ± 9.03 |
| $T_{max}$ (hour) | 16.82 ± 3.44 | 2.92 ± 1.48 |
| $t_{1/2}$ (hour) | 10.07 ± 2.48 | 8.24 ± 2.07 |
| $K_{el}$ (hour$^{-1}$) | 0.074 ± 0.021 | 0.089 ± 0.021 |
| MRT (hours) | 5.53 ± 3.43 | 3.42 ± 2.49 |
| M/P ratio (based on $AUC_{0-inf}$) | 0.1901 ± 0.0771 | 0.1926 ± 0.0712 |

TABLE 12L (Pharmacokinetic Parameters for O,N-di-desmethyltramadol (M5) Multiple-Dose)

| Pharmacokinetic Parameter | Tramadol HCl 200 mg Extended Release Tablets (A) N = 32 Mean ± SD | ULTRAM ® 4 × 50 mg Tablets (B) N = 32 Mean ± SD |
|---|---|---|
| $AUC_\tau$ (ng.hr/mL) | 984.90 ± 345.84 | 1078.57 ± 341.59 |
| $C_{max}$ (ng/mL) | 49.74 ± 16.87 | 51.13 ± 15.15 |
| $C_{min}$ (ng/mL) | 38.31 ± 17.32 | 43.58 ± 15.86 |
| $T_{max}$ (hour) | 16.69 ± 3.50 | 2.89 ± 1.41 |
| Degree of Fluctuation (%) | 30.43 ± 21.23 | 18.40 ± 10.52 |
| Degree of Swing (%) | 38.59 ± 35.35 | 19.82 ± 12.08 |
| $C_{avg}$ (ng/mL) | 41.04 ± 14.41 | 44.94 ± 14.23 |
| M/P ratio | 0.1998 ± 0.0758 | 0.1944 ± 0.0708 |

TABLE 12M (Relative Bioavailability Analysis of Tramadol HCl 200 mg Delayed and Extended Release Tablets (A) versus ULTRAM ® 50 mg Tablets (B) for Tramadol Single-Dose)

| | TRAMADOL | | |
|---|---|---|---|
| Parameter | 90% C.I. | Ratio of Means | Intra-Subject CV |
| $AUC_{0-t}$ | 82.69%-98.46% | 90.23% | 20.56% |
| $AUC_{0-inf}$ | 83.28%-99.46% | 91.01% | 20.56% |
| $C_{max}$ | 81.21%-95.84% | 88.23% | 19.52% |

TABLE 12N (Relative Bioavailability Analysis of Tramadol HCl 200 mg Delayed and Extended Release Tablets (A) versus ULTRAM ® 50 mg Tablets (B) for Tramadol Multiple-Dose)

| | TRAMADOL | | |
|---|---|---|---|
| Parameter | 90% C.I. | Ratio of Means | Intra-Subject CV |
| $AUC_\tau$ | 83.97%-93.75% | 88.73% | 12.98% |
| $C_{max}$ | 78.63%-91.63% | 84.88% | 18.02% |

TABLE 12O (Relative Bioavailability Analysis of Tramadol HCl 200 mg Delayed and Extended Release Tablets (A) versus ULTRAM ® 50 mg Tablets (B) for O-Desmethyltramadol (M1) Single-Dose)

| | O-DESMETHYLTRAMADOL (M1) | | |
|---|---|---|---|
| Parameter | 90% C.I. | Ratio of Means | Intra-Subject CV |
| $AUC_{0-t}$ | 79.19%-94.98% | 86.73% | 21.42% |
| $AUC_{0-inf}$ | 80.03%-98.87% | 88.95% | 23.19% |
| $C_{max}$ | 83.50%-98.17% | 90.54% | 19.07% |

TABLE 12P (Relative Bioavailability Analysis of Tramadol HCl 200 mg Delayed and Extended Release Tablets (A) versus ULTRAM ® 50 mg Tablets (B) for O-Desmethyltramadol (M1) Multiple-Dose)

| | O-DESMETHYLTRAMADOL (M1) | | |
|---|---|---|---|
| Parameter | 90% C.I. | Ratio of Means | Intra-Subject CV |
| $AUC_\tau$ | 85.18%-95.85% | 90.35% | 13.90% |
| $C_{max}$ | 85.05%-97.75% | 91.18% | 16.40% |

TABLE 12Q (Relative Bioavailability Analysis of Tramadol HCl 200 mg Delayed and Extended Release Tablets (A) versus ULTRAM ® 50 mg Tablets (B) for O,N-di-Desmethyltramadol (M5) Single-Dose)

| | O,N-DI-DESMETHYLTRAMADOL (M5) | | |
|---|---|---|---|
| Parameter | 90% C.I. | Ratio of Means | Intra-Subject CV |
| AUC0-t | 78.52%-95.44% | 86.56% | 23.00% |
| AUC0-inf | 81.19%-100.64% | 90.39% | 23.87% |
| $C_{max}$ | 83.11%-100.02% | 91.17% | 21.83% |

TABLE 12R (Relative Bioavailability Analysis of Tramadol HCl 200 mg Delayed and Extended Release Tablets (A) versus ULTRAM ® 50 mg Tablets (B) for O,N-di-Desmethyltramadol (M5) Multiple-Dose)

| | O,N-DI-DESMETHYLTRAMADOL (M5) | | |
|---|---|---|---|
| Parameter | 90% C.I. | Ratio of Means | Intra-Subject CV |
| $AUC_\tau$ | 85.55%-95.76% | 90.51% | 13.28% |
| $C_{max}$ | 90.28%-102.31% | 96.10% | 14.74% |

EXAMPLE 13

A Three-Treatment, Open-Label, Multiple-Dose, Fasting, Dose-Escalation Study of Delayed and Extended Release Tramadol Hydrochloride Tablets (100 mg, 200 mg and 400 mg Doses) Given Once Daily In Normal Healthy Non-Smoking Male And Female Subjects was conducted.

The objective of this study was to investigate the dose-proportionality of tramadol over the 100 mg-400 mg dose range for applicants' novel formulation of tramadol HCl 200 mg Delayed and Extended Release tablets of Example 6, given once daily under multiple-dose, fasting conditions, and the tramadol HCl 100 mg Delayed and Extended Release tablets of Example 1, Composition C I. Experimental Design:

A three-treatment, open-label, multiple-dose, dose-escalation, fasting design.

II. Subjects:

Thirty (30) normal, healthy, non-smoking male and female subjects.

III. Drug Administration

Subjects received the following treatments at 0.0 hour, (once daily), specific to each study Dosing Day during the one (1) study period.

Treatment A: Delayed and Extended Release Tramadol HCl 1×100 mg Tablet (Days 1 to 6).

Treatment B: Delayed and Extended Release Tramadol HCl 1×200 mg Tablet (Days 7 to 12).

Treatment C: Delayed and Extended Release Tramadol HCl Extended Release 2×200 mg Tablets (Days 13 to 18).

Days 1 to 6—Treatment A:

One (1) delayed and extended release tramadol HCl 100 mg tablet at 0.0 hour with 240 mL of ambient temperature water following an overnight fast of at least ten (10) hours. (Total Daily Dose=100 mg).

Days 7 to 12—Treatment B:

One (1) delayed and extended release tramadol HCl 200 mg tablet at 0.0 hour with 240 mL of ambient temperature water following an overnight fast of at least ten (10) hours. (Total Daily Dose=200 mg).

Days 13 to 18—Treatment C:

Two (2) delayed and extended release tramadol HCl 200 mg Tablets at 0.0 hour with 240 mL of ambient temperature water after an overnight fast of at least ten (10) hours. (Total Daily Dose=400 mg).

Washout Period:

Not applicable. Subjects were confined for the entire 20-day study period.

Sample Collection:

Fifty-two (52) blood samples (10 mL each) were drawn for the entire study period for drug content analysis relative to the 0.0 hour drug administration at the following times:

Day 1: 0.0 hour (pre-dose)

Day 2: No blood samples.

Day 3, 4, 5: 0.0 hour (pre-dose).

Day 6: 0.0 (pre-dose), 1.0, 2.0, 3.0, 4.0, 5.0, 6.0, 8.0, 10.0, 12.0, 14.0, 16.0 and 20.0 hours post-0.0 hour drug administration.

Day 7: 24.0 hours after 0.0-hour drug administration of Day 6.

Day 8: No blood samples.

Days 9, 10, 11: 0.0 hour (pre-dose).

Day 12: 0.0 (pre-dose), 1.0, 2.0, 3.0, 4.0, 5.0, 6.0, 8.0, 10.0, 12.0, 14.0, 16.0 and 20.0 hours post-0.0 hour drug administration.

Day 13: 24.0 hours after 0.0-hour drug administration of Day 12.

Day 14: No blood samples.

Days 15, 16, 17: 0.0 hour (pre-dose).

Day 18: 0.0 (pre-dose), 1.0, 2.0, 3.0, 4.0, 5.0, 6.0, 8.0, 10.0, 12.0, 14.0, 16.0 and 20.0 hours post-0.0 hour drug administration.

Day 19: 24.0 hours after 0.0-hour drug administration of Day 18.

All blood samples, which coincided with drug administration, were drawn within 10 minutes prior to dosing.

The "Days" referred to in the above section are "Treatment Days" as opposed to "Calendar Days".

The Treatment Day started at the time of each 0.0 hour drug administration. Twenty-five subjects completed the study. Day 3 of dosing for all doses studied achieved steady state. Within the dose range of 100 mg to 400 mg, tramadol $C_{max}$, $C_{min}$ $AUC_{0-\tau}$ ranged from 179.24 ng/mL-910.05 ng/mL, 73.84 ng/mL-438.70 ng/mL, and 2778.41 hr*ng/mL- 15212.75 hr*ng/mL, respectively. For all analytes, $C_{max}$, and $AUC_{0-\tau}$ increased linearly with increasing doses ($R^2>0.85$), while $T_{max}$ did not differ significantly among doses. In conclusion, linear pharmacokinetics of tramadol and its metabolites were observed with the administration of the delayed and extended release tramadol within the investigated dose range of 100 mg to 400 mg.

Tables 13A-F provide the mean plasma concentration time profiles for tramadol, desmethyltramadol, and didesmethyltramadol. Tables 13G-L summarizes the pharmacokinetic parameters for tramadol, desmethyltramadol, and didesmethyltramadol. Table 13M shows the regression analysis results for AUC, and $C_{max}$ after three doses of delayed and extended release of tramadol with Y=a X+b using un-weighted data. Tables 13N-P shows the p value for paired comparisons among treatments A, B, And C for tramadol, desmethyltramadol, and didesmethyltramadol.

TABLE 13A (Mean (±SD) Plasma Concentration-Time Profiles for Tramadol (ng/mL))

| Sample Time | Treatment A (1 × 100 mg) Mean ± SD | Treatment B (1 × 200 mg) Mean ± SD | Treatment B (2 × 200 mg) Mean ± SD |
|---|---|---|---|
| Day 1 | 0.000 ± 0.000 | ND | ND |
| Day 3 | 63.926 ± 45.807 | 141.248 ± 66.083 | 396.043 ± 175.679 |
| Day 4 | 75.826 ± 40.715 | 169.240 ± 87.832 | 437.835 ± 187.946 |
| Day 5 | 73.139 ± 41.564 | 166.284 ± 79.160 | 477.906 ± 228.788 |
| 0.00 | 74.128 ± 36.540 | 175.916 ± 87.745 | 430.698 ± 203.442 |
| 1.0 | 68.521 ± 33.278 | 163.362 ± 83.751 | 405.745 ± 193.451 |
| 2.0 | 68.194 ± 34.949 | 163.204 ± 85.311 | 390.998 ± 185.584 |
| 3.0 | 70.866 ± 36.217 | 171.674 ± 88.248 | 416.134 ± 190.845 |
| 4.0 | 81.087 ± 41.819 | 187.108 ± 91.527 | 453.308 ± 200.774 |
| 5.0 | 103.448 ± 52.495 | 236.551 ± 110.006 | 543.52 ± 236.038 |
| 6.0 | 112.255 ± 63.429 | 254.467 ± 133.270 | 614.884 ± 255.501 |
| 8.0 | 145.486 ± 71.863 | 295.138 ± 177.216 | 733.924 ± 310.137 |
| 10.0 | 162.731 ± 65.861 | 340.792 ± 189.825 | 789.231 ± 290.949 |
| 12.0 | 156.023 ± 54.938 | 364.161 ± 156.391 | 835.051 ± 312.331 |
| 14.0 | 157.853 ± 59.931 | 372.045 ± 152.390 | 848.514 ± 297.779 |
| 16.0 | 133.296 ± 54.713 | 319.281 ± 138.002 | 740.597 ± 278.615 |
| 20.0 | 97.272 ± 43.901 | 233.513 ± 95.802 | 588.186 ± 245.444 |
| 24.0 | 73.843 ± 42.634 | 168.584 ± 72.580 | 438.695 ± 213.201 |

Figure 33:
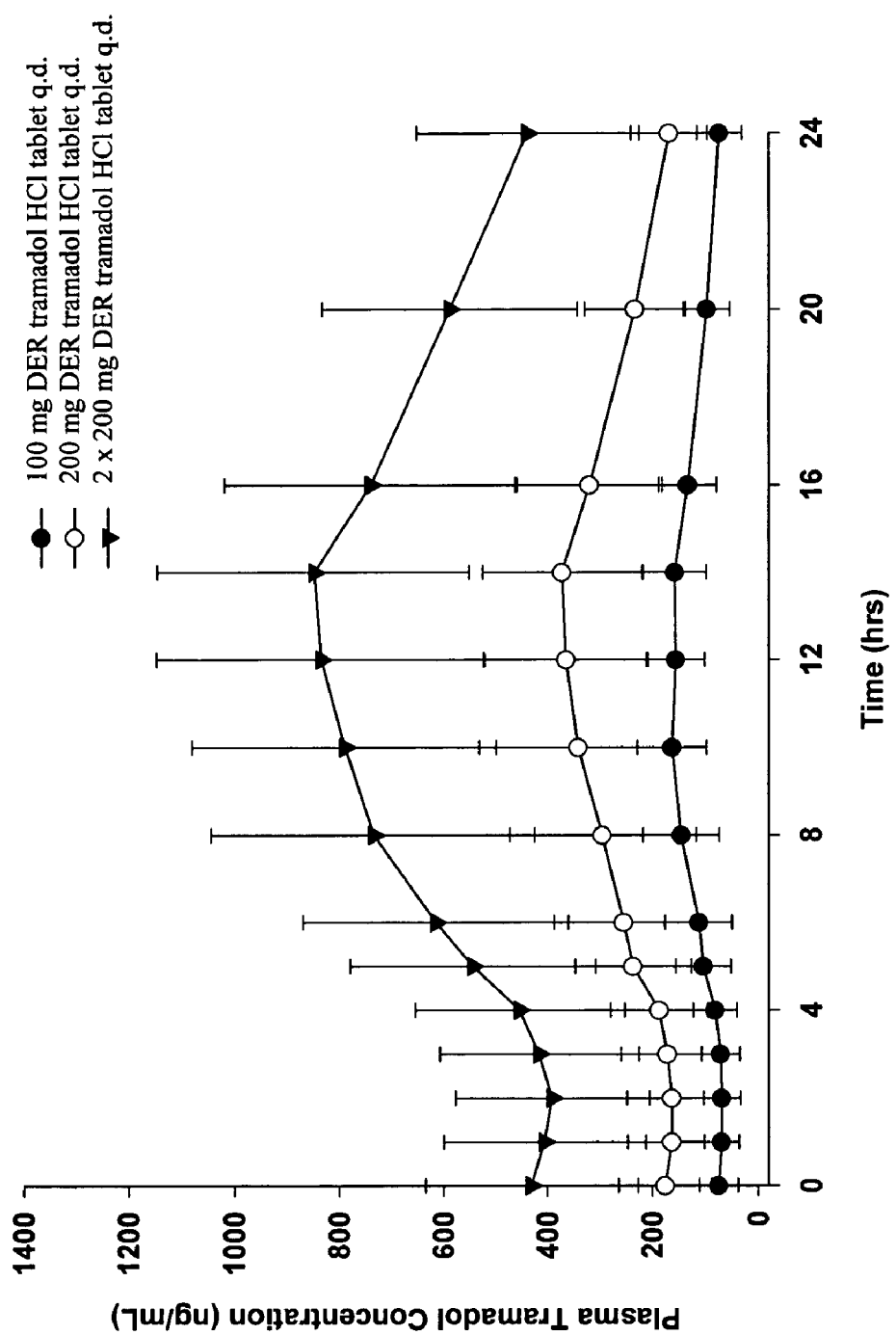
FIG. 33 is a graph illustrating the dose proportionality of the mean plasma tramadol concentrations over time on Day 20 of a 20-day multiple dose study period following administration of either a 1×100 mg, 1×200 mg or 2×200 mg DER tramadol HCl tablet according to an embodiment of the invention under fasting conditions.

Table 13A is presented graphically in FIG. 33.

TABLE 13B (Mean (±SD) Plasma Concentration-Time Profiles for Desmethyltramadol (M1) (ng/mL))

| Sample Time | Treatment A (1 × 100 mg) Mean ± SD | Treatment B (1 × 200 mg) Mean ± SD | Treatment B (2 × 200 mg) Mean ± SD |
|---|---|---|---|
| Day 1 | 0.000 ± 0.000 | ND | ND |
| Day 3 | 26.516 ± 10.390 | 52.815 ± 17.983 | 115.649 ± 37.750 |
| Day 4 | 29.056 ± 8.917 | 56.595 ± 25.362 | 115.547 ± 33.011 |
| Day 5 | 29.139 ± 10.952 | 56.077 ± 20.859 | 122.361 ± 41.044 |
| 0.00 | 28.773 ± 8.524 | 57.516 ± 21.407 | 113.312 ± 38.296 |
| 1.0 | 26.845 ± 8.062 | 53.918 ± 20.241 | 108.733 ± 39.405 |
| 2.0 | 25.654 ± 7.869 | 51.821 ± 19.008 | 101.652 ± 36.696 |
| 3.0 | 25.255 ± 7.943 | 51.812 ± 18.567 | 103.915 ± 37.701 |
| 4.0 | 26.921 ± 8.324 | 54.077 ± 19.696 | 107.460 ± 39.010 |
| 5.0 | 30.337 ± 9.433 | 59.949 ± 20.636 | 113.205 ± 34.186 |
| 6.0 | 30.788 ± 9.515 | 62.006 ± 21.209 | 122.902 ± 38.384 |
| 8.0 | 37.764 ± 10.913 | 68.038 ± 27.448 | 138.077 ± 43.086 |
| 10.0 | 44.136 ± 12.527 | 76.477 ± 30.728 | 148.722 ± 44.515 |
| 12.0 | 42.521 ± 11.377 | 81.970 ± 31.776 | 153.975 ± 46.779 |
| 14.0 | 44.707 ± 11.479 | 86.644 ± 33.491 | 163.923 ± 52.479 |
| 16.0 | 41.353 ± 11.488 | 82.636 ± 33.655 | 153.983 ± 47.657 |
| 20.0 | 33.732 ± 10.466 | 66.544 ± 23.300 | 131.849 ± 43.884 |
| 24.0 | 26.954 ± 10.713 | 53.423 ± 19.003 | 107.232 ± 39.879 |

Figure 34:
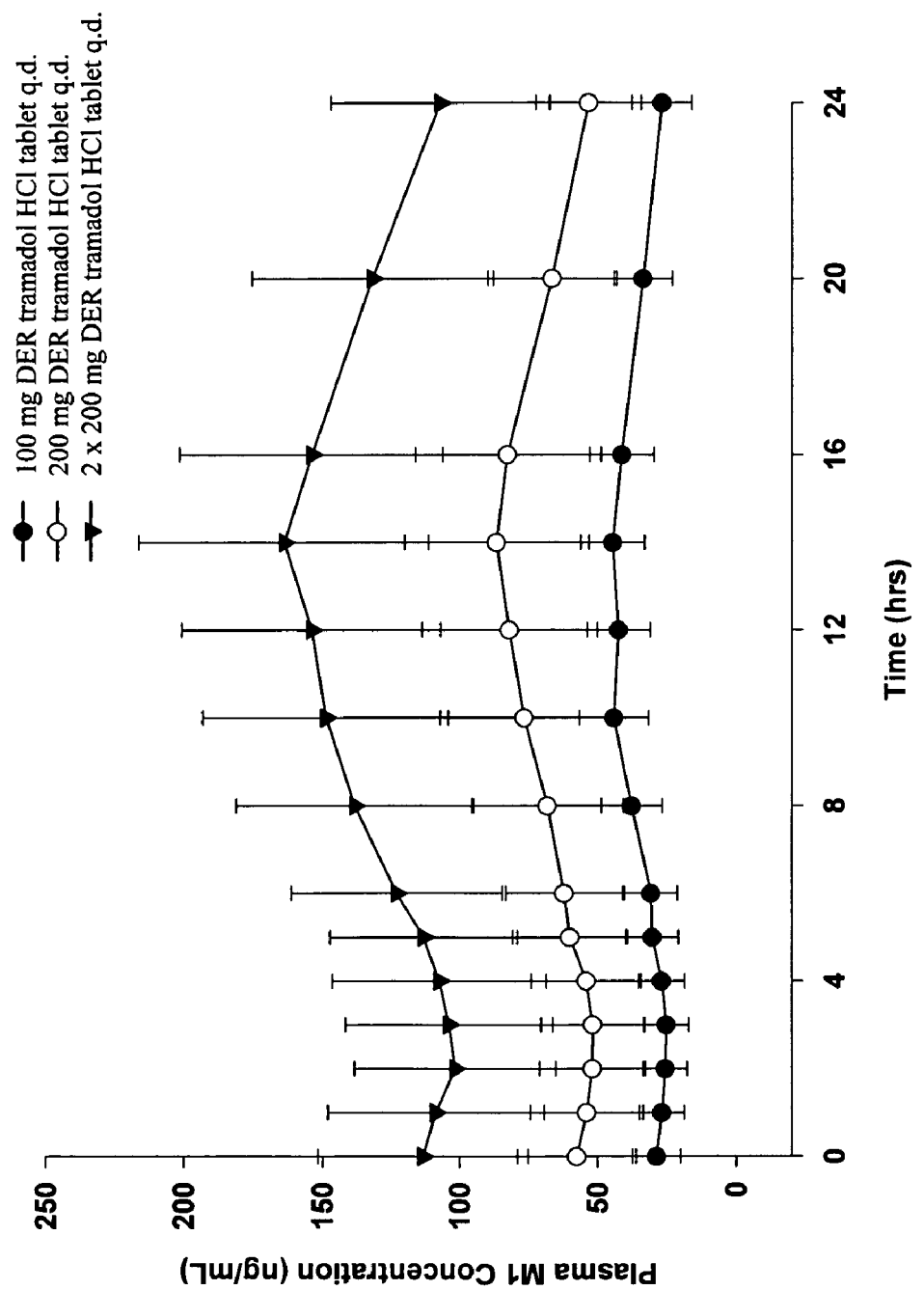
FIG. 34 is a graph illustrating the dose proportionality of the mean plasma desmethyltramadol (M1) concentrations over time on Day 20 of a 20-day multiple dose study period following administration of the tablets of FIG. 33 under fasting conditions.

Table 13B is presented graphically in FIG. 34.

TABLE 13C (Mean (±SD) Plasma Concentration-Time Profiles for Didesmethyltramadol ng/mL))

| Sample Time | Treatment A (1 × 100 mg) Mean ± SD | Treatment B (1 × 200 mg) Mean ± SD | Treatment B (2 × 200 mg) Mean ± SD |
|---|---|---|---|
| Day 1 | 0.000 ± 0.000 | ND | ND |
| Day 3 | 10.757 ± 5.068 | 26.523 ± 10.271 | 67.814 ± 20.900 |
| Day 4 | 12.955 ± 4.787 | 30.241 ± 13.316 | 74.874 ± 21.311 |
| Day 5 | 13.510 ± 5.582 | 31.32 ± 11.601 | 80.068 ± 26.097 |
| 0.00 | 13.689 ± 5.158 | 32.873 ± 12.450 | 80.708 ± 26.820 |
| 1.0 | 12.869 ± 4.670 | 30.384 ± 11.541 | 75.860 ± 26.041 |
| 2.0 | 12.156 ± 4.498 | 29.290 ± 10.938 | 72.371 ± 24.547 |
| 3.0 | 11.722 ± 4.031 | 28.83 ± 10.691 | 72.605 ± 26.205 |
| 4.0 | 12.273 ± 3.938 | 28.919 ± 10.603 | 72.155 ± 25.176 |
| 5.0 | 13.276 ± 4.321 | 30.832 ± 10.362 | 73.872 ± 23.095 |
| 6.0 | 13.550 ± 4.445 | 32.39 ± 11.466 | 75.743 ± 24.242 |
| 8.0 | 16.066 ± 4.904 | 34.301 ± 13.155 | 80.791 ± 23.099 |
| 10.0 | 19.062 ± 5.577 | 38.951 ± 14.763 | 87.193 ± 24.138 |
| 12.0 | 19.061 ± 5.141 | 41.394 ± 15.960 | 91.068 ± 25.275 |
| 14.0 | 20.147 ± 5.199 | 44.586 ± 16.952 | 95.843 ± 27.591 |
| 16.0 | 19.325 ± 4.624 | 45.079 ± 17.894 | 94.608 ± 26.571 |
| 20.0 | 16.486 ± 4.510 | 39.116 ± 14.174 | 87.653 ± 27.320 |
| 24.0 | 13.452 ± 4.882 | 32.661 ± 12.159 | 78.518 ± 27.409 |

Figure 35:
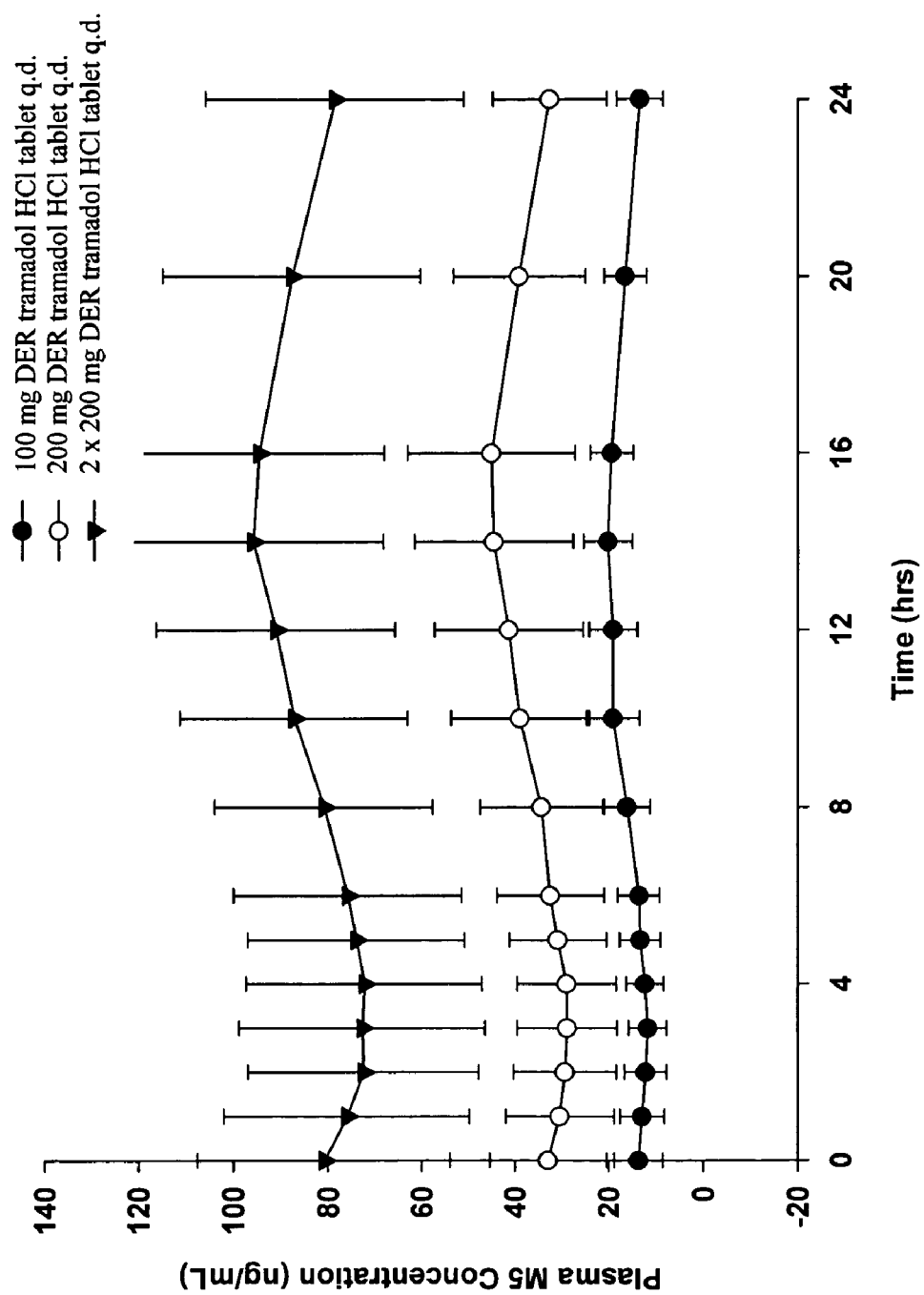
FIG. 35 is a graph illustrating the dose proportionality of the mean plasma didesmethyltramadol (M5) concentrations over time on Day 20 of a 20-day multiple dose study period following administration of the tablets of FIG. 33 under fasting conditions.

Table 13C is presented graphically in FIG. 35.

TABLE 13D (Mean (±SD) Plasma Concentration-Time Profiles for tramadol (ng/mL) (Dose Corrected to 1 × 100 mg strength)

| Sample Time | Treatment A (1 × 100 mg) Mean ± SD | Treatment B (1 × 200 mg) Mean ± SD | Treatment B (2 × 200 mg) Mean ± SD |
|---|---|---|---|
| Day 1 | 0.000 ± 0.000 | ND | ND |
| Day 3 | 63.926 ± 45.807 | 70.624 ± 33.041 | 99.011 ± 43.920 |
| Day 4 | 75.826 ± 40.715 | 84.620 ± 43.916 | 109.459 ± 46.986 |
| Day 5 | 73.139 ± 41.564 | 83.142 ± 39.580 | 119.476 ± 57.197 |
| 0.00 | 74.128 ± 36.540 | 87.958 ± 43.873 | 107.674 ± 50.861 |
| 1.0 | 68.521 ± 33.278 | 81.681 ± 41.875 | 101.436 ± 48.363 |
| 2.0 | 68.194 ± 34.949 | 81.602 ± 42.655 | 97.749 ± 46.396 |
| 3.0 | 70.866 ± 36.217 | 85.837 ± 44.124 | 104.033 ± 47.711 |
| 4.0 | 81.08 ± 41.819 | 93.554 ± 45.764 | 113.327 ± 50.194 |
| 5.0 | 103.448 ± 52.495 | 118.275 ± 55.003 | 135.880 ± 59.010 |
| 6.0 | 112.255 ± 63.429 | 127.234 ± 66.635 | 153.721 ± 63.875 |
| 8.0 | 145.486 ± 71.863 | 147.569 ± 88.608 | 183.481 ± 77.534 |
| 10.0 | 162.731 ± 65.861 | 170.396 ± 94.913 | 197.308 ± 72.737 |
| 12.0 | 156.023 ± 54.938 | 182.080 ± 78.196 | 208.763 ± 78.083 |
| 14.0 | 157.853 ± 59.931 | 186.023 ± 76.195 | 212.128 ± 74.445 |
| 16.0 | 133.296 ± 54.713 | 159.641 ± 69.001 | 185.149 ± 69.654 |
| 20.0 | 97.272 ± 43.901 | 116.757 ± 47.901 | 147.047 ± 61.361 |
| 24.0 | 73.843 ± 42.634 | 84.292 ± 36.290 | 109.674 ± 53.300 |

TABLE 13E (Mean (±SD) Plasma Concentration-Time Profiles for Desmethyltramadol (M1) (ng/mL) (Dose Corrected to 1 × 100 mg strength)

| Sample Time | Treatment A (1 × 100 mg) Mean ± SD | Treatment B (1 × 200mg) Mean ± SD | Treatment B (2 × 200mg) Mean ± SD |
|---|---|---|---|
| Day 1 | 0.000 ± 0.000 | ND | ND |
| Day 3 | 26.516 ± 10.390 | 26.408 ± 8.991 | 28.912 ± 9.437 |
| Day 4 | 29.056 ± 8.917 | 28.298 ± 12.681 | 28.887 ± 8.253 |
| Day 5 | 29.139 ± 10.952 | 28.038 ± 10.430 | 30.590 ± 10.261 |
| 0.00 | 28.773 ± 8.524 | 28.758 ± 10.703 | 28.328 ± 9.574 |
| 1.0 | 26.845 ± 8.062 | 26.959 ± 10.121 | 27.183 ± 9.851 |
| 2.0 | 25.654 ± 7.869 | 25.911 ± 9.504 | 25.413 ± 9.174 |
| 3.0 | 25.255 ± 7.943 | 25.906 ± 9.284 | 25.979 ± 9.425 |

TABLE 13E-continued (Mean (±SD) Plasma Concentration-Time Profiles for Desmethyltramadol (M1) (ng/mL)
(Dose Corrected to 1 × 100 mg strength)

| Sample Time | Treatment A (1 × 100 mg) Mean ± SD | Treatment B (1 × 200mg) Mean ± SD | Treatment B (2 × 200 mg) Mean ± SD |
|---|---|---|---|
| 4.0 | 26.921 ± 8.324 | 27.038 ± 9.848 | 26.865 ± 9.753 |
| 5.0 | 30.337 ± 9.433 | 29.975 ± 10.318 | 28.301 ± 8.547 |
| 6.0 | 30.788 ± 9.515 | 31.003 ± 10.604 | 30.725 ± 9.596 |
| 8.0 | 37.764 ± 10.913 | 34.019 ± 13.724 | 34.519 ± 10.771 |
| 10.0 | 44.136 ± 12.527 | 38.238 ± 15.364 | 37.180 ± 11.129 |
| 12.0 | 42.521 ± 11.377 | 40.985 ± 15.888 | 38.494 ± 11.695 |
| 14.0 | 44.707 ± 11.479 | 43.322 ± 16.746 | 40.981 ± 13.120 |
| 16.0 | 41.353 ± 11.488 | 41.318 ± 16.827 | 38.496 ± 11.914 |
| 20.0 | 33.732 ± 10.466 | 33.272 ± 11.650 | 32.962 ± 10.971 |
| 24.0 | 26.954 ± 10.713 | 26.711 ± 9.501 | 26.808 ± 9.970 |

TABLE 13F (Mean (±SD) Plasma Concentration-Time Profiles for Didesmethyltramadol (M5) (ng/mL)
(Dose Corrected to 1 × 100 mg strength)

| Sample Time | Treatment A (1 × 100 mg) Mean ± SD | Treatment B (1 × 200 mg) Mean ± SD | Treatment B (2 × 200 mg) Mean ± SD |
|---|---|---|---|
| Day 1 | 0.000 ± 0.000 | ND | ND |
| Day 3 | 10.757 ± 5.068 | 13.262 ± 5.135 | 16.953 ± 5.225 |
| Day 4 | 12.955 ± 4.787 | 15.120 ± 6.658 | 18.718 ± 5.328 |
| Day 5 | 13.510 ± 5.582 | 15.663 ± 5.800 | 20.017 ± 6.524 |
| 0.00 | 13.689 ± 5.158 | 16.437 ± 6.225 | 20.177 ± 6.705 |
| 1.0 | 12.869 ± 4.670 | 15.192 ± 5.770 | 18.965 ± 6.510 |
| 2.0 | 12.156 ± 4.498 | 14.645 ± 5.469 | 18.093 ± 6.137 |
| 3.0 | 11.722 ± 4.031 | 14.418 ± 5.345 | 18.151 ± 6.551 |
| 4.0 | 12.273 ± 3.938 | 14.460 ± 5.301 | 18.039 ± 6.294 |
| 5.0 | 13.276 ± 4.321 | 15.416 ± 5.181 | 18.468 ± 5.774 |
| 6.0 | 13.550 ± 4.445 | 16.198 ± 5.733 | 18.936 ± 6.060 |
| 8.0 | 16.066 ± 4.904 | 17.151 ± 6.577 | 20.198 ± 5.775 |
| 10.0 | 19.062 ± 5.577 | 19.475 ± 7.381 | 21.798 ± 6.034 |
| 12.0 | 19.061 ± 5.141 | 20.697 ± 7.980 | 22.767 ± 6.319 |
| 14.0 | 20.147 ± 5.199 | 22.293 ± 8.476 | 23.961 ± 6.898 |
| 16.0 | 19.325 ± 4.624 | 22.539 ± 8.947 | 23.652 ± 6.643 |
| 20.0 | 16.486 ± 4.510 | 19.558 ± 7.087 | 21.913 ± 6.830 |
| 24.0 | 13.452 ± 4.882 | 16.330 ± 6.079 | 19.630 ± 6.852 |

TABLE 13G

Pharmacokinetic Parameters for Tramadol (Without Dose-Corrected Data)

| Pharmacokinetic Parameter | Tramadol HCl 100 mg Extended Release Tablets 1 × 100 mg (A) N = 25 Mean ± SD | Tramadol HCl 200 mg Extended Release Tablets 1 × 200 mg (B) N = 25 Mean ± SD | Tramadol HCl 200 mg Extended Release Tablets 2 × 200 mg (C) N = 25 Mean ± SD |
|---|---|---|---|
| $AUC_\tau$ (ng · hr/mL) | 2778.41 ± 1141.24 | 6364.89 ± 2755.19 | 15212.75 ± 5754.59 |
| $C_{max}$ (ng/mL) | 179.24 ± 62.68 | 408.99 ± 177.71 | 910.05 ± 319.71 |
| $C_{min}$ (ng/mL) | 73.84 ± 42.63 | 168.58 ± 72.58 | 438.70 ± 213.20 |
| $T_{max}$ (hours) | 11.68 ± 2.43 | 12.16 ± 2.23 | 12.00 ± 2.38 |
| Degree of Fluctuation (%) | 98.979 ± 41.628 | 94.697 ± 36.879 | 81.785 ± 38.392 |
| $C_{ave}$ (ng/mL) | 115.77 ± 47.55 | 265.20 ± 114.80 | 633.86 ± 239.77 |

TABLE 13H

Pharmacokinetic Parameters for O-desmethyltramadol (M1) (Without Dose-Corrected Data)

| Pharmacokinetic Parameter | Tramadol HCl 100 mg Extended Release Tablets 1 × 100 mg (A) N = 25 Mean ± SD | Tramadol HCl 200 mg Extended Release Tablets 1 × 200 mg (B) N = 25 Mean ± SD | Tramadol HCl 200 mg Extended Release Tablets 2 × 200 mg (C) N = 25 Mean ± SD |
|---|---|---|---|
| $AUC_\tau$ (ng · hr/mL) | 846.73 ± 210.51 | 1640.53 ± 574.72 | 3189.17 ± 973.87 |
| $C_{max}$ (ng/mL) | 48.01 ± 11.53 | 91.29 ± 34.19 | 169.06 ± 48.75 |
| $C_{min}$ (ng/mL) | 26.95 ± 10.71 | 53.42 ± 19.00 | 107.23 ± 39.88 |
| $T_{max}$ (hours) | 12.32 ± 2.50 | 13.16 ± 2.70 | 14.00 ± 2.83 |
| Degree of Fluctuation (%) | 62.399 ± 32.222 | 56.637 ± 33.742 | 49.717 ± 26.325 |
| $C_{ave}$ (ng/mL) | 35.28 ± 8.77 | 68.36 ± 23.95 | 132.88 ± 40.58 |

TABLE 13I

Pharmacokinetic Parameters for O,N-di-desmethyltramadol (M5) (Without Dose-Corrected Data)

| Pharmacokinetic Parameter | Tramadol HCl 100 mg Extended Release Tablets 1 × 100 mg (A) N = 25 Mean ± SD | Tramadol HCl 200 mg Extended Release Tablets 1 × 200 mg (B) N = 25 Mean ± SD | Tramadol HCl 200 mg Extended Release Tablets 2 × 200 mg (C) N = 25 Mean ± SD |
|---|---|---|---|
| $AUC_\tau$ (ng · hr/mL) | 388.96 ± 99.59 | 888.78 ± 314.74 | 2022.09 ± 589.81 |
| $C_{max}$ (ng/mL) | 21.23 ± 5.30 | 47.19 ± 17.49 | 100.03 ± 27.51 |
| $C_{min}$ (ng/mL) | 13.45 ± 4.88 | 32.66 ± 12.16 | 78.52 ± 27.41 |
| $T_{max}$ (hours) | 13.36 ± 3.09 | 13.44 ± 3.93 | 15.36 ± 2.81 |
| Degree of Fluctuation (%) | 49.959 ± 30.658 | 40.952 ± 29.437 | 28.403 ± 20.472 |
| $C_{ave}$ (ng/mL) | 16.21 ± 4.15 | 37.03 ± 13.11 | 84.25 ± 24.58 |

TABLE 13J

Pharmacokinetic Parameters for Tramadol (With Dose-Corrected Data)

| Pharmacokinetic Parameter | Tramadol HCl 100 mg Extended Release Tablets 1 × 100 mg (A) N = 25 Mean ± SD | Tramadol HCl 200 mg Extended Release Tablets 1 × 200 mg (B) N = 25 Mean ± SD | Tramadol HCl 200 mg Extended Release Tablets 2 × 200 mg (C) N = 25 Mean ± SD |
|---|---|---|---|
| $AUC_\tau$ (ng · hr/mL) | 2778.41 ± 1141.24 | 3182.45 ± 1377.60 | 3803.19 ± 1438.65 |
| $C_{max}$ (ng/mL) | 179.24 ± 62.68 | 204.50 ± 88.85 | 227.51 ± 79.93 |
| $C_{min}$ (ng/mL) | 73.84 ± 42.63 | 84.29 ± 36.29 | 109.67 ± 53.30 |
| $T_{max}$ (hours) | 11.68 ± 2.43 | 12.16 ± 2.23 | 12.00 ± 2.38 |
| Degree of Fluctuation (%) | 98.979 ± 41.628 | 94.697 ± 36.879 | 81.785 ± 38.392 |
| $C_{ave}$ (ng/mL) | 115.77 ± 47.55 | 132.60 ± 57.40 | 158.47 ± 59.94 |

TABLE 13K

Pharmacokinetic Parameters for O-desmethyltramadol (M1)
(With Dose-Corrected Data)

| Pharmacokinetic Parameter | Tramadol HCl 100 mg Extended Release Tablets 1 × 100 mg (A) N = 25 Mean ± SD | Tramadol HCl 200 mg Extended Release Tablets 1 × 200 mg (B) N = 25 Mean ± SD | Tramadol HCl 200 mg Extended Release Tablets 2 × 200 mg (C) N = 25 Mean ± SD |
|---|---|---|---|
| $AUC_\tau$ (ng · hr/mL) | 846.73 ± 210.51 | 820.27 ± 287.36 | 797.29 ± 243.47 |
| $C_{max}$ (ng/mL) | 48.01 ± 11.53 | 45.65 ± 17.09 | 42.26 ± 12.19 |
| $C_{min}$ (ng/mL) | 26.95 ± 10.71 | 26.71 ± 9.50 | 26.81 ± 9.97 |
| $T_{max}$ (hours) | 12.32 ± 2.50 | 13.16 ± 2.70 | 14.00 ± 2.83 |
| Degree of Fluctuation (%) | 62.399 ± 32.222 | 56.637 ± 33.742 | 49.717 ± 26.325 |
| $C_{ave}$ (ng/mL) | 35.28 ± 8.77 | 34.18 ± 11.97 | 33.22 ± 10.14 |
| M/P Ratio | 0.3555 ± 0.1165 | 0.2980 ± 0.0982 | 0.2441 ± 0.0831 |

TABLE 13L

Pharmacokinetic Parameters for O,N-di-desmethyltramadol (M5)
(With Dose-Corrected Data)

| Pharmacokinetic Parameter | Tramadol HCl 100 mg Extended Release Tablets 1 × 100 mg (A) N = 25 Mean ± SD | Tramadol HCl 200 mg Extended Release Tablets 1 × 200 mg (B) N = 25 Mean ± SD | Tramadol HCl 200 mg Extended Release Tablets 2 × 200 mg (C) N = 25 Mean ± SD |
|---|---|---|---|
| $AUC_\tau$ (ng · hr/mL) | 388.96 ± 99.59 | 444.39 ± 157.37 | 505.52 ± 147.45 |
| $C_{max}$ (ng/mL) | 21.23 ± 5.30 | 23.59 ± 8.74 | 25.01 ± 6.88 |
| $C_{min}$ (ng/mL) | 13.45 ± 4.88 | 16.33 ± 6.08 | 19.63 ± 6.85 |
| $T_{max}$ (hours) | 13.36 ± 3.09 | 13.44 ± 3.93 | 15.36 ± 2.81 |
| Degree of Fluctuation (%) | 49.959 ± 30.658 | 40.952 ± 29.437 | 28.403 ± 20.472 |
| $C_{ave}$ (ng/mL) | 16.21 ± 4.15 | 18.52 ± 6.56 | 21.06 ± 6.14 |
| M/P Ratio | 0.1734 ± 0.0653 | 0.1723 ± 0.0666 | 0.1667 ± 0.0682 |

TABLE 13M

Regression Analysis Results for $AUC_\tau$ and $C_{max\ After}$ Three Doses of Tramadol With Y = a X + b Using Un-Weighted Data

| Parameter | Slope | 95% CI | P |
|---|---|---|---|
| $C_{max}$ | 2.4459 | (2.0531, 2.8387) | <0.0001 |
| $AUC_\tau$ | 41.8466 | (34.9723, 48.7208) | <0.0001 |

TABLE 13N

P Value For Paired Comparisons Among Treatments A, B, And C For Tramadol

| Parameter | Trt A – Trt B | Trt A – Trt C | Trt B – Trt C |
|---|---|---|---|
| $C_{max}$ | 0.4532 | 0.0627 | 0.2597 |
| $AUC_\tau$ | 0.4675 | 0.0319 | 0.1491 |

TABLE 13O

P Value For Paired Comparisons Among Treatments A, B, And C For O-Desmethyltramadol (M1)

| Parameter | Trt A – Trt B | Trt A – Trt C | Trt B – Trt C |
|---|---|---|---|
| $C_{max}$ | 0.3011 | 0.1267 | 0.6162 |
| $AUC_\tau$ | 0.4490 | 0.4168 | 0.9560 |

TABLE 13P

P Value For Paired Comparisons Among Treatments A, B, And C For O, N-Di-Desmethyltramadol (M5)

| Parameter | Trt A – Trt B | Trt A – Trt C | Trt B – Trt C |
|---|---|---|---|
| $C_{max}$ | 0.5122 | 0.1035 | 0.3254 |
| $AUC_\tau$ | 0.3743 | 0.0152 | 0.1155 |

EXAMPLE 14

100 mg Tramadol HCl-Controlled Release Matrix Hydrocolloid Tablets

I. Formulation

The following 100 mg tramadol HCl-Controlled Release Matrix Hydrocolloid tablet formulation, which falls within the scope of the teachings of U.S. Pat. No. 5,591,452, was prepared:

TABLE 14A (Controlled Release Matrix Hydrocolloid Formulation)

| Ingredients | Mg/tablet |
|---|---|
| Core | |
| Tramadol HCl | 100 |
| Hydroxypropylmethyl Cellulose (Premium K 100 M CR), USP | 224.40 |
| Lactose Anhydrous, NF | 57.23 |
| Microcrystalline Cellulose (Avicel PH 101), NF | 26.99 |
| Coat | |
| Ethylcellulose (Ethocel Premium 100 FP) NF | 26.99 |
| Magnesium Stearate, NF | 4.35 |
| Opadry II White Y-22-7719 | 15.43 |
| Weight of Coated tablet | 455.39 |

Figure 36:
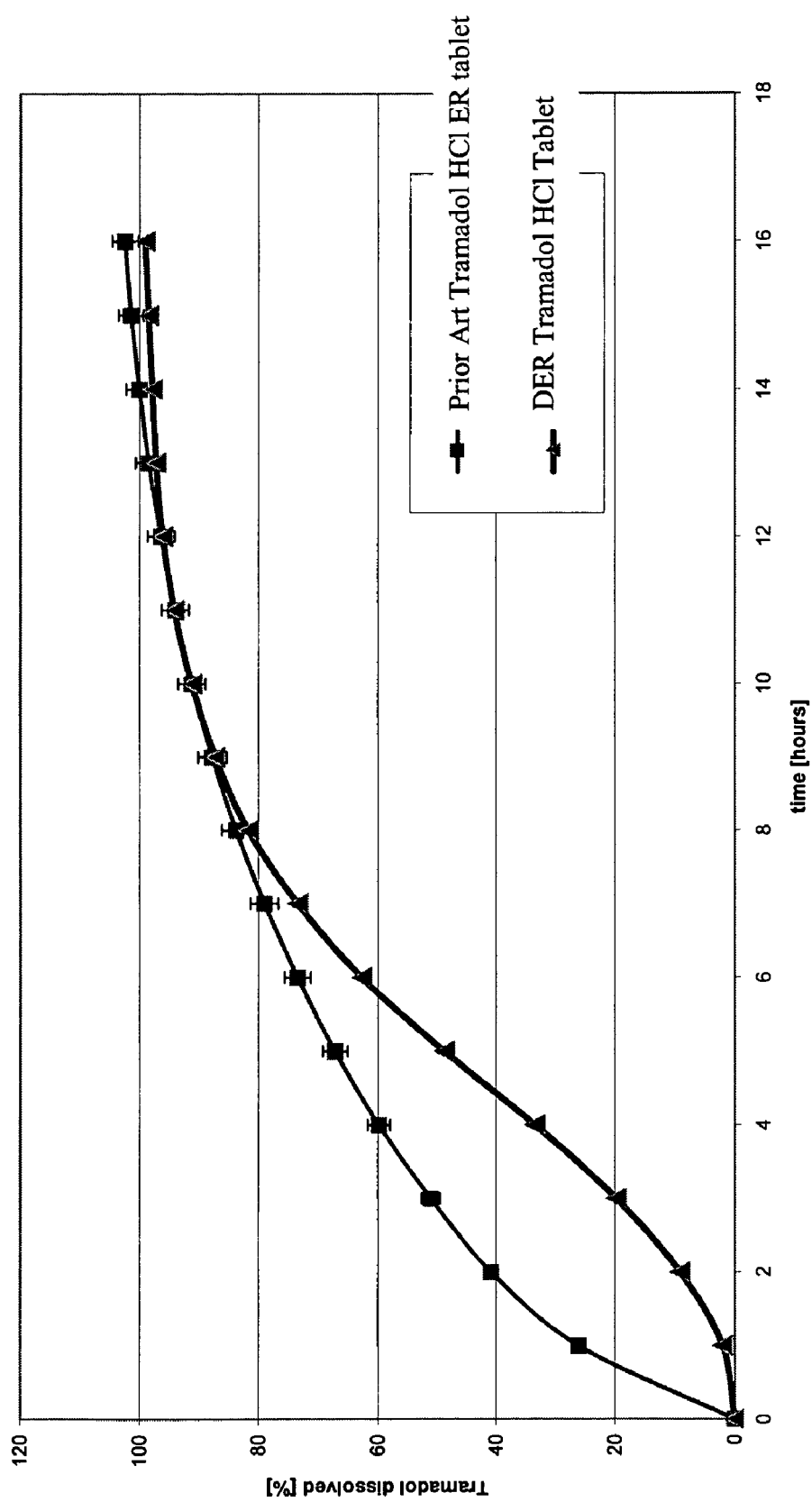
FIG. 36 is a graph illustrating the comparative dissolution curves between a delayed and extended release tramadol HCl composition made according to an embodiment of the invention and a prior art controlled but not delayed release matrix hydrocolloid formulation.

FIG. 36 is a graph comparing the in vitro dissolution profiles of a 100 mg delayed and extended release tramadol HCl composition made according to an embodiment of the invention and the controlled release matrix hydrocolloid composition shown in Table 13A.

II. Pharmacokinetic Study

A three-way, single-dose, open-label, fasting and food effect, comparative bioavailability study of the controlled release matrix hydrocolloid tramadol HCl tablet formulation (100 mg) in normal, healthy, non-smoking male volunteers was conducted.

This study evaluated the effect of food and the time of administration on the relative bioavailability of the controlled release matrix hydrocolloid tramadol HCl tablet formulation (100 mg).

This study was a randomized, three-way crossover study design in twenty-four (24) normal, healthy, non-smoking male volunteers and three (3) alternates.

Twenty-seven (27) subjects were entered into the study. Twenty-seven (27) subjects completed the study; and as per the protocol, there were twenty-four (24) evaluable subjects. All subjects were non-smoking, between 18 and 45 years of age (inclusive), and with body weights no more than ±15% of the ideal weight for the subject's height and frame as determined by the Table of Desirable Weights for Men.

The study periods were separated by a one-week washout period. Blood sampling for drug content analysis was carried out at 0.0 (pre-drug), 1.0, 2.0, 3.0, 4.0, 6.0, 8.0, 10.0, 12.0, 16.0, 20.0, 24.0, 30.0, 36.0, and 48.0 hours post-drug administration.

Treatments:
A: Single dose of the 100 mg controlled release matrix hydrocolloid tramadol HCl tablet, with 240 mL potable water, administered in the morning beginning at approximately 7 AM after an overnight fast of at least 10 hours.
B: Single dose of the 100 mg controlled release matrix hydrocolloid tramadol HCl tablet with 240 mL potable water, administered in the morning beginning at approximately 7 AM after the intake of a high fat-content breakfast.
C: Single dose of the 100 mg controlled release matrix hydrocolloid tramadol HCl tablet, with 240 mL potable water, administered beginning at approximately 10 PM the night before the dosing date of regimens A and B. Food intake was not permitted for 2 hours before and 2 hours after dosing.

In the instant study, the effect of food and time of administration on the formulation used in as pre-emptive dental pain study was evaluated.

Results presented in Tables 14B and 14C indicate that there was no effect of food on the controlled release matrix hydrocolloid tramadol HCl formulation. Similar tramadol, O-desmethyltramadol and M5 pharmacokinetic profiles were achieved when the formulation was administered in the morning or night. Equivalent AUCs and $C_{max}$ values were observed as evidenced by the 90% confidence intervals for the ratio of geometric means falling within 80-125% limits. Table 14B also shows that there was no apparent difference in the ratio of the metabolite ($AUC_\infty$ of M1/tramadol) between the different treatments. The half-life of tramadol was slightly decreased after food (6.18 hours) and nighttime administration (6.74 hours) compared to morning administration (7.64 hours).

Figure 37:
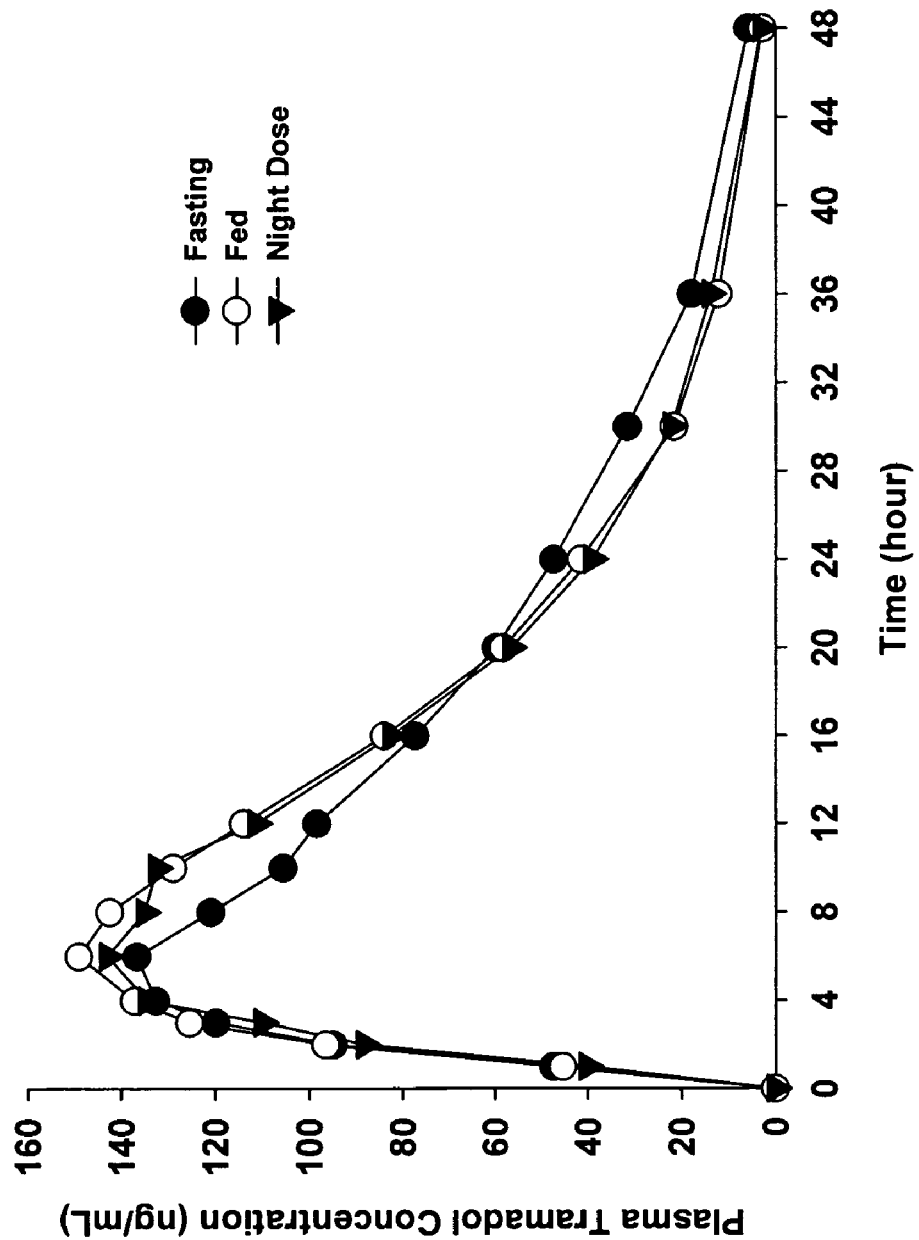
FIG. 37 is a graph illustrating the mean plasma tramadol concentrations over time following once-a-day administration of a 100 mg prior art controlled but not delayed release matrix hydrocolloid formulation.
Figure 38:
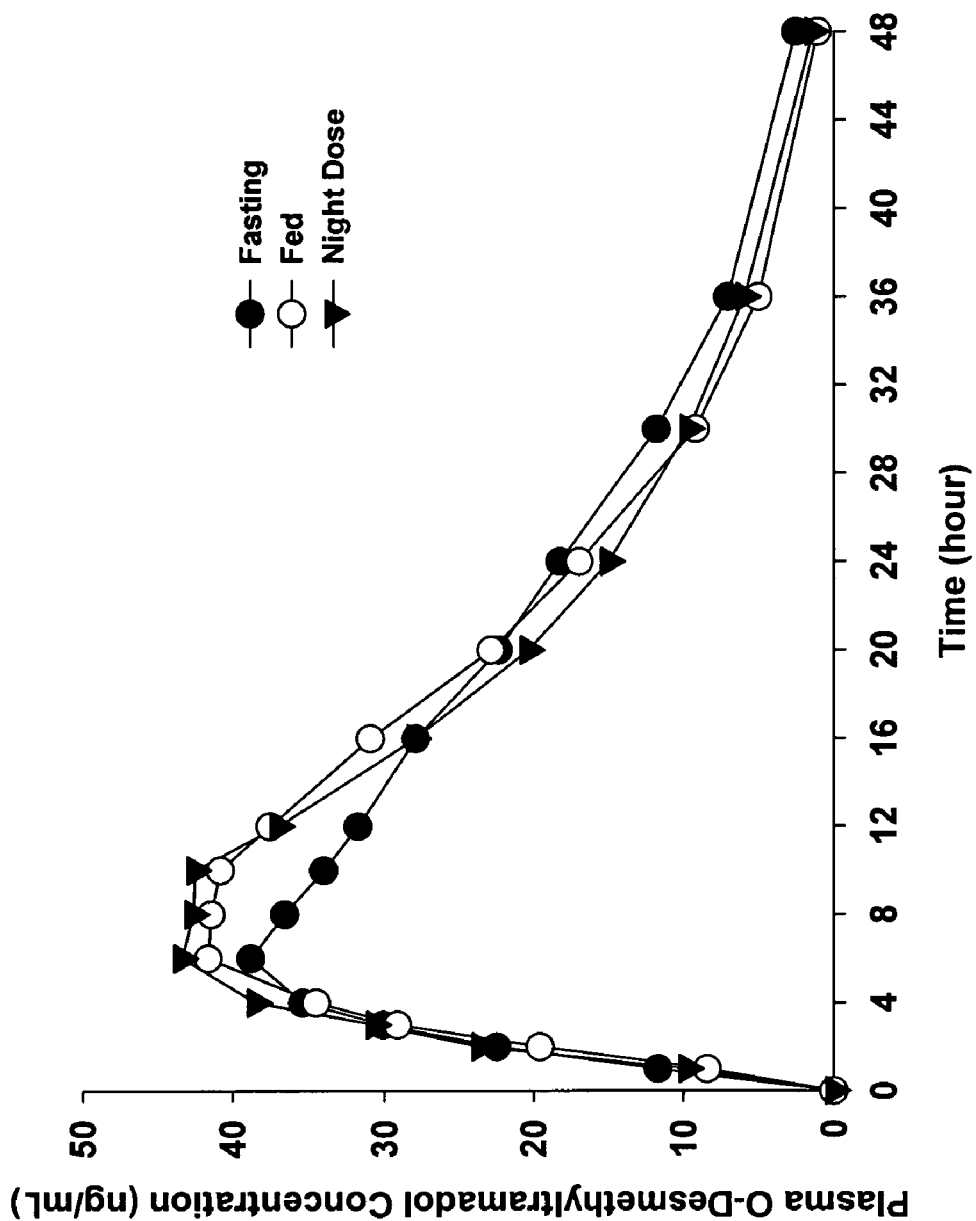
FIG. 38 is a graph illustrating the mean plasma desmethyltramadol concentrations over time following once-a-day administration of the tablet of FIG. 37.
Figure 39:
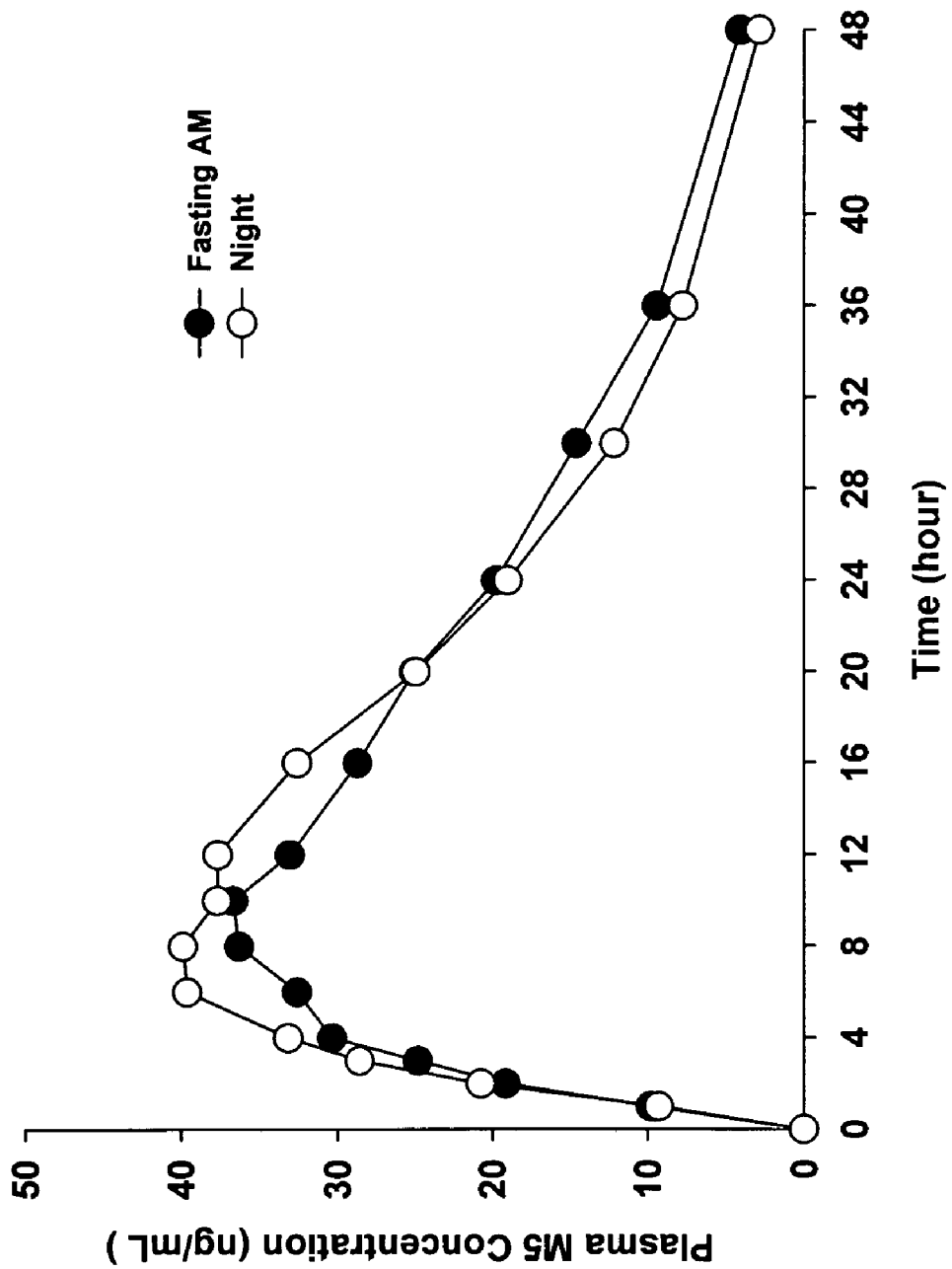
FIG. 39 is a graph illustrating the mean plasma didesmethyltramadol concentrations over time following once-a-day administration of the tablet of FIG. 37.

FIGS. 37-39 show that comparable tramadol, O-desmethyltramadol and M5 levels were obtained regardless of whether the controlled release tramadol formulation was administered in the morning (fasting), morning (fed) or night (fasting).

TABLE 14B (Mean Pharmacokinetic Parameters for Plasma Tramadol (n = 27))

| Parameters | AM Dosing (Fasting) Mean (CV (%)) | AM Dosing (Fed) Mean (CV (%)) | PM Dosing (at least 2 hrs after food) Mean (CV (%)) |
|---|---|---|---|
| $AUC_{0-t}$ (ng · h/mL) | 2655.9 (29.1) | 2691.8 (30.9) | 2622.5 (28.3) |
| $AUC_{0-inf}$ (ng · h/mL) | 2731.5 (30.2) | 2728.0 (32.0) | 2660.3 (28.8) |
| $C_{max}$ (ng/mL) | 144.5 (21.7) | 160.0 (20.3) | 152.5 (24.5) |
| $T_{max}$ (h) | 5.41 (37.4) | 5.85 (32.4) | 5.96 (30.3) |
| $T_{1/2\,el}$ (h) | 7.64 (29.6) | 6.18 (22.8) | 6.74 (18.1) |
| M1/Tramadol Ratio | 0.37 (50.1) | 0.37 (48.7) | 0.38 (51.3) |

TABLE 14C

Ratio of Means & 90% Confidence Interval for Plasma Tramadol

| Statistical Analysis (ANOVA) | Treatment Comparisons | Ratio[1] | 90% Geometric C.I.[2] Lower | Upper |
|---|---|---|---|---|
| $AUC_{0-t}$ | AM Fasting vs AM Fed | 98.64 | 94.03% | 103.47% |
| | AM Fasting vs PM Fasting | 100.99 | 96.28% | 105.94% |
| $AUC_{0-inf}$ | AM Fasting vs AM Fed | 100.05 | 95.40% | 104.92% |
| | AM Fasting vs PM Fasting | 102.18 | 97.43% | 107.15% |
| $C_{max}$ | AM Fasting vs AM Fed | 90.01 | 84.41% | 95.97% |
| | AM Fasting vs PM Fasting | 95.49 | 89.55% | 101.81% |

[1]Ratio of least squares means
[2]Calculated from log-transformed data

TABLE 14D (Mean Pharmacokinetic Parameters for Plasma O-desmethyltramadol (n = 27))

| Parameters | AM Dosing (Fasting) Mean (CV (%)) | AM Dosing (Fed) Mean (CV (%)) | PM Dosing (at least 2 hrs after food) Mean (CV (%)) |
|---|---|---|---|
| $AUC_{0-t}$ (ng · h/mL) | 870.9 (29.1) | 872.0 (30.0) | 871.4 (30.3) |
| $AUC_{0-inf}$ (ng · h/mL) | 909.5 (28.2) | 892.2 (29.5) | 898.5 (28.7) |
| $C_{max}$ (ng/mL) | 40.4 (38.2) | 45.0 (15.7) | 46.9 (37.1) |
| $T_{max}$ (h) | 7.41 (40.2) | 8.37 (28.1) | 7.81 (31.8) |
| $T_{1/2\,el}$ (h) | 8.53 (29.1) | 6.89 (18.2) | 7.68 (23.5) |

TABLE 14E

Ratio of Means & 90% Confidence Interval for Plasma O-desmethyltramadol

| Statistical Analysis (ANOVA) | Treatment Comparisons | Ratio[1] | 90% Geometric C.I.[2] Lower | Upper |
|---|---|---|---|---|
| $AUC_{0-t}$ | AM Fasting vs AM Fed | 99.88 | 96.19% | 103.72% |
| | AM Fasting vs PM Fasting | 100.49 | 96.78% | 104.34% |
| $AUC_{0-inf}$ | AM Fasting vs AM Fed | 102.15 | 98.11% | 106.35% |
| | AM Fasting vs PM Fasting | 101.31 | 97.31% | 105.48% |
| $C_{max}$ | AM Fasting vs AM Fed | 87.96 | 82.56% | 93.72% |
| | AM Fasting vs PM Fasting | 85.38 | 80.13% | 90.96% |

[1]Ratio of least squares means
[2]Calculated from log-transformed data

TABLE 14E (Mean Pharmacokinetic Parameters for Plasma M5 (n = 27))

| Parameters | AM Dosing (Fasting) Mean (CV (%)) | PM Dosing (at least 2 hrs after food) Mean (CV (%)) |
|---|---|---|
| $AUC_{0-t}$ (ng · h/mL) | 917.96 (37.4) | 938.24 (36.4) |
| $AUC_{0-inf}$ (ng · h/mL) | 985.84 (35.4) | 979.38 (35.9) |
| $C_{max}$ (ng/mL) | 40.59 (40.9) | 44.47 (41.2) |
| $T_{max}$ (h) | 9.0 (43.1) | 9.7 950.1) |

EXAMPLE 15

A three-way, single-dose, open-label, fasting and fed, comparative bioavailability study of delayed and extended release tramadol hydrochloride tablets of the invention (2×100 mg) versus the controlled release matrix hydrocolloid formulation tablet of Example 14 involving normal, healthy, non-smoking male and female volunteers was conducted.

This study evaluated the relative bioavailability of delayed and extended release tramadol hydrochloride tablets of the invention (2×100 mg of Example 1, Composition C) versus the controlled release matrix hydrocolloid formulation tablet of Example 14 under fasting (both formulations) and fed (one formulation) conditions.

This study was a randomized, three-way crossover study design in fifteen (15) normal, healthy, non-smoking male and female volunteers and three (3) alternates (total 11 males and 7 females).

Of the 18 volunteers who were dosed, 2 did not complete the study. Subject No. 10 was withdrawn during Period 1 due to adverse events and Subject No. 12's randomization scheme was not respected in Period 1. Thus, 16 subjects completed the study and their data were used for efficacy analysis. Safety analysis and procedures were performed for the 18 subjects who were dosed. All subjects were non-smoking, between 18 and 45 years of age (inclusive), and with body weights no more than ±15% of the ideal weight for the subject's height and frame as determined by the Table of Desirable Weights for Men and Women. All female subjects were non-lactating, had negative pregnancy tests, and were taking an acceptable method of contraception.

The study periods were separated by a one-week washout period. Blood sampling for drug content analysis was carried out at 0.0 (pre-drug), 1.0, 2.0, 3.0, 4.0, 6.0, 8.0, 10.0, 12.0, 16.0, 20.0, 24.0, 30.0, 36.0, and 48.0 hours post-drug administration.

| Treatments: | A: | 2 Tablets of DER tramadol HCl 100 mg tablets of Example 1, Composition C, after a 10-hour overnight fast |
| --- | --- | --- |
| | B: | 2 Tablets of DER tramadol HCl 100 mg tablets of Example 1, Composition C after a high fat high-calorie content breakfast. |
| | C: | 2 Tablets of the controlled release matrix hydrocolloid formulation tablets of Example 14 after a 10-hour overnight fast |

The DER tramadol HCl tablets of the invention which exhibited AUC and $C_{max}$ values comparable to an equivalent dose of ULTRAM® given q.i.d. for one day was evaluated under fasting and fed conditions compared to the controlled release matrix hydrocolloid formulation tablet of Example 14.

All least-squares mean ratios and 90% geometric confidence intervals around the ratios (Treatment A/Treatment B) and (Treatment A/Treatment C) for $AUC_{0-t}$, $AUC_{0-inf}$ and $C_{max}$ were within the 80% to 125% limits for both tramadol and o-desmethyltramadol, with the exception of least-squares mean ratio (Treatment A/Treatment C) for $C_{max}$ for o-desmethyltramadol as well as geometric confidence intervals around the ratio (Treatment A/Treatment C) for $C_{max}$ for tramadol and its metabolite. Moreover, the gender and treatment×gender terms were found to be not significant for $AUC_{0-t}$, $AUC_{0-inf}$ and $C_{max}$, demonstrating that both males and females behaved similarly in regards to the treatment effect.

A total of 100 adverse events occurred during the study. Of the 18 subjects who comprised the safety population, fourteen subjects (77.8%) experienced at least one adverse event. Females seemed to experience more adverse events than males. Seven subjects (3 males and 4 females) randomized to treatment A experienced 27 adverse events (8 for males and 19 for females), 9 subjects (3 males and 6 females) randomized to treatment B experienced 28 adverse events (6 for males and 22 for females), and 10 subjects (5 males and 5 females) randomized to treatment C experienced 45 adverse events (15 for males and 30 for females). No serious adverse events were reported during the study.

Based on these results, the rate and extent of absorption of the DER tramadol hydrochloride 2×100 mg tablets were not significantly affected by food, as evidenced by ratios (Treatment A/Treatment B) of least-squares means for $C_{max}$ and AUCs within the range of 80-125%. For the treatment A and treatment C comparison, these two formulations are comparable regarding the extent of absorption but not the rate of absorption as evidenced by ratios (Treatment A/Treatment C) of least-squares means for AUCs within the range of 80-125% and ratio (Treatment A/Treatment C) of least-squares means for $C_{max}$ outside the range of 80-125%. In addition the mean lag time for treatment C was 0.000 hours for both tramadol and its metabolite, demonstrating that the absorption of this formulation is faster than the DER formulations of the invention. Moreover, the products were well tolerated overall.

The mean pharmacokinetic parameters and 90% confidence interval for the ratio of the geometric mean AUC are presented in Table 15A and 15B for tramadol and 15C and 15D for mono-O-desmethyltramadol.

Figure 40:
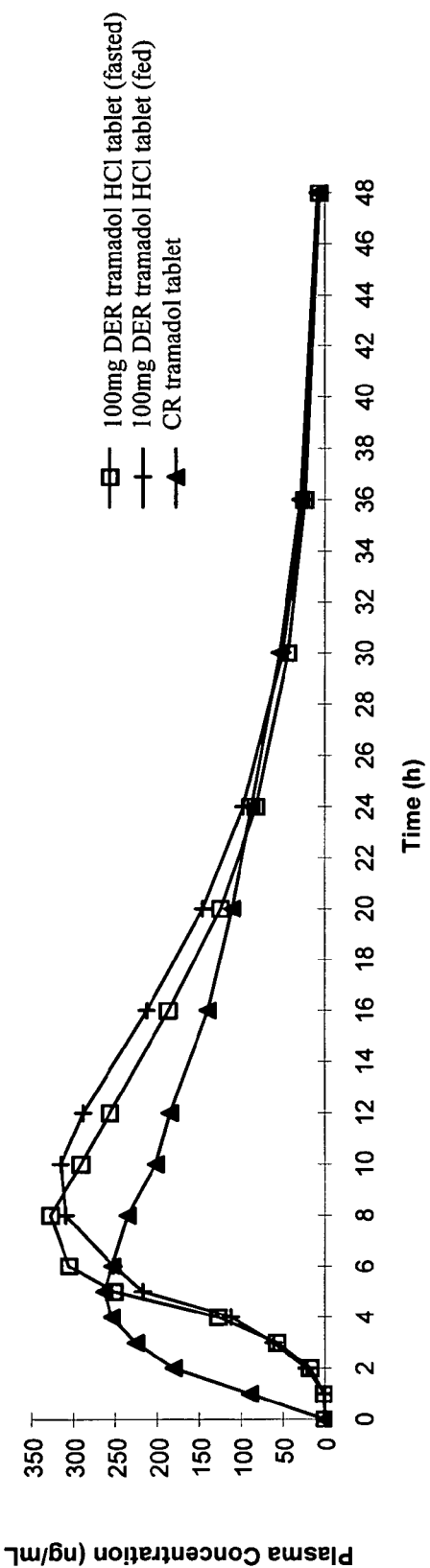
FIG. 40 is a graph illustrating the mean plasma tramadol concentrations over time of a single dose administration of DER Composition A compared to the tablet of FIG. 37 under fed and fasted conditions.
Figure 41:
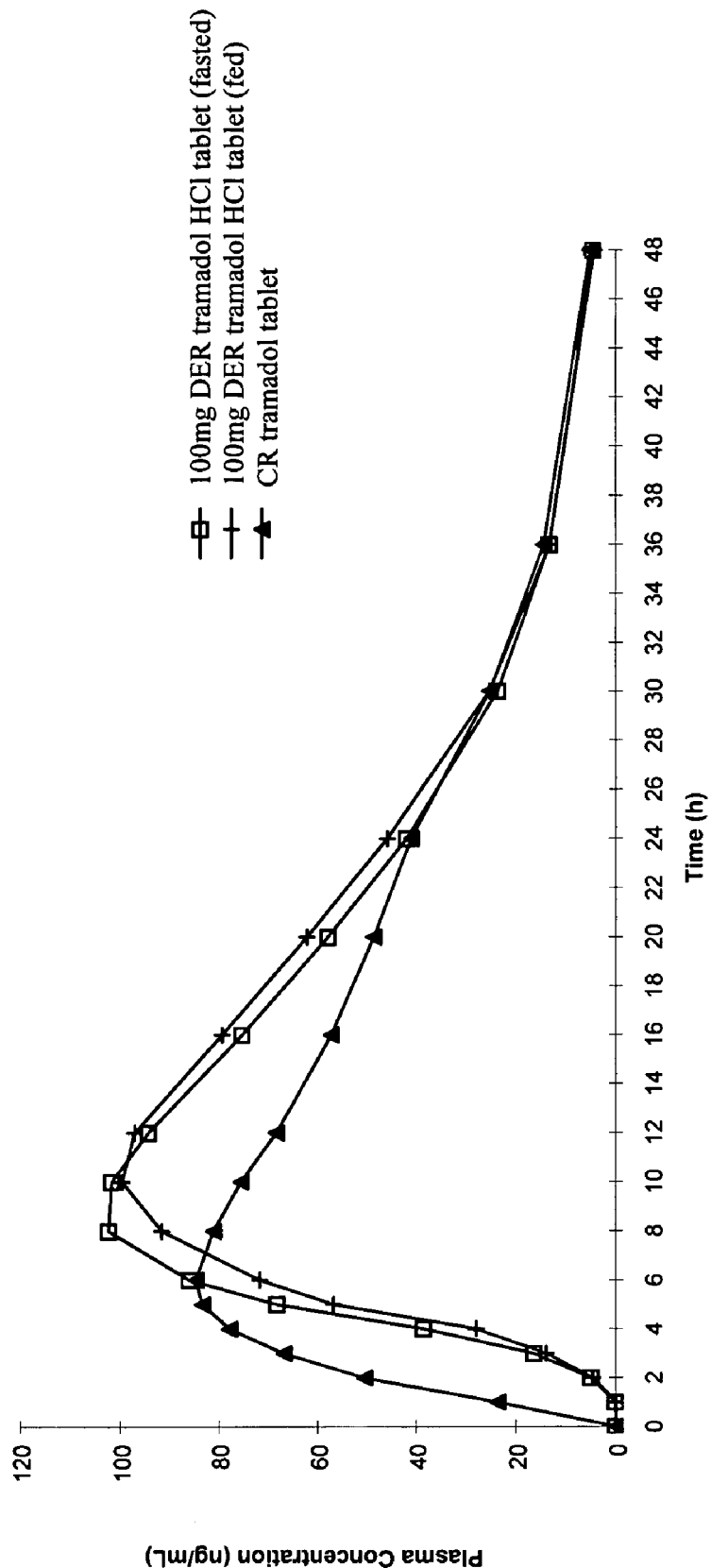
FIG. 41 is a graph comparing the mean plasma desmethyltramadol concentrations over time of a single dose administration of the tablets of FIG. 40 fed and fasted conditions.

FIGS. 40 and 41 depict the tramadol and mono-O-desmethyltramadol plasma levels, respectively, when administered after fasting and fed conditions.

Based upon a longer $T_{max}$ and higher $C_{max}$, the delayed and extended release formulations of the invention exhibits a desirable pharmacokinetic profile for use in pre-emptive dental pain.

TABLE 15A (Mean Pharmacokinetic Parameters for Plasma Tramadol (n = 15))

| Parameters | Treatment A Mean (CV (%)) | Treatment B Mean (CV (%)) | Treatment C Mean (CV (%)) |
| --- | --- | --- | --- |
| $AUC_{0-t}$ (ng · h/mL) | 5078.97 (19.59) | 5391.64 (19.80) | 4892.42 (22.37) |
| $AUC_{0-inf}$ (ng · h/mL) | 5159.41 (19.91) | 5454.67 (20.05) | 4996.98 (22.99) |
| $AUC_{t/inf}$ (%) | 98.51 (1.05) | 98.89 (0.59) | 98.07 (1.48) |
| $C_{max}$ (ng/mL) | 339.00 (25.85) | 338.47 (18.75) | 273.81 (16.95) |
| $T_{max}$ (h) | 7.53 (17.64) | 8.88 (17.75) | 5.12 (25.74) |
| $T_{lag}$ (h) | 0.765 (57.18) | 0.824 (64.19) | 0.000 (—) |
| $T_{1/2\,el}$ (h) | 6.43 (17.65) | 6.18 (12.50) | 6.92 (21.51) |

TABLE 15B (Ratio of Means & 90% Confidence Interval for Plasma Tramadol)

| Statistical Analysis (ANOVA) | Treatment Comparisons | Ratio[1] | 90% Geometric C.I.[2] Lower | Upper |
| --- | --- | --- | --- | --- |
| $AUC_{0-t}$ | Treatment (A) vs Treatment (B) | 93.50% | 86.69% | 100.85% |
| | Treatment (A) vs Treatment (C) | 105.37% | 97.69% | 113.65% |
| $AUC_{0-inf}$ | Treatment (A) vs Treatment (B) | 93.97% | 87.14% | 101.34% |
| | Treatment (A) vs Treatment (C) | 105.10% | 97.46% | 113.34% |
| $C_{max}$ | Treatment (A) vs. Treatment (B) | 100.55% | 89.90% | 112.46% |
| | Treatment (A) vs. Treatment (C) | 121.00% | 108.19% | 135.33% |

[1]Ratio of least squares means
[2]Calculated from log-transformed data

TABLE 15C (Mean Pharmacokinetic Parameters for Plasma O-desmethyltramadol (n = 15))

| Parameters | Treatment A | | Treatment B | | Treatment C | |
|---|---|---|---|---|---|---|
| | Mean | CV (%) | Mean | CV (%) | Mean | CV (%) |
| $AUC_{0-t}$ (ng · h/mL) | 1973.29 | (21.35) | 1976.17 | (23.84) | 1880.16 | (25.04) |
| $AUC_{0-inf}$ (ng · h/mL) | 2027.59 | (21.38) | 2021.39 | (23.95) | 1945.83 | (25.47) |
| $C_{max}$ (ng/mL) | 108.24 | (31.94) | 104.09 | (26.53) | 87.41 | (27.11) |
| $T_{max}$ (h) | 9.41 | (18.04) | 9.65 | (15.08) | 6.71 | (46.79) |
| $T_{lag}$ (h) | 0.941 | (25.77) | 1.059 | (22.91) | 0.000 | — |
| $T_{1/2\ el}$ (h) | 7.29 | (16.14) | 6.96 | (14.86) | 7.71 | (23.43) |

TABLE 15D (Ratio of Means & 90% Confidence Interval for Plasma O-desmethyltramadol)

| Statistical Analysis (ANOVA) | Treatment Comparisons | Ratio[1] | 90% Geometric C.I.[2] | |
|---|---|---|---|---|
| | | | Lower | Upper |
| $AUC_{0-t}$ | Treatment (A) vs Treatment (B) | 100.27% | 93.97% | 106.98% |
| | Treatment (A) vs Treatment (C) | 107.32% | 100.58% | 114.51% |
| $AUC_{0-inf}$ | Treatment (A) vs Treatment (B) | 100.79% | 94.52% | 107.46% |
| | Treatment (A) vs Treatment (C) | 106.87% | 100.23% | 113.95% |
| $C_{max}$ | Treatment (A) vs Treatment (B) | 104.76% | 95.62% | 114.76% |
| | Treatment (A) vs Treatment (C) | 123.59% | 112.81% | 135.39% |

[1]Ratio of least squares means
[2]Calculated from log-transformed data

The incidence of adverse events resulting from the administration of the controlled release matrix hydrocolloid formulation was compared to the incidence of adverse events resulting from the administration of the delayed and extended release tramadol HCl composition described herein and are summarized in Table 15E:

TABLE 15E (Total Number of Adverse Events Resulting From Prior Art Formulation vs. Total Number of Adverse Events Resulting from DER tramadol HCl Tablet of the Invention)

| | N*= | % versus prior art formulation | % Reduction |
|---|---|---|---|
| Total Number of Adverse Events | | | |
| Pre-Dose | 3 | N/A | N/A |
| DER Tramadol HCl 100 mg Tablet, Fasting | 27 | 60.00 | −40.00 |
| DER Tramadol HCl 100 mg Tablet, Fed | 28 | 62.22 | −37.78 |
| Prior Art Tramadol HCl ER 100 mg Tablet, Fasting | 45 | 100.00 | 0.00 |
| Causal Comparable Conditions Number of Adverse Events | | | |
| DER Tramadol HCl 100 mg, Fasting | 23 | 69.70 | −30.30 |
| Prior Art Tramadol HCl ER 100 mg Tablet, Fasting | 33 | 100.00 | 0.00 |

*The reduction in adverse events was found to be statistically significant as determined by a Chi-Square Test and a Binomial Proportion Test.

EXAMPLE 16

The coated cores of Example 3A are placed into gelatin capsules. The capsules filled with the coated cores, when administered to a human, provide a delayed and extended release of tramadol.

EXAMPLE 17

The coated cores of Example 3A are mixed with a binder and compressed into a unitary solid dosage form. The unitary solid dosage form, when administered to a human, provides a delayed and extended release of tramadol.

CONCLUSION

The present invention relates to modified-release compositions for oral administration of at least one form of tramadol, to processes for their preparation and to their medical use. In particular, the present invention relates to a delayed and extended release composition of at least one form of tramadol.

The delayed and extended release composition of the at least one form of tramadol is bioequivalent to the currently marketed immediate-release formulation of tramadol, ULTRAM®, with the mean values for $C_{max}$ and $AUC_{0-t}$ of the preferred formulations falling within the 80-125% range of acceptance. The compositions of the invention provide at least three distinct features: 1) the compositions of the invention provides for a once-a-day administration of the at least one form of tramadol as opposed to the multiple dosing schedule for the immediate-release composition for ULTRAM®, 2) the DER compositions provide for a delay in the time to reach the clinically effective amount of the at least one form of tramadol in the plasma such that a therapeutically effective level is not reached before about 3 hours after the first administration of the composition, and 3) in the fed state the DER composition provides for a delay of at least about 1 hour in the mean time to reach maximum plasma concentrations of the at least one form of tramadol.

Without wishing to be bound to any particular theory, it is believed that when a composition of the present invention is in the presence of an aqueous medium, the water-soluble polymer component of the release-controlling coating hydrates and swells. The hydrated membrane at this point acts as a permeable membrane, and a flux of aqueous medium into the composition is established. This in turn dissolves the at least one form of tramadol from the core. The saturated solution of the at least one form of tramadol inside the coated tablet now establishes a flux gradient of the at least one form of tramadol going outwards through the permeable membrane to the aqueous medium. The flux on either side is controlled by the porosity of the permeable membrane, which in turn depends on the amount of soluble polymer in the membrane. The rate of efflux of the at least one form of tramadol from inside the membrane is initially greater, gradually slowing down until sink conditions are established outside and inside the permeable membrane (following Fick's law of diffusion).

Accordingly, the delayed release characteristics of the formulations of the invention do not depend upon enteric coatings or other pH-dependent release modifying coatings. Rather, the coating of the present invention is believed to respond to osmotic pressure gradients as reflected by the osmolality of the surrounding physiologic fluids. While not wishing to be bound by any particular theory, it is believed that the DER tramadol formulations of the invention show a delay of at least about 1 hour in the mean time to reach maximum plasma concentrations of the at least one form of tramadol in the presence of food because the osmolality of the gastric fluid is altered in the fed state. As a result, less fluid influxes into the formulation, resulting in a greater delay in release of the at least one form of tramadol. As the osmotic pressure gradient across the membrane increases over time after feeding, the release of the at least one form of tramadol concomitantly increases.

While not wishing to be bound to any particular theory, it is believed that due to the delay in the release of the at least one form of tramadol from the delayed and extended release tramadol composition of the invention, and hence very slow but gradual rise in the plasma concentrations of the at least one form of tramadol after first administration of the composition, the incidence of adverse events seen in individuals administered with the compositions of the invention is less than or equal to immediate release tramadol formulations such as ULTRAM®.

A statistically significant reduction in adverse events is seen in comparison with a controlled release matrix hydrocolloid tramadol HCl composition that has no delayed release, which falls within the teachings of the prior art. Even though both the compositions are controlled/extended/sustained release compositions, the primary difference in the plasma tramadol profiles between the DER composition of the invention and that of the controlled release matrix hydrocolloid tramadol HCl formulation is the rise in plasma tramadol concentration such that the clinically effective plasma tramadol concentration is reached after about 3 hours after first administration when the DER compositions of the invention are administered. This feature is not appreciated nor disclosed by any of the prior art formulations.

The invention claimed is:

1. A unit dosage of a delayed and extended release pharmaceutical composition for oral administration once daily, comprising per unit dosage:
   a) an immediate release core comprising about 100 to about 400 mg of tramadol hydrochloride, wherein about 70 to about 98% by weight of the core dry weight is said tramadol hydrochloride and about 2 to about 30% by weight of the core dry weight is a plurality of pharmaceutically acceptable excipients, and
   b) about 8 to about 30% by weight of the core dry weight of a coating completely surrounding said core, said coating comprising a water-insoluble film-forming polymer present in the coating in an amount of from about 20% to about 89% by weight of the coating dry weight, a water-soluble polymer present in the coating in an amount of from about 10% to about 75% of the coating dry weight, and a plasticizer present in the coating from about 1% to about 30% of the coating dry weight,
   wherein said coating becomes permeable to the tramadol hydrochloride in the presence of an aqueous medium; and
   wherein said composition provides a delayed and extended release of the tramadol hydrochloride such that
   (i) the mean plasma concentration of the tramadol hydrochloride reaches a therapeutically effective level at a time which is after at least about 3 hours after first administration of said composition in the fasted state;
   (ii) in the fed state, the mean time to reach maximum plasma concentration of the tramadol hydrochloride after first administration of said composition is delayed by at least about one hour compared to that in the fasted state; and
   (iii) at steady state the composition has a fluctuation index lower than an immediate-release composition of the tramadol hydrochloride administered 3 or 4 times a day.

2. The unit dosage of claim 1, wherein said unit dosage provides an in vitro dissolution profile using the USP Basket Method at 75 rpm in 900 ml 0.1 N HCl at 37° C. such that after about 2 hours, from about 0% to about 22% by weight of the tramadol hydrochloride is released, after about 4 hours from about 5% to about 30% by weight of said tramadol hydrochloride is released, after about 6 hours, from about 15% to about 38% by weight of the tramadol hydrochloride is released, and after about 8 hours, more than about 40% by weight of said tramadol hydrochloride is released.

3. The unit dosage of claim 1, wherein said unit dosage provides an in vitro dissolution profile using the USP Basket Method at 75 rpm in 900 ml 0.1 N HCl at 37° C. such that after about 2 hours, from about 0% to about 10% by weight of the tramadol hydrochloride is released, after about 4 hours from about 12% to about 20% by weight of said tramadol hydrochloride is released, after about 6 hours, from about 30% to about 38% by weight of the tramadol hydrochloride is released, after about 8 hours, from about 48% to about 56% by weight of said tramadol hydrochloride is released, after about 10 hours from about 64% to about 72% by weight of the tramadol hydrochloride is released, and after about 12 hours, more than about 76% by weight of said tramadol hydrochloride is released.

4. The unit dosage of claim 1, wherein said unit dosage when administered to a patient in need thereof provides a mean time to maximum plasma concentration ($T_{max}$) of the tramadol hydrochloride ranging from about four to about fourteen hours.

5. The unit dosage of claim 1, wherein said unit dosage exhibits an incidence of adverse events which is less than or equal to that of an immediate-release composition of the tramadol hydrochloride.

6. The unit dosage of claim 1, wherein said unit dosage exhibits a statistically significant reduction in adverse events when compared to an extended but not delayed release composition of the tramadol hydrochloride.

7. The unit dosage of claim 1, wherein the core of said unit dosage comprises from about 100 mg to about 300 mg of the tramadol hydrochloride.

8. The unit dosage of claim 1, wherein said pharmaceutically acceptable excipients comprising the core are selected from the group consisting of a binder, a lubricant, a filler, a glidant and combinations thereof.

9. The unit dosage of claim 8, wherein the excipients comprise a binder that is a water-soluble polymer.

10. The unit dosage of claim 9, wherein said water-soluble polymer is present in an amount of from about 1% to about 25% by weight of the core dry weight.

11. The unit dosage of claim 10, wherein said water-soluble polymer is selected from the group consisting of a starch derivative gelatin, polyvinylpyrrolidone, polyvinyl alcohol, hydroxypropylmethylcellulose, hydroxypropylcellulose, xanthan gum, a carbomer, caragheen and combinations thereof.

12. The unit dosage of claim 10, wherein said water-soluble polymer is polyvinyl alcohol.

13. The unit dosage of claim 12, wherein said polyvinyl alcohol is present at about 2% by weight of the core dry weight.

14. The unit dosage of claim 8, wherein the excipients comprise a lubricant that is present in an amount from about 0.5% to about 10% by weight of the core dry weight.

15. The unit dosage of claim 14, wherein said lubricant is selected from the group consisting of stearic acid, magnesium stearate, glyceryl behenate, talc, mineral oil (in PEG), sodium stearyl fumarate, a hydrogenated vegetable oil, sodium benzoate, calcium stearate and combinations thereof.

16. The unit dosage of claim 15, wherein said lubricant is sodium stearyl fumarate.

17. The dosage of claim 16, wherein said sodium stearyl fumarate is present at about 1% by weight of the core dry weight.

18. The unit dosage of claim 8, wherein the excipients comprise a filler that is present in an amount from about 1% to about 25% by weight of the core dry weight.

19. The unit dosage of claim 18, wherein said filler is selected from the group consisting of lactose monohydrate, anhydrous lactose, mannitol, sorbitol, microcrystalline cellulose, dibasic calcium, calcium sulfate, pulp cellulose, and combinations thereof.

20. The unit dosage of claim 19, wherein said filler is microcrystalline cellulose.

21. The unit dosage of claim 8, wherein the excipients comprise a glidant that is colloidal silicon dioxide and is present at about 1% by weight of the core dry weight.

22. The unit dosage of claim 1, wherein said water-insoluble film forming polymer is selected from the group consisting of a cellulose ether, a cellulose ester, a methacrylic acid derivative, an aqueous ethylcellulose dispersion, an aqueous acrylic enteric system, a polyvinyl derivative, and combinations thereof.

23. The unit dosage of claim 1, wherein said water-insoluble film-forming polymer is a cellulose ether.

24. The unit dosage of claim 23, wherein said cellulose ether is ethylcellulose.

25. The unit dosage of claim 1, wherein said water-soluble polymer is selected from the group consisting of methylcellulose, hydroxypropylmethylcellulose, hydroxypropylcellulose, hydroxyethylcellulose, polyvinyl alcohol, polyvinylpyrrolidone, and combinations thereof.

26. The unit dosage of claim 1, wherein said water-soluble polymer is polyvinylpyrrolidone.

27. The unit dosage of claim 1, wherein said plasticizer is selected from the group consisting of an ester, an oil, a polyalkylene glycol and combinations thereof.

28. The unit dosage of claim 1, wherein said plasticizer is an ester.

29. The unit dosage of claim 28, wherein said ester is dibutyl sebacate.

30. The unit dosage of claim 1, wherein said water-insoluble film-forming polymer is ethyl cellulose and is present in an amount from about 53% to about 70% of the coating dry weight, said water-soluble polymer is polyvinyl pyrrolidone and is present in an amount from about 20% to about 26% of the coating dry weight, and said plasticizer is dibutyl sebacate and is present from about 14% to about 18% by weight of the coating dry weight.

31. The unit dosage of claim 1 wherein, said coating is present at about 16% by weight of the core dry weight.

32. The unit dosage of claim 1, in the form of a tablet.

33. The unit dosage of claim 1, in the form of a capsule.

34. The unit dosage of claim 1, which upon an in vivo administration releases substantially no tramadol into the plasma until at least 3 hours after administration.

35. The unit dosage of claim 1, wherein the plurality of excipients comprises a lubricant, a binder, and a glidant.

* * * * *